(12) United States Patent
Pedersen

(10) Patent No.: US 10,730,906 B2
(45) Date of Patent: Aug. 4, 2020

(54) MULTI-STEP SYNTHESIS OF TEMPLATED MOLECULES

(75) Inventor: Henrik Pedersen, Bagsvaerd (DK)

(73) Assignee: NUEVOLUTIONS A/S, Copenhagen (DK)

( * ) Notice: Subject to any disclaimer, the term of this patent is extended or adjusted under 35 U.S.C. 154(b) by 2072 days.

(21) Appl. No.: 10/523,006

(22) PCT Filed: Jul. 30, 2003

(86) PCT No.: PCT/DK03/00516
§ 371 (c)(1),
(2), (4) Date: Dec. 16, 2005

(87) PCT Pub. No.: WO2004/013070
PCT Pub. Date: Feb. 12, 2004

(65) Prior Publication Data
US 2006/0121470 A1    Jun. 8, 2006

Related U.S. Application Data

(60) Provisional application No. 60/399,692, filed on Aug. 1, 2002.

(30) Foreign Application Priority Data

Aug. 1, 2002 (DK) .................................. 2002 01171

(51) Int. Cl.
| C40B 40/08 | (2006.01) |
| C40B 40/10 | (2006.01) |
| C07H 21/00 | (2006.01) |
| C12N 15/10 | (2006.01) |

(52) U.S. Cl.
CPC ......... *C07H 21/00* (2013.01); *C12N 15/1068* (2013.01)

(58) Field of Classification Search
None
See application file for complete search history.

(56) References Cited

U.S. PATENT DOCUMENTS

| 4,822,731 A | 4/1989 | Watson et al. |
| 5,013,830 A | 5/1991 | Ohtsuka et al. |
| 5,047,519 A | 9/1991 | Hobbs, Jr. et al. |
| 5,324,829 A | 6/1994 | Bahl et al. |
| 5,432,272 A | 7/1995 | Benner |
| 5,437,977 A | 8/1995 | Segev |
| 5,449,613 A | 9/1995 | Dordick et al. |
| 5,451,503 A | 9/1995 | Hogan et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugarman et al. |
| 5,571,677 A | 11/1996 | Gryaznov |
| 5,571,903 A | 11/1996 | Gryaznov et al. |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,643,722 A | 7/1997 | Rothschild et al. |
| 5,646,265 A | 7/1997 | McGee |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar et al. |
| 5,670,633 A | 9/1997 | Cook et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A * | 3/1998 | Lerner et al. ................... 506/31 |
| 5,739,314 A | 4/1998 | Roy et al. |
| 5,739,386 A | 4/1998 | Holmes et al. |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargilli et al. |
| 5,817,795 A | 6/1998 | Gryaznov et al. |
| 5,780,613 A | 7/1998 | Letsinger et al. |
| 5,789,162 A | 8/1998 | Dower et al. |
| 5,789,172 A | 8/1998 | Still et al. |

(Continued)

FOREIGN PATENT DOCUMENTS

| DE | 19646372 | 6/1997 |
| DE | 196 42 751 | 4/1998 |

(Continued)

OTHER PUBLICATIONS

Doyon, J.B et al. "Highly sensitive in vitro selections for DNA-linked synthetic small molecules with protein binding affinity and specificity" J. Am. Chem. Soc, Sep. 16, 2003.
Kanan, M.W et al. "Reaction discovery enabled by DNA-templated synthesis and in vitro selection" Nature, vol. 431, Sep. 30, 2004.
"Finding reactions in a haystack: Try'em all, see what works" Meeting American Chemical Society, Sep. 10, 2004, vol. 305, Science.
"The Nucleus", Jan. 2004, vol. LXXXII, No. 5, R. Grubina; "Summer Research Report: R. Grubina on DNA Templated Synthesis for Small Molecule Library", p. 10-14.
Nazarenko et al., "A closed tube format for amplification and detection of DNA based on energy transfer", Nucleic Acids Research, 1997, vol. 25, No. 12, p. 2516-2521.

(Continued)

*Primary Examiner* — Tracy Vivlemore
*Assistant Examiner* — Sahana S Kaup
(74) *Attorney, Agent, or Firm* — Merchant & Gould P.C.

(57) ABSTRACT

Disclosed is a method for the manufacture of a library of complexes. The complexes comprise templated molecules attached to the template which directed the synthesis thereof. The templated molecules are produced in a step-by-step fashion which provides for a high local concentration of reactive groups involved in the formation of connections between the individual components of the template molecule.

98 Claims, 61 Drawing Sheets

Specification includes a Sequence Listing.

(56) References Cited

U.S. PATENT DOCUMENTS

| | | |
|---|---|---|
| 5,795,976 A | 8/1998 | Oefner et al. |
| 5,804,563 A | 9/1998 | Li et al. |
| 5,824,471 A | 10/1998 | Mashal et al. |
| 5,830,658 A | 11/1998 | Gryaznov et al. |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,087,112 A | 7/2000 | Dale |
| 6,090,912 A | 7/2000 | Lebl et al. |
| 6,096,500 A | 8/2000 | Oprandy et al. |
| 6,096,875 A | 8/2000 | Khan et al. |
| 6,127,533 A | 10/2000 | Cook et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar et al. |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2* | 6/2010 | Pedersen ............ C07D 405/04 435/5 |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 | 6/2012 | Freskgard et al. |
| 2002/0048760 A1 | 4/2002 | Drmanac et al. |
| 2002/0055125 A1 | 5/2002 | Charych et al. |
| 2002/0007288 A1 | 6/2002 | Endou |
| 2002/0072887 A1 | 6/2002 | Szalma et al. |
| 2002/0081714 A1 | 6/2002 | Jain et al. |
| 2002/0115068 A1 | 8/2002 | Tomlinsen et al. |
| 2002/0127598 A1 | 9/2002 | Zhou et al. |
| 2002/0142335 A1 | 10/2002 | Strittmatter et al. |
| 2003/0004122 A1 | 1/2003 | Beigelman et al. |
| 2003/0050453 A1 | 3/2003 | Sorge |
| 2003/0113738 A1* | 6/2003 | Liu et al. .................. 435/6 |
| 2003/0182068 A1 | 9/2003 | Battersby et al. |
| 2003/0186233 A1 | 10/2003 | Chesnut et al. |
| 2003/0187240 A1 | 10/2003 | Cook et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197804 A1 | 10/2004 | Keefe et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu et al. |
| 2005/0042669 A1 | 2/2005 | Liu et al. |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0023041 A1 | 9/2011 | Lundorf et al. |
| 2011/0230419 A1 | 9/2011 | Lundorf et al. |
| 2012/0002881 A1 | 2/2012 | Freskgard et al. |
| 2012/0028812 A1 | 2/2012 | Freskgard et al. |

FOREIGN PATENT DOCUMENTS

| | | |
|---|---|---|
| EP | 0604552 | 4/1993 |
| EP | 0542770 | 5/1993 |
| EP | 0643778 | 10/1993 |
| EP | 0695305 | 10/1994 |
| EP | 0776330 | 10/1996 |
| EP | 0766826 | 4/1997 |
| EP | 0773227 | 5/1997 |
| EP | 0778280 | 6/1997 |
| EP | 0879219 | 11/1998 |
| EP | 0962527 | 12/1999 |
| EP | 1324045 | 7/2003 |
| EP | 1402024 B1 | 3/2004 |
| EP | 1483585 B1 | 12/2004 |
| EP | 1514938 | 3/2005 |
| EP | 1533385 | 5/2005 |
| EP | 1828381 B1 | 9/2007 |
| EP | 1832567 | 9/2007 |
| EP | 2305808 | 4/2011 |
| JP | 05292967 | 11/1993 |
| JP | 08000268 | 1/1996 |
| WO | 0324616 | 7/1989 |
| WO | 9005785 | 5/1990 |
| WO | 9303172 | 2/1991 |
| WO | 9105058 | 4/1991 |
| WO | WO 1991/19818 | 12/1991 |
| WO | WO 1992/00091 | 1/1992 |
| WO | WO 1992/02536 | 2/1992 |
| WO | WO1992/22875 | 12/1992 |
| WO | WO 1993/06121 A1 | 4/1993 |
| WO | WO 1993/20242 | 10/1993 |
| WO | WO 1994/08051 | 4/1994 |
| WO | WO 1994/13623 | 6/1994 |
| WO | WO 1994/24143 | 10/1994 |
| WO | WO 1995/04160 | 2/1995 |
| WO | WO 1995/06293 | 3/1995 |

(56) References Cited

FOREIGN PATENT DOCUMENTS

| | | |
|---|---|---|
| WO | 9512608 | 5/1995 |
| WO | WO 1996/03418 | 2/1996 |
| WO | 9609316 | 3/1996 |
| WO | 9612014 | 4/1996 |
| WO | WO 1996/11878 | 4/1996 |
| WO | WO 1996/24061 | 8/1996 |
| WO | WO 1996/24847 | 8/1996 |
| WO | 9635699 | 11/1996 |
| WO | WO96035699 A1 * | 11/1996 |
| WO | WO 1996/40201 | 12/1996 |
| WO | WO 1996/41011 | 12/1996 |
| WO | WO 1997/04131 | 2/1997 |
| WO | WO 1997/11958 | 4/1997 |
| WO | WO 1997/19039 | 5/1997 |
| WO | WO 1997/27317 | 7/1997 |
| WO | WO 1997/35198 | 9/1997 |
| WO | WO 1998/01562 | 1/1998 |
| WO | 9831700 | 7/1998 |
| WO | WO 1998/47613 | 10/1998 |
| WO | 9856904 | 12/1998 |
| WO | WO 1998/58256 | 12/1998 |
| WO | WO 1999/42605 | 8/1999 |
| WO | 9951546 | 10/1999 |
| WO | WO 1999/51773 | 10/1999 |
| WO | WO 1999/64378 | 12/1999 |
| WO | 0021909 | 4/2000 |
| WO | 0023458 | 4/2000 |
| WO | WO 2000/020639 | 4/2000 |
| WO | WO 2000/23456 | 4/2000 |
| WO | WO 2000/023458 | 4/2000 |
| WO | WO 2000/24882 | 5/2000 |
| WO | 0032823 | 6/2000 |
| WO | 2000/40695 | 7/2000 |
| WO | WO 2000/40695 | 7/2000 |
| WO | 0047775 | 8/2000 |
| WO | 0061775 | 10/2000 |
| WO | 0100876 | 1/2001 |
| WO | WO 2001/07657 | 2/2001 |
| WO | WO 2001/07690 | 2/2001 |
| WO | WO 2001/53539 | 7/2001 |
| WO | WO 2001/56955 | 8/2001 |
| WO | WO 2001/90414 | 11/2001 |
| WO | WO 2002/03067 | 1/2002 |
| WO | WO 2002/10186 | 2/2002 |
| WO | WO 2002/34948 | 5/2002 |
| WO | WO 2002/40664 | 5/2002 |
| WO | 02074929 | 9/2002 |
| WO | WO 2002/074978 | 9/2002 |
| WO | WO02074929 * | 9/2002 |
| WO | WO2002074929 * | 9/2002 |
| WO | WO 2002/083951 | 10/2002 |
| WO | WO2002090581 * | 11/2002 |
| WO | 02102820 | 12/2002 |
| WO | 02103008 | 12/2002 |
| WO | WO 2002/099078 | 12/2002 |
| WO | WO 2002/103008 | 12/2002 |
| WO | WO02103008 A2 * | 12/2002 |
| WO | WO 2003/025567 | 3/2003 |
| WO | WO 2003/062417 | 7/2003 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | WO 2003/076943 | 9/2003 |
| WO | 03082901 | 10/2003 |
| WO | 2004001042 | 12/2003 |
| WO | WO 2003/106679 | 12/2003 |
| WO | 2004009814 | 1/2004 |
| WO | WO 2004/007529 | 1/2004 |
| WO | 2004016767 | 2/2004 |
| WO | WO 2004/013070 | 2/2004 |
| WO | 2004024929 | 3/2004 |
| WO | 2004039825 | 5/2004 |
| WO | WO 2004/039962 | 5/2004 |
| WO | WO 2004/042019 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004110964 | 12/2004 |
| WO | WO 2005/003778 | 1/2005 |
| WO | WO 2005/008240 | 1/2005 |
| WO | 2005026387 | 3/2005 |
| WO | WO 2005/058479 | 6/2005 |
| WO | WO 2005/078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 A2 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 A2 | 5/2007 |
| WO | 2007/062664 | 6/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO2008/094599 | 8/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

Chan et al., "Intra-tRNA distance measurements for nucleocapsid protein-dependent tRNA unwinding during priming of HIV reverse transcription", PNAS vol. 96, p. 459-464, Jan. 1999.

DNA-templated synthesis as a basis for the evolution of synthetic molecules. Liu DR, Gartner ZJ, Kanan MW, Calderone CT Abstracts of Papers of the American Chemical Society 225: 612-ORGN, Part 2, Mar. 2003.

Rodriguez et al., "Template-directed extension of a guanosine 5'-phosphate covalently attached to an oligodeoxycytidylate template", J Mol Evol (1991) 33:477-482.

Inoue et al, Oligomerization of (Guanosine 5'-phosphor)-2-methylimidazolide on Poly(C), J. Mol. Biol. (1982), 162, 201-217.

C. B. Chen et al., "Template-directed synthesis on Oligodeoxycytidylate and Polydeoxycytidylate templates" J. Mol. Biol. 1985, 181, 271.

H. Rembold et al., "Single-strand regions of Poly(G) act as templates for oligo(C) synthesis" J. Mol. Evol. 1994, 38, 205.

T. Inoue et al., "A nonenzymatic RNA polymerase model", Science 1983, 219, p. 859-862.

O. L. Acevedo et al., "Non-enzymatic transcription of an oligonucleotide 14 residues long", J. Mol. Biol. 1987, 197, p. 187-193.

C. Böhler et al.,"Template switching between PNA and RNA oligonucleotides", Nature 1995, 376, 578-581.

Acevedo et al., "Template-directed oligonucleotide ligation on hydroxylapatite", Nature vol. 321, Jun. 19, 1986, p. 790-792.

Piccirilli, "RNA seeks its maker", Nature vol. 376, Aug. 17, 1995, p. 548-.

A. W. Schwartz et al., "Template-directed synthesis of novel, nucleic acid-like structures", Science 1985, 228, 585-7.

Halpin et al.: DNA display III. Solid-phase organic synthesis on unprotected DNA. PLoS Biol. Jul. 2004;2(7):E175. Epub Jun. 22, 2004.

(56) References Cited

OTHER PUBLICATIONS

Halpin et al.: DNA display II. Genetic manipulation of combinatorial chemistry libraries for small-molecule evolution. PLoS Biol. Jul. 2004;2(7):E174. Epub Jun. 22, 2004.
Halpin et al.: DNA display I. Sequence-encoded routing of DNA populations. PLoS Biol. Jul. 2004;2(7):E173. Epub Jun. 22, 2004.
"Highly Sensitive In Vitro Selections for DNA-Linked Synthetic Small Molecules with Protein Binding Affinity and Specificity" Doyon, J. B.; Snyder, T. M.; Liu, D. R. J. Am. Chem. Soc. 125, 12372-12373 (2003).
"Translation of DNA into Synthetic N-Acyloxazolidines" Li, X.; Gartner, Z. J.; Tse, B. N.; Liu, D. R. J. Am. Chem. Soc. 126, 5090-5092 (2004).
"DNA-Templated Organic Synthesis: Nature's Strategy for Controlling Chemical Reactivity Applied to Synthetic Molecules" Li, X.; Liu, D. R. Angew. Chem. Int. Ed. 43, 4848-4870 (2004).
"DNA-Templated Organic Synthesis and Selection of a Library of Macrocycles" Gartner, Z. J.; Tse, B. N.; Grubina, R.; Doyon, J. B.; Snyder, T. M.; Liu, D. R. Science 305, 1601-1605 (2004).
"Nucleic Acid-Templated Synthesis as a Model System for Ancient Translation" Calderone, C. T. and Liu, D. R. Curr. Opin. Chem. Biol. 8, 645-653 (2004).
"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).
"Translating DNA into synthetic Molecules", David R. Liu, PLoS Biology, Jul. 2004, vol. 2, Iss. 7, p. 905-6.
"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.
Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.
Nemoto, N et al. "In vitro virus: bonding of mRNA bearing puromycin at the 3'-terminal end to the C-terminal end of its encoded protein on the ribosome in vitro". FEBS Lett. Sep. 8, 1997;414(2):405-8.
Roberts, RW et al. "RNA-peptide fusions for the in vitro selection of peptides and proteins". Proc Natl Acad Sci U S A. Nov. 11, 1997;94(23):12297-302.
Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.
Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.
Keiler et al. "Role of a peptide tagging system in degradation of proteins synthesized from damaged messenger RNA". Science. Feb. 16, 1996;271(5251):990-3.
Benner, SA. "Expanding the genetic lexicon: incorporating non-standard amino acids into proteins by ribosome-based synthesis". Trends Biotechnol. May 1994:12(5):158-63.
Mendel, D. "Site-directed mutagenesis with an expanded genetic code". Annu. Rev. Biophys. Biomol. Struc. 1995. 24:463-93.
Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.
Liu DR et al. "Progress toward the evolution of an organism with an expanded genetic code". Proc Natl Acad Sci USA. Apr. 27, 1999;96(9):4780-5.
Liu, R et al. "Optimized synthesis of RNA-protein fusions for in vitro protein selection". Methods Enzymol. 2000;318:268-93.
Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.
Ellman J.A., et al. "Biosynthetic method for introducing Unnatural Amino acids site specifically into proteins". Methods Enzymol. 202, 301-336 (1992).
José Salas et al. "Biosynthetic Poiydeoxynucleotides as Direct Templates for Polypeptide Synthesis". J. of Biological Chemistry, vol. 243, No. 6, 1968, p. 1012-1015.
Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci U S A. Jan. 1979;76(1):51-5.
Bruick et al. "Template-directed ligation of peptides to oligonucleotides" Chemistry and Biology, vol. 3, No. 1, Jan. 1996, p. 49-56.
Tamura K, Schimmel P. "Oligonucleotide-directed peptide synthesis in a ribosome- and ribozyme-free system". Proc Natl Acad Sci USA. Feb. 13, 2001;98(4):1393-7.
Lewis RJ, Hanawalt PC. "Ligation of oligonucleotides by pyrimidine dimers—a missing 'link' in the origin of life?"22;298(5872):393-6.
Liu J, Taylor JS. "Template-directed photoligation of oligodeoxyribonucleotides via 4-thiothymidine". Nucleic Acids Res. Jul. 1, 1998;26(13):3300-4.
Fujimoto et al. "Template-directed photoreversible ligation of deoxyoligonucleotides via 5-Vinyldeoxyuridine" J. Am. Soc. 2000, 122, 5646-5647.
Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000, 41:33:6451-6454.
Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron letters 2000, 41:49:9437-40.
Letsinger et al. "Chemical Ligation of oligonucleotides in the presence and absence of a template". J. Amer. Chem. Soc. 1993, 115, 3808-9.
Gryaznov SM, Letsinger RL. "Template controlled coupling and recombination of oligonucleotide blocks containing thiophosphoryl groups". Nucleic Acids Res. Mar. 25, 1993;21(6):1403-8.
Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.
Herrlein MK, Letsinger RL. "Selective chemical autoligation on a double-stranded DNA template". Nucleic Acids Res. Nov. 25, 1994;22(23):5076-8.
Letsinger, RL; Wu, T; Elghanian, R "Chemical and photochemical ligation of oligonucleotide blocks". Nucleosides and nucleotides, 16(5&6), 643-652 (1997).
Visscher J, Schwartz AW "Template-directed synthesis of acyclic oligonucleotide analogues". J Mol Evol. Dec. 1988-Feb. 1989;28(1-2):3-6.
Visscher J, Bakker CG, van der Woerd R, Schwartz AW "Template-directed oligomerization catalyzed by a polynucleotide analog". Science. Apr. 21, 1989;244(4902):329-31.
Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.
Zhan, ZJ and Lynn, DG "Chemical Amplification through template-directed synthesis". J. Am. Chem. Soc. 1997, 119, 12420-1.
Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.
Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

(56) References Cited

OTHER PUBLICATIONS

Xu, Y and Kool, E "Rapid and Selective selenium-mediated autoligation of DNA strands" J. Am. Chem. Soc. 2000, 122, 9040-1 Pub. on web Aug. 31, 2000.
Xu Y, Karalkar NB, Kool ET. "Nonenzymatic autoligation in direct three-color detection of RNA and DNA point mutations". Nat Biotechnol. Feb. 2001;19(2):148-52.
Li X, Zhan ZY, Knipe R, Lynn DG. "DNA-catalyzed polymerization". J Am Chem Soc. Feb. 6, 2002;124(5):746-7.
Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.
Leitzel JC, Lynn DG "Template-directed ligation: from DNA towards different versatile templates". Chem Rec. 2001;1(1):53-62. Published online Jan. 30, 2001.
Schmidt JG, Nielsen PE, Orgel LE. "Information transfer from peptide nucleic acids to RNA by template-directed syntheses". Nucleic Acids Res. Dec. 1, 1997;25(23):4797-802.
Dower, WJ et al. "In vitro selection as a powerful tool for the applied evolution of proteins and peptides".Current Opinion in Chemical Biology, 2002, 6:390-398.
Brenner, S and Lerner, RA . "Encoded combinatorial chemistry" Proc. Natl. Acad. Sci. USA. vol. 89, p. 5381-3, Jun. 1992.
Gartner, Z; Liu, DR "The generality of DNA-templated synthesis as a basis for evolving non-natural small molecules". J Am Chem Soc. Jul. 18, 2001;123(28):6961-3.
David Liu. "Expanding the reaction scope of DNA-templated synthesis Angew". Chem. Int. Ed. 2002, 41, No. 10 pp. 1796-1800. Published May 15, 2002.
Gartner, ZJ et al. "Multistep small-molecule synthesis programmed by DNA templates". J. Am. Chem. Soc. vol. 124, No. 35, 2002, 10304-10306.
Calderone, CT et al. "Directing otherwise incompatible reactions in a single solution by using DNA-templated organic synthesis". Angew Chem Int Ed, 2002, 41, No. 21. 4104-4108.
Bittker, JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.
Summerer,D and Marx, A "DNA-templated synthesis: more versatile than expected". Angew Chem Int Ed Engl. Jan. 4, 2002;41(1):89-90. Review.
Gartner, ZJ et al. "Two enabling architectures for DNA-templated organic synthesis". Angew. Chem Int. Ed. 2003, 42, No. 12, 1370-1375.
Rosenbaum, DM et al. "Efficient and sequence-specific DNA-templated polymerization of peptide nucleic acid aldehydes". J. Am. Chem. Soc. vol. 125, No. 46, 2003, 13924-13925.
Li, X et al. "Stereoselectivity in DNA-templated organic synthesis and its origins". J. Am. Chem. Soc. vol. 125, No. 34, 2003, 10188-10189.
Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.
Otto, S et al. S "Recent developments in dynamic combinatorial chemistry". Current opinion in Chemical Biology 2002, 6: 321-327.
Pavia, MR. "The Chemical generation of molecular diversity". http://www.netsci.org/Science/Combichem/feature01.html.
Braun, E, et al. "DNA-templated assembly and electrode attachment of a conducting silver wire". Nature, vol. 391, Feb. 19, 1998, 775-778.
Tanaka, K et al. "Synthesis of a novel nucleoside for alternative DNA base pairing through metal complexation" J. Org. Chem. 1999, 64, 5002-5003.
Beger, M et al. "Universal bases for hybridization, replication and chain termination", Nucleic acids research, Oxford University Press, vol. 28, No. 15, pub. Aug. 1, 2000, p. 2911-2914.
Weizman, H et al. "2,2'-Bipyridine ligandoside: a novel building block for modifying DNA with intra-duplex metal complexes". J. Am. Chem. Soc. 2001, 123, 3375-3376.

Frutos, AG et al. "Demonstration of a word design strategy for DNA computing on surfaces". Nucleic Acids Research, 1997, vol. 25, No. 23, 4748-4757.
Loweth, CJ et al. "DNA-based assembly of gold nanocrystals". Angew. Chem. Int. Ed. 1999, 38, No. 12. 1808-1812.
Elghanian, R et al. "Selective colorimetric detection of polynucleotides based on the distance-dependent optical properties of gold nanoparticles". Science, vol. 277, Aug. 22, 1997.
Storhoff, JJ and Mirkin, CA. "Programmed Materials Synthesis with DNA". Chem Rev. Jul. 14, 1999;99(7):1849-1862.
Mirkin CA. "Programming the assembly of two- and three-dimensional architectures with DNA and nanoscale inorganic building blocks". Inorg Chem. May 29, 2000;39(11):2258-72.
Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.
Bruce Smith and Markus Krummenacker "DNA-guided assembly of proteins as a pathway to an assembler" (http://www.wadsworth.org/albcon97/abstract/krummena.htm) The 1997 Albany Conference: Biomolecular Motors and Nanomachines.
DeWitt, SH et al. "Diversomers: an approach to nonpeptide, nonoligomeric chemical diversity". Proc. Natl. Acad. Sci, USA, vol. 90, pp. 6909-6913, Aug. 1993.
Nielsen, J et al. "Synthetic methods for the implementation of encoded combinatorial chemistry". J. Am. Chem. Soc. 1993, 115, 9812-9813.
Ohlmeyer, MHJ et al. "Complex synthetic chemical libraries indexed with molecular tags". Proc. Natl. Acad, Sci, USA, vol. 90, pp. 10922-10926, Dec. 1993, Chemistry.
Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.
Luo, P et al. "Analysis of the structure and stability of a backbone-modified oligonucleotide: implications for avoiding product inhibition in catalytic template-directed synthesis". J. Am. Chem. Soc. 1998, 120, 3019-3031.
Luther, A et al. "Surface-promoted replication and exponential amplification of DNA analogues". Nature, vol. 396, Nov. 19, 1998, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramström, O et al. "In situ generation and screening of a dynamic combinatorial carbohydrate library against concanavalin A". ChemBioChem, 2000, 1, 41-48.
Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.
Roberts, SI et al. "Simultaneous selection, amplification and isolation of a pseudo-peptide receptor by an immobilised N-methyl ammonium ion template". Chem. Commun., 2002, 938-939.
Annex II: Vipergen Technology Paper—The YoctoReactor drug discovery technology platform. 2 pages. Aug. 2008.
"DNA Phosphoramidites & CPG's"; http://www.qualitysystems.com.tw/proligo/dna%20phosphoamidites%20&%20cpg's.htm Dec. 2, 2010.
"Dokl Akad Nauk SSSR", vol. 258, 1242-1245, Krynetskya NF Tumanov YV (1981).
"Ligase", Answers.com: http://www.answers.com/topic/ligase, [accessed Dec. 10, 2009].
"Organic Chemistry", Wikipedia, [accessed Dec. 10, 2009]: http://en.wikipedia.org/wiki/organic_chemistry (10 pages).
"Orthogonal Protection Protecting Group", Wikipedia: http://en.Wikipedia.org/wiki/protecting_group#Orthogonal_protection [accessed Apr. 15, 2010].

(56) References Cited

OTHER PUBLICATIONS

Abravaya et al. "Detection of point mutation with a modified ligase chain reaction (GAP-LCR)", *Nucleic Acids Research*, vol. 23, No. 4, 675-682 (1995).
Acinas et al. "PCR-Induced Sequence Artifacts and Bias: Insights from Comparison of Two 16S rRNA Clone Libraries Constructed from the same Sample", *Applied and Environmental Microbiology*, vol. 71, No. 12, 8966-8969, (2005).
Agarwal, et al. "Total Synthesis of the gene for an alanine transfer ribonucleic acid from yeast", Abstract only, *Nature*, 227, 27-34 (1970).
Anonymous. "5,6-Dihydro-Pyrimidines, 2'-Phosphoramidites", *Glen Research Report*, vol. 10, 11 (Dec. 1997 issue).
Anonymous. "Cytofectin GSV Transfection Protocol", *Glen Research Report*, vol. 10, 4-6 (Dec. 1997 issue).
Anonymous. "DCI—A Logical Alternative Aviator", *Glen Research Report*, vol. 10, No. 1, 1-12 (1997).
Anonymous. "More Novel Monomers-4-Thio-dU, 5'-Amino-dT, 2'-F-Pyrimidines", *Glen Research Report*, vol. 10, 10 (Dec. 1997 issue).
Anonymous. "New Fluorescent Reagents—Tamra CPG, Fluorescein-dt", *Glen Research Report*, vol. 10, 7 (Dec. 1997 issue).
Anonymous. "Non-enzymatic Ligation of Single-Stranded and Duplex DNA", *Glen Research Report*, vol. 10, 12 (Dec. 1997 issue).
Anonymous. "Preparing Oligonucleotides for Antisensen Experiments", *Glen Research Report*, vol. 10, 3 (Dec. 1997 issue).
Anonymous. "Q-Supports Reduce Cleavage Time to 2 Minutes", *Glen Research Report*, vol. 10, 9 (Dec. 1997 issue).
Anonymous. "Universal Support Replaces Individual Columns", *Glen Research Report*, vol. 10, 8 (Dec. 1997 issue).
Baldwin, "Design, Synthesis and use of binary encoded synthetic chemical libraries", *Molecular Diversity*, 2, 81-88 (1996).
Baldwin, JJ et al. "Synthesis of a Small Molecule Combinatorial Library Encoded with Molecular Tags", *J. Am. Chem. Soc.* 117, 5588-5589 (1995).
Baran et al. "Total Synthesis of Marine natural products without using protecting groups", *Nature*, vol. 446, 404-408 (2007).
Barany, "Genetic disease detection and DNA amplification using cloned thermostable ligase", *Proc. Natl. Acad.*, vol. 88, 189-193 (1991).
Barany, F. "The ligase chain reaction in a PCR world", *Genome Res.* vol. 1, 5-16 (1991).
Barany, F. "The TaqI star reaction: strand preferences reveal hydrogen-bond donor and acceptor sites in canonical sequence recognition", *Gene* vol. 65 149-165 (1988).
Battersby, et al. "Optical encoding of micro-beads for gene screening: alternatives to micro-arrays", *Drug Discovery Today*, vol. 6, supp 1, p. 519-526 (Jun. 1, 2001).
Bayer, E. et al. "Liquid Phase Synthesis of Peptides", *Nature* vol. 237; (Jun. 30, 1972).
Bittker, et al. "Nucleic Acid Evolution and Minimization by Non-homologous Random Recombination", *Nature Biotechnology* 20, 1024-1029 (2002).
Bonora, et al. "Large Scale, PEG-supported DNA Synthesis"; *Nucleosides & Nucleotides*, 10 (1-3), (1991).
Borman, "Combinatorial chemists focus on small molecules, molecular recognition, and automation", *Chemical & Engineering News*, Feb. 12, 1996.
Braasch, et al. "Locked nucleic acids (LNA): fine-tuning the recognition of DNA and RNA", *Elsevier, Chemistry & Biology*, 8, 1-7 (2001).
Brenner, et al. "Encoded Combinatorial Chemistry", *Proc Natl. Acad. Sci. USA*, vol. 89, pp. 5381-5383 (Jun. 1992).
Broude, Natalie E. "Stem-loop oligonucleotides: a robust tool for molecule biology and biotechnology", *Trends in Biotechnology*, vol. 20, No. 6, Jun. 2002 (22-06) pp. 249-256.
Buller et al., "Drug Discovery with DNA-Encoded Chemical Libraries", *Bioconjugate Chem.*, vol. 21 (9), pp. 1571-1580, (2010).

Buller, F. et al., "Design and synthesis of a novel DNA-encoded chemical library using Diels-Alder cycloadditions", *Bioorg Med Chem Lett* 18, 5926 (2008).
Buller, F. et al. "Discovery of TNF inhibitors from an DNA-encoded chemical library based on Diels-Alder cycloaddition", *Chem Biol* 16, 1075 (2009).
Bunin, et al. "[26] Synthesis and Evaluation of 1,4-Benzodiazepine Libraries", *Methods in Enzymology*, vol. 267, pp. 448-465 (1996).
Bunin, et al. "The combinatorial synthesis and chemical and biological evaluation of a 1,4-benzodiazepine library", *Proc. Natl. Acad. Sci. USA*, vol. 91, pp. 4708-4712 (May 1994).
Buskirk, et al. "Engineering a Ligand-Dependent RNA Transcriptional Activator", *Chem. Biol.* 11, 1157-1163 (2004), This work is featured in a Research Highlight in Nature Methods 1, 6-7 (2004).
Canne et al. "Chemical Protein Synthesis by Solid Phase Ligation of Unprotected Peptide Segments", *J. Am. Chem. Soc.*, 121, 8720-8727 (1999).
Chen, et al. "Enzyme Engineering for Nonaqueous Solvents: Random Mutagenesis to Enchance Activity of Subtilisin E in Polar Organic Media"; *Bio/Technology* 9, 1073-1077 (1991)—Abstract.
Chen, et al. "Enzymes in Nonaqueous Solvents; Applications in Carbohydrate and Peptide Preparation", *Methods in Biotechnology*, vol. 15, 373-374 (2001).
Chu et al. "Ligation of oligonucleotides to nucleic acids or proteins via disulfide bonds." *Nucleic Acids Research.* vol. 16. No. 9. pp. 3671-3691 (1998).
Clark et al. "Design, synthesis and selection of DNA-encoded small-molecule libraries", *Nat Chem Biol* 5, 647 (2009).
Clark, Matthew A. "Selecting chemicals: the emerging utility of DNA-encoded libraries", *Molecular Discovery Research, GlaxoSmithKline, Walthm, MA, USA*. Current Opinion in Chemical Biology (2010), 14(3), 396-403. Publisher: Elsevier B.V.
Colombo, R. et al. "Synthesis of leucin-enkephalin and methionineenkephalin . . . ", *Hoppe-Seyler's Z.Physiol.Chem.* vol. 363 (1981).
Constantino, L et al. "Privileged structures as leads in medicinal chemistry", *Curr Med Chem* 13, 65, (2006).
Cotton, et al. "Reactivity of cytosine and thymine in single-base-pair mismatches with hydroxylamine and osmium tetroxide and its application to the study of mutations", *Proc Natl Acad Sci (US)*, 85, 4397-401 (1988).
Czarnik, A. W. "Encoding strategies in combinatorial chemistry", *Proc. Natl. Acad. Sci. USA*, vol. 94, pp. 12738-12739 (Nov. 1997).
Czarnik, et al. "Encoding methods for combinatorial chemistry", *Current Opinion in Chemical Biology*, vol. 1, Iss 1, p. 60-66 (Jun. 1997).
Degn, Hans, et al. "Enzyme Activity in Organic Solvent as a Function of Water Activity Determined by Membrane Inlet Mass Spectometry"; *Biotechnology Techniques* vol. 6; No. 2; pp. 161-164 (Mar./Apr. 1992).
Denapoli, et al. "PEG-supported Synthesis of Cyclic Oligodeoxyribonucleotides", *Nucleosides & Nucleotides*, vol. 12, No. 1 (1993).
Dolinnaya, et al. "Chemical ligation as a method for the assembly of double-stranded nucleic acids: Modifications and local structure studies", *Russian Chemical Bulletin*, vol. 45, No. 8 (1996).
Dolinnaya, et al. "Structural and kinetic aspects of chemical reactions in DNA duplexes. Information on DNA local structure obtained from chemical ligation data", *Nucleic Acids Research*, vol. 19, No. 11, 3073-3080 (1991).
Douglas, et al. "Polymer-supported solution synthesis of oligosaccharides", *J. Am. Chem. Soc.*, vol. 113 (1991).
Drabovich, et al. "Selection of Smart Small-Molecule Ligands: The Proof of Principle", *Analytical Chemistry*, vol. 81, No. 1, 490-494 (2009).
Drews "Drug Discovery: A Historical Perspective", *Science* vol. 287, pp. 1960-1964 (2000).
Dreyer, et al. "Enzyme Catalysis in Nonaqueous Media: Past, Present and Future" *in Patel (ed.)*, "Biocatalysis in the Pharmaceutical and Biotechnology Industries", 819-820 (2006).
Ecker, David J, et al. "Rational screening of oligonucleotide combinatorial libraries for drug discovery", *Nucleic Acids Research*, vol. 21, No. 8, pp. 1853-1856 (1993).

(56) References Cited

OTHER PUBLICATIONS

Fack, Fred, et al. "Heteroduplex mobility assay (HMA) pre-screening: An improved strategy for the rapid identification of inserts selected from phage-displayed peptide libraries", *Molecular Diversity*, vol. 5, No. 1; pp. 7-12 (2000).
Fegan et al. "Rigid cyanine dye nucleic acid labels", *Chem Commun* May 7; (17) 2004-6 (2008).
Ficht, Simon, et al. "As Fast and Selective as Enzymatic Ligations: Upaired Nucleobases Increase the Selectivity of DNA-Controlled Native Chemical PNA Ligation"; *ChemBioChem*: vol. 6, Issue 11, pp. 2098-2103 (2005).
Fredriksson, et al. "Protein detection using proximity-dependent DNA ligation assays", *Nature Biotechnology*, vol. 20, p. 473-477 (May 2002).
Furka, A, "Combinatorial Chemistry: 20 years on . . . ", *Drug Discovery* today vol. 7, No. 1, p. 1-4 (2002).
Furka, et al. "Combinatorial Libraries by Portioning and Mixing", *Combinatorial Chemistry & High Throughput Screening*, 2, 105-122 (1999).
Geysen, et al. "Combinatorial Compound Libraries for Drug Discovery: An Ongoing Challenge", *Nature Reviews*, Drug Discovery, vol. 2, p. 222-223, (Mar. 2003).
Grange, et al. "Detection of point mutations in type I collagen by RNase digestion of RNA/RNA hybrids", *Nucleic Acids Research* 18: 4227-36 (1990).
Gruen, et al. "An In Vivo Selection System for Homing Endonuclease Activity", *Nucleic Acids Research* 30, e29 (2002).
Gumport, et al. "T4 RNA Ligase as a Nucleic Acids Synthesis and Modification Reagent", *Elsevier North Holland, Inc.*, 314-345 (1981).
Guo, T. et al. "Preparation of Encoded Combinatorial Libraries for Drug Discovery", *Methods in Molecular Biology, Combinatorial Library Methods and Protocols*, pp. 23-39(2002).
Hansen, M. "A Yoctoliter-scale DNA reactor for small-molecule evolution", *J Am Chem Soc.* 131, 1322 (2009).
Harada, et al. "Unexpected substrate specificity of T4 DNA ligase revealed by in vitro selection", *Nucleic Acids Research*, vol. 21, No. 10, 2287-2291 (1993).
Harada "In vitro selection of optimal DNS substrates for ligation by a water-soluble carbodiimide", *J Mol Evol.*, 38, 6, 558-560 (1994).
Harada, et al. "In vitro selection of optimal DNA substrates for t4 RNA ligase", *Proc. Natl. Acad. Sci. USA*, vol. 90, pp. 1576-1579 (Feb. 1993).
Herpin, et al. "Synthesis of a 10000 member 1,5-Benzodiazepine-2-one Library by the Directed Sorting Method", *J. Comb. Chem.*, 2, 513-521 (2000).
Higgins, et al. "Addition of Oligonucleotides to the 5'-Terminus of DNA by T4 RNA Ligase", *Nucleic Acids Research*, 6(3): 1013-1024 (1979).
Higgins, et al. "DNA joining Enzymes: A Review", *Methods in Enzymology*, vol. 68, pp. 50-71 (1979).
Hinton, et al. "T4 RNA Ligase Joins 2'-Deoxyribonucleoside 3', 5'-Bisphosphates to Oligodeoxyribonucleotides", *Biochemistry* vol. 17, No. 24, pp. 5091-5097 (1978).
Holmes, CP "Model Studies for New o-Nitrobenzyl Photolabile Linkers: Substituent Effects on the Rates of Photochemical Cleavage", *J. Org. Chem.* 62, 2370-2380 (1997).
Housby, Nicholas J, et al. "Fidelity of DNA ligation: a novel experimental approach based on the polymerisation of libraries of oligonucleotides", *Nucleic Acids Research*, vol. 26, No. 18, pp. 4259-4266 (1998).
Hsu "Detection of DNA point mutations with DNA mismatch repair enzymes" *Carcinogenesis* 15:1657-62 (1994).
Ito et al. Tag-reporter and Resin Capture ± Release Strategy in Oligosaccharide Synthesis. Chemistry—A European Journal 8(14):3077-3084 (2002).
James, Kenneth D. et al. "The Fidelity of Template-Directed Oligonucleotide Ligation and the Inevitability of Polymerase Function", *Origins of Life and Evolution of the Biosphere* 29, 1999 *Kluwer Academic Publishers*; pp. 375-390.
Janda, Kim D. "Tagged versus untagged libraries: Methods for the generation and screening of combinatorial chemical libraries", *Proc. Natl. Acad. Sci. USA*, vol. 91, pp. 10779-10785 (Nov. 1994).
Jäschke, Andres, et al. "Evolution of DNA and RNA as catalysts for chemical reactions"; Current Opinion in Chemical Biology 4; pp. 257-262 (2000).
Jäschke, et al. "Synthesis and properties of oligodeoxyribonucleotide-polyethylene glycol conjugates", *Nucleic Acids Research*, vol. 22, No. 22, pp. 4810-4817 (1994).
Jones, et al. "Enzymes in organic synthesis 22. Effects of organic solvents on horse liver alcohol dehyrogense-catalyzed reduction"; *Can. J. Chem.* 60 pp. 335-338 (1982).
Kahn, Jason "DNA-ligases": http://adnadn.umd.edu/biochem/kahn/molmachines/replication/DNA%20ligase.htm downloaded Dec. 10, 2009.
Kanagawa, Takahiro Bias and Artifacts in Multitemplate Polymerase Chain Reactions (PCR), *Journal of Bioscience and Bioengineering*, vol. 96, No. 4, pp. 317-323 (2003).
Kanan, et al. "Reaction Discovery Enabled by DNA-Templated Synthesis and In Vitro Selection", Supplementary Information, pp. 1-20.
Kerr, JM et al. "Encoded Combinatorial Peptide Libraries Containing Non-Natural Amino Acids", *J. Am. Chem. Soc.* 115, 2529-2531 (1993).
Kinoshita, et al. "Enzymatic Synthesis of Code Regions for Encoded Combinatorial Chemistry", *Nucleic Acids Symposium Series*, 34: 201-202 (1995).
Kinoshita, Y. et al. "Strand ligation in a double-stranded DNA by T4 RNA ligase", *Department of Functional Materials Science*, Saitama University, Urawa, Japan. Chemistry Letters (9), 797-798 (1996).
Klibanov, Alexander M. "Why are enzymes less active in organic solvent than water?", *Trends in Biotechnology*; vol. 15, Issue 3, 97-101; (Mar. 1, 1997)—Abstract.
Krishna, Sajja Hari "Developments and trends in enzyme catalysis in nonconventional media", *Biotechnology Advances*; vol. 20; Issues 3-4; pp. 239-267 (Nov. 2002)—Abstract.
Krug, et al. "Reversal of T4 RNA Ligase", *Biochemistry* vol. 21, No. 8, pp. 1858-1864 (1982).
Kurz, M. et al. "cDNA—protein fusions: covalent protein—gene conjugates for the in vitro selection of peptides and proteins", *Chembiochem—A European Journal of Chemical Biology*, Wiley VCH, Weinheim, DE, vol. 2, No. 9, Sep. 3, 2001 (Sep. 3, 2001), pp. 666-672, XP002332971, ISSN: 1439-4227.
Lebl, Michal "Parallel Personal Comments on "Classical" Papers in Combinatorial Chemistry", *J. Comb. Chem.* 1, pp. 3-24 (1999).
Lehman, I.R. "DNA ligase: Structure, Mechanism, and Function; The joining of DNA chains by DNA ligase is an essential component of DNA repair, replication, and recombination", *Science* vol. 186; pp. 790-797 (1974).
Lim, Carols S. et al. "Syntehsis of DNA Dumbbells: Chemical vs. Enzymatic Ligation of Self-Complementary Oligonucleotides", Abstract only, *Nucleotides and Nucleic Acids*; vol. 16, Issue 1 & 2 pp. 41-51 (Jan. 1997).
Lindström, Ulf M. et al. "An orthogonal oligonucleotide protecting group strategy that enables assembly of repetitive or highly structured DNAs"; *Nucleic Acids Research*. Oct. 1, 2002; 30(19), e101; 2002 Oxford University Press.
Liu, D.R. "Development of Amplifiable and Evolvable Unnatural Molecules", website of Dr. D. R. Liu, publicly available Mar. 11, 2000. http://web.archive.org/web/20000311112631/http://evolve.havard.edu.
McGregor, et al. "Interaction-Dependent PCR: Identification of Ligand-Target Pairs from Libraries of Ligands and Libraries of Targets in a Single Solution-Phase Experiment", *J. Am. Chem. Soc.* 132, pp. 15522-15524 (2010).
Gorin, et al. "Reactivity-Dependent PCR: Direct, Solution-Phase in Vitro Selection for Bond Formation", *J. Am. Chem. Soc.* 131, pp. 9189-9191 (2009).
Liu, D.R. "The Chemistry and Chemical Biology of molecular Evolution", Liu Group Research Summary from the website of Professor David R. Liu, obtained from the website in Feb. 2005.

(56) References Cited

OTHER PUBLICATIONS

Magliery, et al. "Expanding the Genetic Code In Vitro and In Vivo", The Genetic Code and the Origin of Life, Ed. Ribas de Pouplana, L. Landes Bioscience, In Press (2004).
Lobanov *Trends in Biotechnology*, vol. 20, No. 2, pp. 86-87 (Feb. 2002).
Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).
Loughlin, Wendy A. "Biotransformations in organic synthesis"; Bioresource Technology 74, pp. 49-62 (2000)).
Lowe, et al. "Combinatorial Libraries for Studying Molecular Recognition", URL: iupac.org/symposia/proceedings/phuket97/lowe.html, downloaded in Jun. 2005.
Luebke, Kevin J. et al. "Nonenzymatic ligation of double-helical DNA by alternate-strand triple helix formation"; Nucleic Acids Research; vol. 20, No. 12; pp. 3005-3009 (1992).
MacLean, Derek, et al. "Encoded Combinatorial Chemistry: Synthesis and screening of a library of highly functionalized pyrrolidines", *Proc. Natl. Acad. Sci.* USA, vol. 94, pp. 2805-2810 (Apr. 1997).
Makara, Gergely M. et al. "Improving Success rates for lead generation using affinity binding technologies", *Current Opinion in Biotechnology* 16:666-673 (2005).
Mannocci, L. "DNA-Encoded affinity maturation libraries", *Proc Natl Acad Sci USA* 105, 17670 (2008).
Mannocci, Lucca "DNA-Encoded Chemical Libraries", Diss. ETH No. 18153 (2009).
Margulies, M. et al., "Genome sequencing in microfabricated high-density picolitre reactors", *Nature* 437, 376 (2005).
Mashal, et al. "Detection of mutations by cleavage of DNA heteroduplexes with bacteriophage resolvases", *Nature Genetics* 9:177-83 (1995).
Matsuda, et al. "Low Fidelity DNA Synthesis by Human DNA Polymerase-?", *Nature*, 404: 1011-1013 (Apr. 27, 2000).
Matsuura, K., et al. "Construction of glyco-clusters by self-organization of site-specifically glycosylated oligonucleotides and their cooperative amplification of lectin-recognition." *Journal of the American Chemical Society*, vol. 123, No. 2, pp. 357-358 (Jan. 17, 2001).
McCoy, et al. "T4 Ribonucleic Acid Ligase Joins Single-Strand Oligo(deoxyribonucleotides)", *Biochemistry* vol. 19, No. 4, 635-642 (1980).
Melkko, Samu. et al. "Lead discovery by DNA-encoded chemical libraries", *Drug Discovery Today*, vol. 12, No. 11/12, pp. 465-471 (Jun. 2007).
Mendel, D. "Site-directed mutagenesis with an expanded genetic code". Annu. Rev. Biophys. Biomol. Struc. 24:435-62 (1995).
Miller, Scott J. "DNA as a template for reaction discovery", *Nature Biotechnology*, vol. 22, No. 11, pp. 1378-1379 (Nov. 2004).
Mudrakovskaya, et al. "Solid-Phase Enzymatic Synthesis of Oligoribonucleotides", *Bioorg Khim* vol. 17, No. 6, pp. 469-472 (1991).
Mutter, M. et al. "Functionalized polyethylene glycols and polypeptides in organic synthesis and catalysis", Reactive Polymers, vol. 6, pp. 99-107 (1987).
Myers, et al. "Detection of single base substitutions by ribonuclease cleavage at mismatches in RNA:DNA duplexes" *Science* 230: 1242-6 (1985).
Needels, CM, et al. "Generation and screening of an oligonucleotide-encoded synthetic peptide library", *Proc. Natl. Acad. Sci., USA*, vol. 90, pp. 10700-10704. (Nov. 1993).
Nestler, HP et al. "A General Method for Molecular Tagging of Encoded Combinatorial Chemistry Libraries", *J. Org. Chem.*, 59, 4723-4724 (1994).
Nielsen "Combinatorial chemistry and automation", DDT, vol. 1, No. 11, pp. 458-460 (Nov. 1996).
Nikolaiev, V et al. "Peptide-Encoding for structure determination of nonsequenceable polymers within libraries synthesized and tested on solid-phase supports", *Peptide Research*, vol. 6, No. 3, pp. 161-170 (1993).
Nishigaki, Koichi, et al. "Y-ligation: an efficient method for ligating single stranded DNAs and RNAs with T4 RNA ligase", Department of Functional Materials Science, Saitama University, Urawa, Japan. *Molecular Diversity* vol. 4(3), 187-190 (2000)).
O'Donovan MC, et al. "Blind analysis of denaturing high-perfomance liquid chromatography as a tool for mutation detection", *Genomics*. 52:4449 (1998).
Persichetti, et al. "Cross-Linked Enzyme Crystals (CLECs) of Thermolysin in the Synthesis of Peptides", *Journal of the American Chemical Society*, 117: 2732-2737 (1995).
Pochet, et al. "Solid-Supported Ligation Primer", *Nucleic Acids Research*, 16(4): 1619 (1988).
Polsky-Cynkin et al. "Use of DNA immobilized on platic and agarose supports to detect DNA by sandwich hybridization", *Clin. Chem.* 31(9): 1438-43 (Sep. 1985).
Porco, Jr. "Synthesis Undressed", *Nature* 446, 383-5 (Mar. 22, 2007).
Purmal, Andrei A., et al. "A new affinity reagent for the site-specific, covalent attachment of DNA to active-site nucleophiles: application to the EcoRI and Rsrl restriction and modification enzymes", *Nucleic Acids Research*; vol. 20, No. 14; 1992 Oxford University Press; pp. 3713-3719.
Robertson, Dan "Direct Evolution Process for Robust Enzyme Catalysis in Organic Solvents"; Report date: Sep. 1996. pp. 1-14.
Robinson "A Synthesis of Tropinone", *Journal of the Chemical Society Transactions*, vol. 111, pp. 762-768, (1917).
Romaniuk, et al. "Joining of RNA molecules with RNA ligase", *Methods in Enzymology*, vol. 100, pp. 52-59, (1983).
Saiki et al. "Genetic analysis of amplified DNA with immobilized sequence-specific oligonucleotide probes" *PNAS* 86(16): 6230-6234 (1989).
Sarmento, et al. "Cardosins A and B, Two New Enzymes Available for Peptide Synthesis", *Journal of Molecular Catalysis B: Enzymatic*, 5: 327-330 (1998).
Scheuermann, Jörg, et al. "DNA-encoded chemical libraries", *Journal of Biotechnology* 126 568-581 (2006).
Scheuermann, Jörg, et al. "DNA-encoded chemical libraries: A tool for drug discovery and for chemical biology", *ChemBioChem* 0000, 00, 1-8 (2010).
Schmidt, JG, et al., "Information transfer from peptide nucleic acids to RNA by template-directed syntheses", *Nucleic Acids Res.*, vol. 25 (23), pp. 4792-4796 (Dec. 1, 1997).
Schmitz, et al. "Solid-Phase Enzymatic Synthesis of Oligonucleotides", *Organic Letters*, 1(11): 1729-1731 (1999).
Schoenleber, R.O. et al. "Photochemical release of amines by C,N-bond cleavage", *Synlett* 501-504 (2003).
Schultz, et al. "The Combinatorial Library: A Multifunctional Resource", *Biotechnol. Prog.* 12, 729-743 (1996).
Shabarova, et al. "Chemical ligation of DNA: the first non-enzymatic assembly of a biologically active gene", Nucl. Acids Res., 19:4247-51 (1991).
Sharifian, Hoda. "Errors induced during PCR amplification", May 30, 2010.
Shchepinov, et al. "Trityl tags for encoding in combinatorial synthesis", *Tetrahedron* 56 2713-2724 (2000).
Shuman, Stewart. "DNA ligases: Progress and Prospects"; jbc.org/content/284/26/17365. full downloaded Feb. 10, 2009.
Snyder, T. "Ordered multistep synthesis in a single solution directed by DNA templates", *Angew Chem* Int Ed Engl 44, 7379 (2005.
Sokolova, N.I., et al. "Chemical reactions within DNA duplexes; Cyanogen bromide as an effective oligodeoxyribonucleotide coupling agent"; *FEBS letters*, vol. 232, No. 1, pp. 153-155 (May 1988).
Still, W. Clark "Career-In-Review (CIR)", BJ Wright, Synthesis Literacy Group, Columbia University Chemistry, Mar. 30, 2007.
Tabor, Stanley "DNA-ligases"; *Current Protocols in Molecular Biology* 3.14.1-3.14.4 (1987).

(56) References Cited

OTHER PUBLICATIONS

Takemori, Shigeki, et al. "Stabilization of Enzyme Activity by an Organic Solvent", Abstract only, *Nature* 215, 417-419 (Jul. 22, 1967).
Tan et al. "Natural-product inhibitors of human DNA ligase P", *Biochemical Journal* 314: 993-1000 (1996).
Tan, Derek S. et al. "Ligand discovery using encoded combinatorial libraries", *Current Opinion in Drug Discovery & Development*, 3(4), p. 439-53 (Jul. 2000).
Tessier, et al. "Ligation of Single-Stranded Oligodeoxyribonucleotides by T4 RNA Ligase", *Analytical Biochemistry* 158, 171-178 (1986).
Tse, B. "Translation of DNA into a library of 13,000 synthetic small-molecule macrocycles suitable for in vitro selection", *J Am Chem Soc* 130, 15611 (2008).
Uhlenbeck, et al. "T4 RNA Ligase", The Enzymes, vol. XV, pp. 31-58 (1982).
Unknown "Science & Technology: Concentrates", *Chem. & Eng. News* 82 [40] 31 (2004).
Vágner, et al. "Enzyme-mediated spatial segregation on individual polymeric support beads: Application to generation and screening of encoded combinatorial libraries", *Proc. Natl. Acad. Sci. USA*, vol. 93, pp. 8194-8199, (Aug. 1996).
Vaisman, et al. "Human DNA polymerase, promiscuous mismatch extension", JBC 276: 30615-30622 (2001).
Vratskikh, et al. "Solid-phase synthesis of oligoribonucleotides using T4 RNA ligase and T4 polynucleotide kinase", *Biochimie* 77, 227-232 (1995).
Wagner, et al. "Mutation detection using immobilized mismatch binding protein (MutS)" *Nucleic Acids Research* 22, 3944-3948 (1995).
Walder, JA., et al. "Complementary carrier Peptide Synthesis: General Strategy and Implications for Prebiotic Origin of Peptide Synthesis", *Department of Chemistry, and Department of Biochemistry and Molecular Biology, Northwestern University*, Evanston, Illinois 60201, vol. 76, No. 1, p. 51-55, (1979).
Wang, S., et al. "Circular RNA oligonucleotides. Synthesis, nucleic acid binding properties, and a comparison with circular DNAs"; Nucleic Acids Research , 1994, vol. 22, No. 12; *1994 Oxford University Press*; pp. 2326-2333.
Washington, et al. "Mismatch extension ability of yeast and human DNA polymerase n", JBC 276: 2263-2266 (2001).
Weiss, et al. "Enzymatic Breakage and Joining of Deoxyribonucleic Acid, I. Repair of Single-Strand Breaks in DNA by an Enzyme System From *Escherichia coli* Infected With T4 Bacteriophage*" *PNAS* 57, (4): 1021-1028 (1967).
Whitesides, et al. "Enzymes as Catalysts in Organic Synthesis", *Aldrichimica Acta.*, vol. 16, No. 2, pp. 27-34, (1983).
Winzeler, et al. "Fluorescence-based expression monitoring using microarrays", *Methods Enzymol.* 306: 3-18 (1999).
Wong, Daphne M. et al. "Branch capture reactions: displacers derived from assymmetric PCR"; 1991 *Oxford University Press; Nucleic Acids Research*; vol. 19; No. 9; pp. 2251-2259 (1991).
Xu, Y, et al. "A Novel 5'-Iodonucleoside Allows Efficient Non-enzymatic Ligation of Single-Stranded and Duplex DNA", Abstract, *Glen Research Catalog, Tetrahedron Letters* 38:5595-5598 (1997).
Xu, Y, et al. "High sequence fidelity in a non-enzymatic DNA autoligation reaction", *Nucleic Acids Research*, vol. 27, No. 3; pp. 875-881 (1999).
Zhu, et al. A Primer-dependent Polymerase Function of Pseudomonas aeruginosa ATP-dependent DNA ligase (LigD). *Journal of Biological Chemistry* 280(1): 418-427 (2005).
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Dec. 16, 2003.
Website of prof. David R. Liu, publicly available Feb. 10, 2004.
Website of prof. David R. Liu, publicly available Feb. 15, 2001.
Website of prof. David R. Liu, publicly available Feb. 8, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov 29, 2002.
Website of prof. David R. Liu, publicly available Nov. 30, 2001.
Website of prof. David R. Liu, publicly available Oct. 17, 2002.
Decision to Grant from European Application No. EP 02740409.4 dated Jul. 26, 2007.
European Office Action from European Application No. EP 02740409.4 dated Sep. 1, 2005.
Reply to European Office Action from European Application No. EP 02740409.4 dated Jun. 16, 2006.
Intent to Grant from European Application No. EP 02740409.4 printed Oct. 13, 2006.
Extended European Search Report from European Application No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 dated Apr. 6, 2005.
Response to Restriction Requirement from U.S. Appl. No. 10/175,539 dated May 6, 2005.
Office Action (Non-Final Rejection) from U.S. Appl. No. 10/175,539 dated May 13, 2005.
Response to Office Action (Non-Final Rejection) from U.S. Appl. No. 10/175,539 dated Apr. 13, 2006.
Office Action (Non-Final Rejection) from U.S. Appl. No. 10/175,539 dated May 14, 2007.
Response to Office Action (Non-Final Rejection) from U.S. Appl. No. 10/175,539 dated Sep. 13, 2007.
Office Action (Final Rejection) from U.S. Appl. No. 10/175,539 dated May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 dated Nov. 27, 2007.
Response to Ex Parte Quayle Action from U.S. Appl. No. 10/175,539, filed Feb. 27, 2008.
Notice of Allowance from U.S. Appl. No. 10/175,539 dated May 30, 2008.
Issue Notification U.S. Appl. No. 10/175,539 dated Jun. 1, 2010.
Office Action (Non-Final Rejection) from U.S. Appl. No. 12/330,709 dated Oct. 27, 2009.
Response to Office Action (Non-Final Rejection) from U.S. Appl. No. 12/330,709, filed Apr. 21, 2010.
Notice of Allowance from U.S. Appl. No. 12/330,709 dated Mar. 3, 2011.
Request for Continued Examination and supplemental IDS from U.S. Appl. No. 12/330,709, filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 10, 2006.
Amendment after Intention to Grant from European Application No. 03709676.5 dated Nov. 16, 2007.
Decision to Grant from European Application No. 03709676.5 dated Oct. 23, 2008.

(56) References Cited

OTHER PUBLICATIONS

European Search Report from European Application No. 08 16 9346 dated Apr. 13, 2010.
1st Office Action from European Application No. 08169346.7 dated Apr. 19, 2011.
Response filed in European Application No. 08169346.7 dated Mar. 23, 2011.
International Search Report for PCT Application No. PCT/DK03/00172 dated Nov. 3, 2003.
Office Action (Non-Final) for U.S. Appl. No. 10/507,121 dated Feb. 8, 2007.
Response to Office Action for U.S. Appl. No. 10/507,121 dated Jun. 7, 2007.
Office Action (Final Rejection) for U.S. Appl. No. 10/507,121 dated Sep. 7, 2007.
Request for Continued Examination and supplemental amendment for U.S. Appl. No. 10/507,121, filed Feb. 13, 2008.
Notice of Allowance for U.S. Appl. No. 10/507,121 dated Mar. 20, 2008.
Office Action (Non-Final) from U.S. Appl. No. 12/179,323 dated Jan. 27, 2010.
Response to Office Action from U.S. Appl. No. 12/179,323, filed Jun. 24, 2010.
Office Action (Final Rejection) for U.S. Appl. No. 12/179,323 dated Sep. 15, 2010.
Notice of Appeal from U.S. Appl. No. 12/179,323, filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 dated Feb. 18, 2004.
1st Restriction Requirement from U.S. Appl. No. 10/523,006 dated Apr. 4, 2008.
Response to 1st Restriction Requirement from U.S. Appl. No. 10/523,006, filed Oct. 1, 2008.
2nd Restriction Requirement from U.S. Appl. No. 10/523,006 dated Dec. 9, 2009.
Response to 2nd Restriction Requirement from U.S. Appl. No. 10/523,006, filed May 5, 2010.
3rd Restriction Requirement from U.S. Appl. No. 10/523,006 dated Aug. 3, 2010.
Response to 3rd Restriction Requirement from U.S. Appl. No. 10/523,006, filed Feb. 1, 2011.
Office Action (Non-Final) from U.S. Appl. No. 10/523,006 dated Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 dated Jun. 22, 2004.
Restriction Requirement for U.S. Appl. No. 10/539,288 dated Aug. 2, 2010.
Response to Restriction Requirement for U.S. Appl. No. 10/539,288, filed Jan. 31, 2011.
Office Action (Non-Final) for U.S. Appl. No. 10/539,288 dated Apr. 25, 2011.
1st Office Action for European Application No. 03729906.6 dated May 17, 2006.
Reply to 1st Office Action for European Application No. 03729906.6 dated Mar. 9, 2007.
2nd Office Action for European Application No. 03729906.6 dated Sep. 22, 2009.
Reply to 2nd Office Action for European Application No. 03729906.6 dated May 6, 2010.
International Search Report for PCT Application No. PCT/DK03/00417 dated Feb. 10, 2004.
Restriction Requirement for U.S. Appl. No. 10/518,056 dated Jan. 4, 2008.
Response to Restriction Requirement for U.S. Appl. No. 10/518,056, filed Jun. 2, 2008.
Office Action (Non-Final) for U.S. Appl. No. 10/518,056 dated Oct. 8, 2008.
Reply to Office Action for U.S. Appl. No. 10/518,056, filed Feb. 17, 2009.
Office Action (Final Rejection) for U.S. Appl. No. 10/518,056 dated May 27, 2009.
Notice of Appeal for U.S. Appl. No. 10/518,056 dated Oct. 27, 2009.
Amendment After Appeal for U.S. Appl. No. 10/518,056, filed Nov. 17, 2009.
Advisory Action for U.S. Appl. No. 10/518,056 dated Jan. 7, 2010.
Request for Continued Examination and IDS for U.S. Appl. No. 10/518,056, filed Mar. 22, 2010.
1st Office Action for European Application No. 04713515.7 dated Oct. 19, 2006.
Reply to 1st Office Action for European Application No. 04713515.7 dated Aug. 20, 2007.
2nd Office Action for European Application No. 04713515.7 dated Mar. 31, 2008.
Reply to 2nd Office Action for European Application No. 04713515.7 dated Dec. 5, 2008.
3rd Office Action for European Application No. 04713515.7 dated Sep. 6, 2010.
Reply to 3rd Office Action for European Application No. 04713515.7 dated Jun. 21, 2011.
International Search Report for PCT Application No. PCT/DK2004/000116 dated Aug. 23, 2004.
Office Action (Non-Final) for U.S. Appl. No. 10/545,795 dated Mar. 31, 2008.
Response filed for U.S. Appl. No. 10/545,795, filed Sep. 30, 2008.
Office Action for U.S. Appl. No. 10/545,795 dated Jan. 27, 2009.
Notice of Appeal filed for U.S. Appl. No. 10/545,795, filed Jul. 27, 2009.
Amendment after Appeal for U.S. Appl. No. 10/545,795, filed Sep. 28, 2009.
Office Action (Advisory Action) for U.S. Appl. No. 10/545,795 dated Sep. 29, 2009.
Request for Continued Examination and IDS for U.S. Appl. No. 10/545,795, filed Oct. 27, 2009.
Office Action (Non-Final) for U.S. Appl. No. 10/545,795 dated Nov. 16, 2009.
Office Action (Non-Final) for U.S. Appl. No. 10/545,795 dated Mar. 30, 2010.
Office Action (Interview Summary) for U.S. Appl. No. 10/545,795 dated Jul. 30, 2010.
Response filed for U.S. Appl. No. 10/545,795, filed Aug. 30, 2010.

(56) References Cited

OTHER PUBLICATIONS

Office Action (Final rejection) for U.S. Appl. No. 10/545,795 dated Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/DK2004/000117 dated Aug. 19, 2004.
Restriction Requirement for U.S. Appl. No. 10/546,538 dated Jul. 31, 2008.
Response to Restriction Requirement for U.S. Appl. No. 10/546,538, filed Dec. 24, 2008.
Office Action (Non-Final) for U.S. Appl. No. 10/546,538 dated Jun. 10, 2009.
Response to Office Action for U.S. Appl. No. 10/546,538, filed Dec. 9, 2009.
Office Action (Final Rejection) for U.S. Appl. No. 10/546,538 dated Jun. 8, 2010.
Response to Office Action (Notice of Appeal) for U.S. Appl. No. 10/546,538, filed Dec. 8, 2010.
Office Action (Communication re: Appeal) for U.S. Appl. No. 10/546,538 dated Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 dated Sep. 15, 2010.
International Search Report for International Application No. PCT/DK2004/000195 dated Dec. 27, 2004.
Restriction Requirement for U.S. Appl. No. 10/549,619 dated Apr. 21, 2008.
Response to Restriction Requirement for U.S. Appl. No. 10/549,619, filed Sep. 22, 2008.
Office Action (Non-Final) for U.S. Appl. No. 10/549,619 dated Apr. 28, 2009.
Response to Office Action for U.S. Appl. No. 10/549,619, filed Oct. 26, 2009.
Office Action (Interview Summary) for U.S. Appl. No. 10/549,619 dated Mar. 3, 2010.
Amendment filed for U.S. Appl. No. 10/549,619, filed Oct. 21, 2010.
Notice of Allowance for U.S. Appl. No. 10/549,619 dated Jul. 7, 2010.
Amendment After Allowance for U.S. Appl. No. 10/549,619, filed Oct. 6, 2010.
Issue Notification for U.S. Appl. No. 10/549,619 dated Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after ESP for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
International Search Report for International Application No. PCT/DK03/00739 dated Aug. 30, 2004.
Restriction Requirement for U.S. Appl. No. 10/525,817 dated May 9, 2007.
Response to Restriction Requirement for U.S. Appl. No. 10/525,817, filed Sep. 10, 2007.
Restriction Requirement for U.S. Appl. No. 10/525,817 dated Nov. 28, 2007.
Response to Restriction Requirement for U.S. Appl. No. 10/525,817, filed Feb. 28, 2008.
Restriction Requirement for U.S. Appl. No. 10/525,817 dated Jul. 7, 2009.
Response to Restriction Requirement for U.S. Appl. No. 10/525,817, filed Oct. 5, 2009.
Office Action (Non-Final) for U.S. Appl. No. 10/525,817 dated Apr. 1, 2010.
Supplemental Office Action for U.S. Appl. No. 10/525,817 dated Apr. 5, 2010.
Response filed for U.S. Appl. No. 10/525,817, filed Jul. 27, 2010.
Office Action (Non-Final) for U.S. Appl. No. 10/525,817 dated Jan. 5, 2011.
Office Action (Interview Summary) for U.S. Appl. No. 10/525,817 dated Jul. 1, 2011.
Response filed for U.S. Appl. No. 10/525,817, filed Jul. 5, 2011.
Restriction Requirement for U.S. Appl. No. 11/402,957 dated Jun. 25, 2008.
Response to Restriction Requirement for U.S. Appl. No. 11/402,957, filed Aug. 25, 2008.
Office Action (Non-Final) for U.S. Appl. No. 11/402,957 dated Nov. 28, 2008.
Response filed for U.S. Appl. No. 11/402,957, filed May 15, 2009.
Office Action (Non-Final) for U.S. Appl. No. 11/402,957 dated Jul. 6, 2009.
Response filed for U.S. Appl. No. 11/402,957, filed Dec. 7, 2009.
Office Action (Final Rejection) for U.S. Appl. No. 11/402,957 dated Feb. 16, 2010.
Response filed for U.S. Appl. No. 11/402,957, filed Jul. 28, 2010.
Notice of Appeal filed for U.S. Appl. No. 11/402,957, filed Aug. 16, 2010.
Notice of Allowance for U.S. Appl. No. 11/402,957 dated Sep. 2, 2010.

(56) References Cited

OTHER PUBLICATIONS

Request for Continued Examination filed for U.S. Appl. No. 11/402,957, filed Dec. 2, 2010.
Second Notice of Allowance for U.S. Appl. No. 11/402,957 dated Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 dated Feb. 14, 2005.
Restriction Requirement for U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644, filed Jan. 19, 2011.
Office Action (Non-Final) for U.S. Appl. No. 10/572,644 dated Oct. 29, 2009.
Response to Office Action for U.S. Appl. No. 10/572,644, filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000199 dated Jan. 23, 2006.
Office Action for U.S. Appl. No. 10/593,868 dated Mar. 30, 2009.
Response to Office Action for U.S. Appl. No. 10/593,868, filed Jul. 28, 2009.
Notice of Allowance for U.S. Appl. No. 10/593,868 dated Nov. 16, 2009.
Amendment after Allowance for U.S. Appl. No. 10/593,868, filed Feb. 16, 2010.
Issue Notification for U.S. Appl. No. 10/593,868 dated Apr. 7, 2010.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2005/000106 dated Sep. 12, 2005.
Restriction Requirement for U.S. Appl. No. 10/589,551 dated Apr. 7, 2011.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 dated May 24, 2011.
Invitation to Identify Subject Matter for European Application No. 10 192 717.6 dated Jun. 1, 2011.
International Search Report for International Application No. PCT/DK2006/000685 dated Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
International Search Report for International Application No. PCT/DK2009/050129 dated Aug. 21, 2009.
Barrio, et al., "Synthesis of modified nucleoside 3',5'-bisphophates and their incorporation into oligoribonucleotides with T4 RNA Ligase", American Chemical Society, vol. 17, No. 11, 1978.
Chan, et al., "Altered DNA ligase I activity in Bloom's syndrome cells", Nature, vol. 325, pp. 357-359, 1987.
Cranston, et al., "Studies on ribonucleic acid ligase", J.Biol.Chem., vol. 249, No. 23, pp. 7447-7456, 1974.
England, et al., "Enzymatic oligoribonucleotide synthesis with T4 RNA ligase", American Chemical Society, vol. 17, No. 11, 1978.
Gassen, et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth, et al., "Interaction of *Escherichia coli* host factor protein with oligoriboadenylates", Biochemistry, 19, pp. 6138-6146, 1980.
Hoffman, et al., "Polynucleotide phosphorylase covalently bound to cellulose and its use in the preparation of homopolynucleotides", Biochemical and biophysical research communications, vol. 41, No. 3, pp. 710-714, 1970.
Kiebom, "Enzymes that do not work in organic solvents: Too polar substrates give too tight enzyme-product complexes", Recl. Tray. Chim. Pays-Bas, 107, pp. 347-348, 1988.
Middleton, et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson, et al., "Synthesis of biologically active portions of an intercistronic region by use of a new 3'-phosphate incorporation method to protect 3'-OH and their binding to ribosomes", Eur. J. Biochem., 99, pp. 429-437, 1979.
Ochoa, et al., "Enzymatic synthesis of polynucleotides", J.Biol. Chem., vol. 236, 12, pp. 3303-3311, 1961.
Willis, et al., "DNA ligase I deficiency in Bloom's syndrome", Nature, vol. 325, pp. 355-357, 1987.
Decision to Grant dated Oct. 10, 2013 re European patent appliction No. 09154197.9.
Decision to Grant EP 10183942.1 dated Nov. 14, 2013.

(56) References Cited

OTHER PUBLICATIONS

Communication pursuant to Rule 161(1) and 162 for European Application No. 11720372.9 dated Dec. 12, 2012.
Final rejection dated Oct. 28, 2013 re U.S. Appl. No. 12/330,709.
Non final rejection dated Nov. 15, 2013 re U.S. Appl. No. 10/539,288.
Non-final rejection dated Nov. 15, 2013 re U.S. Appl. No. 13/455,223.
Non-final rejection dated Oct. 8, 2013 re U.S. Appl. No. 12/095,778.
Examiner's amendment communication dated May 12, 2011 re U.S. Appl. No. 10/525,817.
d'Angelo, et al., "HIV-1 integrase: the next target for AIDS therapy?", Pathol. Biol., 2001, 49, pp. 237-246.
http://www.piercenet.com/method/avidin-biotin-interaction retrieved Nov. 5, 2013.
Response to 1st Office Action dated Jul. 30, 2012 in EP 10192716.8 submitted May 28, 2013.
1st office action dated Nov. 20, 2013 re Chinese patent application No. 201210222023.8.
Schreiber, "The small-molecule approach to biology—Chemical genetics and diversity-oriented organic synthesis make possible the systematic exploration of biology", C&EN, Mar. 3, 2003, pp. 51-61.
Balasubramanian, "The science of chemical discovery: probing the unknown with new technologies", DDT, vol. 5, No. 12, Dec. 2000, pp. 533-534.
Wills, et al., "Recent developments in linker design and application", Current Opinion in Chemical Biology, 2003, 7, pp. 346-352.
Balasubramanian, "Solid phase chemical technologies for combinatorial chemistry", J. Cell. Biochem. Suppl., 37, 2001, pp. 28-33.
Response to 2nd Office Action dated Feb. 6 in EP 10184311.8 submitted Dec. 8, 2013.
Response to 3rd Office Action dated Jan. 29, 2013 in EP 08169346.7 submitted Nov. 25, 2013.
Reply to 5th Office Action dated May 31, 2012 in EP 03766117.0 submitted Mar. 11, 2013.
Reply to 6th Office Action dated Mar. 26, 2013 in EP 03766117.0 submitted Jan. 8, 2014.
Further submissions re EP 1558744 submitted Nov. 6, 2013 by proprietor.
Result of oral proceedings of Nov. 20, 2013 re European Patent No. 1558744.
Provision of the minutes of Dec. 13, 2013 of oral proceedings re European Patent No. 1558744.
Grounds and Decision for revoking the European Patent No. 1558744 dated Dec. 13, 2013.
Notice of Allowance dated Dec. 5, 2013 re U.S. Appl. No. 11/402,957.
Millward, S.W. et al. "A General Route for Post-Translational Cyclization of mRNA Display Libraries", *Journal of the American Chemical Society*: vol. 127, 14142-14143, (2005).
Millward, S.W. et al. "Design of Cyclic Peptides That Bind Protein Surfaces with Antibody-Like Affinity", *ACS Chemical Biology*: vol. 2, No. 9, 625-634, (2007).
Giebel, L.B. et al. "Screening of Cyclic Peptide Phage Libraries Identifies Ligands That Bind Streptavidin with High Affinities", *Biochemistry*: vol. 34, No. 47; 15430-15435, (1995).
Ladner, R.C. "Constrained peptides as binding entities", *Elsevier Science Ltd., Trends in Biotechnology*: vol. 13, 426-430, (1995).
Koivunen, E. et al. "Phage Libraries Displaying Cyclic Peptides with Different Ring Sizes: Ligand Specificities of the RGD-Directed Integrins", *Bio/Technology*: vol. 13, 265-270, (1995).
Office Action in European patent application No. 10184311.8, dated Mar. 19, 2012, with Annex.
Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
Office Action in Israeli patent application No. 207673 dated May 28, 2013.
Office Action dated Jan. 29, 2013 re Japanese patent application No. 2010-226107.
Decision of dismissal of amendment dated Aug. 20, 2013 re Japanese patent application No. 2010-226107.
Restriction Requirement dated Apr. 6, 2005 re U.S. Appl. No. 10/175,539.
Response to Restriction Requirement dated May 6, 2005 re U.S. Appl. No. 10/175,539.
Non-final Rejection dated Oct. 13, 2005 re U.S. Appl. No. 10/175,539.
Response submitted Apr. 13, 2006 to Non-final Rejection re U.S. Appl. No. 10/175,539.
Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.
Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 30, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/175,539.
Non-final Rejection dated Oct. 27, 2009 re U.S. Appl. No. 12/330,709.
Response submitted Apr. 21, 2010 to Non-final Rejection re U.S. Appl. No. 12/330,709.
Supplemental response submitted Jun. 2, 2010 re U.S. Appl. No. 12/330,709.
Ex parte Quyale Action datedJul. 27, 2010 re U.S. Appl. No. 12/330,709.
Response of Jan. 10, 2011 to Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Issue Notification for U.S. Appl. No. 10/507,121 dated Jul. 30, 2008.
Non-final Rejection dated Jan. 27, 2010 re U.S. Appl. No. 12/179,323.
Response dated Jun. 24, 2010 to Non-final Rejection re U.S. Appl. No. 12/179,323.
Final Rejection dated Sep. 15, 2010 re U.S. Appl. No. 12/179,323.

(56) References Cited

OTHER PUBLICATIONS

Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
Restriction Requirement dated Aug. 2, 2010 re U.S. Appl. No. 10/539,288.
Response to Restriction Requirement dated Jan. 31, 2011 re U.S. Appl. No. 10/539,288.
Non-final Rejection dated Apr. 25, 2011 re U.S. Appl. No. 10/539,288.
Response after Non-final rejection dated Oct. 25, 2011 re U.S. Appl. No. 10/539,288.
Final rejection dated Dec. 22, 2011 re U.S. Appl. No. 10/539,288.
Notice of Appeal filed Jun. 18, 2012 re U.S. Appl. No. 10/539,288.
RCE filed Aug. 20, 2012 re U.S. Appl. No. 10/539,288.
Non final rejection dated Sep. 21, 2012 re U.S. Appl. No. 10/539,288.
Response after Non-final rejection dated Feb. 28, 2013 re U.S. Appl. No. 10/539,288.
Liu, D.R. "The Chemistry and Chemical Biology of Molecular Evolution", website of Dr. D. R. Liu, publicly available Mar. 1, 2001. www.web.archive.org/web/20010301175107/http://evolve.havard.edu.
Liu, D.R. "The Chemistry and Chemical Biology of Molecular Evolution", website of Dr. D. R. Liu, publicly available Oct. 15, 2003 (A). Www.web.archive.org/web/20031015114255/http://evolve.havard.edu.
Liu, D.R. "The Chemistry and Chemical Biology of Molecular Evolution", website of Dr. D. R. Liu, publicly available Nov. 20, 2002. www.web.archive.org/web/20021120104204/http://evolve.havard.edu.
Liu, D.R. "The Chemistry of Molecular Evolution", website of Dr. D. R. Liu, publicly available Oct. 15, 2000 (B). www.web.archive.org/web/20001015144553/http://evolve.havard.edu.
Liu, W, et al. "Denaturing high perfomance liquid chromatography (DHPLC) used in the detection of germline and somatic mutations", Nucleic Acids Research. 26:1396-1400 1998 (B).
Office Actions from European Patent Application No. 03757752.5 (dated Jun. 17, 2005, Mar. 16, 2006, Feb. 15, 2007, Jan. 26, 2007, Jan. 14, 2009, Jul. 20, 2009, May 12, 2008 and Aug. 11, 2008.
1st Office Action in EP 07114663.3 dated Sep. 12, 2011.
Response to Office Action in EP 07114663.3 dated May 17, 2013.
3rd Office Action in European patent application No. 07114663.3 dated Jun. 3, 2013.
EESR Response to ESR dated Feb. 6, 2012.
Response to 1st Office Action dated Mar. 19, 2012 in EP 10184311.8 submitted Jan. 18, 2013.
2nd Office action dated Feb. 6, 2013 in EP 10184311.8.
Response to Office Action filed Feb. 10, 2012.
2nd Office Action dated Feb. 24, 2012.
Response to 2nd Office Action dated Feb. 24, 2012 in EP 08169346.7 submitted Dec. 21, 2012.
3rd Office Action dated Jan. 29, 2013 in EP 08169346.7.
Response to 4th Office Action dated Jun. 25, 2012 in EP 03766117.0 submitted Mar. 14, 2012.
5th Office Action from European Appllication No. 03766117.0 dated May 31, 2012.
Office Action from European Application No. 03766117.0 dated Mar. 26, 2013.
EESR Response to Office Action filed Aug. 5, 2011.
Office Action w. Annex dated Sep. 12, 2011.
Opposition against EP 1558744 filed by Strawman Limited on Mar. 12, 2013.
Opposition against EP 1558744 by HGF on Mar. 14, 2012.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
European Search Report dated Feb. 21, 2012 & Search Opinion.
Response to ESR of re European Patent Application No. 10183942.1 submitted Jan. 9, 2013.
1st Office Action for European Patent Application No. 10183942.1 dated Feb. 11, 2013.
Communication re Partial European Search Report dated Feb. 10, 2012 re European Patent Application No. 10184069.2.
Partial European Search Report dated Feb. 3, 2012.
European Search Report dated Jun. 6, 2012 re EP 10184069.2.
Response dated Apr. 12, 2013 to European Search Report issued in European Patent Application No. 10184069.2.
1st Office Action for European Patent Application No. 10184069.2 dated Jul. 3, 2013.
EESR Office Action in European patent application No. 10192716.8 dated Jul. 3, 2013.
Response to Invitation dated Aug. 5, 2011.
Comm. re partial ESR w. partial European Search Report dated Oct. 7, 2011.
Response to partial ESR dated Dec. 8, 2011.
ESR and Search Opinion dated Jan. 25, 2012.
Response to ESR dated Sep. 26, 2012 submitted Dec. 5, 2012.
Office Action dated Jul. 16, 2013 re European patent application No. 10192717.6.
European Office Action from EP 09765460.2 dated May 7, 2012.
Response to office action re 09765460.2 dated Feb. 22, 2013.
International Search Report dated Aug. 23, 2011 re PCT/DK2011/000031.
Notice of Acceptance for Australian Application No. 2003273792 dated Jun. 22, 2011.
Office action dated Aug. 20, 2012 re Canadian patent application No. 2,544,153.
Notice of Allowance dated Sep. 3, 2012 re Chinese patent application No. 200380104764.5.
Office Action in Israeli patent application No. 207672 dated May 28, 2013.
Non-final rejection dated Apr. 16, 2013 re U.S. Appl. No. 10/539,288.
Response to Non-final rejection dated Sep. 16, 2013 re U.S. Appl. No. 10/539,288.
Restriction Requirement dated Jan. 4, 2008 re U.S. Appl. No. 10/518,056.
Response to Restriction Requirement dated Jun. 2, 2008 re U.S. Appl. No. 10/518,056.
Non-final Rejection dated Oct. 8, 2008 re U.S. Appl. No. 10/518,056.
Response after Non-final Rejection dated Feb. 17, 2009 re U.S. Appl. No. 10/518,056.
Final Rejection dated May 27, 2009 re U.S. Appl. No. 10/518,056.
Notice of Appeal filed Oct. 27, 2009 re U.S. Appl. No. 10/518,056.
Amendments after Final Rejection dated Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection dated Mar. 31, 2008 re U.S. Appl. No. 10/545,795.
Response after Non-final Rejection dated Sep. 30, 2008 re U.S. Appl. No. 10/545,795.
Final Rejection dated Jan. 27, 2009 re U.S. Appl. No. 10/545,795.
Notice of Appeal filed Jul. 27, 2009 re U.S. Appl. No. 10/545,795.
Amendments after Final Rejection dated Sep. 28, 2009 re U.S. Appl. No. 10/545,795.
Advisory Action dated Sep. 29, 2009 re U.S. Appl. No. 10/545,795.
Second amendment after Notice of Appeal submitted Oct. 27, 2009 re U.S. Appl. No. 10/545,795.
Advisory Action dated Oct. 21, 2009 re U.S. Appl. No. 10/545,795.
RCE submitted Oct. 27, 2009 re U.S. Appl. No. 10/545,795.
Non-final Rejection dated Nov. 16, 2009 re U.S. Appl. No. 10/545,795.
Non-final Rejection dated Mar. 30, 2010 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.

(56) References Cited

OTHER PUBLICATIONS

Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection dated Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement dated Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Restriction Requirement dated Apr. 21, 2008 re U.S. Appl. No. 10/549,619.
Response filed Sep. 22, 2009 to Restriction Requirement re U.S. Appl. No. 10/549,619.
Non-final Rejection dated Apr. 28, 2009 re U.S. Appl. No. 10/549,619.
Response after Non-final Rejection dated Oct. 26, 2009 re U.S. Appl. No. 10/549,619.
Interview summary dated Mar. 3, 2010 re U.S. Appl. No. 10/549,619.
Notice of Allowance re U.S. Appl. No. 10/549,619.
Amendments after Notice of Allowance dated Oct. 6, 2010 re U.S. Appl. No. 10/549,619.
Second amendment after Notice of Allowance dated Oct. 21, 2010 re U.S. Appl. No. 10/549,619.
Issue Notification of dated Mar. 9, 2011 re U.S. Appl. No. 10/549,619.
First Restriction Requirement dated May 9, 2007 re U.S. Appl. No. 10/525,817.
Bain et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., Novel Solution Phase Strategy for the Synthesis of Chemical Libraries Containing Small Organic Molecules, J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-772, 2009.
Curran, "Strategy-Level Separations in Organic Synthesis: From Planning to Practise", Angew. Chem. Int. Ed., vol. 37, 1174-1196, 1998.
Declaration by Dr. Dennis Benjamin (including curriculum vitae).
Frutos et al. "Enzymatic Ligation Reactions of DNA "Words" on Surfaces for DNA Computing", J. Am. Chem. Soc., vol. 120, No. 40, 10277-10282, 1998.
Gait, "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4).
Glen Research Report, "Advances in RNA Synthesis and Structural Analysis", vol. 11, No. 2, (Dec. 1998).
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries", PNAS USA, vol. 91,10779-10785, 1994.
Kelemen et al., "Hypersensitive Substrate for Ribonucleases", Nucl. Acids. Res., vol. 27, No. 18, 3696-3701, 1999.
Kempe et al., "Chemical and Enzymatic Biotin-labeling of Oligodeoxyribonucleotides", Nucl. Acids Res., vol. 13, No. 1, 45-57, 1985.
Kinoshita et al., "Enzymatic Synthesis of Sequencing Primers Based on a Library of Tetramers", Chem. Express, No. 7, 149-152, 1992.
Kinoshita et al., "Strand Ligation in a Double-stranded DNA by T4 RNA Ligase", Chem. Lett., No. 9, 797-799, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-Specific Modification of Pre-mRNA: the 2'-Hydroxyl Groups at the Splice Sites", Science, vol. 256, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Toward Chemical Implementation of Encoded Combinatorial Libraries", Methods: A Companion to Meth: Enzymol., vol. 6, 361-371, 1994.
Roux, "Optimization and Troubleshooting in PCR", PCR Methods Appl., vol. 4, S185-S194, 1995.
Schmitz et al., "Solid-Phase Enzymatic Synthesis of Oligonucleotides", Org. Lett., vol. 1, 1729-1731, 1999.
Seelig et al., "Site-Specific Modification of Enzymatically Synthesized RNA: Transcription Initiation and Diels-Alder Reaction", Tetrahed. Lett., vol. 38, 7729-7732, 1997.
Seo et al., "Click Chemistry to Construct Fluorescent Oligonucelotides for DNA Sequencing", J. Org. Chem., vol. 68, 2003.
Sherlin et al., "Chemical and Enzymatic Synthesis of tRNAs for High-throughput Crystallization", RNA, vol. 7, 1671-1678, 2001.
Tabuchi et al., "An Efficient Ligation Method in the Making of an in vitro Virus for in vitro Protein Evolution", Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed on the Surface of Encoded Bacteriophage", Chem. Biol., 847-858, (Sep. 2003).
Wojczewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series vol. 12, Pergamon, Elsevier Science Lrd. (Oxford, England) 1994, pp. Xiii-xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Notice of Allowance dated Nov. 16, 2009 re U.S. Appl. No. 10/593,868.
Amendments after Notice of Allowance dated Feb. 16, 2010 re U.S. Appl. No. 10/593,868.
Issue Notification dated Apr. 7, 2010 re U.S. Appl. No. 10/593,868.
Restriction Requirement dated Apr. 7, 2011 re U.S. Appl. No. 10/589,551.

(56) References Cited

OTHER PUBLICATIONS

Response submitted Oct. 7, 2011 to Restriction Requirement re U.S. Appl. No. 10/589,551.
Non-final rejection dated Oct. 26, 2011 re U.S. Appl. No. 10/589,551.
1st Restriction requirement dated Oct. 5, 2011 re U.S. Appl. No. 12/095,778.
Response dated Mar. 5, 2012 to 1st Restriction Requirement re U.S. Appl. No. 12/095,778.
2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Adang et al., "The Contribution of Combinatorial Chemistry to Lead Generation: An Interim Analysis", Current Medicinal Chemistry, 2001, 8, 985-998.
Affleck, "Solutions for library encoding to create collections of discrete compounds", Current Opinion in Chemical Biology, 2001, 5:257-263.
Bain et al., "Biosynthetic Site-Specific Incorporation of a Non-Natural Amino Acid into a Polypeptide", J. Am. Chem. Soc., 1989, 111, 8013-8014.
Barnes et al., "Recent developments in the encoding and deconvolution of combinatorial libraries", Current Opinion in Chemical Biology 2000, 4:346-350.
Chen et al., "Total Synthesis of Naturally Occurring Prostaglandin F2a on a Non-Cross-Linked Polystyrene Support", Tetrahedron Letters, 39, (1998) 3943-3946.
Coe et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res, 37, 1991, 487-493.
Gallop et al., "Applications of Combinatorial Technologies to Drug Discovery. 1. Background and Peptide Combinatorial Libraries", Journal of Medicinal Chemistr-y, 1994, vol. 37, No. 9, pp. 1233-1251.
Guillen Schlippe et al., "In Vitro Selection of Highly Modified Cyclic Peptides That Act as Tight Binding Inhibitors", J. Am. Chem. Soc. 2012, 134, 10469-10477.
Han et al., "Liquid-phase combinatorial synthesis", Proc. Natl. Acad. Sci. USA, vol. 92, pp. 6419-6423, 1995.
www.wikipedia.org/wiki/DNA-encoded chemical library Oct. 2, 2012, pp. 1-12.
http://www2.umt.edu/medchem/teaching/medchem/mclect14.htm, Thompson C. M., Medical Chemistry, lecture 14, Pharmaceutical Sciences 621 & Chemistry 569.
Li et al., "Kinetics of RNA Degradation by Specific Base Catalysis of Transesterification Involving the 2'-Hydroxyl Group", J. Am. Chem. Soc., 1999, 121, pp. 5364-5372.
Ma et al., "In Vitro Selection of Unnatural Cyclic Peptide Libraries via mRNA Display", Book Ribosome Display and Related Technologies, ch. 21, pp. 367-390.
MacLean et al., "Glossary of Terms Used in Combinatorial Chemistry", Pure Appl. Chem., vol. 71, No. 12, pp. 2349-2365, 1999.
Meier et al, "Combinatorial Methods, Automated Synthesis and High-Throughput Screening in Polymer Research: the Evolution Continues", Macromol. Rapid Commun., 2004, 25, 21-33.

Chorghade, "Drug Discovery and Development", 2006, ISBN-13: 978-0-471-39848-6, Published by John Wiley & Sons, Inc., Hoboken, New Jersey.
Needels et al., "Generation and screening of an oligonucleotide-encoded synthetic peptide library", Proc. Natl. Acad. Sci. USA, vol. 90, pp. 10700-10704, Nov. 1993.
Ni et al., "Versatile Approach to Encoding Combinatorial Organic Syntheses Using Chemically Robust Secondary Amine Tags", J. Med. Chem. 1996, 39, 1601-1608.
"Nicolaou et al., "Radiofrequency Encoded Combinatorial Chemistry", Angew. Chem. Int. Ed. Engl., 1995, 34, No. 20, pp. 2289-2291."
Noren et al., "A General Method for Site-Specific Incorporation of Unnatural Aminoacids into Protein", Science, American Association for the advancement of science, Washington, DC, vol. 244, 1989, pp. 182-188.
Starck et al., "The Puromycin Route to Assess Stereo- and Regiochemical Constraints on Peptide Bond Formation in Eukaryotic Ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial Synthesis the Design of Compound Libraries and their Application to Drug Discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Wermuth et al., "Glossary of Terms Used in Medical Chemistry", Pure & Appl. Chem, 1998, vol. 70, No. 5, pp. 1129-1143.
Ymane et al., "Discrimination between D- and L-Tyrosyl Transfer Ribonucleic Acids in Peptide Chain Elongation", Biochemistry, vol. 20, No. 25, Dec. 8, 1981, pp. 7059-7064.
Lipinski et al., "Experimental and computational approaches to estimate solubility and permeability in drug discovery and development settings", Adv. Drug Deliv. Rev., vol. 46, 2001, pp. 3-26.
Lipinski, "Lead- and drug-like compounds: the rule-of-five revolution", Drug Discovery Today: Technologies, vol. 1, No. 4, 2004, pp. 337-341.
Kleiner et al., "Small-molecule discovery from DNA-encoded chemical libraries", Chem. Soc. Rev., 2011, 40, pp. 5707-5717.
http://en.wikipedia.org/wiki/Scaffold_protein.
Balkenhohl et al., "Combinatorial Synthesis of Small Organic Molecules", Angew Chem Int. Ed Engl. 1996, 35, pp. 2288-2337.
Strachan, "Human Molecular Genetics", 2nd edition, textbook published by Wiley-Liss, 1999.
Response submitted to First Restriction Requirement dated Sep. 10, 2007 re U.S. Appl. No. 10/525,817.
Second Restriction Requirement dated Nov. 28, 2007 re U.S. Appl. No. 10/525,817.
Response to second Restriction Requirement dated Feb. 28, 2008 re U.S. Appl. No. 10/525,817.
Third Restriction Requirement dated Jul. 7, 2009 re U.S. Appl. No. 10/525,817.
Response to third Restriction Requirement dated Oct. 5, 2009 re U.S. Appl. No. 10/525,817.
Non-final rejection dated Apr. 1, 2010 re U.S. Appl. No. 10/525,817.
Supplemental Non-final Action dated Apr. 5, 2010 re U.S. Appl. No. 10/525,817.
Response submitted Jul. 27, 2010 to Non-final Action dated Apr. 5, 2010 re U.S. Appl. No. 10/525,817.
Non-final rejection dated Jan. 5, 2011 re U.S. Appl. No. 10/525,817.
Interview Summary dated Jul. 1, 2011 re U.S. Appl. No. 10/525,817.
Response submitted Jul. 5, 2011 to Non-final Action re U.S. Appl. No. 10/525,817.
Examiner's amendment communication dated Dec. 2, 2011 re U.S. Appl. No. 10/525,817.
Notice of Allowance dated Oct. 14, 2011 re U.S. Appl. No. 10/525,817.
Notice of Allowance dated Jan. 19, 2012 re U.S. Appl. No. 10/525,817.
RCE dated Mar. 19, 2012 re U.S. Appl. No. 10/525,817.
Notice of Allowance dated Mar. 30, 2012 re U.S. Appl. No. 10/525,817.

(56) References Cited

OTHER PUBLICATIONS

Issue Notification dated Jun. 6, 2012 re U.S. Appl. No. 10/525,817.
Restriction Requirement dated Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 14, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 1/1402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
RCE dated Dec. 2, 2010 re U.S. Appl. No. 11/402,957.
Second Notice of Allowance dated Apr. 29, 2011 re U.S. Appl. No. 11/402,957.
RCE dated Jul. 28, 2011 re U.S. Appl. No. 11/402,957.
Third Notice of Allowance dated Oct. 31, 2011 re U.S. Appl. No. 11/402,957.
RCE dated Dec. 12, 2011 re U.S. Appl. No. 11/402,957.
Preliminary amendment dated Nov. 21, 2012 re U.S. Appl. No. 11/402,957.
Non-final Rejection dated May 22, 2013 re U.S. Appl. No. 11/402,957.
Response to Non-final rejection dated Sep. 23, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
First Restriction Requirement dated Feb. 4, 2009 re U.S. Appl. No. 10/572,644.
Reponse submitted Jul. 29, 2009 to First Restriction Requirement re U.S. Appl. No. 10/572,644.
Non-final rejection dated Oct. 29, 2009 re U.S. Appl. No. 10/572,644.
Response submitted Apr. 28, 2010 to Non-final rejection re U.S. Appl. No. 10/572,644.
Second Restriction Requirement dated Jul. 21, 2010 re U.S. Appl. No. 10/572,644.
Response submitted Jan. 19, 2011 to Second Restriction Requirement re U.S. Appl. No. 10/572,644.
Non-final rejection dated Mar. 31, 2011 re U.S. Appl. No. 10/572,644.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Non-final rejection dated Mar. 30, 2009 re U.S. Appl. No. 10/593,868.
Response submitted Jul. 28, 2009 to Non-final rejection re U.S. Appl. No. 10/593,868.
Communication (office action) by the European Patent Office dated Mar. 24, 2016 in relation to European Patent Application No. 10741877.4.
Glen Research (Catalogue No. 10-1014-XX)—Mar. 8, 2005 + Material Safety Data Sheet on Catalogue No. 10-1014-xx—Sep. 11, 2004.
Glen Research (Catalogue No. 10-1054-XX)—Mar. 8, 2005 + Material Safety Data Sheet on Catalogue No. 10-1054-xx—Oct. 28, 2004.
Glen Research (Catalogue No. 10-1092-XX)—Apr. 28, 2005 + Material Safety Data Sheet on Catalogue No. 10-1092-xx—Oct. 28, 2004.
Glen Research (Catalogue No. 10-1590-XX)—Aug. 21, 2008 + Further Info on 10-1590-xx—Dec. 12, 2008.
Han et al., "Quantum-dot-tagged microbeads for multiplexed optical coding of biomolecules", Nature Biotechnology, 2001, vol. 19, pp. 631-635.
Korshun et al., "5-(1-Pyrenylethynyl)-2'-Deoxyuridine, A N Ovel Fluorescent Nucleosideanalog", Bioorganiceskaa himia, 22(12), 1996, pp. 923-925. (English abstract only).
Mullah et al., "Efficient synthesis of double dye-labeled oligodeoxyribonucleotide probes and their application in a real time PCR assay", Nucleic Acids Research, 1998, vol. 26, No. 4, pp. 1026-1031.
Thelwell, "Mode of action and application of Scorpion primers to mutation detection", Nucleic Acids Research, 2000, vol. 28, No. 19, pp. 3752-3761.
Third Party observation filed with the European Patent Office on Mar. 14, 2016 in relation to European Patent Application No. 10741877.4 (X-Chem Inc.).
Wagner, "Gene inhibition using antisense oligodeoxynucleotides", Nature, 1994, vol. 372, pp. 333-335.
Wagner, "Antisense gene inhibition by oligonucleotides containing C-5 propyne pyrimidines", Science, 1993, vol. 260, pp. 1510-1513.
Yamana et al., "Synthesis and Binding Properties of Oligonucleotides Containing an Azobenzene Linker", Nucleosides & Nucleotides, 1998, vol. 17, No. 1-3, pp. 233-242.
Zammatteo et al., "Amination of polystyrene microwells: Application to the covalent grafting of DNA probes for hybridization assays", Analytical Biochemistry, 236, pp. 85-94, 1996.
Blondal et al., "Isolation and characterization of a thermostable RNA ligase 1 from a Thermus scotoductus bacteriophage TS2126 with good single-stranded DNA ligation properties", Nucl. Acids. Res. 2005, vol. 33, No. 1, pp. 135-142.
Brennan & Gumport, "T4 RNA ligase catalyzed synthesis of base analogue-containing oligodeoxyribonucleotides and a characterization of their thermal stabilities", Nucleic Acids Res., 1985, vol. 13, No. 24, pp. 8665-8684.
Cummins et al., "Characterization of fully 2'-modified oligoribonucleotide hetero- and homoduplex hybridization and nuclease sensitivity", Nucl. Acids Res. 1995, vol. 23, No. 11, pp. 2019-2024.
Inoue et al., "Synthesis and hybridization studies on two complementary nona(2'-O-methyl)ribonucleotides", Nucleic Acids Res. 1987, vol. 15, No. 15, pp. 6131-6148.
Lesnik et al., "Oligodeoxynucleotides containing 2'-O-modified adenosine: Synthesis and effects on stability of DNA: RNA duplexes", Biochemistry, 1993, vol. 32, pp. 7832-7838.
Verma et al., "Functional tuning of nucleic acids by chemical modifications: tailored oligonucleotides as drugs, devices, and diagnostics", Chem Rec. 2003, 3(1), pp. 51-60.

* cited by examiner

Fig. 3. An oligonucleotide-based building block. Example of coding region design, allowing for high building block diversity.

A. 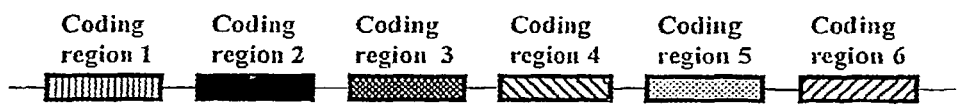

| Coding region | sequence | number of unique codons |
|---|---|---|
| 1 | XXXXXATATTTXXXXX | 1024 |
| 2 | XXXATTTTAXXXXXXX | 1024 |
| 3 | XTAATTTXXXXXXXXX | 1024 |
| 4 | XXATXXATXXATXXXX | 1024 |
| 5 | GCCCGATTAAAXXCCG | 4 |
| 6 | XAXAXTTXTTXXXGGG | 128 |

X = G or C

B.
    Codon 1     GCGCGATATTTGGGCC
    Anti-codon 1 CGCGCTATAAACCCGG

Codon 6     GAGAGTTCTTCGCGGG
    Anti-codon 6 CTCTCAAGAAGCGCCC

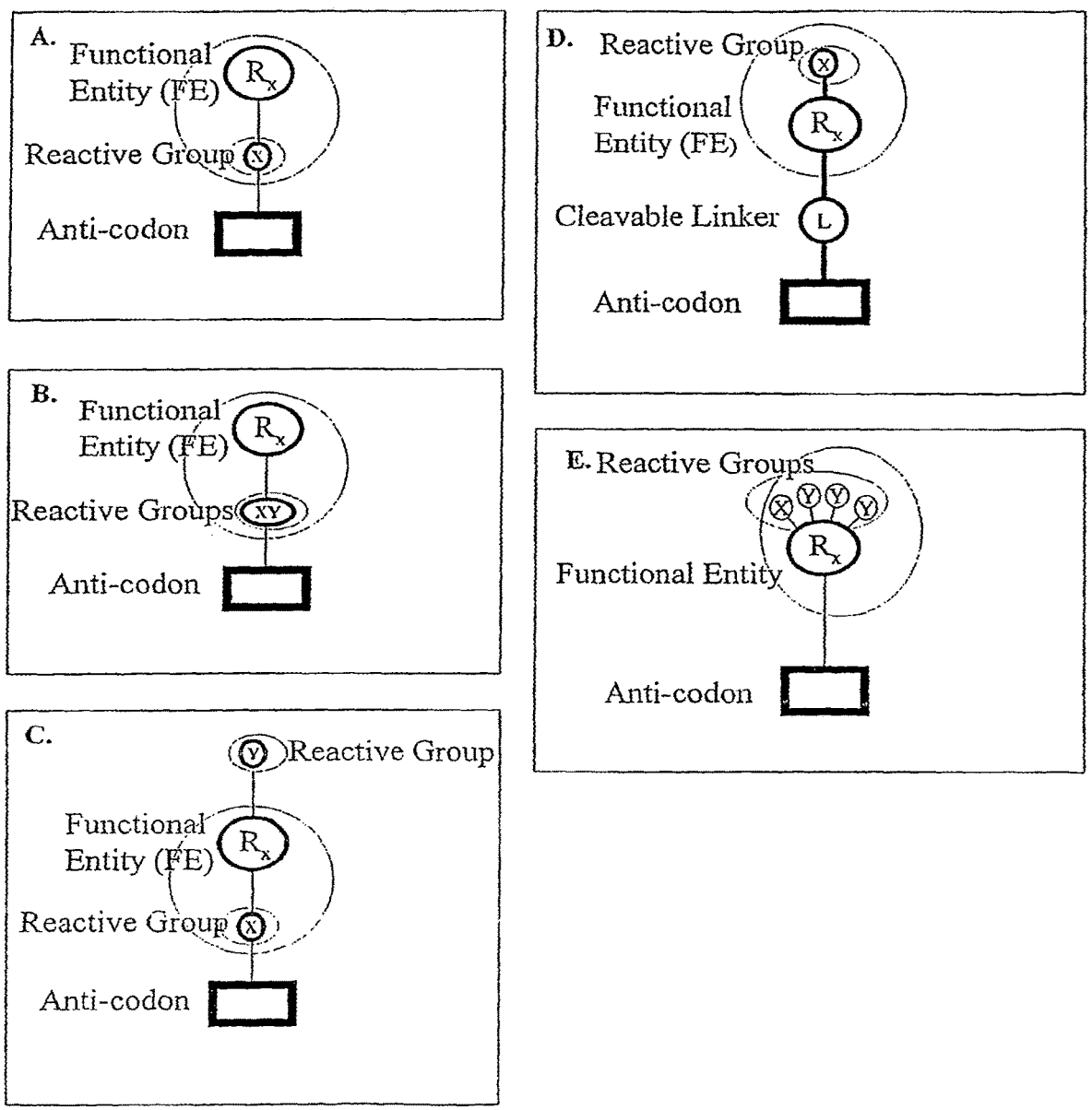
Fig. 4. Building blocks.

Fig. 5. Exemplary monomer Building Blocks.
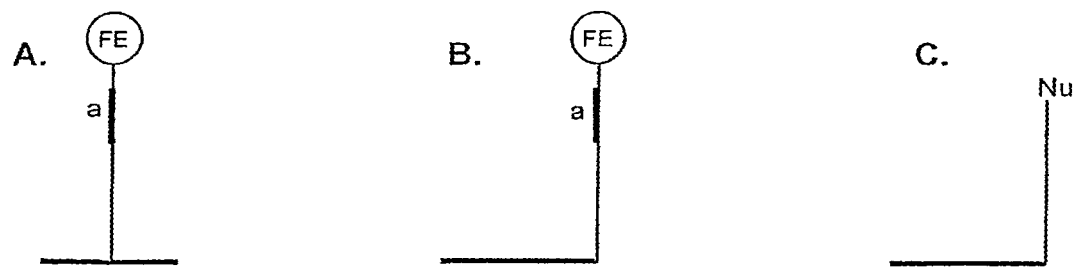

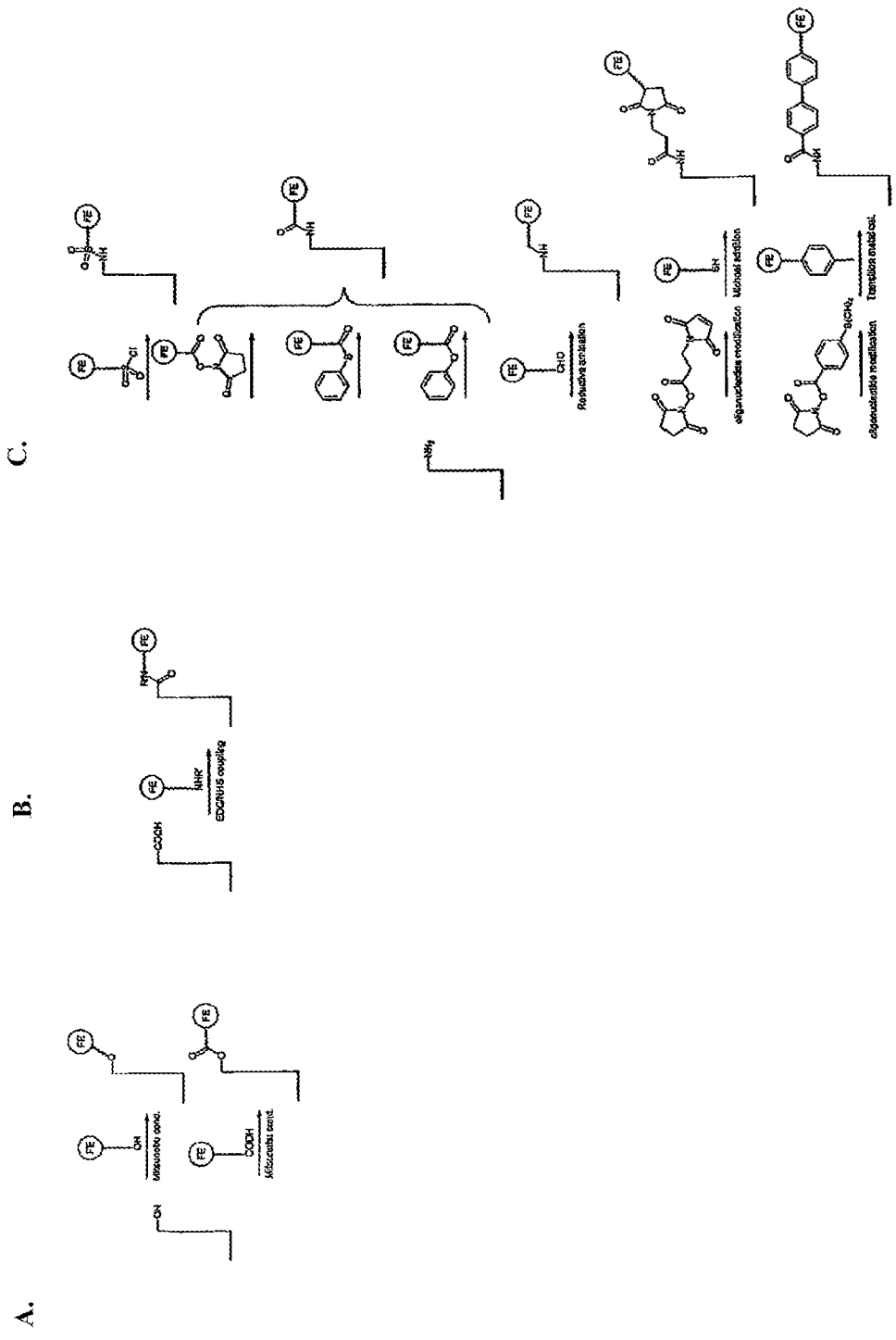
Fig. 6 Preparation of Building Blocks. General examples

Fig. 6 Preparation of Building Blocks. General examples (continued)
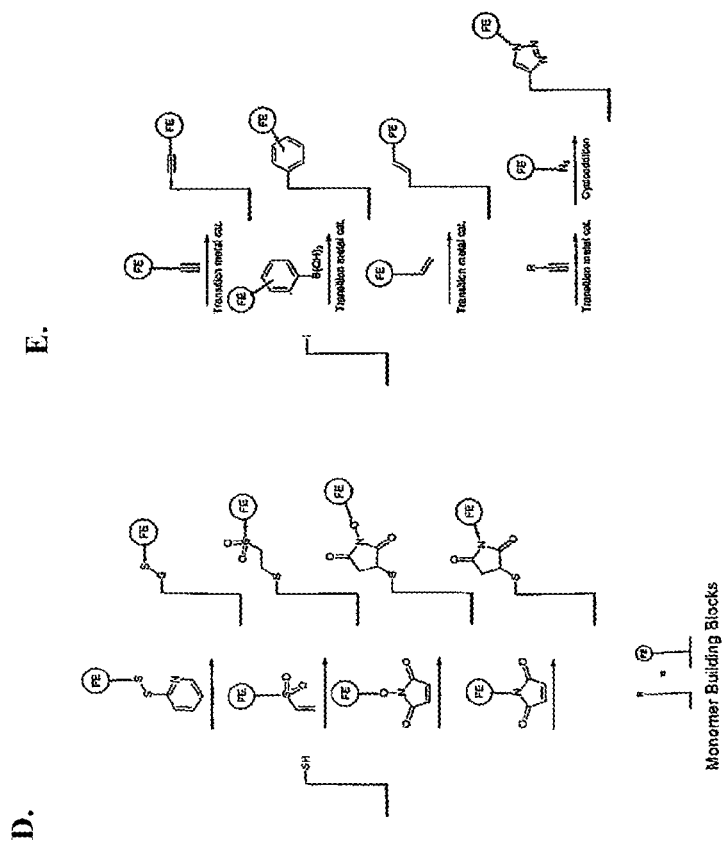

Fig. 7. Design and synthesis of specific building blocks
A.
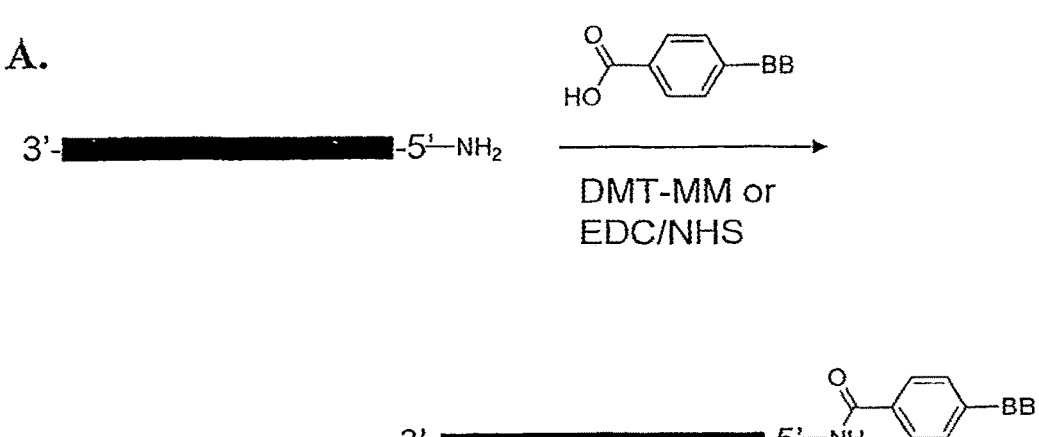
B.
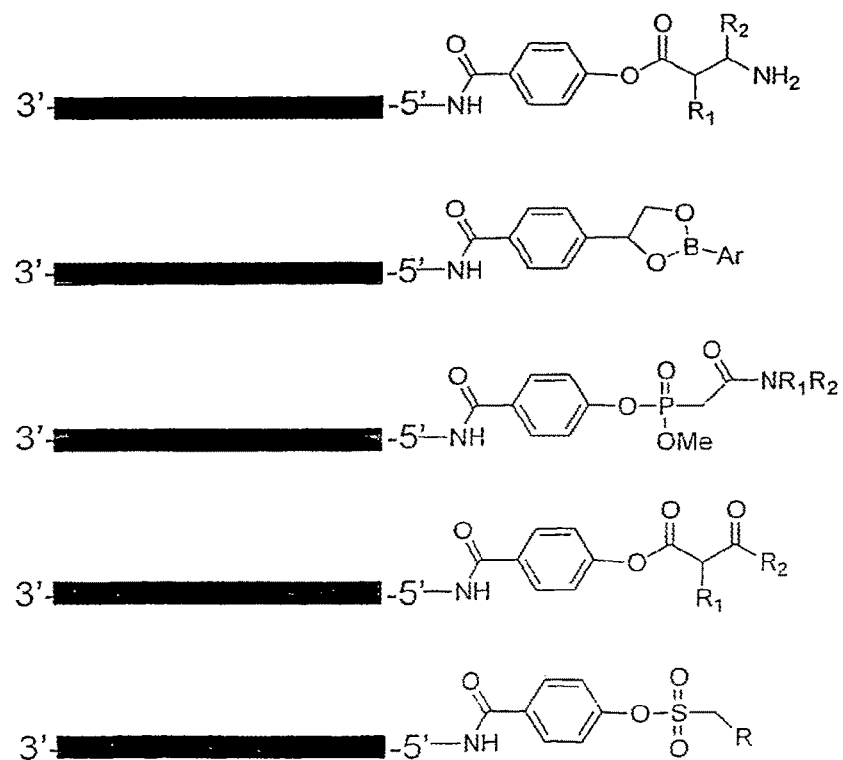

Fig. 8. Templated synthesis of a polymer.
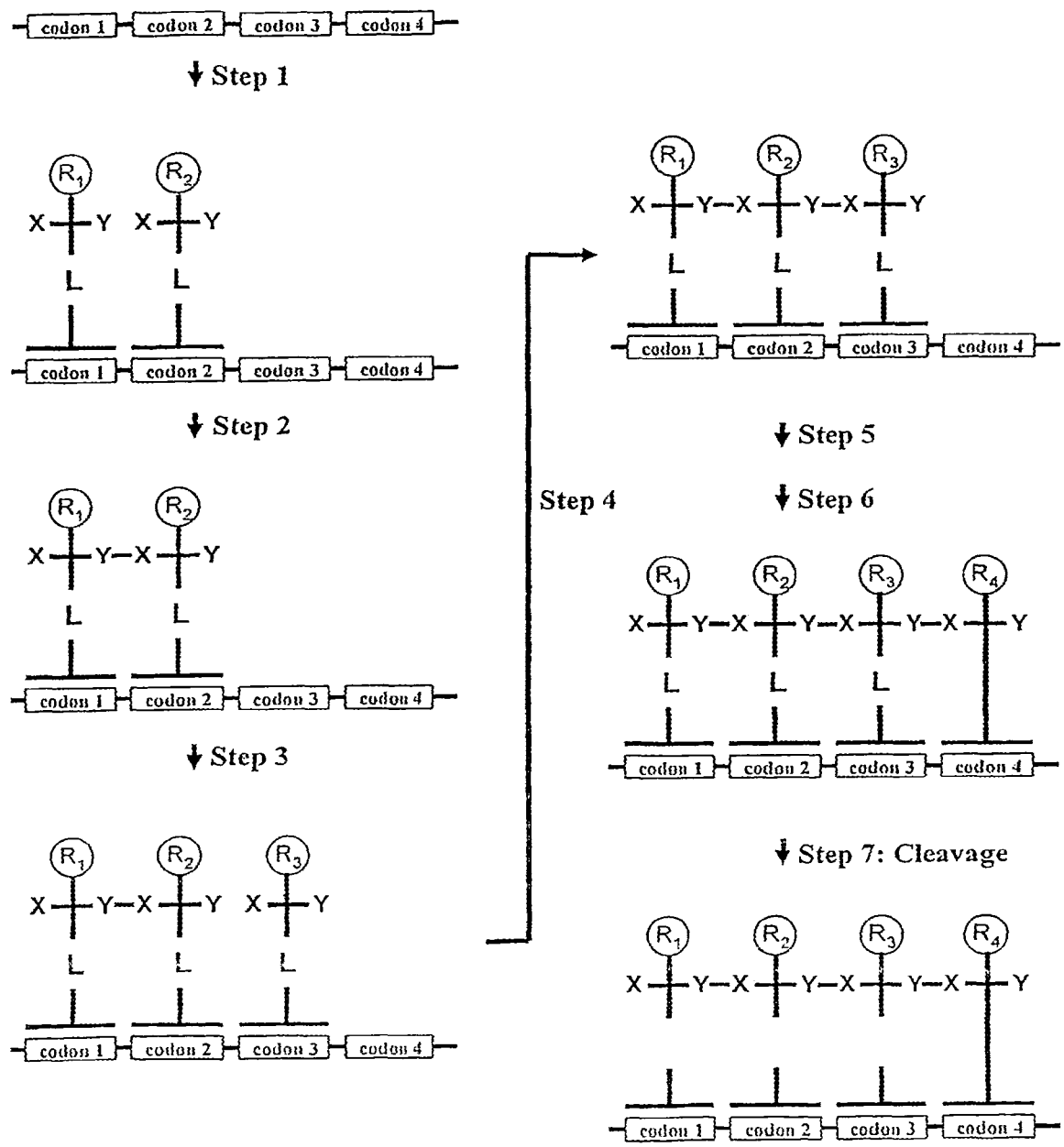

Fig. 9    Light-induced reaction between symmetric building blocks: Coumarin derivatives.
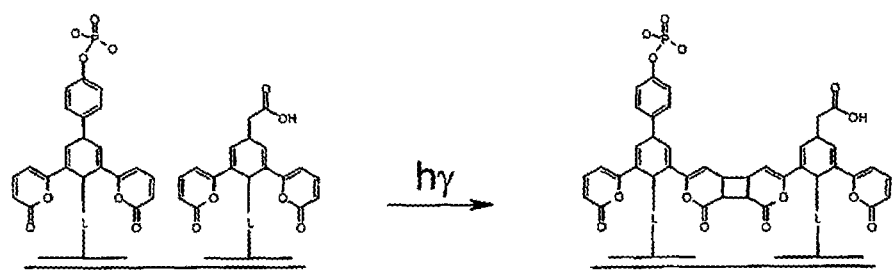

Fig. 10 Templated synthesis of a polymer by simultaneous reaction and cleavage.
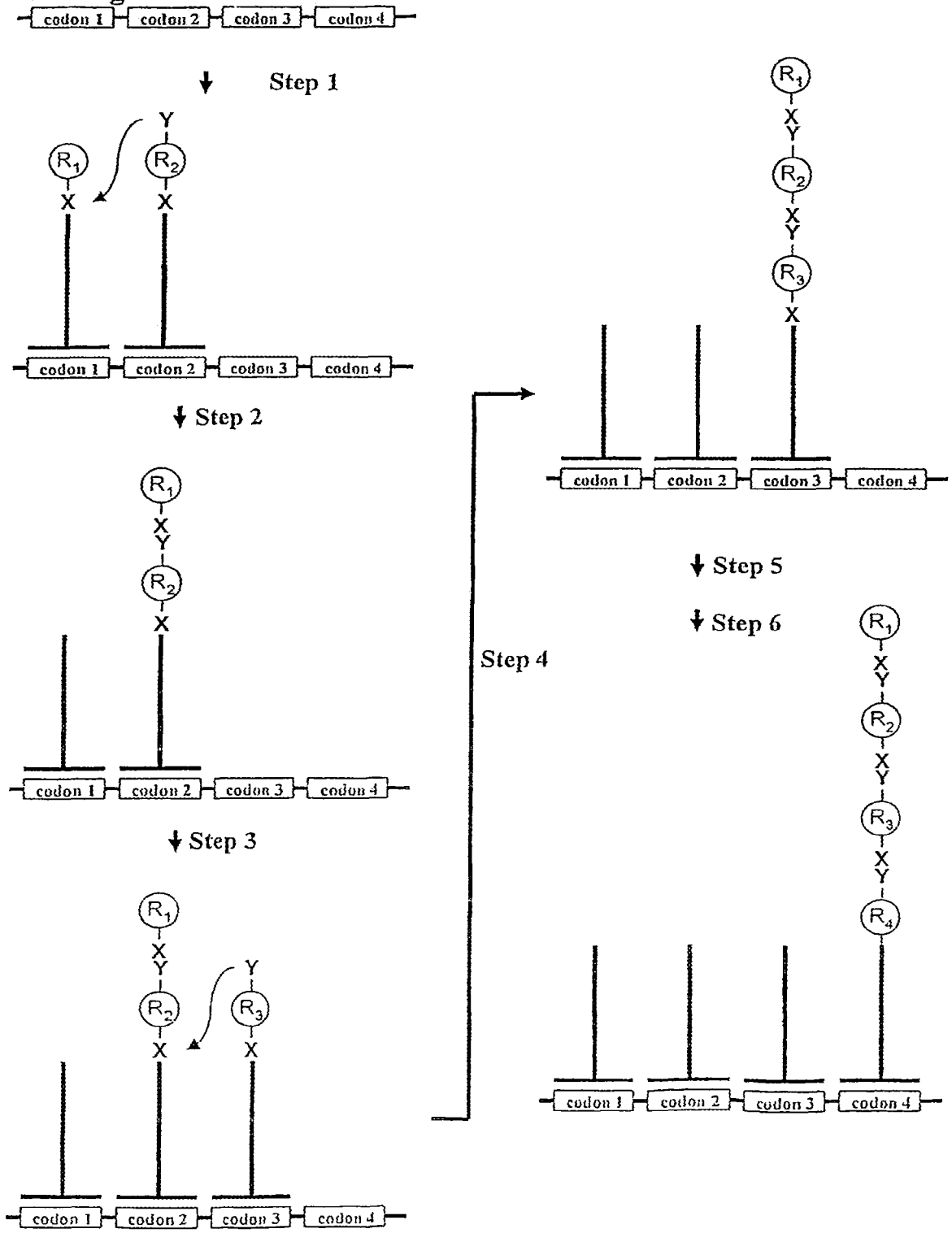

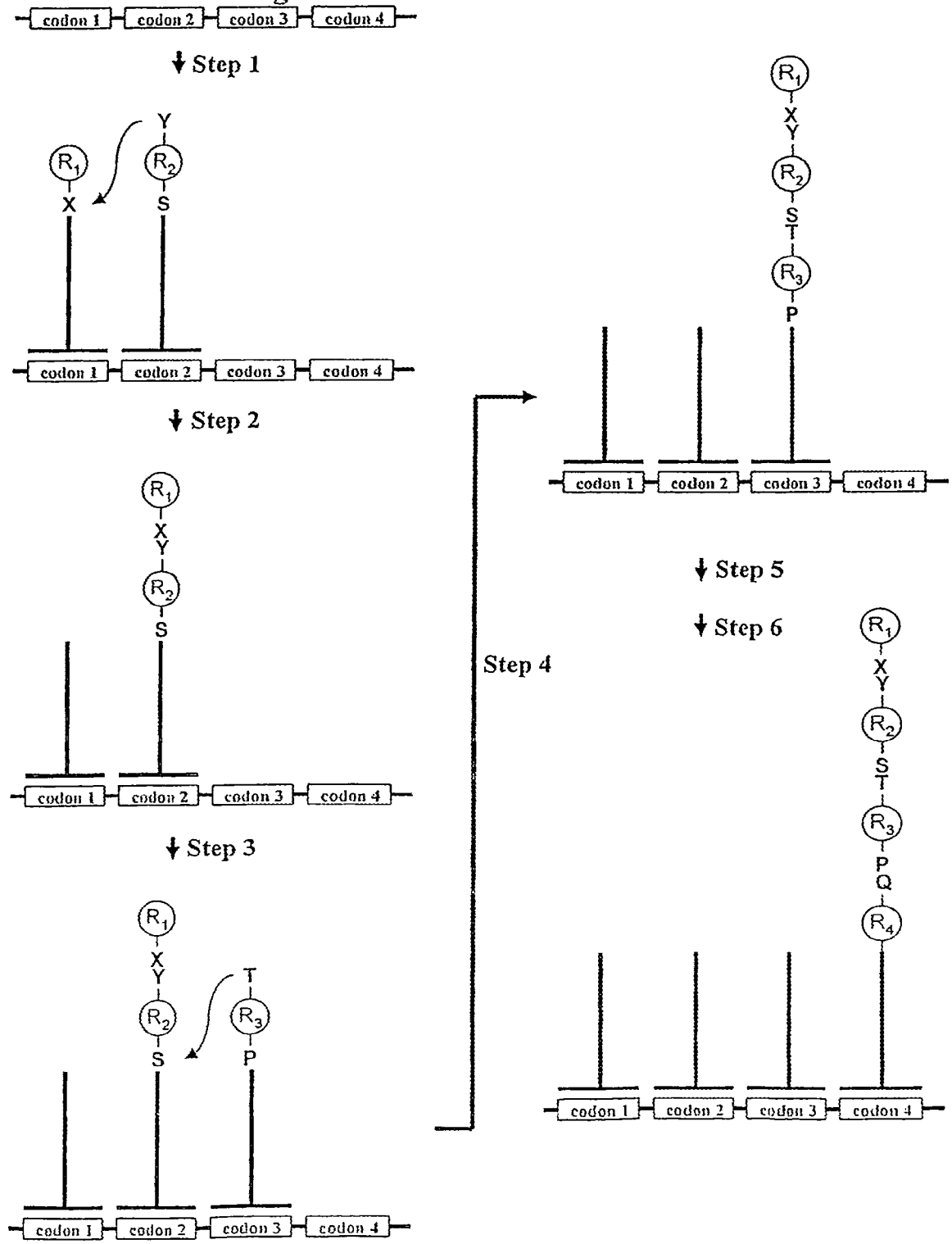
Fig. 11 Templated synthesis of a mixed polymer by simultaneous reaction and cleavage.

Fig. 12  Simultaneous reaction and cleavage: Formation of (A) an alpha-peptide, and (C) a polyamine.
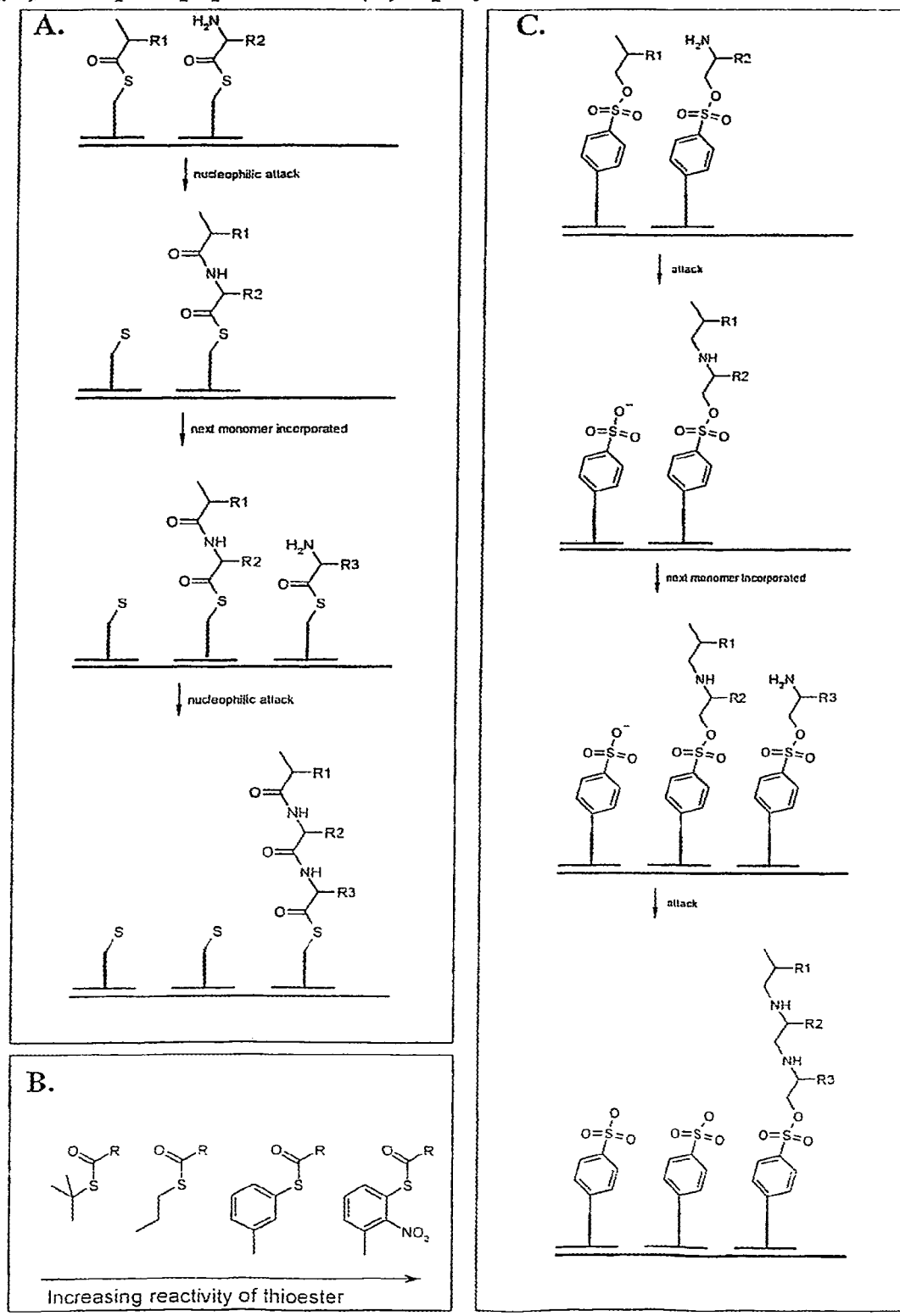

Fig. 13    Simultaneous reaction and cleavage: Formation of
(A) a peptoid or an alpha- or beta-peptide, and (B) a hydrazino peptide.
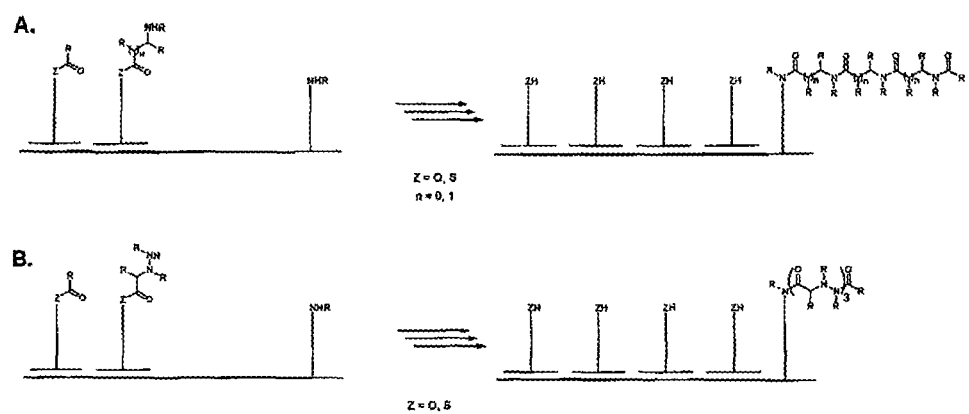

Fig. 14 Templated synthesis of a polymer, using non-simultaneous reaction and cleavage.
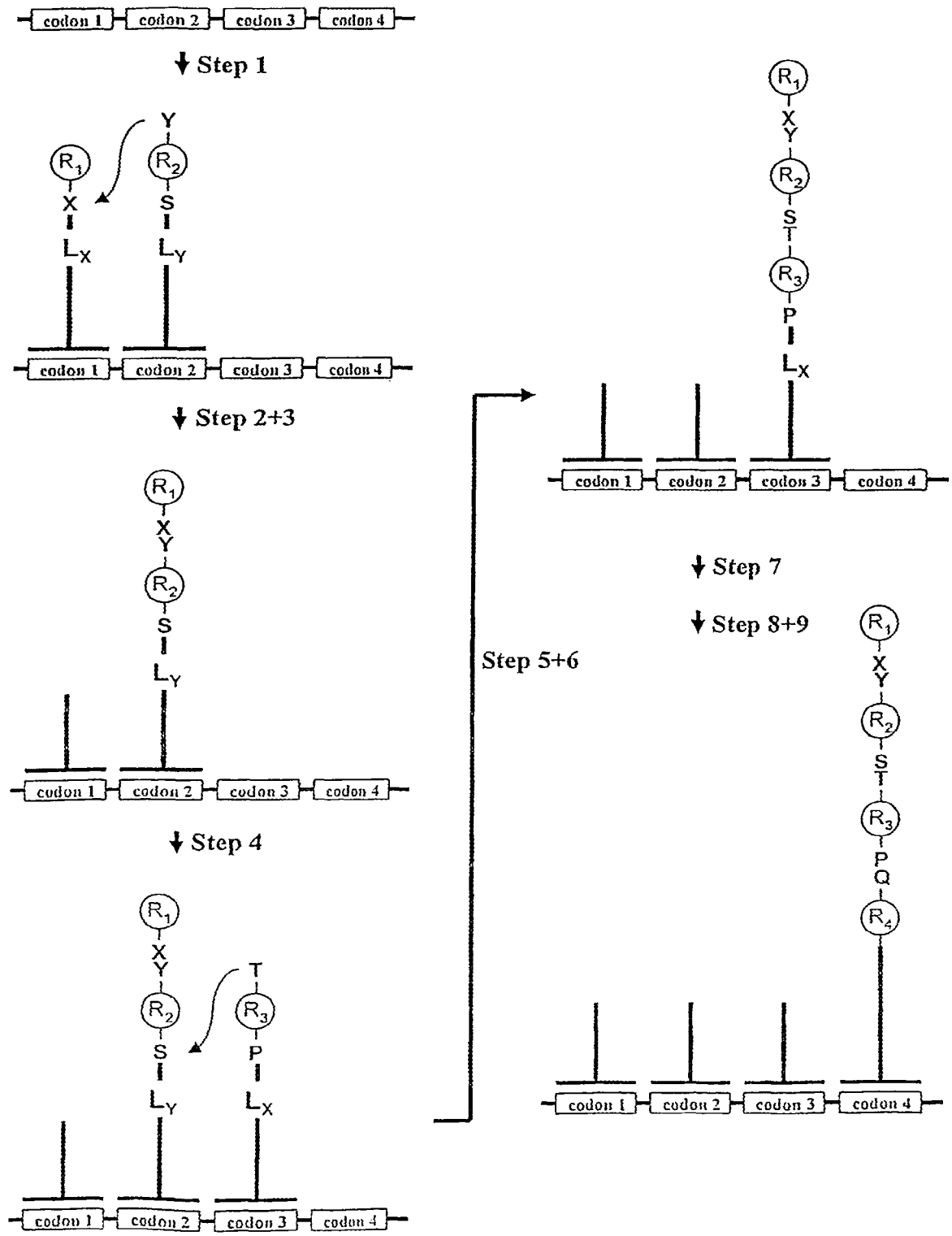

Fig. 15 Activation of reactive group and release from anti-codon by ring opening.
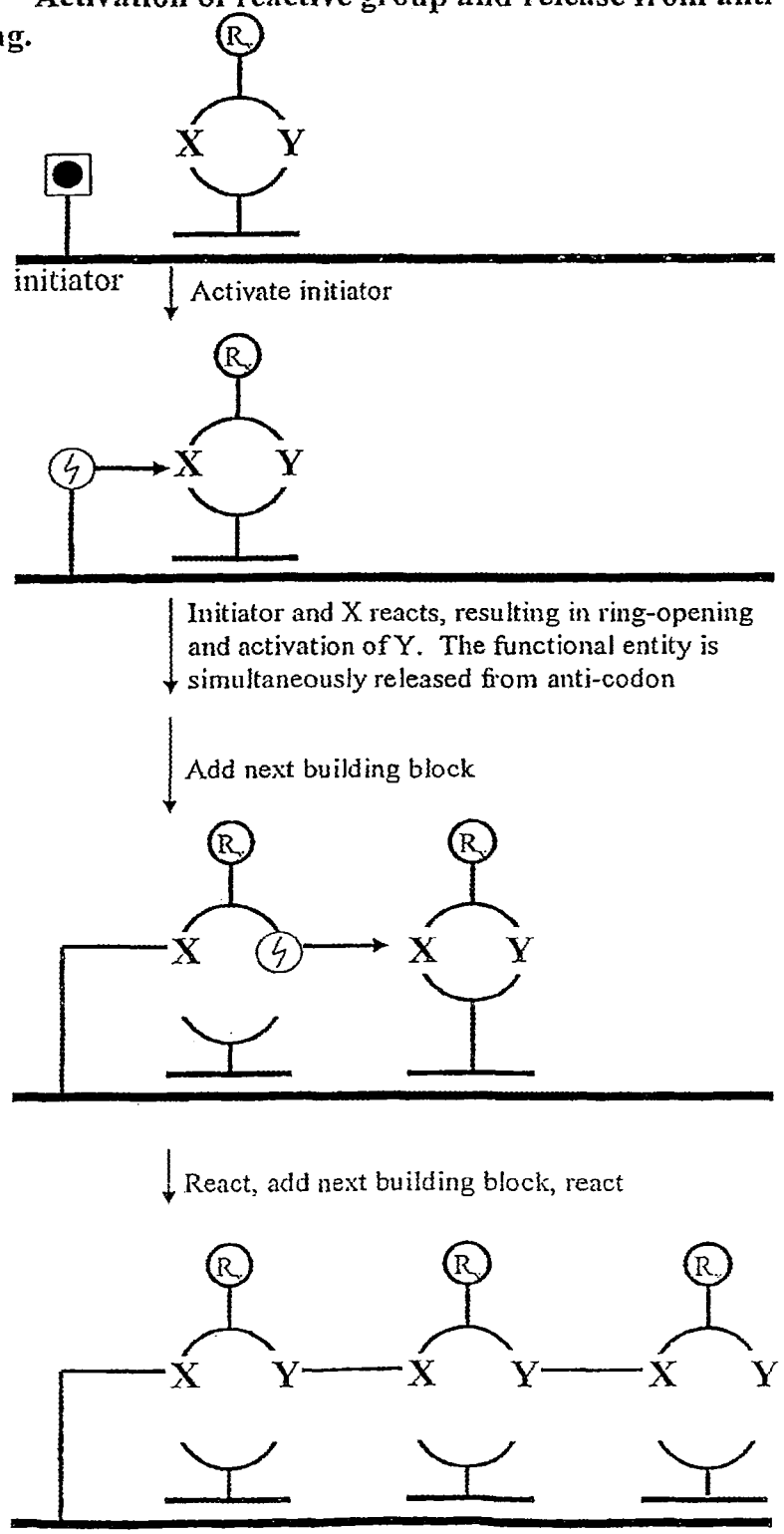

Fig. 16  Symmetric fill-in reaction (symmetric XX building blocks).
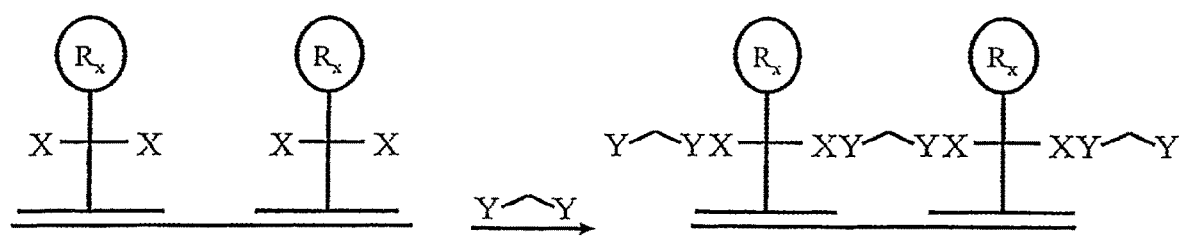
Fig. 17  Imine formation by fill-in.
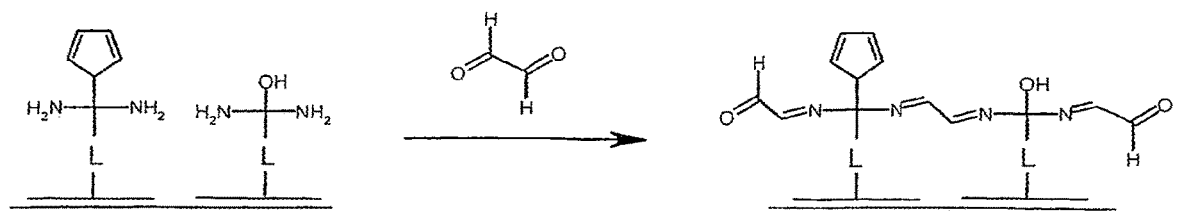

Fig. 18  Amide formation.
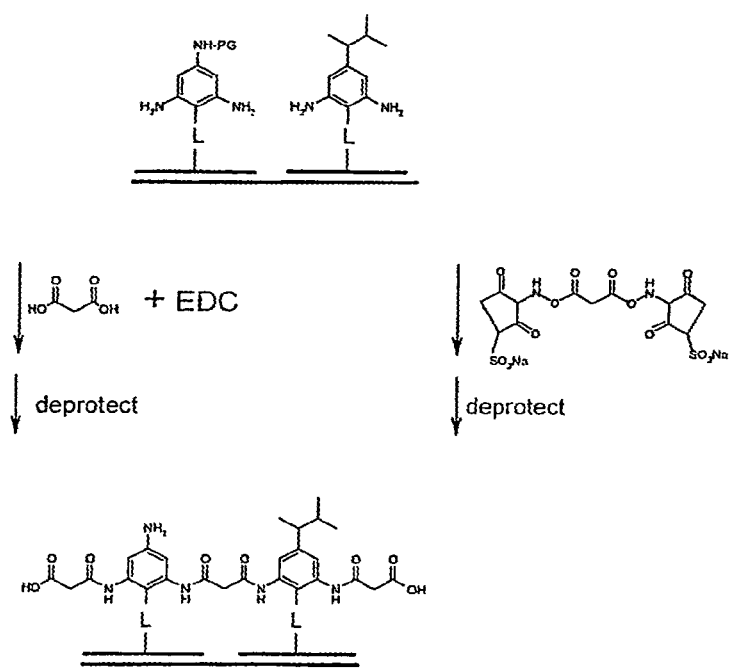
Fig. 19  Urea formation
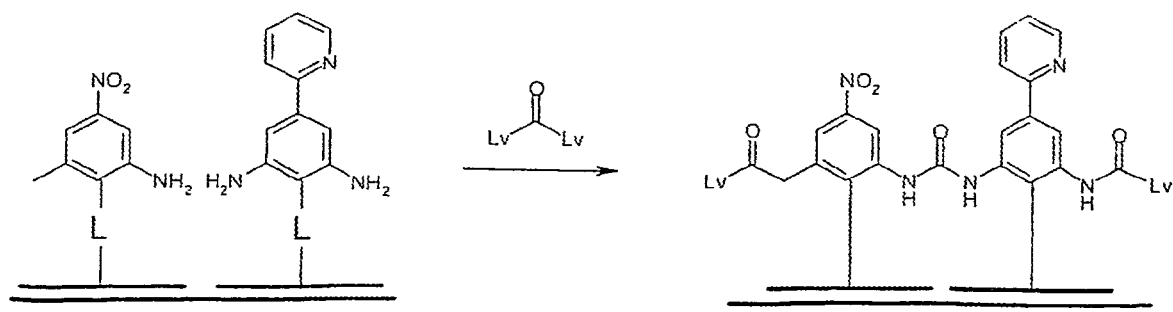

Fig. 20
Synthesis of the functional entity 13.3.1A:
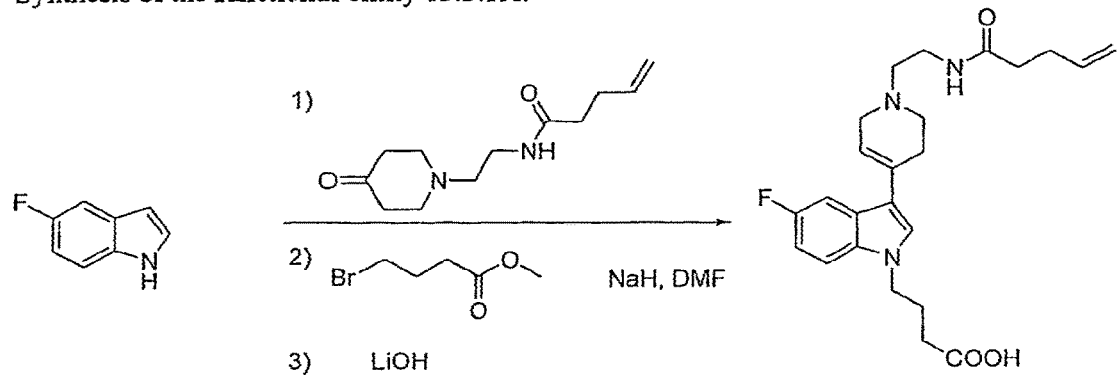
Synthesis of the functional entity 13.3.1B:
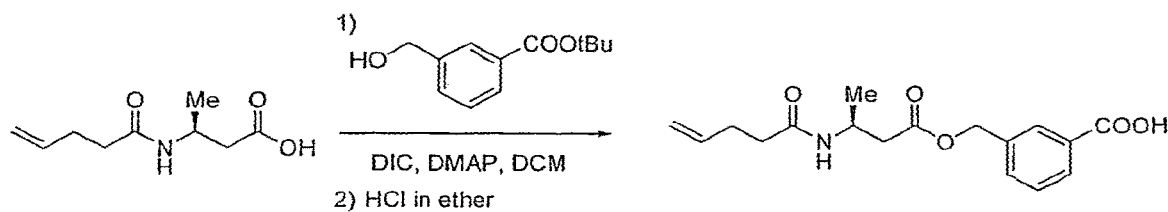
Fill in experiment using functional entity 13.3.1A and 13.3.1B:
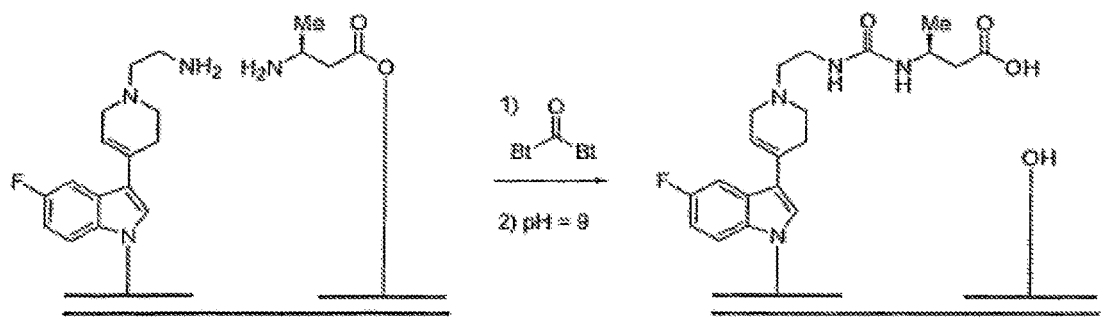

Fig. 21　　Chiral and non-chiral templated molecule
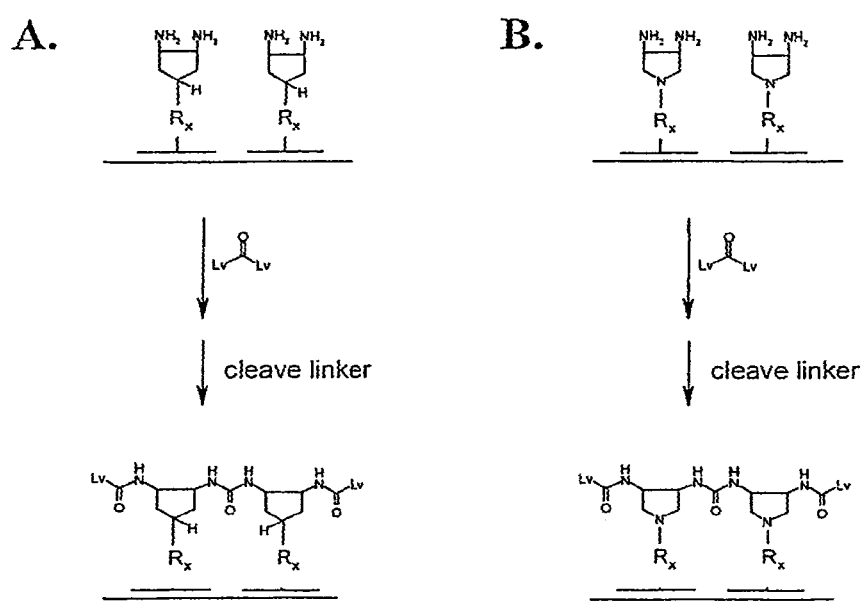

Fig. 22  Symmetric fill-in: Formation of a phophodiester bond.
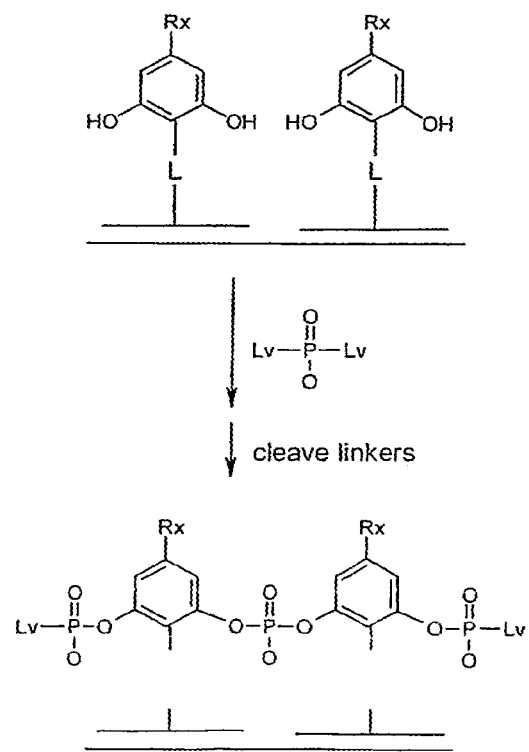

Fig. 23    Fill-in: Phophodiester formation with one reactive group in each building block
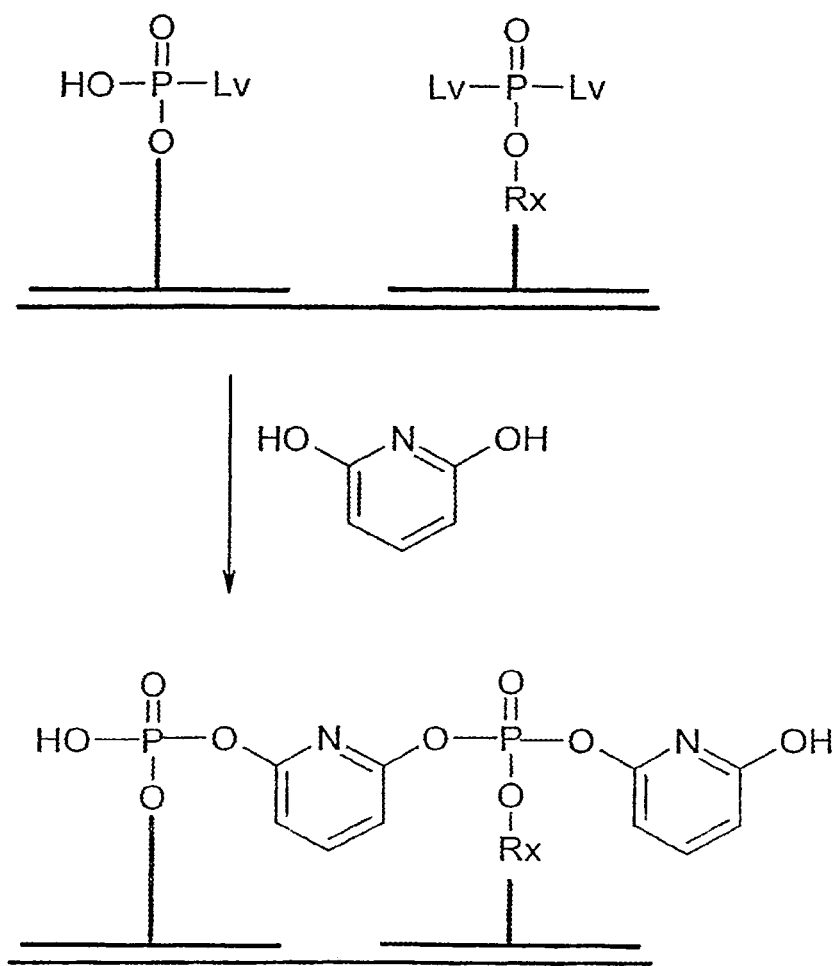

Fig. 24    Pericyclic reaction.
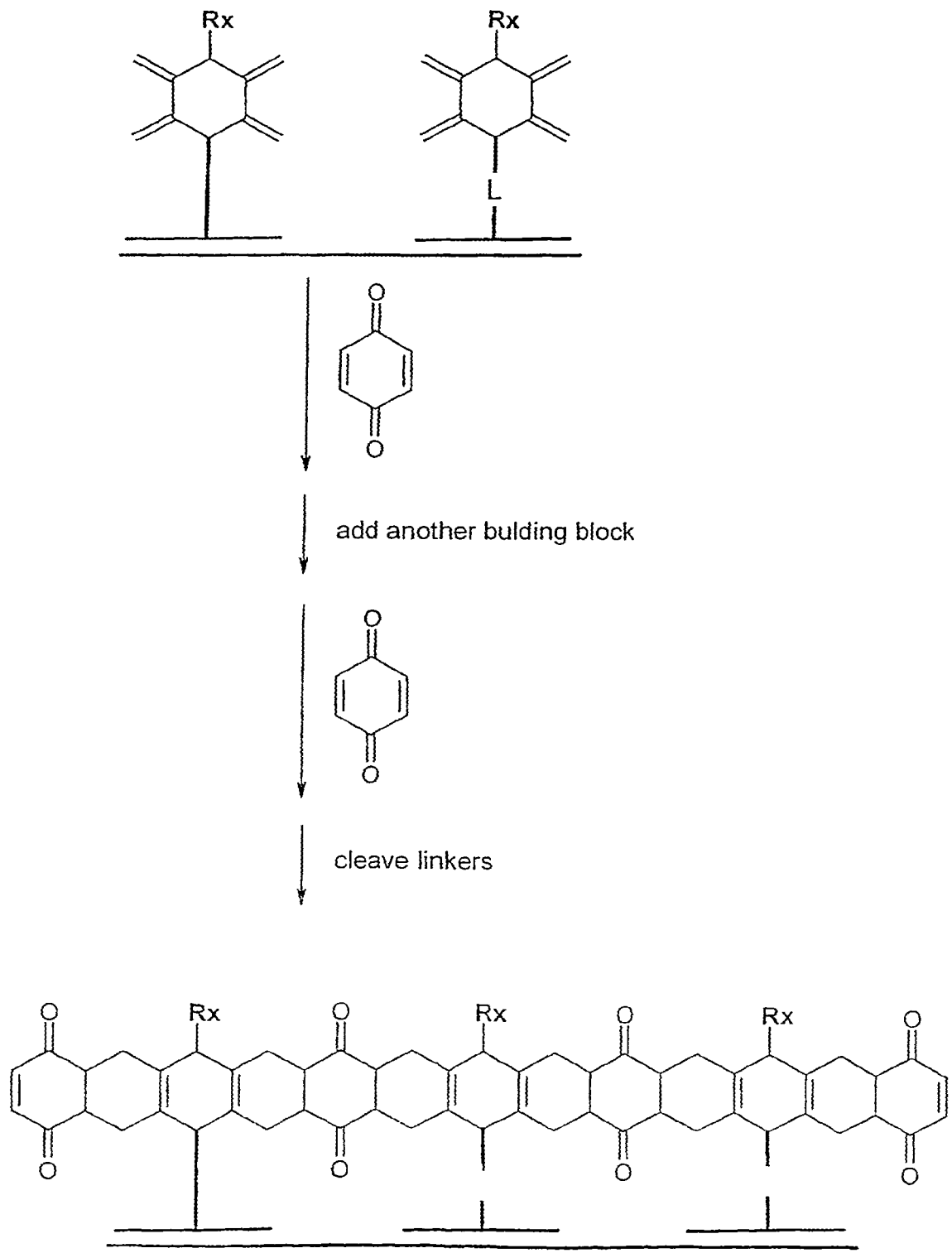

Fig. 25        Pericyclic reaction
Synthesis of the functional entity 13.7.1A:
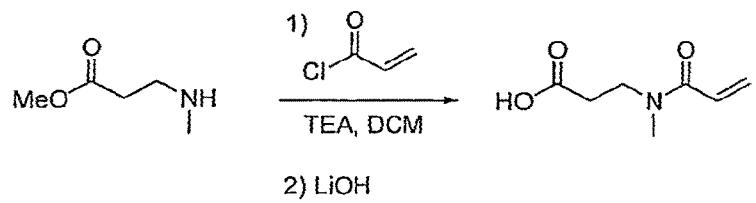
Synthesis of the functional entity 13.7.1B:
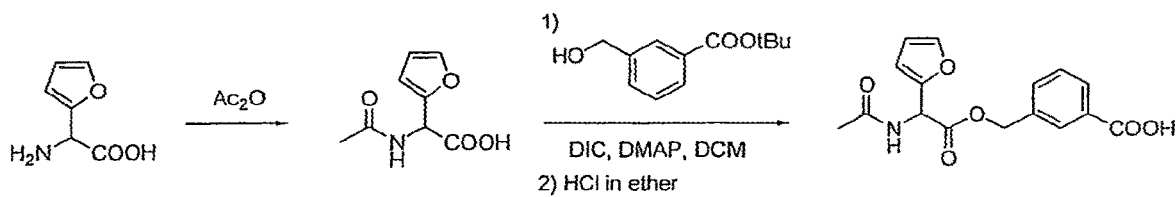
Pericyclic reaction experiment using functional entity 13.7.1A and 13.7.1B:
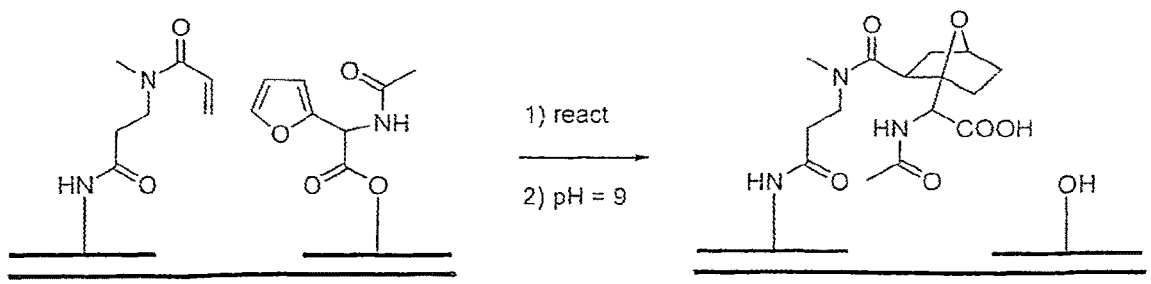

Fig. 26 "Fill-in" reaction (asymmetric XS monomers).
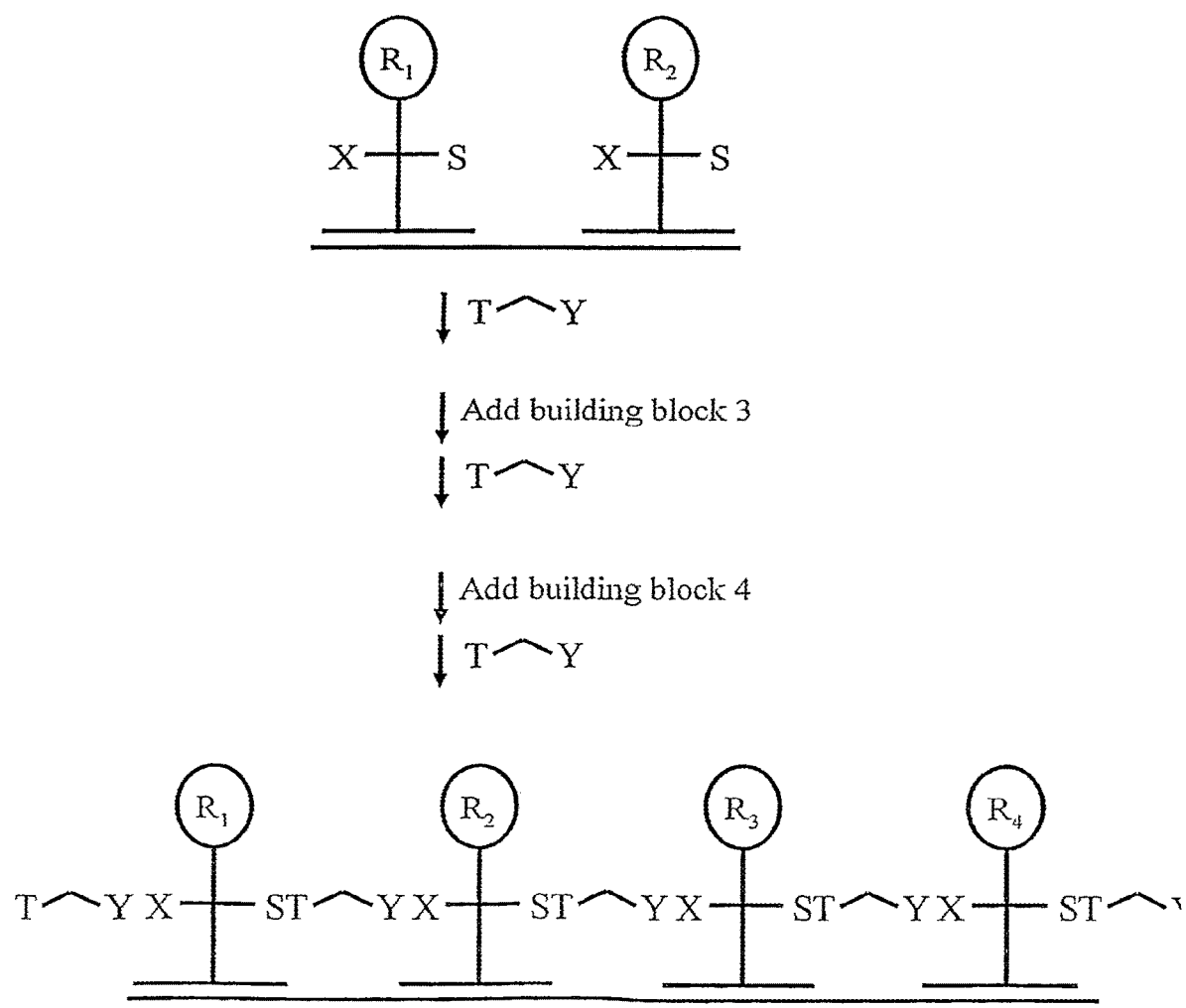

Fig. 28  Templated synthesis of a non-linear molecule.

Fig. 29 Templated synthesis of a non-linear molecule, employing reactive groups of different classes, and non-simultaneous reaction and cleavage.

Fig. 30  Migrating scaffold. Templated synthesis of a non-linear molecule, by exploiting the increased proximity effect that arises from a "migrating" scaffold.

Fig. 31 Templated synthesis of non-linear molecules, examples.

Fig. 33 Templated synthesis in whiche the reaction step is performed under conditions where specific annealing of building block to template is inefficient.
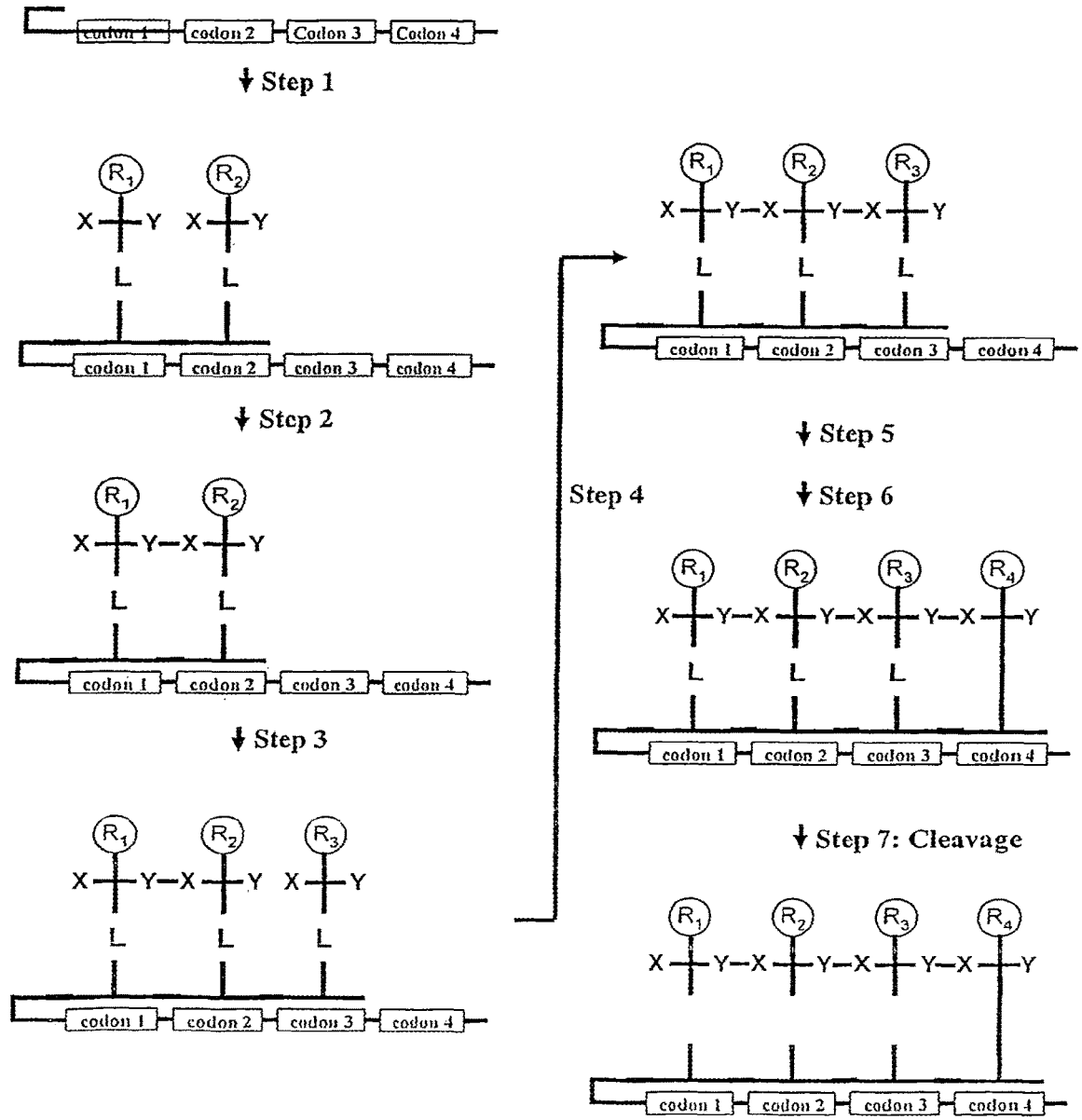

Fig. 34  Reaction types allowing simultaneous reaction and activation.

Nucleophilic substitution using activation of electrophiles

A. Acylating monomer building blocks - principle

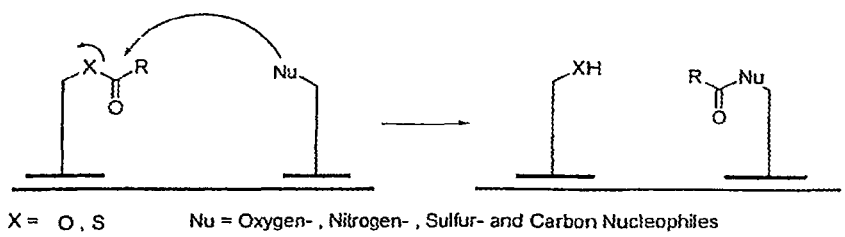

X = O, S       Nu = Oxygen-, Nitrogen-, Sulfur- and Carbon Nucleophiles

B. Acylation
Amide formation by reaction of amines with activated esters

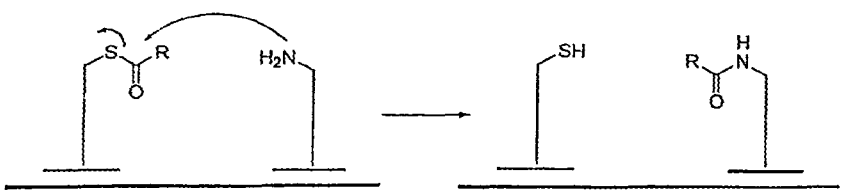

C. Acylation
Pyrazolone formation by reaction of hydrazines with β-Ketoesters

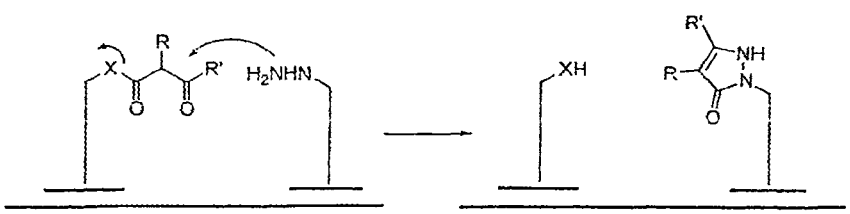

D. Acylation
Isoxazolone formation by reaction of hydroxylamines with β-Ketoesters

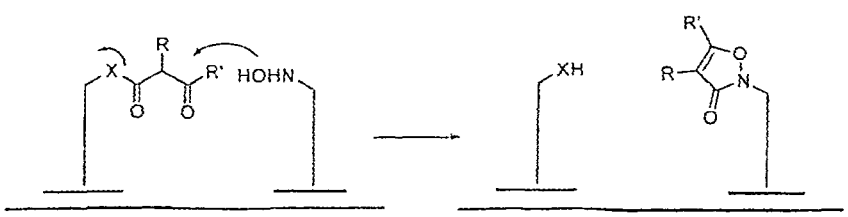

Fig. 35
E. Acylation
Pyrimidine formation by reaction of thioureas with β—Ketoesters

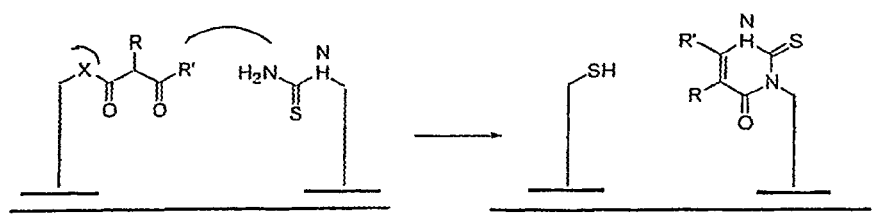

F. Acylation
Pyrimidine formation by reaction of ureas with Malonates

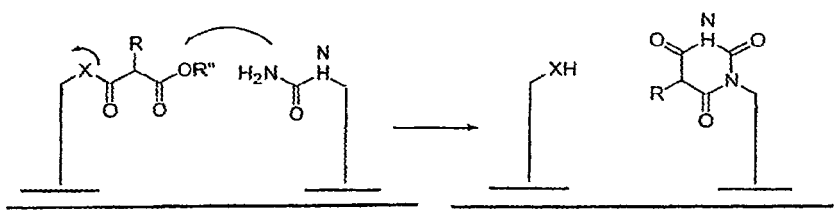

G. Acylation
Coumarine or quinolinon formation by a Heck reaction followed by a nucleophilic substitution

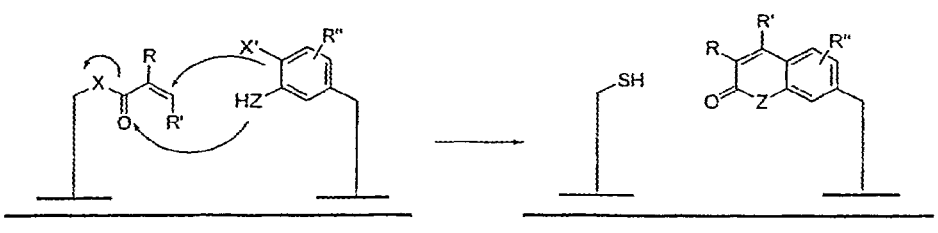

X = O,S     X' = Halogen, OTf, OMs     Z = O, NH

H. Acylation
Phthalhydrazide formation by reaction of Hydrazines and Phthalimides

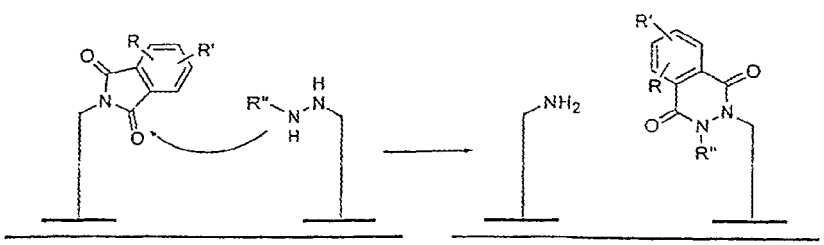

Fig. 36

I. Acylation
Diketopiperazine formation by reaction of Amino Acid Esters

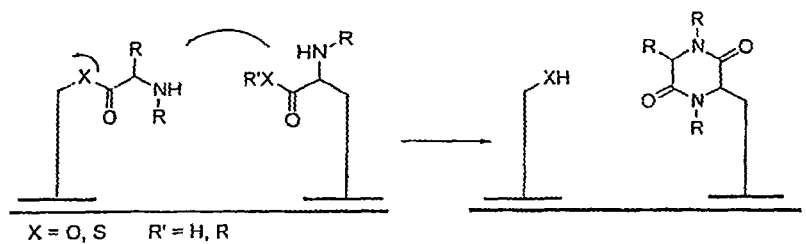

X = O, S     R' = H, R

J. Acylation
Hydantoin formation by reaction of Urea and α-substituted Esters

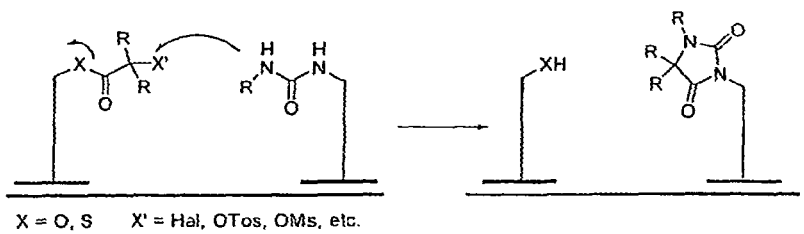

X = O, S     X' = Hal, OTos, OMs, etc.

K. Alkylating monomer building blocks - principle
Alkylated compounds by reaction of Sulfonates with Nucleofiles

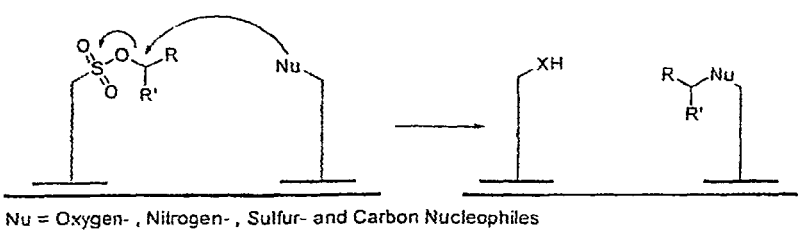

Nu = Oxygen- , Nitrogen- , Sulfur- and Carbon Nucleophiles

L. Vinylating monomer building blocks - principle

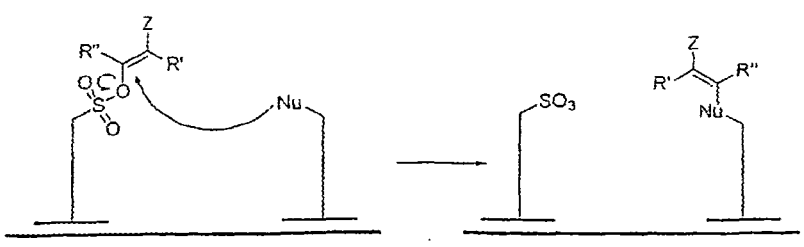

Z = CN, COOR, COR, $NO_2$, $SO_2R$, S(=O)R, $SO_2NR_2$, F
Nu = Oxygen- , Nitrogen- , Sulfur- and Carbon Nucleophiles

Fig. 37

M. Heteroatom electrophiles
Disulfide formation by reaction of Pyridyl disulfide with Mercaptanes

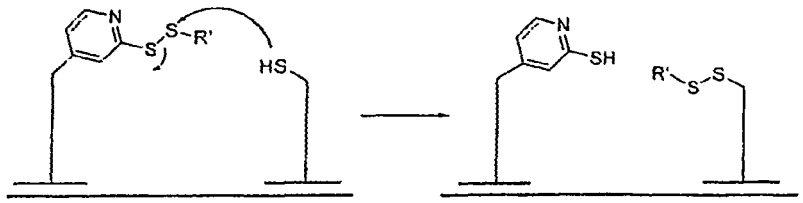

N. Acylation
Benzodiazepinone formation by reaction of Amino Acid Esters and Amino Ketones

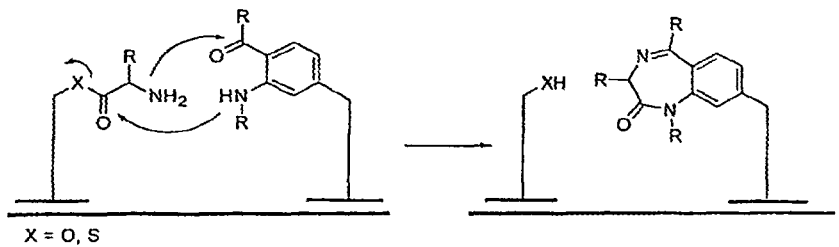

X = O, S

Addition to carbon-hetero multiple bonds

O. Wittig/Horner-Wittig-Emmons reagents
Substituted alkene formation by reaction of Phosphonates with Aldehydes or Ketones

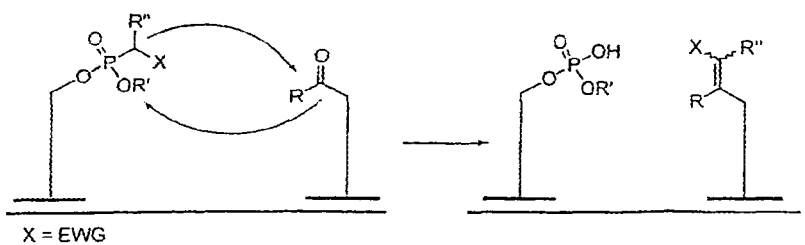

X = EWG

Fig. 38
Transition metal catalysed reactions
P. Arylation
Biaryl formation by the reaction of Boronates with Aryls or Heteroaryls
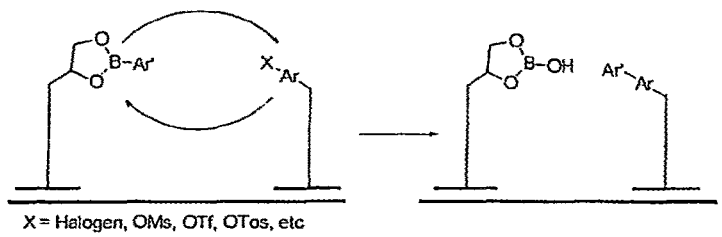
X = Halogen, OMs, OTf, OTos, etc
Q. Arylation
Biaryl formation by the reaction of Boronates with Aryls or Heteroaryls
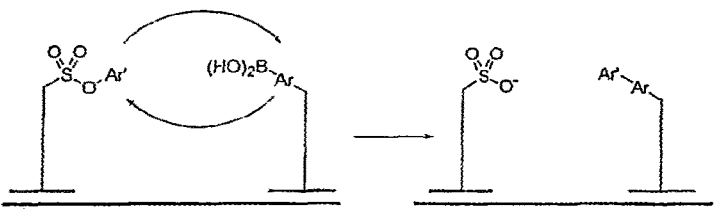
R. Arylation
Vinylarene formation by the reaction of alkenes with Aryls or Heteroaryls
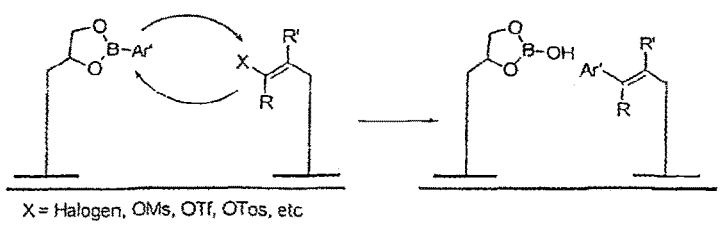
X = Halogen, OMs, OTf, OTos, etc

Fig. 39

S. Alkylation
Alkylation of arenes/hetarens by the reaction with Alkyl boronates

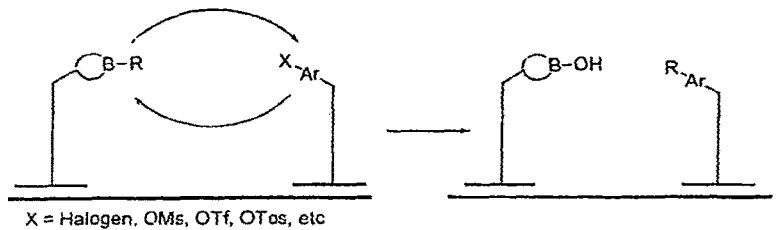

X = Halogen, OMs, OTf, OTos, etc

T. Alkylation
Alkylation of arenas/hetarenes by reaction with enolethers

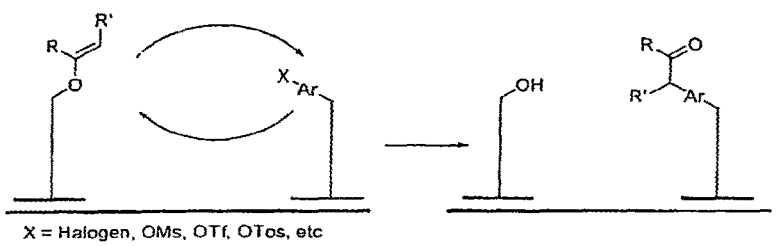

X = Halogen, OMs, OTf, OTos, etc

Nucleophilic substitution using activation of nucleophiles

U. Condensations
Alkylation of aldehydes with enolethers or enamines

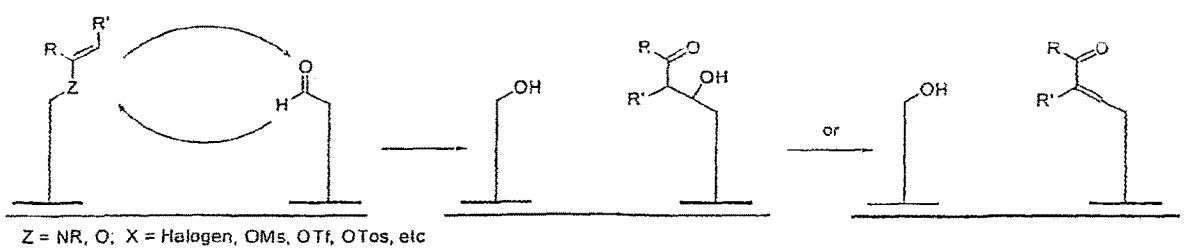

Z = NR, O; X = Halogen, OMs, OTf, OTos, etc

Fig. 40
V. Alkylation
Alkylation of aliphatic halides or tosylates with enolethers or enamines
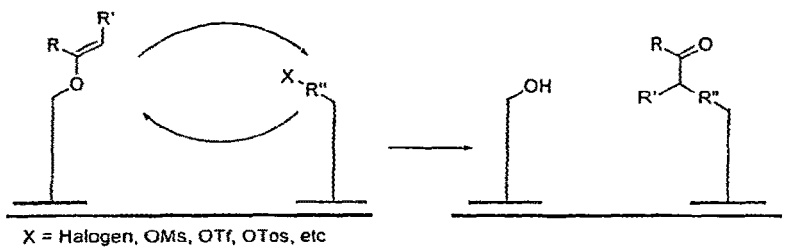
X = Halogen, OMs, OTf, OTos, etc
Cycloadditions
W. [2+4] Cycloadditions
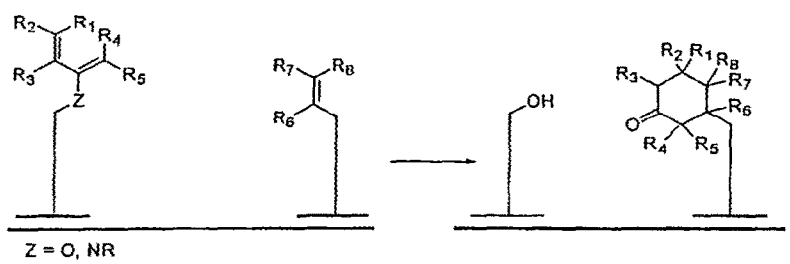
Z = O, NR
X. [2+4] Cycloadditions
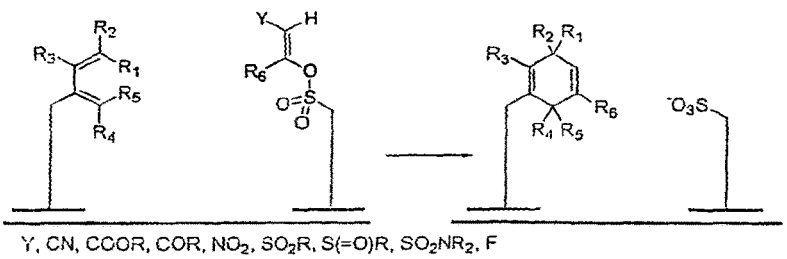
Y, CN, COOR, COR, $NO_2$, $SO_2R$, S(=O)R, $SO_2NR_2$, F
Y. [3+2] Cycloadditions
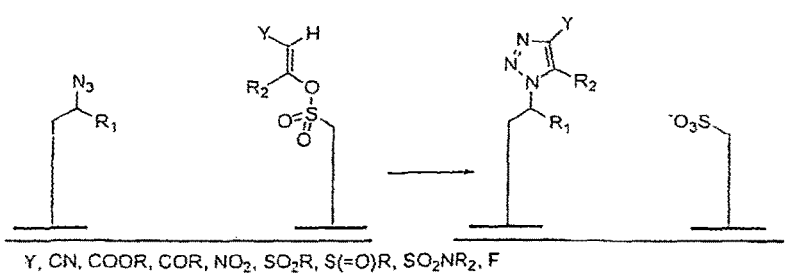
Y, CN, COOR, COR, $NO_2$, $SO_2R$, S(=O)R, $SO_2NR_2$, F Z. [3+2] Cycloadditions

Y, CN, COOR, COR, NO₂, SO₂R, S(=O)R, SO₂NR₂, F

Fig. 42 Pairs of reactive groups X,Y and the resulting bond XY.
Nucleophilic substitution reaction
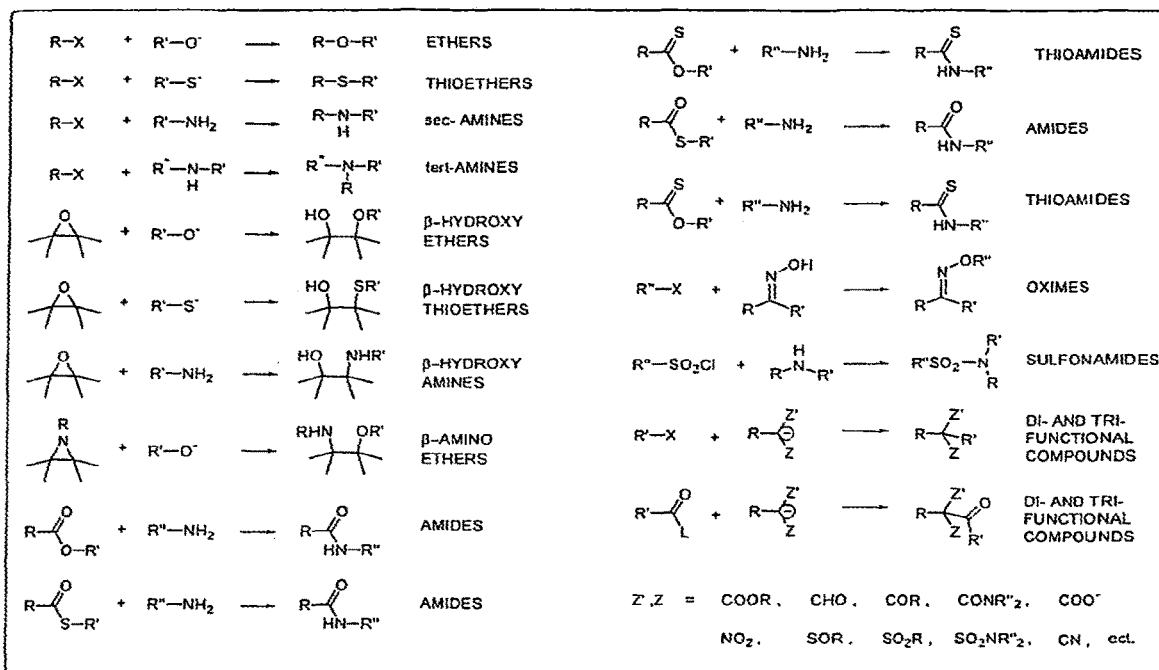
Aromatic nucleophilic substitution
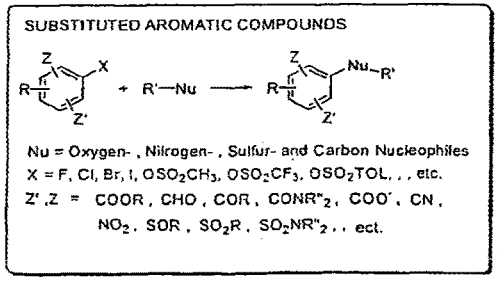
Transition metal catalysed reactions
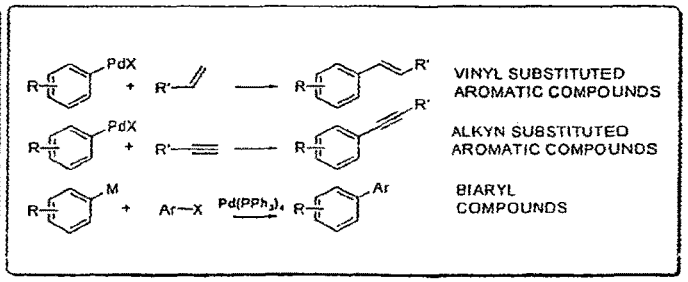

Fig. 43
Addition to carbon-carbon multiplebonds
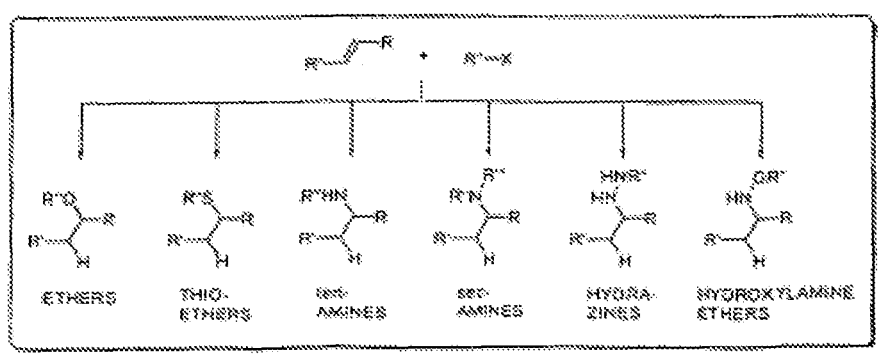
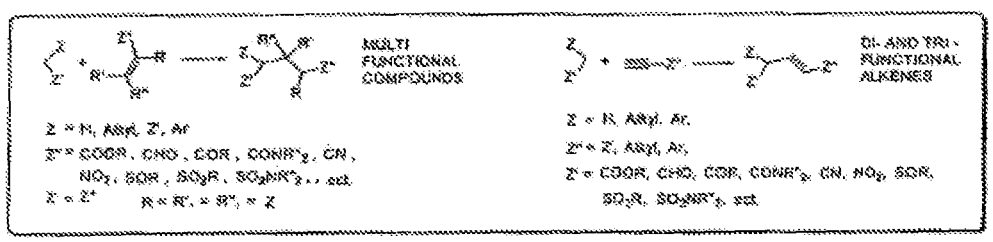

Fig. 44
Cycloaddition to multiple bounds
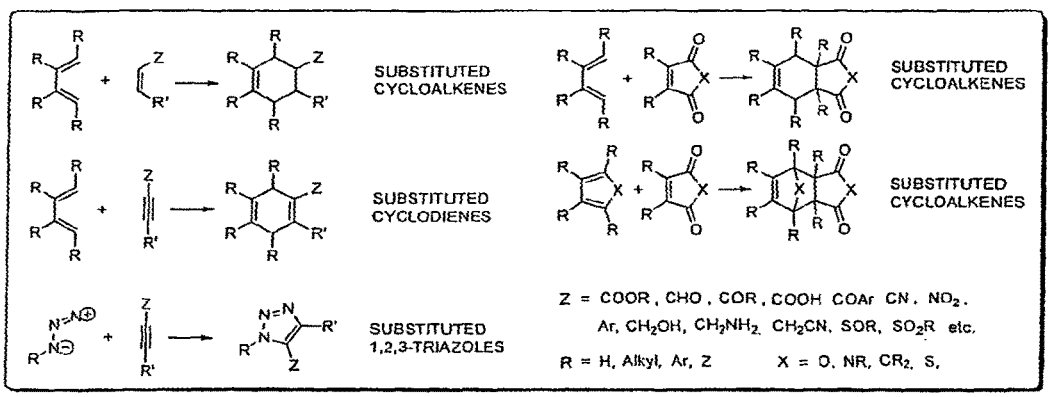
Addition to carbon-hetero multiple bonds
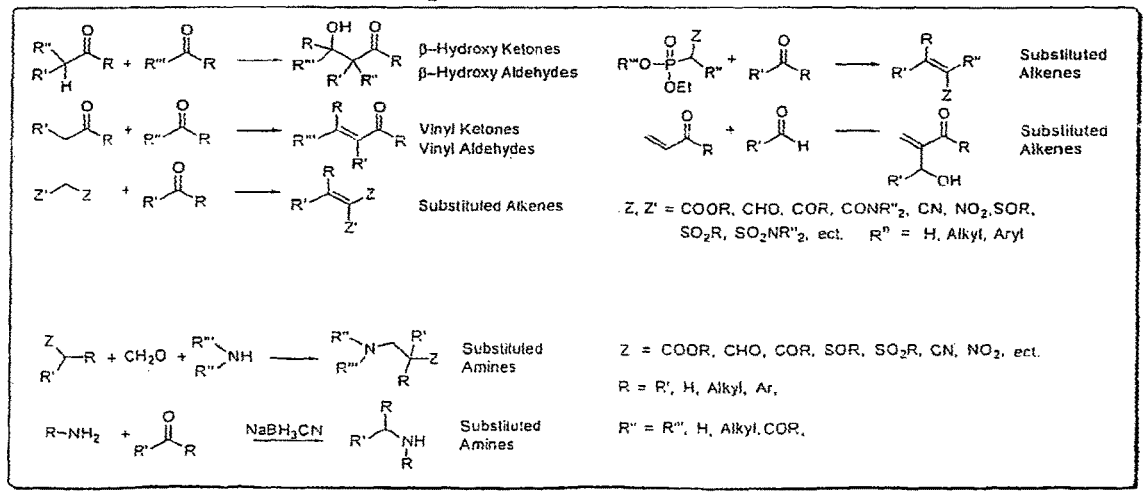

Fig. 45 Increasing the proximity effect: Zipper box.
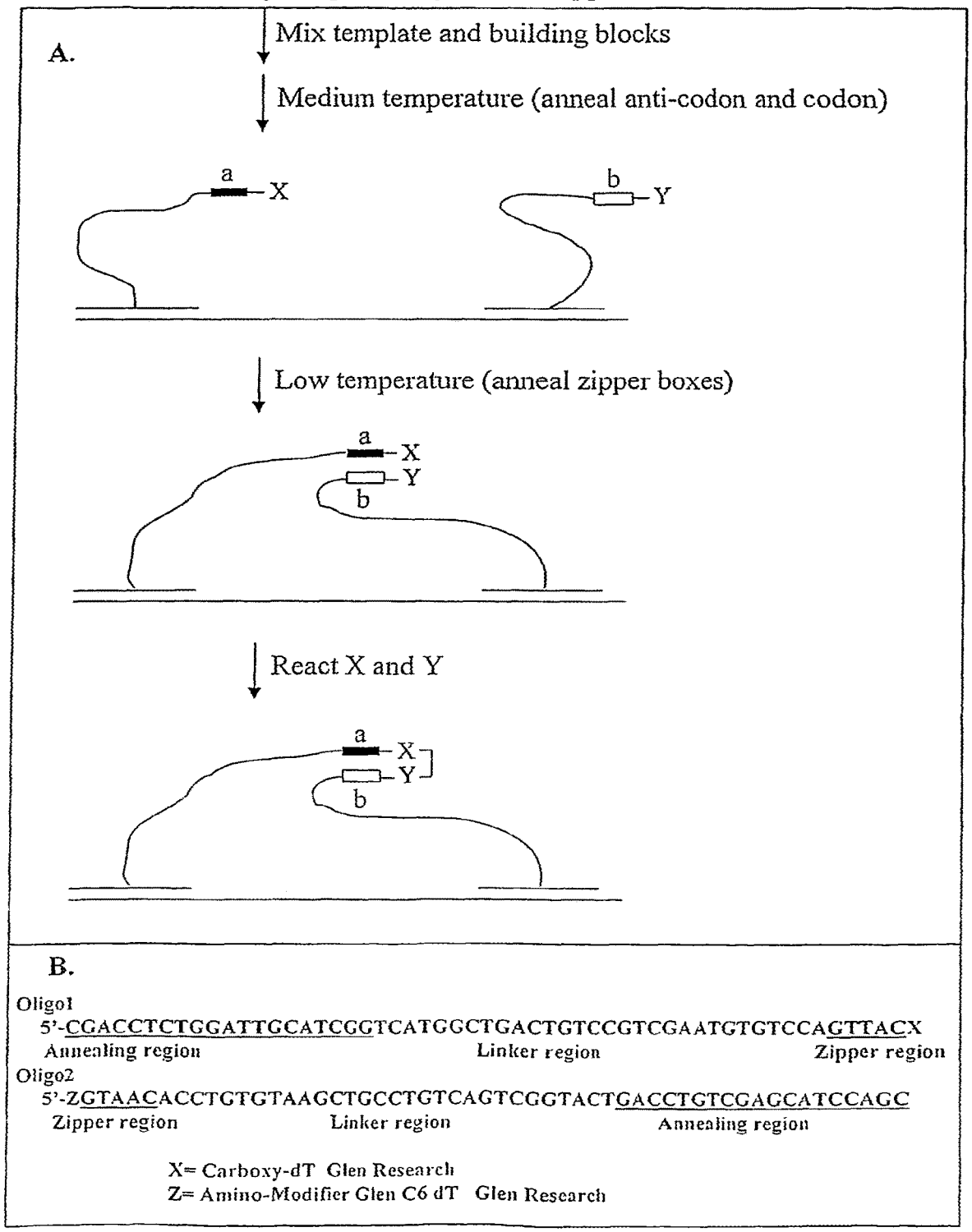

Fig. 46  Increasing the proximity effect: Helix Stacking (A), Ligation (B), and (C) Rigid linkers
A. Double helix stacking.
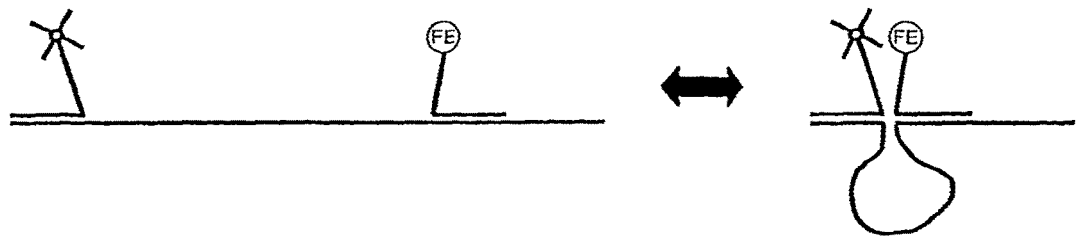
B. Ligation.
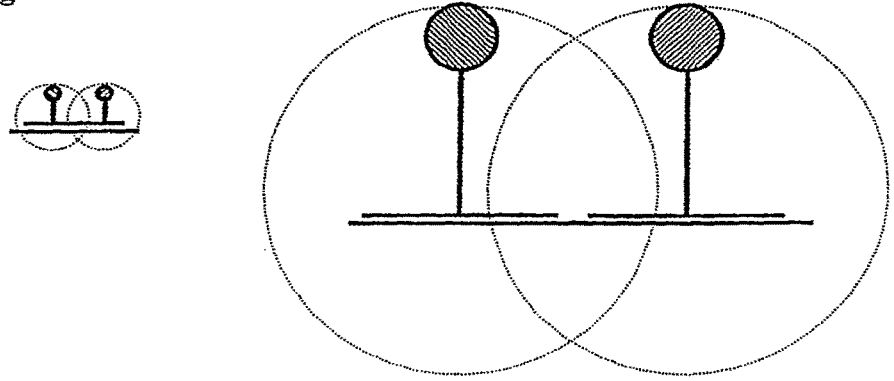
C. Rigid linkers.
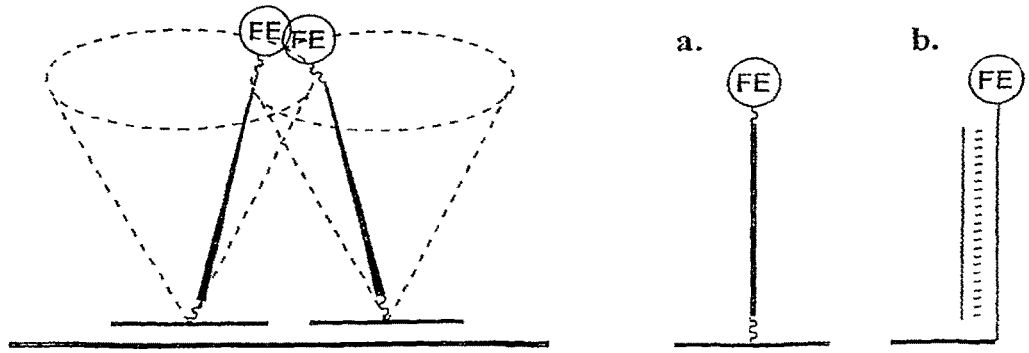

Fig. 47 Cleavable Linkers

A. Linker for the formation of Ketones, Aldehydes, Amides and Acids

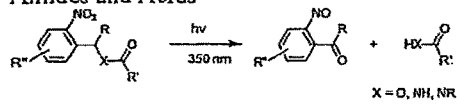

B. Linker for the formation of Ketones, Amides and Acids

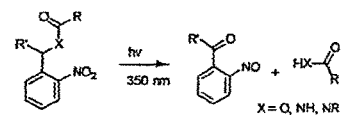

C. Linker for the formation of Aldehydes and Ketones

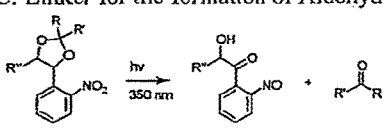

D. Linker for the formation of Alcohols and Acids

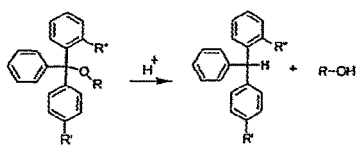

E. Linker for the formation of Amines and Alcohols

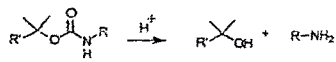

F. Linker for the formation of Esters, Thioesters, Amides and Alcohols

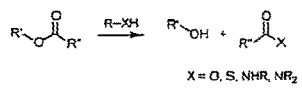

G. Linker for the formation of Sulfonamides and Alcohols

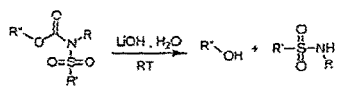

H. Linker for the formation of Ketones, Amines and Alcohols

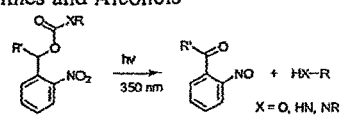

I. Linker for the formation of Ketones, Amines, Alcohols and Mercaptanes

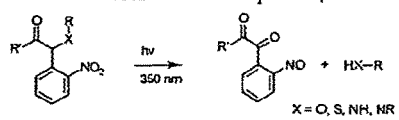

J. Linker for the formation of Biaryl and Bihetaryl

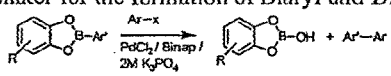

K. Linker for the formation of Benzyles, Amines, Anilins Alcohols and Phenoles

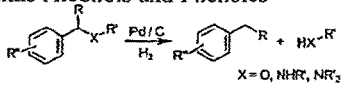

L. Linker for the formation of Mercaptanes

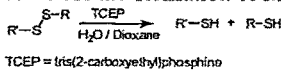

TCEP = tris(2-carboxyethyl)phosphine

M. Linker for the formation of Glycosides

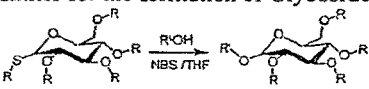

N. Linker for the formation of Aldehydes and Glyoxylamides

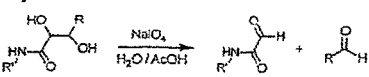

O. Linker for the formation of Aldehydes, Ketones And Aminoalcohols

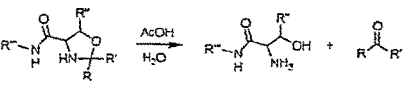

Fig. 48 Templated synthesis by generating a new reactive group.
A.
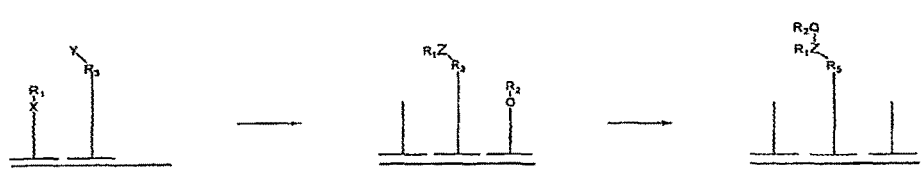
B.
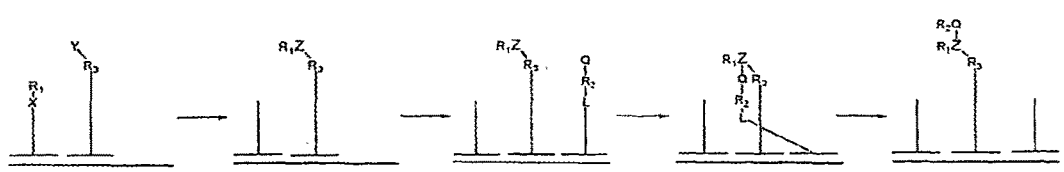

Fig. 49  Generation of reactive groups in the first reaction round, followed by reaction of the generated reactive groups with introduced reactive groups.
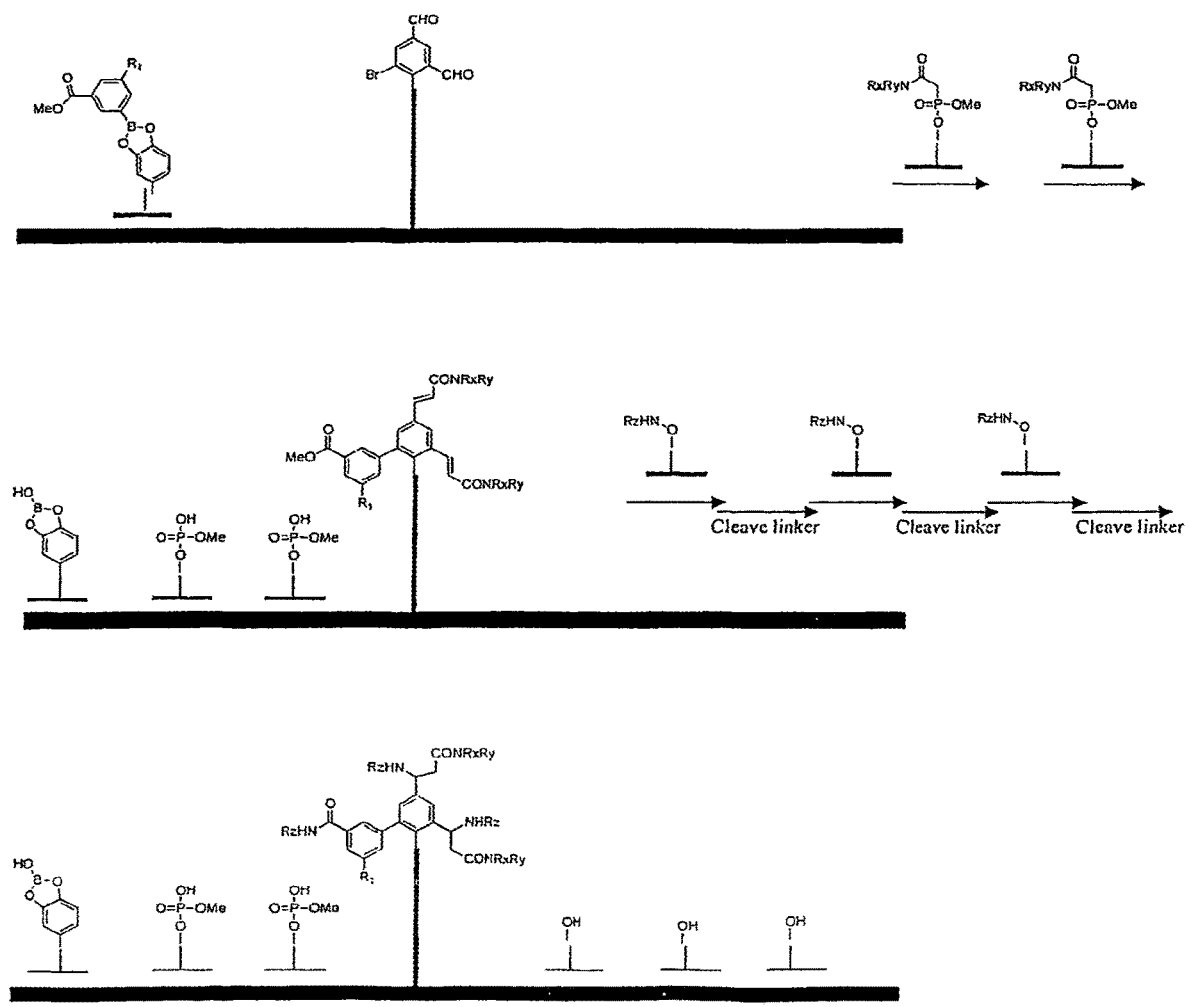

Fig. 50  Post-templating modification of templated molecule
A Rearrangement and cleavage in one step, eg:
A1 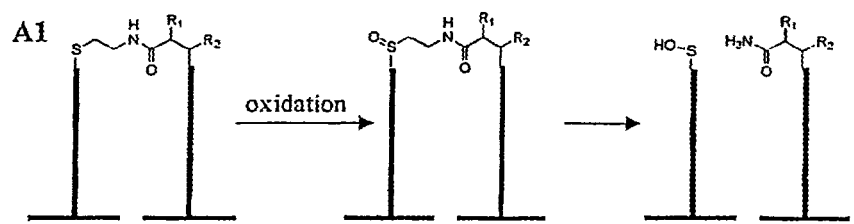
A2 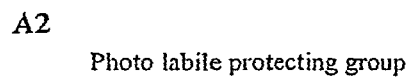
Photo labile protecting group
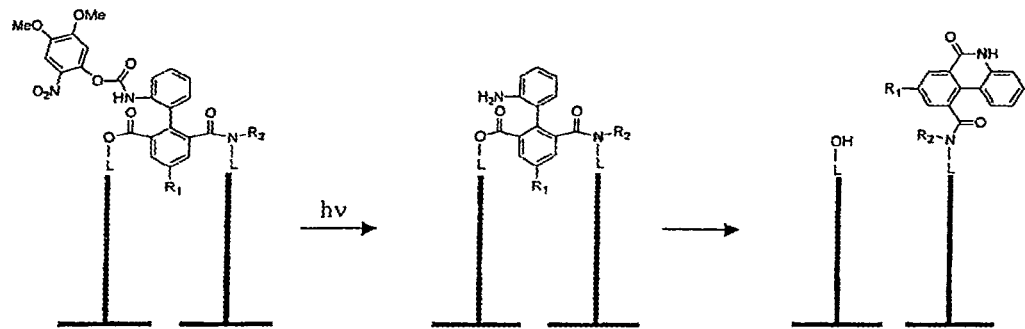

Fig. 51
B Reaction of functional groups present in a templated molecule
B1 Intramolecular Michael addition:
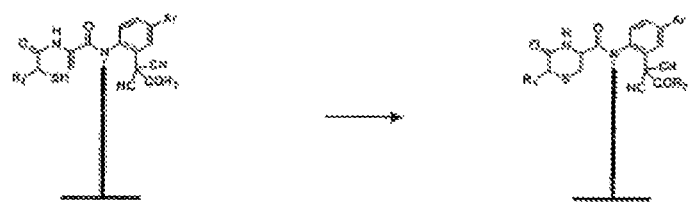
B2 Intermolecular Michael addition:
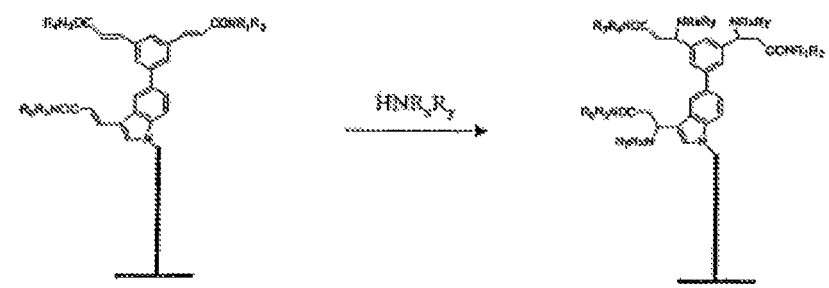

Fig. 52
B3 Reaction of phenylenediamines and aldehydes to form benzimidazoles:
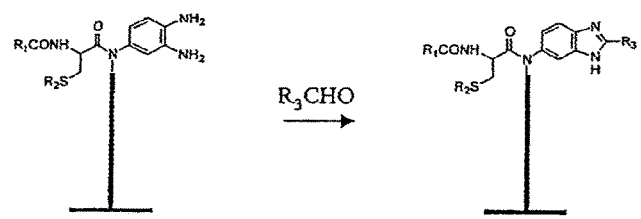
B4 Reduction of multiple bonds:
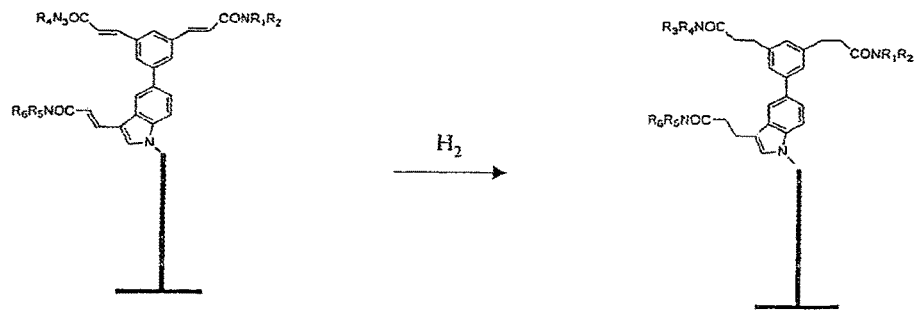
C Post templating modification of linker to extend the spacing between the template and the templated molecule.
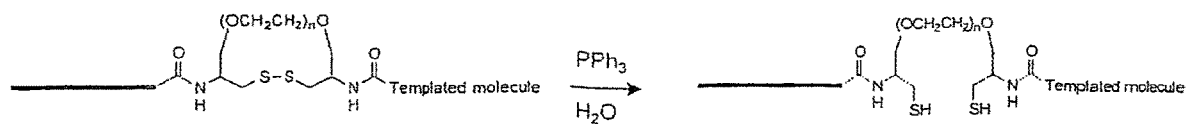

MULTI-STEP SYNTHESIS OF TEMPLATED MOLECULES

TECHNICAL FIELD

The present invention relates to a method for the manufacture of a library of complexes. Each complex in the library comprises a templated molecule attached to the template which directed the synthesis thereof. The library of the invention is useful in the quest for new biological active compounds, such as drugs.

BACKGROUND ART

The generation of molecules carrying new properties remains a challenging task. Recently, a number of procedures have been suggested that should allow a more efficient generation and screening of a larger number of molecules. The approaches taken involve the encoding and/or templating of molecules other than natural biopolymers such as peptide, RNA and DNA. These approaches allow the researcher to generate and screen a huge number of molecules in a short time. This should lead to better molecules carrying the desired properties.

The central dogma of biology describes the one-way flow of information from DNA to RNA to protein. Recently, methods such as phage display, peptides-on-plasmids, ribosome display and mRNA-protein fusion have been developed, allowing the transfer of information from the level of protein/peptide to RNA or DNA. This has enabled the use of molecular evolution to be applied on huge numbers of peptides that are exposed to an enrichment process, where after the enriched pool of molecules (enriched for a particular feature, such as binding to receptor protein) are amplified, by exploiting information flow from the peptide to DNA and then amplifying the DNA.

More recently, approaches have been developed that allow the encoding of polypeptides and other biochemical polymers. An example of this approach is disclosed in U.S. Pat. No. 5,723,598, which pertains to the identification of a biochemical polymer that participates in a preselected binding interaction with a target to form a binding reaction complex. The prior art method encompasses the generation of a library of bifunctional molecules. One part of the bifunctional molecule is the biochemical polymer and the other part is an identifier oligonucleotide comprising a sequence of nucleotides which encodes and identifies the biochemical polymer. Following the generation of the library of the bifunctional molecules, a partitioning with respect to affinity towards the target is conducted and the identifier oligonucleotide part of the bifunctional molecule is amplified by means of PCR. Eventually, the PCR amplicons are sequenced and decoded for identification of the biochemical polymer. This approach suffers from the draw-back that it is necessary with a laborius decoding step following each round of selection. Thus the flow of information from the identifier sequence to the biochemical polymer is restrained.

Halpin and Harbury have in WO 00/23458 suggested an improvement to the approach stipulated immediately above, wherein the molecules formed are not only identified but also directed by the nucleic acid tag. The approach is based on the traditional split-and-combine strategy for synthesis of combinatorial libraries comprising two or more synthetic steps. Plurality nucleic acid templates are used, each having at one end a chemical reactive site and dispersed throughout the stand a plurality of codons regions, each of said codon regions in turn specifying different codons. Separately, each of the strands, identified by a first codon region, is reacted at the chemical reaction sites with specific selected reagents. Subsequently, all the strands are pooled and subjected to a second partitioning based on a second codon region. The split-and-combine method is conducted an appropriate number of times to produce a library of typically between $10^3$ and $10^6$ different compounds. The split-and-combine method is cumbersome and generates only a relatively small library.

The present invention aims at obtaining a library of compounds which are not only encoded by a suitable tag attached to each compound, but also directed. The directed synthesis of the compounds of the library allows for renewed synthesis of templated molecules following a selection round. Furthermore, the present invention increases the probability of connection of molecular entities eventually appearing in the templated molecule due to a higher local concentration of the reactive groups involved in the formation of the connection.

DISCLOSURE OF THE INVENTION

The present invention relates to a method for the manufacture of a library of complexes comprising templated molecules, said method comprises the steps of
  a) providing a plurality of different templates comprising a number of coding regions and a reactive group, wherein each coding region of a specific template specifies a unique codon,
  b) providing a plurality of different building blocks, each building block comprising an anti-codon, a functional entity and a linker connecting the anti-codon and the functional entity, wherein the anti-codon of each building block complements a unique codon of a template, and the functional entity comprises at least one reactive group,
  c) contacting the plurality of different templates with a subset of the plurality of different building blocks, said subset having anti-codons which complement the unique codons of a specific coding region, said contacting being performed under conditions which allow specific hybridisation of the anti-codons to the unique codons of the templates,
  d) reacting the reactive group of the template and the reactive group of the building block to obtaining a chemical connection,
  e) contacting under conditions allowing specific hybridisation, the plurality of different templates harbouring the nascent templated molecules with a further subset of the plurality of building blocks, said subset having anti-codons complementary to the unique codons of a coding region in the vicinity of the coding region harbouring the nascent templated molecules,
  f) allowing the functional entities of the subset of further building blocks to form a chemical connection to the nascent templated molecules,
  g) optionally, cleaving one or more of the linkers, provided that at least one linker remains to connect the nascent templated molecule with the template which directed the synthesis thereof,
  h) optionally repeating steps e) through g),
  i) obtaining a templated molecule attached via the linker one or more building blocks to the template which directed the synthesis thereof.

The present invention allow for a multi-step templated synthesis of a library of molecules without the need for a laborious and time consuming split step of the traditional split and-mix-method. The method furthermore provides for the possibility of bringing the functional entities of building blocks in close proximity, thus allowing facilitated connection of functional entities in the vicinity of each other. The bringing in close proximity of building blocks provide for an increased local concentration of the active chemical groups, thus increasing the probability that two reactive groups will be so close that a reaction actually will occur.

The various templates of the present invention are in general constructed to follow a general scheme. According to the scheme, a number of coding regions are provided on the template. In turn, each of the coding regions specifies one or more unique codons. Thus, a specific template comprises a given number of unique codons. The plurality of templates can, taken as a whole, be characterized as a library comprising the total amount of the different combinations of unique codons possible, or any subset thereof. The coding regions are suitable positioned in a linear sequence, such that the individual coding regions are positioned immediately next to each other. In some embodiments, it may be of advantage to use a branched template to ensure proximity of reactive groups, the introduction of catalysts in the vicinity of the reactive groups or the introduction of as third reactant.

Besides the coding regions, the templates used in the present invention include a reactive group. The reactive group comprised by the template may be covalently or non-covalently attached to the template. Covalent attachment may be preferred when the templated molecule is to be effectively attached to the template, because a covalent bonding will allow affinity selection using more harsh conditions. The covalent attachment of the reactive group may be done at a terminal region of the template or at a central region thereof. In an aspect of the invention, the reactive group is non-covalently attached to the template using a complementing element hybridised to the template. More particularly, it is preferred that the reactive group of the template is part of a building block hybridised to the template.

The coding regions may be spaced with a suitable spacer region. The spacer region may be an indentifier for the coding region of may be a region not carrying any information but serving to bring the functional entities into the desired proximity or to provide the template with a desired physical characteristic like a stiff connection of coding regions, or alternative, a flexible connection between two coding regions.

The template may comprise flanking regions. One of the flanking regions can in an aspect of the invention serve to immobilize the template to a surface of a solid support. In another aspect of the invention the flanking region can encompasses a signal group, such a flourophor or a radio active group, to allow a direct detection of the presence of the template.

The plurality of templates used in the present invention may in one embodiment be represented by the general formula:

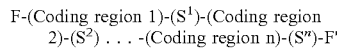

F-(Coding region 1)-($S^1$)-(Coding region 2)-($S^2$) . . . -(Coding region n)-($S''$)-F'

Wherein
Each of Coding region I through Coding region n independently specifies m unique codons,
F and F' are optional flanking regions,
$S^1$ to $S''$ are optional spacing groups,
n is an integer of at least 2, and
m is an integer of at least 1.

The unique codons of the templates are preferably composed of a sequence of nucleic acid monomers, such as nucleotides. Each codon is unique in the sense that within the same coding region no other codons have an identical sequence and length of nucleic acid monomers. Preferably, a unique codon does not have a corresponding sequence anywhere in the plurality of templates. To avoid hybridisation between individual templates it is also desirable to design each of the unique codons such that the complementary sequence thereof does not exist on any other templates.

The number of coding regions may be selected in accordance with inter alia the number of the desired final templated compounds, the building blocks available and the envisaged structure of the templated compound. According to the invention the number of coding regions is preferably at least 3 to achieve the desired diversity. The upper limit for the number of coding regions has not yet been elucidated; however it is believed that a number exceeding 100 may give practical problems. Generally, it is preferred to use templates having between 3 and 50 coding regions, more preferably between 3 and 30 and still more preferred between 4 and 15.

Within each of the coding regions the number of unique codons may be selected according to the need for diversity. The number of unique codons in each of the coding regions may be similar or different. The number of unique codons can be as low as one. This may be the choice when a so-called scaffold is involved in the evolving templated molecule. The upper limit for the number of unique codons may be chosen quit high as long as specific hybridisation of oligonucleotides of the anti-codons to their complements on the templates occurs. An example of an upper limit may be 10,000, but may be chosen below this limit or above according to the need.

The building blocks essential for the present invention, are generally composed of three elements, viz. an anti-codon, a functional entity, and a linker which connects the anti-codon and the functional entity. The anti-codon is a sequence of nucleic acid monomers complementary to the sequence of a unique codon on at least one of the plurality of templates. In one aspect of the invention, building blocks are provided which possesses anti-codons complementing all the unique codons of the variety of templates. In another aspect, some of the building blocks carrying anti-codons for selected unique codons are not present. The latter situation may occur when termination of the synthesis is desired at different stages or when the absences of certain functional entities on the templated molecule are desirable. Furthermore, anti-codons not associated with any functional entity may be present for steric reasons or to avoid unintended hybridisation events.

The design of the anti-codons and the complementing unique codons may be aimed at obtaining essentially the same annealing temperature for all or some of the codon: anti-codon hybrids to ensure that all the anti-codons have been annealed to the template before the functional entities are connected to each other through a chemical reaction. In an aspect of the invention, the annealing temperature of the codon:anti-codon hybrids within the same coding region is designed to have different annealing temperature. The separate reaction may be accompliced by initially raising the temperature above the annealing temperature for all the hybrids and slowly decreasing the temperature until the first set of anti-codons anneal to its templates. Following the connection of the functional entity to another functional entity or a nascent templated molecule, the temperature is decreased sufficient for allowing another building blocks to anneal to a coding region in the vicinity. The above design provides for the possibility that functional groups of different templates but within the same coding region are subjected to different reaction conditions.

A further design involves annealing temperatures different for each of the coding regions but similar within a specific coding region. Upon proper design it is possible step-wise to anneal the individual building blocks by gradually decreasing the temperature from above the annealing temperature for the total of the codon:anti-codon hybrids to a temperature at or below a temperature where all the codon:anti-codon hybrids have been formed within the same coding region. Subsequently or simultaneously with the temperature regime selected, a connection between the functional entities and the other functional entities or nascent templated molecules is performed. At each step of the step-wise decrease of the temperature, a new building block is annealed to the template and a subsequent connection is performed. This design allows for the simultaneous addition of all the building blocks to the plurality of templates and, thus, omitting the step-wise addition of building blocks.

It is within the capability of the skilled person in the art to construct the desired design. When a specific annealing temperature is desired it is a standard procedure to suggest appropriate compositions of nucleic acid monomers and the length thereof. The construction of an appropriate design may be assisted by software, such as Vector NTI Suite or the public database at the internet address http://www.nwfsc-.noaa.gov/protocols/oligoTMcalc.html.

The functional entity of the building block serves the function of being a precursor for the structural entity eventually incorporated into the templated molecule.

The functional entity is designed to be capable of being connected to a functional entity of another building block or a nascent templated molecule. The connection is aided by one or more reactive groups of the functional entity. The number of reactive groups which appear on the functional entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. Two or more reactive groups intended for the formation of connections, are typically present on scaffolds. A scaffold is a core structure, which forms the basis for the creation of multiple variants. The variant forms of the scaffold is typically formed through reaction of reactive groups of the scaffold with reactive groups of other building blocks, optionally mediated by fill-in groups or catalysts, under the creation of a connection between the entities. The functional entities to be connected to the scaffold may contain one, two or several reactive groups able to form connections.

Some of the linkers are durable during the entire synthesis to ensure the connection between the scaffolded molecule and the template. It is essential for the invention that at least one linker is maintained in order to ensure the coupling of the templated molecule to the template which directed the synthesis thereof. In a final state of the production of the templated molecule the at least one linker emanating from a building block may be substituted by another entity securing the adherence of the template molecule to the template. The durable linkers are preferably cleavable at a final stage to separate the templated molecule from the template or a complementary template. Therefore, the durable linkers may be referred to as selectively cleavable linkers. Preferably, some of the linkers of the building blocks are also cleavable during the synthesis of the templated molecule, i.e. the functional entity may be released from the building block to allow the synthesis of the templated molecule.

The linker may be attached to the anti-codon at a central area thereof or at one of the ends. In one aspect of the invention, the anti-codon and the linker is a contiguous oligonucleotide, i.e. a part of the nucleotide complements a sequence of the template and another part is non-complementing avoiding the hybridisation of the oligonucleotide part to the template. This design of the building blocks is a convenient way of design as no separate reaction step is required for the attachment of the linker to the anti-codon. In another aspect of the invention the linker is attached to a central part of the anti-codon to allow for the ligation of neighbouring anti-codons using suitable enzymes to produce a complementary template.

The linker can be attached to the functional entity according to the functionalities desired. In one aspect, the linker is attached to the functional entity through a reactive group capable of forming a connection to another functional entity or a nascent templated molecule. Examples of suitable reactive groups are imine groups (—NH—) and disulfide groups (—S—S—). The bonding of the functional entity to the linker can be cleaved simultaneously with the reaction of the inter-spacing reactive group or the cleavage can be performed in a separate step. In the following, linkers connected to a functional entity through a reactive group which is cleaved simultaneously with the formation of the connection, are referred to as translocating linkers. Translocating linkers allow for the production of templated polymers, which are connected to the template that directed the synthesis thereof via the terminal building block, when a reactive group on a functional entity in the vicinity reacts to form a connection. The separate formation of the connection between a functional entity and another functional entity or evolving templated molecule and the cleavage of the linker is an advantage because more than one connection may be formed prior to the cleavage.

A subset of the building blocks is contacted with the plurality of templates in the initial phase of the production of the library. The subset of the total amount of building blocks is selected to have anti-codons which complement unique codons of a specific coding region on the template. It may be of advantage to have the building blocks in the vicinity of the reactive group of the template. In the event, the reactive group of the template is a part of a building block, it is preferred that the building blocks to be linked together is attached in the vicinity of each other to ensure a sufficient proximity of the functional entities. Preferably, the subset comprises building blocks having anti-codons which form hybrids with unique codons in two neighbouring coding regions. The subset may be provided by adding the building blocks separately, or alternatively, by adding all the building blocks or a major portion thereof and then direct the annealing of the individual building blocks by proper design of the codon:anti-codon hybrids, as depicted above.

The conditions which allow specific hybridisation of the unique codons and the anti-codons are influenced by a number of factors including temperature, salt concentration, type of puffer, and acidity. It is within the capabilities of the person skilled in the art to select appropriate conditions to ensure that the contacting between the templates and the building blocks are performed at hybridisation conditions.

When two building blocks in the initial stage of the present method are hybridised to a template the functional entities of each of the building blocks are allowed to form a chemical connection. The connection between two functional entities usually occurs by a reaction between reactive groups present on each functional entity. It may, however, be desirable to make the bridging between two reactive groups on separate functional entities through a suitable fill-in group. The latter situation may occur, for example, when two similar reactive groups, such as a two amine groups, are not able to react with each other directly. The two amine groups may, however, be connected to each other through a di-carboxylic acid, such as oxalic acid, to create amide bondings.

Following the successful connection of two entities for the formation of the nascent templated compound, one of the linkers connected thereto may be cleaved. However, this step is optional. It is possible to continue with the incorporation of further building blocks without this cleaving step. In one aspect of the invention, the connection of the functional entities and the cleavage of one of the linkers occur simultaneously. This aspect of the invention is of particular relevance when the reactive group able to react with another reactive group of a functional entity in the vicinity thereof, is the bridging group to the linker.

The propagation part of the method is initiated by contacting the plurality of different templates harbouring the nascent templated compound with a further subset of the plurality of building blocks, said subset having anti-codons complementary to the unique codons of a coding region in the vicinity of the coding region(s) harbouring the nascent templated molecules. To increase the proximity, it can be suitable to hybridise the further building blocks to a coding region neighbouring the building block(s) harbouring the nascent templated molecule. The subset of building blocks may be provided by adding building blocks separately which hybridise to a specific coding region. Alternatively, different stringency conditions combined with appropriate design of the individual codon:anti-codon hybrids can be selected to allow the predominate annealing of a subset of building blocks to selected codon regions. The alternative way of forming a subset has the advantage that all or at least a major part of the building blocks can be added to the reaction vessel. An example of directing the annealing is to design the first two coding regions such that they have a relatively high annealing temperature, whereas the subsequent building blocks to be annealed have a gradually decreasing annealing temperature.

When the further building block is hybridised to a template also harbouring the evolving templated molecule, the functional entity of the further building block is allowed to form a chemical connection to the nascent templated molecule. The formation of the chemical connection normally proceeds by reaction between reactive groups present on the functional entity and the nascent templated molecule, respectively. It may, however, be desirable to make the bridging between two reactive groups through a suitable spacer group. The latter situation may for example occur when two similar reactive groups, such as a two amine groups, are not able to react with each other directly. The two amine groups may, however, be connected to each other through a di-carboxylic acid, such as oxalic acid, to create amide bondings.

After the connection between the nascent templated molecule and the further functional entity one or more of the linkers may optionally be cleaved, however ensuring that at least one linker is durable. The propagation part of the method may be repeated a desired number of times to evolve the templated molecule. Each repetition of the propagation is initiated by contacting the templated with a new subset of further building blocks.

After the propagation stage follows the termination stage. Depending on the degree of cleavage during the propagation, the attachment of the templated molecule or the complementary template, is different. At one extreme none of the linkers are cleaved during the synthesis, which is when the optional cleavage of linkers of step g) is not performed. This may lead to a templated molecule attached to a number of linker similar to the number of building blocks involved in the synthesis. At the other extreme, the complexes obtained in step i) comprise templated molecules attached to the template which templated the syntheses thereof via the linker of a single building block. The number of linkers may be anywhere between these two extremes in the templated molecule. In some applications it is of advantage to have more than one linker, e.g. when the conformation of the templated molecule can be stabilized or even altered. In general, it is sufficient for the templated molecule to be attached to the template through a single linker to allow the subsequent enrichment process to proceed efficiently.

The attachment via a building block involves the use of hydrogen bondings between the codon and the anti-codon to ensure the coupling of the template and the templated molecule. As is well-known within the art, hydrogen bondings are weak bondings that may easily be disrupted. Therefore, in an aspect of the invention, the building block finally harbouring the templated molecule, may be attached to the template through a codon:anti-codon hybrid having a higher annealing temperature than the other codon:anti-codon hybrids of the template. Alternatively, and in some applications preferably, the templated molecule is connected with the template which directed the syntheses thereof via a covalent link. The covalent link may be in addition to the hydrogen bondings or the covalent link may be a substitution. The presence of a covalent link allows for a more harsh chemical treatment of the complex. In one aspect of the invention, the covalent link is selectively cleavable to provide for a separation of the templated molecule from the complementary template.

The method according to the present invention may involve the further step of cleaving all but one linker after the formation of the templated molecule. This further step implies that some or all of the linkers in step g) are not cleaved during the synthesis of the templated molecule.

The method according to the invention may, as a further step, involve the transfer of the templated molecule to an anchorage point on the template, or a sequence complementing the template, to establish an effective chemical connection between the template and the templated molecule. An effective coupling of the templated molecule to the template or a sequence complementary to the template can be desirable to allow for denaturing enrichment conditions or denaturing post-templating modification of the manufactured molecule. The anchorage may involve the presence of a reactive group on the templated molecule and a reaction partner on the template, whereby the reaction between these reactive groups will establish a covalent link. Alternatively, the anchorage point may be present on a complementary sequence hybridised to the template. In a preferred embodiment the complementing sequence has a higher annealing temperature than one or more of the building blocks, notably the terminal building block, to enable usage of a higher stringency during enrichment and , optionally, clearance of used building blocks.

The anti-codons can, after the cleavage of the linker, remain hybridised to the unique codons or can be detached from the template. When it is chosen to detach the anti-codons, they are preferably cleared from the solution to avoid any re-hybridisation or interference with nucleic acids intended to participate in an hybridisation event. In an aspect of the invention, the anti-codons following the cleavage of the linker attached thereto, remain hybridised to the unique codons because the anti-codons attached to the templates can be ligated together to create a complementary template. The ligation of the anti-codons may be performed after all or the majority of building blocks have been incorporated or, in the alternative, the ligation can be performed after the incorporation of each new building block. Furthermore, in some occasions, it may be of advantage to ligate the anti-codons together prior to the cleavage of the linkers. The ligation of the all the anti-codons provide a direct covalent link between the complementing template and the templated molecule. The covalent link is preferably designed to allow the separation of the templated molecule from the complementing template. The separation of the templated molecule will in general during an enrichment process appear as one of the later steps. Therefore, it is of importance in most applications that the covalent link is selectively cleavable, i.e. cleavable under certain chemical conditions not used in the prior steps of enrichment. In one aspect of the invention the templated molecule is released by the use of enzymes. As an example, restriction nucleases may be used by the incorporation of a restriction site close to the templated molecule. Another example is to use a phosphodiesterase to perform a total or partly digest of the template or complementing template.

The use of ligation also have another advantage, because it is possible to use anti-codons having a shorter sequence of nucleotides. An example of a typically anti-codon will have 15 to 25 nucleotides in sequence to obtain an appropriate annealing temperature of around 40 to 70° C. By ligating building blocks in the vicinity of each other using a ligase or a chemical crosslink, it becomes possible to incorporate very small anti-codons (e.g. 4-10 nucleotides) with high specificity and efficiency. The ligation of a small anti-codon to another anti-codon or a complementing template increases the total annealing temperature. A result of using smaller anti-codons is that, the local concentration of functional entities is increased, and therefore, the efficiency of the reaction between the reactive groups becomes more efficient.

Another way to increase the proximity further is to provide building blocks intended to interact with each other, with a reversible interacting molecule pair. The molecule pair allows a building block to form a reversible coupling to another building block in the vicinity thereof through the interaction of the two parts of the pair situated on each building block. Preferably, the molecule pair is also termed a dimerisation domain and is located in the functional entity or is a portion of the linker that is close to the functional entity. The dimerisation domains of two building blocks intended to react with each other are designed to have an affinity to each other. Examples of dimerisation domains include leucine-rich areas, coiled-coil structures, antibody-antigen pairs, complementing sequences of nucleotides, ect. The affinity of the dimerisation of two building blocks are preferably lower than the affinity between the codon and the anti-codon to allow for shifting dimerisation partners though performing temperature cycles. When the dimerisation domains of two building blocks intended to interact are sequences of nucleotides, the length of the sequences may be chosen to obtain an annealing temperature below room temperature but preferably above 5° C., e.g. between 10° C. and 20° C. When the dimerisation domain includes two complementing oligonucleotides, the domain is also referred to as a "zipper box".

A suitable temperature scheme for the propagation step of the present invention is to add a building block to the template at a temperature above the annealing temperature for said building block. Then the temperature is lowered below the annealing temperature to allow the new building block as well as the building block harbouring the nascent templated molecule to find and bind to their respective parts of the template. Excess building blocks and debris are then preferably washed away. Then the temperature is decreased below the annealing temperature of the dimerisation domain and consequently the probability that the functional entities are connected is increased. Potentially, the conditions in the reaction vessel, other than the temperature, may be changed to provide for the connection. Following the connection between the functional entities/templated molecules, the temperature is raised and the temperature scheme is repeated.

Another method of increasing the proximity further is to apply a "rigid" linker attached to the anti-codon with molecular hinges. A result of using a rigid linker is that a smaller three dimensional space is sampled by the functional entity. Thereby the probability is increased that two functional entities in the vicinity of each other and attached to a rigid linker will be close enough to each other for a reaction to proceed. A rigid linker may be prepared by various methods available to the skilled person in the art. An example is to use a double stranded oligonucleotide. In a preferred embodiment, the anti-codon and the linker is performed of a contiguous oligonucleotide, wherein the anti-codon domain of the oligonucleotide is able to hybridise to a unique codon of a template and a stiffer domain is able to hybridise to a further oligonucleotide complementary thereto. The hinges may be provided by any group allowing essentially unhindered rotation about at least one bonding. A hinge may be provided in the above preferred embodiment by separation of the anti-codon domain and the stiffer domain with at least one nucleotide. In other words, a hinge may be provided by a single stranded region positioned between the double stranded unique codon:anti-codon hybrid and the double stranded rigid linker.

In one aspect of the invention, the template is covalently connected to the complementing template. The connection may be performed by covalently bonding the two hybridised strings to each other. In the alternatively, the template may at one end be designed with a hair pin loop to enable the ligation of the template end to an anti-codon. According to this aspect, the templated molecule will be linked to a double stranded template. The double stranded template may be an advantage because it is more stable allowing more versatile chemical reactions.

In one aspect of the invention a library of complexes is obtainable from the above methods.

The library may be used for a variety of applications, including the search for compounds for use in therapeutic or diagnostic methods and plant protection compounds, like pesticides, fungicides ect. The library may comprise any number of complexes according to the invention. At one extreme, the library consists of only two complexes. At the other extreme, the library can consist of up to $10^{18}$ complexes. Usually, the number of complexes is to be selected between these to extremes.

One method to identify the most active compounds which can be used in e.g. therapeutic applications is to subject the library to an enrichment treatment. According to one aspect of the invention an enrichment of a library of complexes comprising templated molecules with respect to a predetermined activity, comprises the steps of:

i) establishing a first library of complexes comprising templated molecules, said library being obtainable according to any of the methods of the invention,
ii) exposing the library to conditions enriching the library with complexes having the predetermined activity,
iii) amplifying the complexes of the enriched library,
iv) optionally, repeating step ii) to iii), and
v) obtaining an enriched library having a higher ratio of complexes comprising templated molecules with the predetermined activity.

The amplification is normally preferred, though not always necessary. Especially, when several cycles of enrichments are conducted it is of advantage to make an amplification to obtain sufficient complexes. In a preferred aspect of the invention, the amplification of the complexes of the enriched library comprises the steps of contacting the library of complexes with amplification means, amplifying the templates or the complementing templates, and conducting the method according to the invention using the amplification product as templates. The amplification means can be any of the nucleic acid amplification means suitable for the amplification of the template, such as PCR. Preferably, the amplification of the complex comprises a $10^1$ to $10^{15}$-fold amplification.

To allow for multiple enrichment cycles the steps ii) and iii) are repeated at least 2, 3, 5 times, such as at least 10 times, such as at least 15 times. The complexes may be identified after the completion of each cycle or may be only be identified after the last cycle. There is no explicit need for intermediate identifications as the amplification can be performed without knowing the sequence of the template or a sequence complementing the template, if the template or the complement thereof is provided with suitable primer regions. The identification after the enrichment process involves the determination of the sequence of the template and/or the structural determination of the templated molecule and/or the entire complex having the predetermined activity.

Preferably, the conditions enriching the library comprise contacting a binding partner to the templated molecules of interest. The binding partner may be in solution or may be directly or indirectly immobilised on a support. The enrichment is in general performed using an affinity or activity assay. In one aspect of the invention, the enrichment is conducted by screening for complexes having an affinity for—or an effect on—a target molecule or a target entity. In another aspect the enrichment is conducted by selection for catalytic activity. Alternatively, the conditions enriching the library involves any one or more of electrophoretic separation, gelfiltration, immunoprecipitation, isoelectric focusing, centrifugation, and immobilization.

The enrichment process can involve cells. Thus, in one embodiment, the conditions enriching the library comprises providing cells capable of internalising the templated molecule, or performing an interaction with the templated molecule having the desired predetermined activity.

When the library of complexes have been enriched to a small pool comprising complexes displaying a predetermined activity, it is desirable to obtain each of the complexes separately. Thus, the invention also entails to a method for the manufacture of a complex of a templated molecule attached to the template which directed the synthesis thereof, said method comprises the steps of a) providing a template comprising a number of coding regions and a reactive group, wherein each coding region specifies a unique codon,
b) providing a plurality of different building blocks, each building block comprising an anti-codon, a functional entity and a linker connecting the anti-codon and the functional entity, wherein the anti-codon of each building block complements a unique codon of the template, and the functional entity comprises at least one reactive group,
c) contacting the template with a building block having an anti-codon which complements the unique codon of a specific coding region, said contacting being performed under conditions which allow specific hybridisation of the anti-codon to the unique codon of the templates,
d) reacting the reactive group of the template and the reactive group of the building block to obtaining a chemical connection,
e) contacting under conditions allowing specific hybridisation, the template harbouring the nascent templated molecule with a further building block having an anti-codon complementary to the unique codon of a coding region in the vicinity of the coding region harbouring the nascent templated molecule,
f) allowing the functional entity of the further building block to form a chemical connection to the nascent templated molecule,
g) optionally, cleaving one or more of the linkers, provided that at least one linker remains to connect the nascent templated molecule with the template which directed the synthesis thereof,
h) optionally repeating steps e) through g),
i) obtaining a templated molecule attached via the linker of one or more building blocks to the template which directed the synthesis thereof.

The templated molecule can be obtained from the complex by cleaving the linker(s) of the one or more building blocks to release the templated molecule from the template.

DETAILED DISCLOSURE OF THE INVENTION

Codon

The codons occurring in nature consist of a sequence of three nucleic acid monomers. The length of the codon sequence may be of the same order in accordance with the present invention but is preferably longer to obtain a suitable annealing temperature. Preferably the sequence is selected to produce an annealing temperature above normal room temperature. Herein the terms annealing temperature and melting temperature may be used interchangeably said temperature being defined as the maximum of the first derivative of the absorbance vs. temperature curve. The different codons need no to be of the same lengths, that is to comprise the same number of nucleic acid monomers. However, a typically number of nucleic acid monomers in the codon sequence is normally above 6 but below 25.

Each nucleic acid monomer is normally composed of three parts, namely a nucleobase moiety, a sugar moiety and a internucleoside linker.

The nucleobase moiety may be selected among naturally occurring nucleobases as well as non-naturally occurring nucleobases. It should be clear to the person skilled in the art that various nucleobases which previously have been considered "nonnaturally occurring" have subsequently been found in nature. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$, $N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat No. 5,432,272. The term "nucleobase" is intended to cover every and all of these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

The sugar moiety is suitably a pentose but may be the appropriate part of an PNA. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine.

Each codon is complemented by an anti-codon. The anticodon has the ability specifically to engage with the codon which it complements. The affinity between the codon and the complementing anti-codon is affected through hydrogen bondings following the well-known Watson-Crick base pairing system. Thus, the anti-codon may be composed of the same kind of nucleic acid monomers as the codon itself.

Linkers

Linkers connecting the anti-codon and functional entity of building blocks may be selected from a variety of possibilities. Linkers may include one or more reactive groups in order to obtain a selectively cleavable linker, a cleavable linker, and a translocating linkers. Suitable linkers may be selected from but are not limited to, the group comprising: carbohydrates and substituted carbohydrates; vinyl, polyvinyl and substituted polyvinyl; acetylene, polyacetylene; aryl/hetaryl, polyaryl/hetaryl and substituted polyaryl/polyhetaryl; ethers, polyethers such as e.g. polyethylenglycol and substituted polyethers; amines, polyamines and substituted polyamines; double stranded, single stranded or partially double stranded natural and unnatural polynucleotides and substituted double stranded, single stranded or partially double stranded natural and unnatural polynucleotides; and polyamides and natural and unnatural polypeptides and substituted polyamides and natural and unnatural polypeptides.

Functional Groups

The functional entity may comprise one or more functional groups, i.e. groups which eventually form part of the templated molecule. The templated molecule may comprise one or more of the following functional groups either alone or in combination:

1. Hydroxyls
2. Primary, secondary, tertiary amines
3. Carboxylic acids
4. Phosphates, phosphonates
5. Sulfonates, sulfonamides
6. Amides
7. Carbamates
8. Carbonates
9. Ureas
10. Alkanes, Alkenes, Alkynes
11. Anhydrides
12. Ketones
13. Aldehydes
14. Nitatrates, nitrites
15. Imines
16. Phenyl and other aromatic groups
17. Pyridines, pyrimidines, purines, indole, imidazole, and heterocyclic bases
18. Heterocycles
19. polycycles
20. Flavins
21. Halides
22. Metals
23. Chelates
24. Mechanism based inhibitors
25. Small molecule catalysts
26. Dextrins, saccharides
27. Fluorescein, Rhodamine and other fluorophores
28. Polyketides, peptides, various polymers
29. Enzymes and ribozymes and other biological catalysts
30. Functional groups for post-polymerization/post activation coupling of functional groups
31. Drugs, e.g., taxol moiety, acyclovir moiety, "natural products"
32. Supramolecular structures, e.g. nanoclusters
33. Lipids
34. Oligonucleotides, oligonucleotide analogs (e.g., PNA, LNA, morpholinos)
35. Hydrogen Reactive Groups Reactive groups relates among other things to groups which form part of the functional entity and are capable of participating in a reaction that form a connection between two functional entities, either directly or via a suitable bridging molecular entity. Examples of reactive groups are listed below:

1. N-carboxyanhydrides (NCA)
2. N-thiocarboxyanhydrides (NTA)
3. Amines
4. Carboxylic acids
5. Ketones
6. Aldehydes
7. Hydroxyls
8. Thiols
9. Esters
10. Thioesters
11. conjugated system of double bonds
12. Alkyl halides
13. Hydrazines
14. N-hydroxysuccinimide esters
15. Epoxides
16. Haloacetyls
17. UDP-activated saccharides
18. Sulfides 19. Cyanates
20. Carbonylimidazole
21. Thiazinanones
22. Phosphines
23. Hydroxylamines
24. Sulfonates
25. Activated nucleotides
26. Vinylchloride
27. Alkenes, quinones Templated Molecules According to the present invention, virtually any molecule may be templated using the general method disclosed herein. Examples of compounds which it is anticipated can be synthesised includes, but are not limited to, the compounds listed below:

alpha-, beta-, gamma-, and omega-peptides Mono-, di- and tri-substituted peptides; L- and D-form peptides; Cyclohexane- and cyclopentane-backbone modified beta-peptides; Vinylogous polypeptides; glycopolypeptides; polyamides; vinylogous sulfonamide peptide; polysulfonamide; conjugated peptide (i.e., having prosthetic groups); polyesters; polysaccharides; polycarbamates; polycarbonates; polyureas; poly-peptidylphosphonates; azatides; peptoids (oligo N-substituted glycines); polyethers; ethoxyformacetal oligomers; polythioethers; polyethylene glycols (PEG); polyethylenes; polydisulfides; polyarylene sulfides; polynucleotides; PNAs; LNAs; morpholinos; oligo pyrrolinone; polyoximes; polyimines; polyethyleneimine; polyacetates; polystyrenes; polyacetylene; polyvinyl; lipids; phospholipids; glycolipids; polycycles (aliphatic); polycycles (aromatic); polyheterocycles; proteoglycan; polysiloxanes; polyisocyanides; polyisocyanates; polymethacrylates; monofunctional, Difunctional, Trifunctional and Oligofunctional open-chain hydrocarbons; monofunctional, difunctional, trifunctional and oligofunctional nonaromatic carbocycles; monocyclic, bicyclic, tricyclic and polycyclic hydrocarbons; bridged polycyclic hydrocarbons; monofunctional, difunctional, trifunctional, and oligofunctional nonaromatic heterocycles; monocyclic, bicyclic, tricyclic, and polycyclic heterocycles, bridged polycyclic heterocycles; monofunctional, difunctional, trifunctional and oligofunctional aromatic carbocycles; monocyclic, bicyclic, tricyclic, and polycyclic aromatic carbocycles; monofunctional, difunctional, trifunctional and oligofunctional aromatic heterocycles; monocyclic, bicyclic, tricyclic and polycyclic heterocycles; chelates; fullerenes; steroids; cyclosporin analogs; as well as any combination of the above molecular moieties.

Use of Library

Selection or screening, commonly referred to as enrichment, of the library of complexes comprising templated molecules with respect to desired activities (for example binding to particular target, catalytic activity, or a particular effect in an activity assay) may be performed according to any standard protocol. For example, affinity selections may be performed according to the principles used for phage displayed, polysome-displayed or mRNA-protein fusion displayed peptides. Selection for catalytic activity may be performed by affinity selections on transition-state analogue affinity columns (Baca et al., Proc. Natl. Acad. Sci USA. 1997; 94(19):10063-8), or by function-based selection schemes (Pedersen et al., Proc. Natl. Acad. Sci. USA. 1998, 95(18):10523-8). Screening for a desired characteristic may be performed according to standard microtiter plate-based assays, or by FACS-sorting assays.

Generally, affinity selections involve the immobilisation of a target or a binding partner on a solid support, such as a column. Subsequently, the complex manufactured according to the invention is added to the column under conditions allowing a part of the complexes to bind to the target. The complexes not bound to the target is eluted out of the column and discharged. The part of the complexes attached to the target may be amplified using the template or complementing template associated with the templated molecule.

The choice of amplification method depends on the choice of codons and anti-codons. Natural oligonucleotides can be amplified by any state of the art method. These methods include, but is not limited to the polymerase chain reaction (PCR); as wells as e.g. nucleic acid sequence-based amplification (e.g. Compton, Nature 350, 91-92 (1991)), amplified anti-sense RNA (e.g. van Gelder et al., PNAS 85: 77652-77656 (1988)); self-sustained sequence replication system (e.g. Gnatelli et al., PNAS 87: 1874-1878 (1990)); polymerase independent amplification as described in e.g. Schmidt et al., NAR 25: 4797-4802 (1997), as well as in vivo amplification of plasmids carrying cloned DNA fragments. Ligase-mediated amplification methods may also be used, e.g., LCR (Ligase Chain Reaction).

For non-natural nucleotides the choices of efficient amplification procedures are fewer. As non-natural nucleotides per definition can be incorporated by certain enzymes including polymerases, it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al., NAR 25: 4797-4802 (1997)). For backbone-modified oligonucleotide analogs such as PNA and LNA, this amplification method may be used. Before or during amplification the templates or complementing templates may be mutagenized or recombined in order to create a larger diversity for the next round of selection or screening.

Following the amplification of the template part or complementing template part of the complex, the method according to the invention is conducted using the amplification product as the templates. The result is a reduced or enriched library of complexes of a template attached to a template molecule.

The selection and amplification steps may be repeated if considered necessary to further enrich the library. When the selection and amplification steps are repeated, the binding step involving the target and the complexes, is preferably performed under more strict conditions ensuring that only a part of the complexes adhere to the target.

The enrichment cycles may be performed 2 to 15 times or even more with enrichment in each cycle of 10 to 1000 times. In one approach, the starting library amounts to $10^{14}$ complexes. After seven cycles of enrichments with a 100 fold concentration in each cycle, the complex with the highest affinity to the target should, theoretically, be obtained. However, it is more likely that the final cycles deliver a small pool of interesting complexes, which have to be examined by other means.

After the final round of selection, it is often desirable to sequence individual templates, in order to determine the composition of individual templated molecules. If the template contains natural nucleotides, it is a standard routine to optionally PCR amplify the isolated templates (if the template is an RNA molecule, it is necessary to use reverse transcriptase to produce cDNA prior to the PCR-amplification), and then clone the DNA fragments into for example plasmids, transform these and then sequence individual plasmid-clones containing one or multiple tandem DNA sequences. In this case, it is practical to design a restriction site in both of the flanking sequences to the central random or partly random sequence of the template (i.e., in the primer binding sites). This will allow easy cloning of the isolated nucleotides. Sequencing can be done by the standard dideoxy chain termination method, or by more classical means such as Maxam-Gilbert sequencing.

If the template contains non-natural nucleotides, it may not be feasible to clone individual sequences by transfer through a microbial host. However, using bead populations where each bead carries one oligonucleotide sequence, it is possible to clone in vitro, where after all the nucleotides attached to a specific bead may be optionally amplified and then sequenced (Brenner et al., 2000, Proc. Natl. Acad. Sci. USA 97, 1665-1670). Alternatively, one may dilute the population of isolates adequately, and then aliquot into microtiter plates so that the wells on average contain for example 0.1 templates. By amplifying the single templates by for example PCR, it will now be possible to sequence using standard methods. Of course, this requires that the non-natural nucleotides are substrates for the thermostable polymerase used in the PCR.

If alternative methods are used that require shorter oligonucleotides it may be desirable to design the starting template so as to contain restriction sites on either side of the encoding/templating region of the template. Thereby, after the final selection round, the templates can be restricted, to obtain a short oligonucleotide encoding the templated polymer, and then these short oligonucleotides can be applied to various analytical procedures.

It is also possible to sequence the isolates by the use of a DNA array of oligonucleotides with random but predetermined sequences.

It may also be desirable to sequence the population of isolates as a pool, for example if the sequences are expected to be in register, for example because the initial library consisted of a degenerate sequence based on a polymer sequence with a known (relatively high) desired activity. Therefore, it is then expected that all the isolates have sequences similar to the initial sequence of the templates before selection. Thus, the population of isolates can be sequenced as a whole, to obtain a consensus sequence for the population as a whole.

Selection of Template-displaying Molecules that Will Bind to Known Targets

The present invention is also directed to approaches that allow selection of small molecules capable of binding to different targets. The template-displaying molecule technology contains a built-in function for direct selection and amplification. The binding of the selected molecule should be selective in that they only coordinate to a specific target and thereby prevent or induce a specific biological effect. Ultimately, these binding molecules should be possible to use e.g. as therapeutic agents, or as diagnostic agents.

Template-displaying molecule libraries can easily be combined with screenings, selections, or assays to assess the effect of binding of a molecule ligand on the function of the target. In a more specific embodiment, the template-displaying method provides a rapid means for isolating and identifying molecule ligands which bind to supra-molecular, macro-supra-molecular, macro-molecular and low-molecular structures (e.g. nucleic acids and proteins, including enzymes, receptors, antibodies, and glycoproteins); signal molecules (e.g. cAMP, inositol triphosphate., peptides, prostaglandins); and surfaces (e.g. metal, plastic, composite, glass, ceramics, rubber, skin, tissue).

Specifically, selection or partitioning in this context means any process whereby the template-displaying molecule complex bound to a target molecule, the complex-target pair, can be separated from template-displaying molecules not bound to the target molecule. Selection can be accomplished by various methods known in the art.

The selection strategy can be carried out so it allows selection against almost any target. Importantly, no steps in this selection strategy need any detailed structural information of the target or the molecules in the libraries. The entire process is driven by the binding affinity involved in the specific recognition/coordination of the molecules in the library to a given target. However, in some applications, if needed, functionality can also be included analogous to selection for catalytic activity using phage display (Soumillion et al. (1994) J. Mol. Biol. 237: 415-22; Pedersen et al. (1998) PNAS. 18: 10523-10528). Example of various selection procedures are described below.

This built-in template-displaying molecule selection process is well suited for optimizations, where the selection steps are made in series starting with the selection of binding molecules and ends with the optimized binding molecule. The single procedures in each step are possible to automate using various robotic systems. This is because there is a sequential flow of events and where each event can be performed separately. In a most preferable setting, a suitable template-displaying molecule library and the target molecule are supplied to a fully automatic system which finally generates the optimized binding molecule. Even more preferably, this process should run without any need of external work outside the robotic system during the entire procedure.

The libraries of template-displayed molecules will contain molecules that could potentially coordinate to any known or unknown target. The region of binding on a target could be into a catalytic site of an enzyme, a binding pocket on a receptor (e.g. GPCR), a protein surface area involved in protein-protein interaction (especially a hot-spot region), and a specific site on DNA (e.g. the major groove). The template-displaying molecule technology will primarily identify molecules that coordinate to the target molecule. The natural function of the target could either be stimulated (agonized) or reduced (antagonized) or be unaffected by the binding of the template-displaying molecules. This will be dependent on the precise binding mode and the particular binding-site the template-displaying molecules occupy on the target. However, it is known that functional sites (e.g. protein-protein interaction or catalytic sites) on different proteins are more prone to bind molecules that other more neutral surface areas on a protein. In addition, these functional sites normally contain a smaller region that seems to be primarily responsible for the binding energy, the so called hot-spot regions (Wells, et al. (1993) Recent Prog. Hormone Res. 48; 253-262). This phenomenon will increase the possibility to directly select for small molecules that will affect the biological function of a certain target.

The template-displaying molecule technology of the invention will permit selection procedures analogous to other display methods such as phage display (Smith (1985) Science 228: 1315-1317). Phage display selection has been used successfully on peptides (Wells & Lowman. (1992) Curr. Op. Struct. Biol. 2, 597-604) proteins (Marks et al. (1992) J. Biol. Chem. 267: 16007-16010) and antibodies (Winter et al. (1994) Annu. Rev. Immunol. 12: 433-455). Similar selection procedures are also exploited for other types of display systems such as ribosome display (Mattheakis et al. (1994) Proc. Natl. Acad. Sci. 91: 9022-9026) and mRNA display (Roberts, et al. (1997) Proc. Natl.

Acad. Sci. 94: 12297-302). However, the template-displaying molecule technology of the invention, will for the first time allow direct selection of target-specific small non-peptide molecules independently of the translation process on the ribosome complex. The necessary steps included in this invention are the amplification of the templates and incorporation and reaction of the monomer building blocks. The amplification and incorporation and the incorporation and reaction are either done in the same step or in a sequential process.

The linkage between the templated molecule (displayed molecule) and DNA replication unit (coding template) allows a rapid identification of binding molecules using various selection strategies. This invention allows a broad strategy in identifying binding molecules against any known target. In addition, this technology will also allow discovery of novel unknown targets by isolating binding molecules against unknown antigens (epitopes) and use these binding molecules for identification and validation (see section "Target identification and validation").

As will be understood, selection of binding molecules from the template-displaying molecule libraries can be performed in any format to identify optimal binding molecules. A typical selection procedure against a purified target will include the following major steps: Generation of a template-displaying molecule library: Immobilization of the target molecule using a suitable immobilization approach; Adding the library to allow binding of the template-displayed molecules; Removing of the non-binding template-displayed molecules; Elution of the template-displayed molecules bound to the immobilized target; Amplification of enriched template-displaying molecules for identification by sequencing or to input for the next round of selection. The general steps are schematically shown in FIG. 53.

In a preferred embodiment, a standard selection protocol using a template-displaying molecule library is to use the bio-panning method. In this technique, the target (e.g. protein or peptide conjugate) is immobilized onto a solid support and the template-displayed molecules that potentially coordinate to the target are the ones that are selected and enriched. However, the selection procedure requires that the bound template-displayed molecules can be separated from the unbound ones, i.e. those in solution. There are many ways in which this might be accomplished as known to ordinary skilled in the art.

The first step in the affinity enrichment cycle (one round as described in FIG. 53) is when the template-displayed molecules showing low affinity for an immobilized target are washed away, leaving the strongly binding template-displayed molecules attached to the target. The enriched population, remaining bound to the target after the stringent washing, is then eluted with, e.g. acid, chaotropic salts, heat, competitive elution with the known ligand or proteolytic release of the target/template molecules. The eluted template-displayed molecules are suitable for PCR, leading to many orders of amplification, i.e. every single template-displayed molecule enriched in the first selection round participates in the further rounds of selection at a greatly increased copy number. After typically three to ten rounds of enrichment a population of molecules is obtained which is greatly enriched for the template-displayed molecules which bind most strongly to the target. This is followed quantitatively by assaying the proportion of template-displaying molecules which remain bound to the immobilized target. The variant template sequences are then individually sequenced.

Immobilisation of the target (peptide, protein, DNA or other antigen) on beads might be useful where there is doubt that the target will adsorb to the tube (e.g. unfolded targets eluted from SDS-PAGE gels). The derivatised beads can then be used to select from the template-displaying molecules, simply by sedimenting the beads in a bench centrifuge. Alternatively, the beads can be used to make an affinity column and the template-displaying libraries suspension recirculated through the column. There are many reactive matrices available for immobilizing the target molecule, including for instance attachment to —$NH_2$ groups and —SH groups. Magnetic beads are essentially a variant on the above; the target is attached to magnetic beads which are then used in the selection. Activated beads are available with attachment sites for —$NH_2$ or —COOH groups (which can be used for coupling). The target can be also be blotted onto nitrocellulose or PVDF. When using a blotting strategy, it is important to make sure the strip of blot used is blocked after immobilization of the target (e.g. with BSA or similar protein).

In another preferred embodiment, the selection or partitioning can also be performed using for example: Immunoprecipitation or indirect immunoprecipitation were the target molecule is captured together with template-displaying binding molecules; affinity column chromatography were the target is immobilized on a column and the template-displaying libraries are flowed through to capture target-binding molecules; gel-shift (agarose or polyacrylamide) were the selected template-displaying molecules migrate together with the target in the gel; FACS sorting to localize cells that coordinates template-displaying molecules; CsCl gradient centrifugation to isolate the target molecule together template-displaying binding molecules; Mass spectroscopy to identify target molecules which are labelled with template-displaying molecules; etc., without limitation. In general, any method where the template-displaying molecule/target complex can be separated from template-displaying molecules not bound to the target is useful.

TABLE 1

Examples of selection method possible to use to identify binding molecules using the template-displaying technology.

| Type of Target | Method of choice |
| --- | --- |
| Soluble receptors | Direct immobilization, Immunoprecipitation, affinity column, FACS sorting, MS. |
| Cell surface receptor | Cell-surface subtraction selection, FACS sorting, Affinity column. |
| Enzyme inhibitors | Direct immobilization, Immunoprecipitation, affinity column, FACS sorting, MS. |
| Surface epitopes | Cell-surface subtraction selection, in-vivo selection, FACS sorting, Affinity column. |

Elution of template-displayed molecules can be performed in different ways. The binding molecules can be released from the target molecule by denaturation, acid, or chaotropic salts and then transferred to another vial for amplification. Alternatively, the elution can be more specific to reduce the background. Elution can be accomplished using proteolysis to cleave a linker between the target and the immobilizing surface or between the displaying molecule and the template. Also, elution can be accomplished by competition with a known ligand. Alternatively, the PCR reaction can be performed directly in the washed wells at the end of the selection reaction.

A possible feature of the invention is the fact that the binding molecules need not be elutable from the target to be selectable since only the encoding template DNA is needed for further amplification or cloning, not the binding molecule itself. It is known that some selection procedure can bind the most avid ligands so tightly as to be very difficult to elute. However the method of the invention can successfully be practiced to yield avid ligands, even covalent binding ligands.

Alternative selection protocol includes a known ligand as fragment of each displayed molecule in the library. That known ligand will guide the selection by coordinate to a defined part on the target molecule and focus the selection to molecules that binds to the same region. This could be especially useful for increasing the affinity for a ligand with a desired biological function but with a too low potency.

A further aspect of the present invention relates to methods of increasing the diversity or complexity of a single or a mixture of selected binding molecules. After the initial selection, the enriched molecules can be altered to further increase the chemical diversity or complexity of the displayed molecules. This can be performed using various methods known to the art. For example, using synthesized randomized oligonucleotides, spiked oligonucleotides or random mutagenesis. The randomization can be focused to allow preferable codons or localized to a predetermined portion or sub-sequence of the template nucleotide sequence. Other preferable method is to recombine templates coding for the binding molecules in a similar manner as DNA shuffling is used on homologous genes for proteins (Stemmer (1994) Nature 370:389-91). This approach can be used to recombine initial libraries or more preferably to recombine enriched encoding templates.

In another embodiment of the invention when binding molecules against specific antigens that is only possible to express on a cell surface, e.g. ion channels or transmembrane receptors, is required, the cells particle themselves can be used as the selection agent. In this sort of approach, cells lacking the specific target should be used to do one or more rounds of negative selection or be present in large excess in the selection process. Here, irrelevant template-displayed molecules are removed. For example, for a positive selection against a receptor expressed on whole cells, the negative selection would be against the untransformed cells. This approach is also called subtraction selection and has successfully been used for phage display on antibody libraries (Hoogenboom et al. (1998) Immunotech. 4: 1-20).

A specific example of a selection procedure can involve selection against cell surface receptors that become internalized from the membrane so that the receptor together with the selected binding molecule can make its way into the cell cytoplasm or cell nucleus. Depending on the dissociation rate constant for specific selected binding molecules, these molecules largely reside after uptake in either the cytoplasm or the nucleus.

The skilled person in the art will acknowledge that the selection process can be performed in any setup where the target is used as the bait onto which the template-displaying molecules can coordinate.

The selection methods of the present invention can be combined with secondary selection or screening to identify molecule ligands capable of modifying target molecule function upon binding. Thus, the methods described herein can be employed to isolate or produce binding molecules which bind to and modify the function of any protein or nucleic acid. It is contemplated that the method of the present invention can be employed to identify, isolate or produce binding molecules which will affect catalytic activity of target enzymes, i.e., inhibit catalysis or modifying substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

A still further aspect of the present invention relates to methods allowing functionality in the selection process can also be included. For example, when enrichment against a certain target have been performed generation a number of different hits, these hits can then directly be tested for functionality (e.g. cell signalling). This can for example be performed using fluorescence-activated cell sorting (FACS).

The altered phenotype may be detected in a wide variety of ways. Generally, the changed phenotype is detected using, for example: microscopic analysis of cell morphology; standard cell viability assays, including both increased cell death and increased cell viability; standard labelling assays such as fluorometric indicator assays for the presence of level of particular cell or molecule, including FACS or other dye staining techniques; biochemical detection of the expression of target compounds after killing the cells; etc. In some cases, specific signalling pathways can be probed using various reporter gene constructs.

Secondary selection methods that can be combined with template-displaying molecule technology include among others selections or screens for enzyme inhibition, alteration or substrate binding, loss of functionality, disruption of structure, etc. Those of ordinary skill in the art are able to select among various alternatives of selection or screening methods that are compatible with the methods described herein.

The binding molecules of the invention can be selected for other properties in addition to binding, For example, during selection; stability to certain conditions of the desired working environment of the end product can be included as a selection criterion. If binding molecules which are stable in the presence of a certain protease is desired, that protease can be part of the buffer medium used during selection. Similarly, the selection can also be performed in serum or cell extracts or any type of media. As will be understood, when utilizing this template-displaying approach, conditions which disrupt or degrade the template should be avoided to allow amplification. Other desired properties can be incorporated, directly into the displaying molecules as will be understood by those skilled in the art. For example, membrane affinity can be included as a property by employing building blocks with high hydrophobicity.

Molecules selected by the template-displaying molecule technology can be produced by various synthetic methods. Chemical synthesis can be accomplished since the structure of selected binding molecules is readily obtained form the nucleic acid sequence of the coding template. Chemical synthesis of the selected molecules is also possible because the building blocks that compose the binding molecules are also known in addition to the chemical reactions that assemble them together.

In a preferred embodiment, the selected binding molecules is synthesized and tested in various appropriate in vitro and in vivo testing to verify the selected candidates for biological effects and potency. This may be done in a variety of ways, as will be appreciated by those in the art, and may depend on the composition of the bioactive molecule.

Target Identification and Validation

In another aspect, the present invention provides methods to identify or isolate targets that are involved in pathological processes or other biological events. In this aspect, the target molecules are again preferably proteins or nucleic acids, but can also include, among others, carbohydrates and various molecules to which specific molecule ligand binding can be achieved. In principal, the template-displaying molecule technology could be used to select for specific epitopes on antigens found on cells, tissues or in vivo. These epitopes might belong to a target that is involved in important biological events. In addition, these epitopes might also be involved in the biological function of the target.

Phage display with antibodies and peptide libraries has been used numerous times successfully in identifying new cellular antigens. (e.g. Pasqualini et al. (1996) Nature 380: 364-366; Pasqualini et al. (2000) Cancer Res. 60: 722-727; Scheffer et al. (2002) Br J Cancer 86: 954-962; Kupsch et al. (1999) Clin Cancer Res. 5: 925-931; Tseng-Law et al. (1999) Exp. Hematol. 27: 936-945; Gevorkian et al. (1998) Clin. Immunol. Immunopathol. 86: 305-309). Especially effective have been selection directly on cells suspected to express cell-specific antigens. Importantly, when selecting for cell-surface antigen, the template molecule can be maintained outside the cell. This will increase the probability that the template molecule will be intact after release for the cell surface.

In vivo selection of template-displayed molecules has tremendous potential. By selecting from libraries of template-displayed molecules in vivo it is possible to isolate molecules capable of homing specifically to normal tissues and other pathological tissues (e.g. tumours). This principle has been illustrated using phage display of peptide libraries (Pasqualini & Ruoslathi (1996) Nature 280: 364-366). This system has also been used in humans to identify peptide motifs that localized to different organs (Arap et al. (2002) Nat. Med. 2:121-127). A similar selection procedure could be used for the template-displaying libraries. The coding DNA in phage display is protected effectively by the phage particle allows selection in vivo. Accordingly, the stability of the template in vivo will be important for amplification and identification. The template can be stabilised using various nucleotide derivatives in a similar way as have been used to stabilise aptamers for in vivo applications (Nolte (1996) Nature Biotechnol. 14: 1116-1121; Pagratis et al. (1997) Nature Biotechnol. 15: 68-72). However, it is reasonable to believe that the template structure will be stabilized against degradation due to the modified bases used for encoding the displayed molecule. Other types of protection are also possible where the template molecule is shielded for the solution using various methods. This could include for example liposomes, pegylation, binding proteins or other sorts of protection. The template molecule could also be integrated into another designed structure that protects the template form external manipulation. Fort example, the linker can be design to be incorporated in vesicles to position the templates inside the vesicle and the displaying molecules on the outside. The arrangement will protect the template molecules from external manipulate and at the same time allow exposure of the displaying molecules to permit selection.

Most antibodies have a large concave binding area which requires to some degree protruding epitopes on the antigens. Also, the antibody molecule is a large macromolecule (150 KDa) which will sterically reduce the access for a number of different antigens (e.g. on a cell surface). The template-displaying technology should be able to access and recognize epitopes inaccessible to antibodies. The small binding molecules will be able to bind into active sites, grooves and other areas on an antigen. The coding template element is also smaller that an antibody which will increase the physical access of the template-binding molecule par. In addition, the diversity and complexity of the template-displaying molecule libraries will be much greater compare to peptide libraries. This will increase the possibility to find molecules that can coordinate to epitopes inaccessible to peptides due to inadequate chemistry. All together, the template-displaying molecule technology has the potential to identify novel antigens which is not possible to identify with antibodies or peptides. One of ordinary skill in the art will acknowledge that various types of cells can be used in the selection procedure. It will also be understood that the selection for new antigens can be performed using subtraction methods as described previously.

Another aspect of the present invention relates to methods to validate the identified target. The identified binding molecules can directly be used if they change the biological response of the target. This can be done either in vitro using any direct or cell-based assay or directly in vivo studying any phenotypic response. The strength of this approach is that the same molecules are used both for identification and validation of various targets. Most favourable, the binding molecules could also directly be used as therapeutic agents.

In another preferred embodiment, the template-displaying molecules are used to pull out the target molecules. This can for instance be achieved by selection against a cDNA library expressed on bacteriophage (libraries vs. libraries). By mixing a template-displaying molecule library with a cDNA library it will be possible to find binding pairs between the small molecules in the template-displaying molecule library and proteins from the cDNA library. One possibility is to mix a phage display library with a template display library and do a selection for either the phage or template library. The selected library is then plated to localized phage clones and the DNA coding for the phage and template displayed molecules can then be identified using PCR. Other types of libraries than cDNA could also be used such as nucleic acids, carbohydrates, synthetic polymer.

In another embodiment of the invention the template-displaying molecule technology can be used to account for in vivo and in vitro drug metabolism. That could include both phase I (activation) and phase II (detoxification) reactions. The major classes of reactions are oxidation, reduction, and hydrolysis. Other enzymes catalyze conjugations. These enzymes could be used as targets in a selection process to eliminate displayed molecule that are prone to coordinate to these enzymes. The templates corresponding to these displayed molecules could subsequently be used to compete or eliminate these molecules when making template-displaying molecule libraries. These obtained libraries will then be free of molecules that will have a tendency of binding to enzymes involved in phase I-II and possible be faster eliminated. For instance, a selection on each separate enzyme or any combination of cytochrome P450 enzymes, flavin monooxygenase, monoamine oxidase, esterases, amidases, hydrolases, reductases, dehydrogenases, oxidases UDP-glucuronosyltransferases, glutathione S-transferases as well as other relevant enzymes could be performed to identify these binding molecules that are prone to coordinate to these metabolic enzymes. Inhibitors are easily selected for due to their binding affinity but substrates need at least micro molar affinity to be identified.

Another interesting embodiment of this invention is the possibility to directly select for molecules that passively or actively becomes transported across epithelial plasma membrane, or other membranes. One possible selection assay is to use CaCO-2 cells, a human colon epithelial cell line, which is general, accepted as a good model for the epithelial barrier in the gastrointestinal guts. The CaCO-2 assay involves growing a human colon epithelial cell line on tissue culture well inserts, such that the resultant monolayer forms a biological barrier between apical and basolateral compartments. The template-displaying molecule libraries are placed either side of the cell monolayer and the molecules that can permeate the cell monolayer is collected and amplified. This process can be repeated until active molecules have been identified. Other cell line or setup of this assay is possible and is obvious for skill in the art.

A still further aspect of the present invention relates methods of selecting for stability of the selected molecules. This could be performed by subjecting an enriched pool of binding molecules to an environment that will possibly degrade or change the structure of the binding molecules. Various conditions could be certain proteases or a mixture of protease, cell extract, and various fluids from for example the gastrointestinal gut. Other conditions could be various salts or acid milieu or elevated temperature. Another possibility is to generate a library of known ligands and subject that library to stability tests and selection to identify stable molecules under certain conditions as describe above.

Therapeutic Applications

The potential therapeutic applications of the invention are great. For example, the template-displaying molecule technology of the invention may be used for blocking or stimulating various targets. A therapeutically relevant target is a substance that is known or suspected to be involved in a regulating process that is malfunctioning and thus leads to a disease state. Examples of such processes are receptor-ligand interaction, transcription-DNA interaction, and cell-cell interaction involving adhesion molecules, cofactor-enzyme interaction, and protein-protein interaction in intracellular signalling. Target molecule means any compound of interest for which a molecule ligand is desired. Thus, target can, for example, include a chemical compound, a mixture of chemical compounds, an array of spatially localized compounds, a biological macromolecule, such as DNA or mRNA, a bacteriophage peptide display library, a ribosome peptide display library, an extract made from biological materials such as bacteria, plants, fungi, or animal (e.g. mammalian) cells or tissue, protein, fusion protein, peptide, enzyme, receptor, receptor ligand, hormone, antigen, antibody, drug, dye, growth factor, lipid, substrate, toxin, virus, or the like etc., without limitation. Other examples of targets include, e.g. a whole cell, a whole tissue, a mixture of related or unrelated proteins, a mixture of viruses or bacterial strains or the like. etc., without limitation.

Therapeutic drug targets can be divided into different classes according to function; receptors, enzymes, hormones, transcription factors, ion channels, nuclear receptors, DNA, (Drews, J. (2000) Science 287:1960-1964). Among those, receptors, nuclear receptors, and metabolic enzymes constitute overwhelmingly the majority of known targets for existing drugs. Especially, G Protein-Coupled Receptors (GPCR) constitutes one of the most important classes of drug targets together with proteases for pharmacological intervention. Although the above examples are focused on the most relevant targets, it will be self-evident for a person skilled in the art that any other therapeutic target may be of interest.

The present invention employing the template-displaying molecule technology can be utilized to identify agonists or antagonists for all these classes of drug targets, dependent on the specific properties each target holds. Most of the targets are possible to obtain in a purified form for direct selection procedures. Other targets have to be used when they are in their native environments such as imbedded cell surface receptors. In those situations the selection using the template-displaying molecule libraries can be performed using subtraction-selection described previously.

One specific application of the template-displaying molecule technology of the invention is to generate molecules that can function as antagonists, where the molecules block the interaction between a receptor and one or more ligands. Another application includes cell targeting. For example, the generated molecules recognizing specific surface proteins or receptors will be able to bind to certain cell types. Such molecules may in addition carry another therapeutic agent to increase the potency and reduce the side-effects (for example cancer treatment). Applications involving antiviral agents are also included. For example, a generated molecule, which binds strongly to epitopes on the virus particle, may be useful as an antiviral agent. Another specific application of the template-displaying molecule technology of the invention is to generate molecules that can function as agonists, where the molecules stimulate or activate a receptor to initiate a cellular signalling pathway.

BRIEF DESCRIPTION OF THE FIGURES

FIG. 3 shows an example as designs of templates for the generation of a library. In panel A, coding regions 1-6 are SEQ ID NOs:29-34, respectively. In panel B, codon 1 is SEQ ID NO:35, anti-codon 1 is SEQ ID NO:36, codon 6 is SEQ ID NO:37, and anti-codon 6 is SEQ ID NO:38.

FIG. 4 shows examples of building blocks for use in the preparation of a library of templated molecules.

FIG. 5 shows further examples of building blocks.

FIGS. 6A, 6B, 6C, 6D and 6E show examples of the preparation of building blocks.

FIG. 7 shows examples of the preparation of building blocks starting from a 5'-NH$_2$ derivatized oligonucleotide.

FIG. 8 shows a general procedure of performing one embodiment for the formation of the templated molecule.

FIG. 9 shows an example of the embodiment shown in FIG. 8 involving light induced reaction between symmetrical building blocks.

FIG. 10 shows a general procedure of performing one embodiment for the formation of the templated molecule.

FIG. 11 shows a general procedure of performing one embodiment of the invention for the formation of a mixed polymer templated molecule.

FIG. 12 shows examples of simultaneous reaction and cleavage of neighbouring of functional entities for the formation of and alpha-peptide (FIG. 12A) and a polyamine (FIG. 12C).

FIG. 13 shows examples of simultaneous reaction and cleavage of neighbouring functional entities for the formation of a peptoid, or an α- or β-peptide (FIG. 13A), and a hydrazino peptide (FIG. 13B).

FIG. 14 depicts a templated synthesis of a polymer, using non-simultaneous reaction and cleavage.

FIG. 15 depicts formation of a templated molecule due to activation of reactive groups and partly release of the templated molecule for the template by ring-opening.

FIG. 16 shows the connection of two functional entities by the fill-in of connecting moiety.

FIG. 17, example 1, discloses an exemplification of FIG. 16, in which an imine is formed by a fill-in reaction.

FIG. 18, example 2, shows an exemplification of FIG. 16, in which an amide is formed.

FIG. 19, example 3, shows an exemplification of FIG. 16, in which an urea bonding is formed.

FIG. 20, example 3.1, shows an exemplification of FIG. 16 in which functional entities 13.3.1.A and 13.3.1.B are synthesised.

Figure 1:
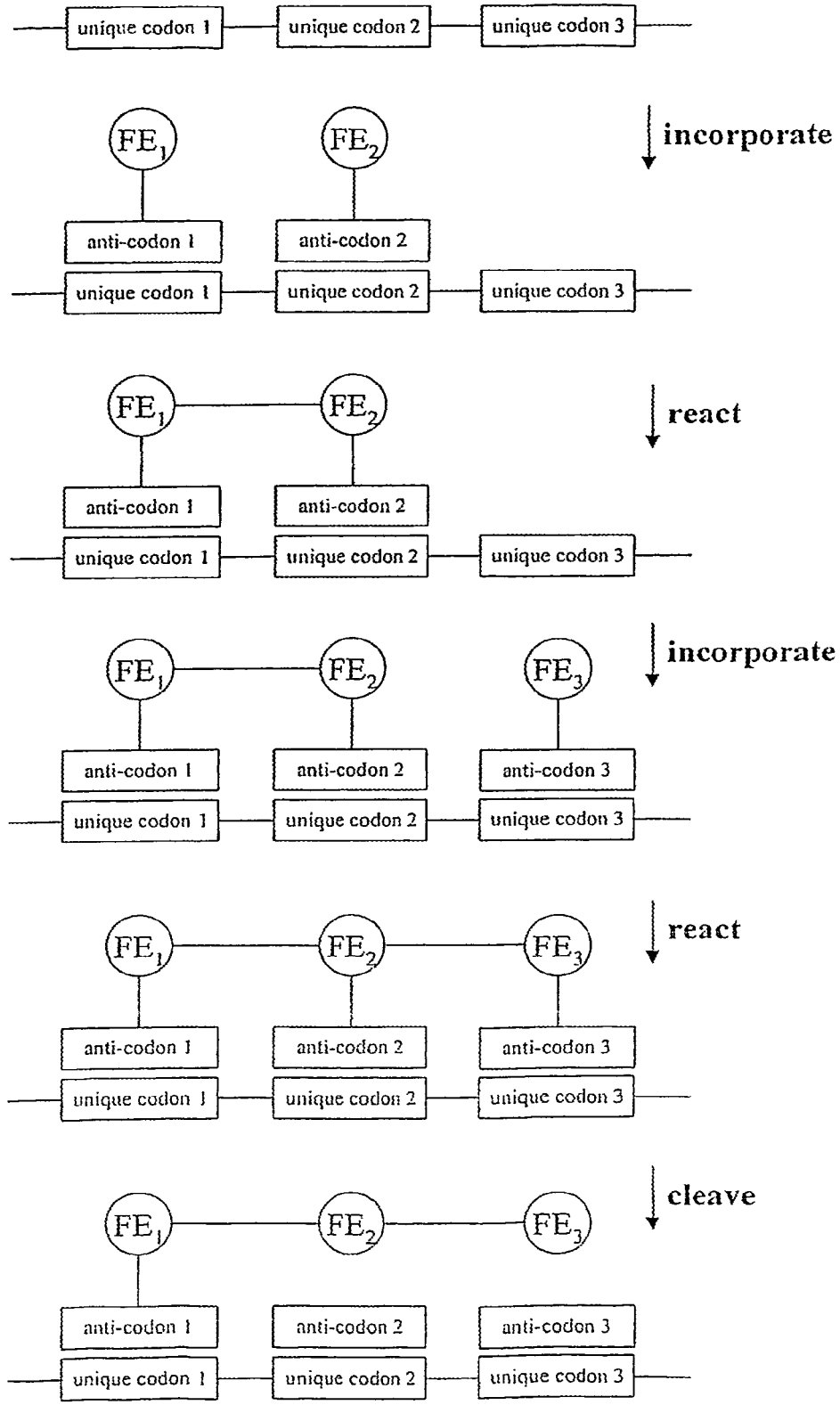
FIG. 1 shows the general principle for one embodiment of the present invention for the multi-step synthesis of templated molecules.

Synthesis of the functional entity 13.3.1A:

5-Fluoroindole (1eq) is dissolved in ethanol and treated with pent-4-enoic acid [2-(4-oxo-piperidin-1-yl)-ethyl]-amide (1.2 eq) and 2N KOH. The mixture is stirred o/n at reflux. The crude is evaporated and purified by silica gel filtration. The purified materiel is treated with methyl 3-bromobutanoate (1.2 eq) and NaH (1.5 eq) in DMF at rt. After 5 hours LiOH (10 eq) and water is added and the reaction mixture is stirred at rt o/n. The final product is purified by LC-MS and loaded on a DNA oligo containing an amino function.

Synthesis of the functional entity 13.3.1B:

3-Pent-4-enoylamino-butyric acid (1 eq) is treated with 3-hydroxymethyl-benzoic acid tert-butyl ester (1.2 eq), DIC (1.2 eq) and DMAP (0.2 eq) in DCM. The reaction mixture is stirred o/n at rt. The crude is evaporated and purified by silica gel filtration. The purified material is dissolved in diethyl ether and treated with HCl in diethyl ether. After stirring for 3 hours the mixture is evaporated and the crude material loaded on a DNA oligo containing an amino function.

Fill in experiment using functional entity 13.3.1A and 13.3.1B:

The two loaded oligos are mixed with a template oligo in in hepes buffer (pH=7.5) and 100 mM NaCl. 1,1'-Carbonylbisbenzotriazole (0.1M in MeOH) is added and the mixture is left at rt for 4 hours. pH is then adjusted to 9 and the mixture is left at rt o/n.

FIG. 21, shows the formation of chiral and achiral templated molecules.

FIG. 22, shows the formation of a phosphodiester bond by symmetric fill-in.

FIG. 23, shows the formation of a phosphodiester bond by a fill-in reaction, wherein the building block comprises a single reactive group.

FIG. 24, shows a pericyclic fill-in reaction.

FIG. 25, shows an exemplification of FIG. 16, in which functional entities 13.7.1A and 13.7.1.B are synthesised.

Synthesis of the functional entity 13.7.1A:

3-Methylamino-propionic acid methyl ester (1eq) is dissolved in DCM and triethylamine (2eq). The mixture is cooled to 0° and treated with acryloyl chloride (1.5 eq). After 2 hours the reaction mixture is evaporated, redissolved in THF and treated with LiOH (10 eq) and water. The mixture is left at rt for 3 hours. The crude is extracted with EtOAc (2x). The combined organic phases are dried over MgSO4 and evaporated. The product is purified by LC-MS and loaded on a DNA oligo containing an amino function.

Synthesis of the functional entity 13.7.1B:

Amino-furan-2-yl-acetic acid (1 eq) is treated with acetic anhydride (3 eq) at rt for 1 hour. The crude is evaporated and the product purified by LC-MS and then treated with 3-hydroxymethyl-benzoic acid tert-butyl ester (1.2 eq), DIC (1.2 eq) and DMAP (0.2 eq) in DCM. The reaction mixture is stirred o/n at rt. The crude is evaporated and purified by silica gel filtration. The purified material is dissolved in diethyl ether and treated with HCl in diethyl ether. After stirring for 3 hours the mixture is evaporated and the crude material loaded on a DNA oligo containing an amino function.

Pericyclic reaction experiment using functional entity 13.7.1A and 13.7.1B:

The two loaded ( )idos are mixed with a template oligo in in hepes buffer (pH=7.5) and 100 mM. The mixture is left at rt for 4 hours. pH is then adjusted to 9 and the mixture is left at rt o/n.

FIG. 26 shows a schematic representation of a fill-in reaction using asymmetric monomers.

Figure 27:
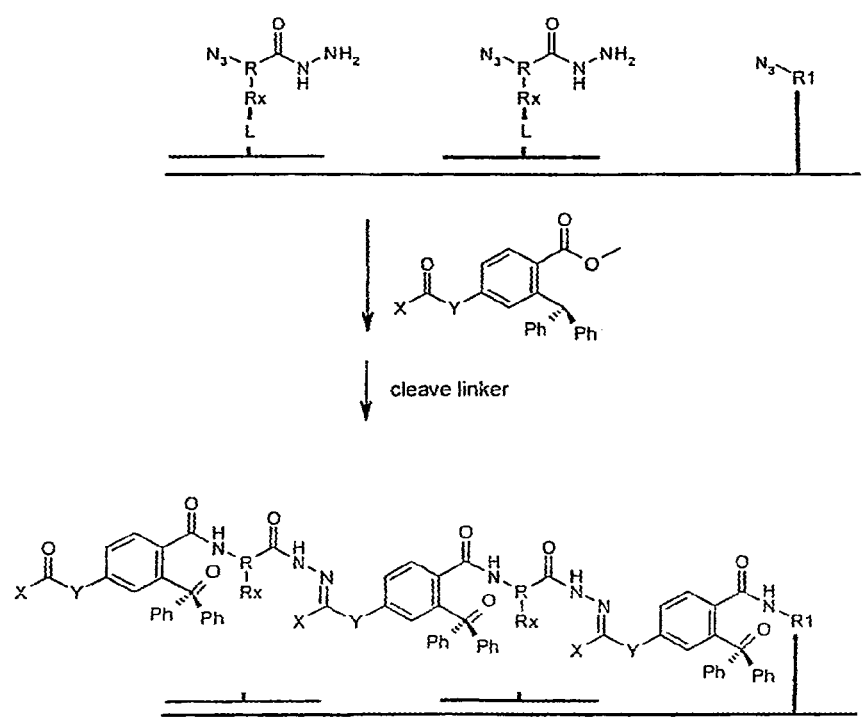

FIG. 27 shows an asymmetric fill-in reaction using modified Staudinger ligation and ketone-hydrazide reaction.

Figure 28:
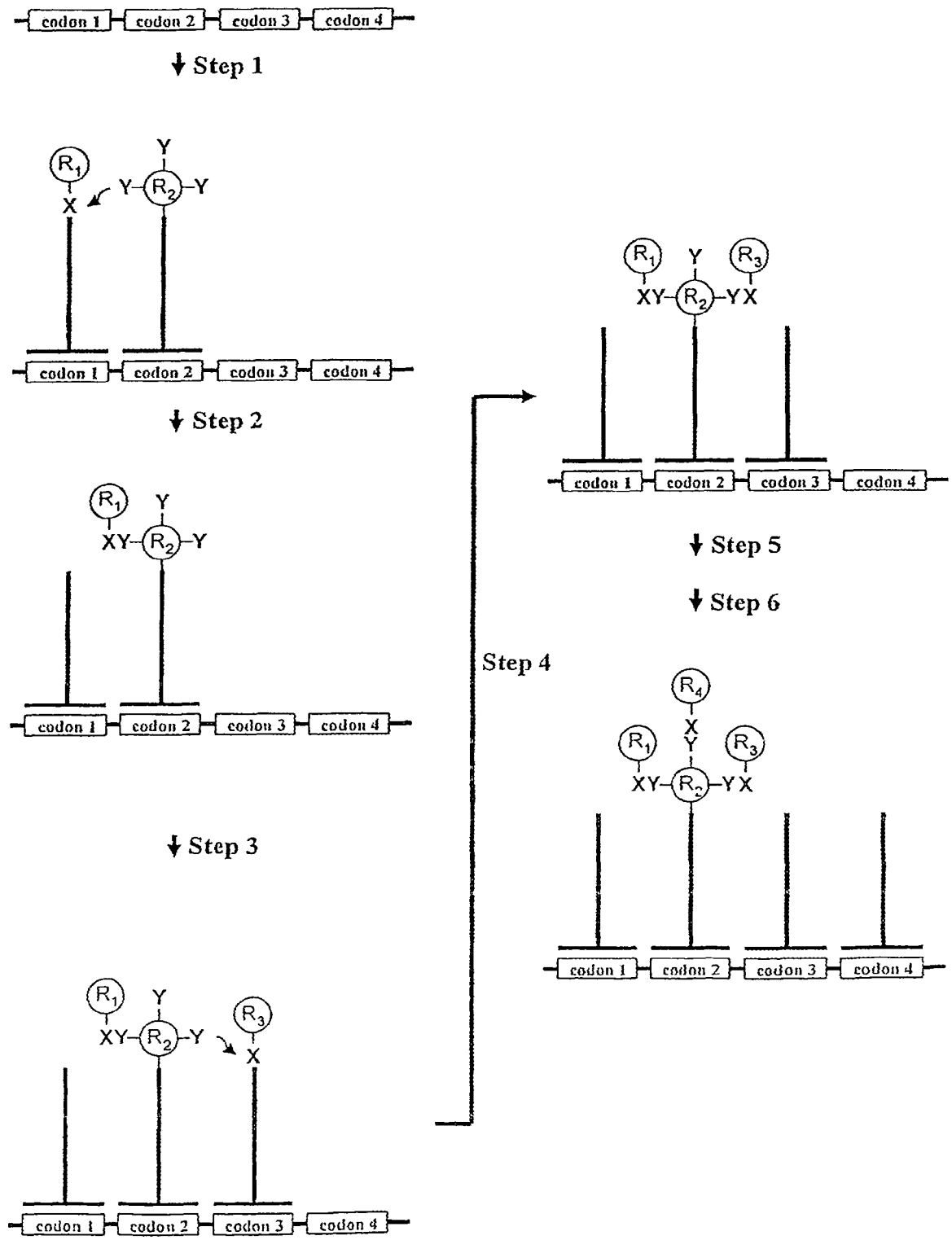

FIG. 28 shows a schematic representation of a templated synthesis of a non-linear molecule.

Figure 29:
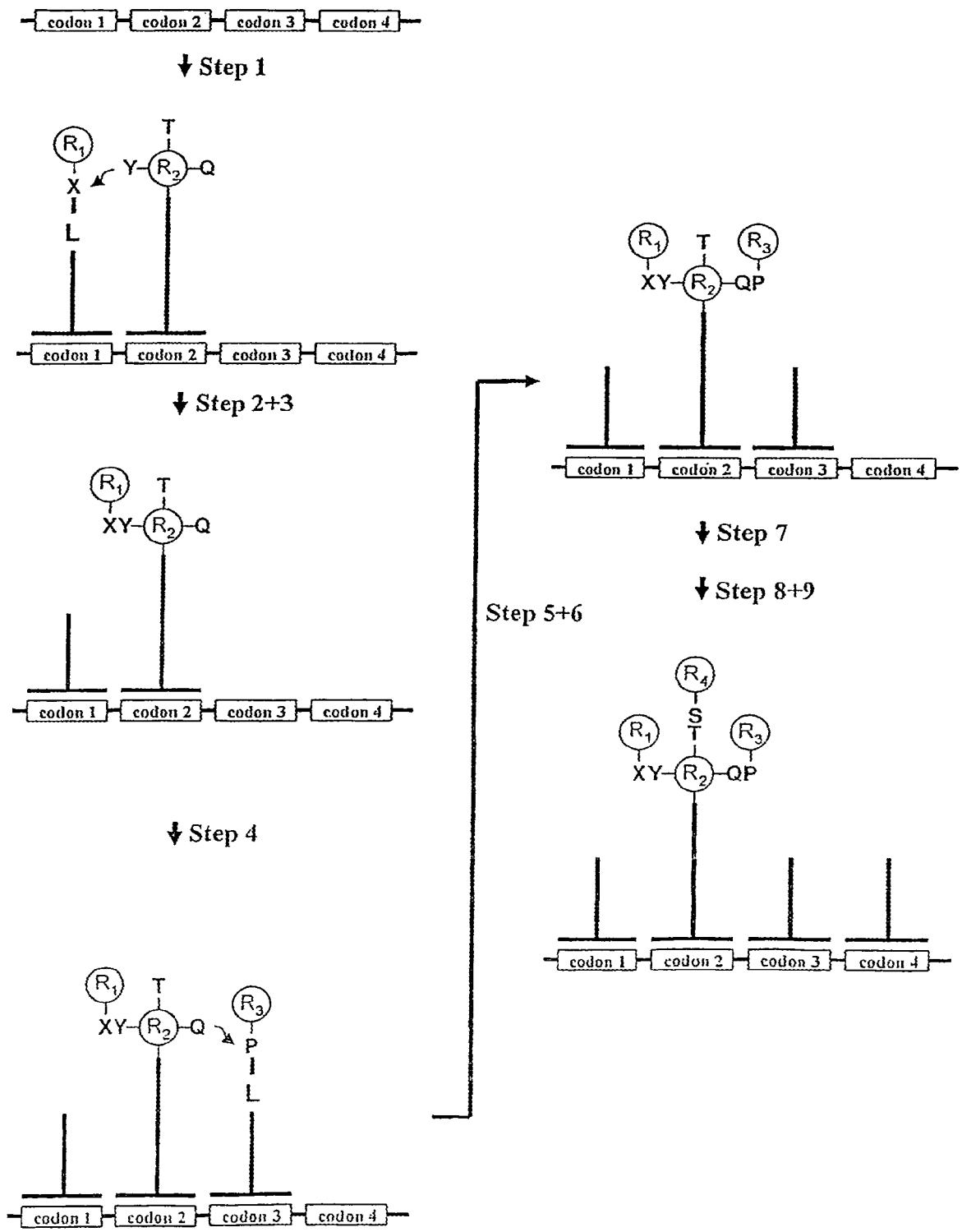

FIG. 29 shows a representation of the templated synthesis of a non-linear molecule employing reactive groups of different classes and non-simultaneous reaction and cleavage.

Figure 30:
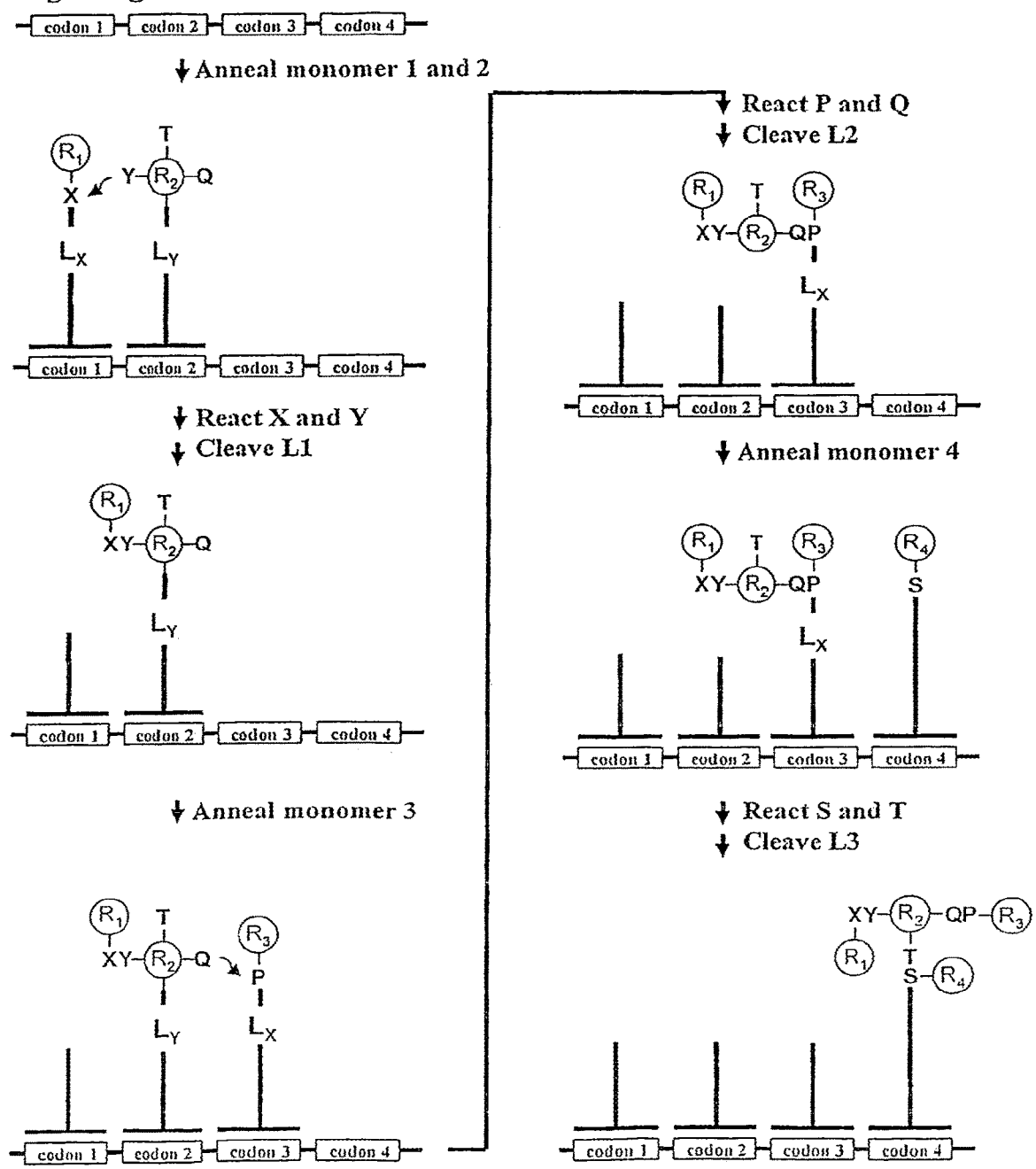

FIG. 30 depicts a templated synthesis of a non-linear molecule, by exploiting the increased proximity effect that arises from a "migrating" scaffold.

Figure 31:
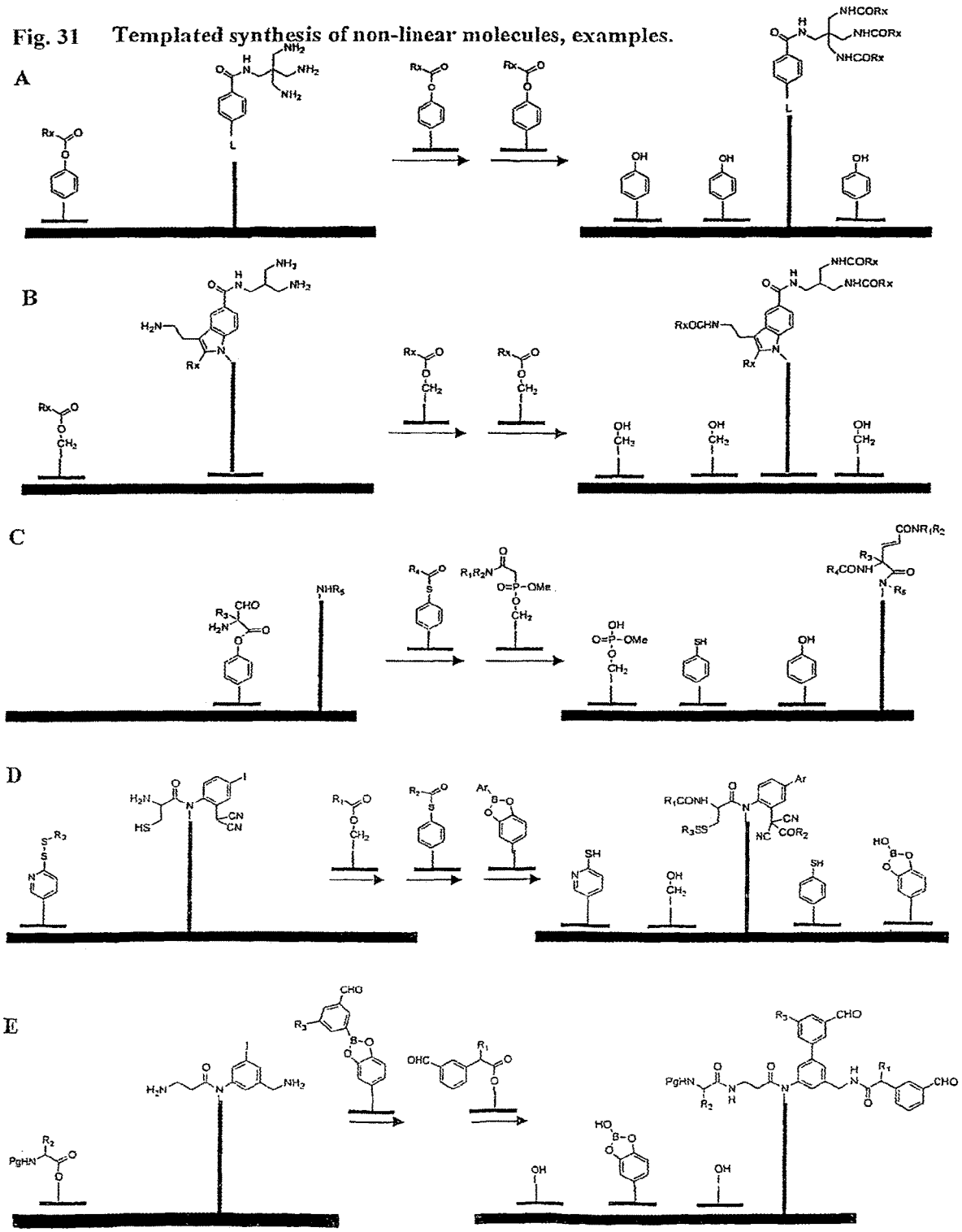
Figure 32:
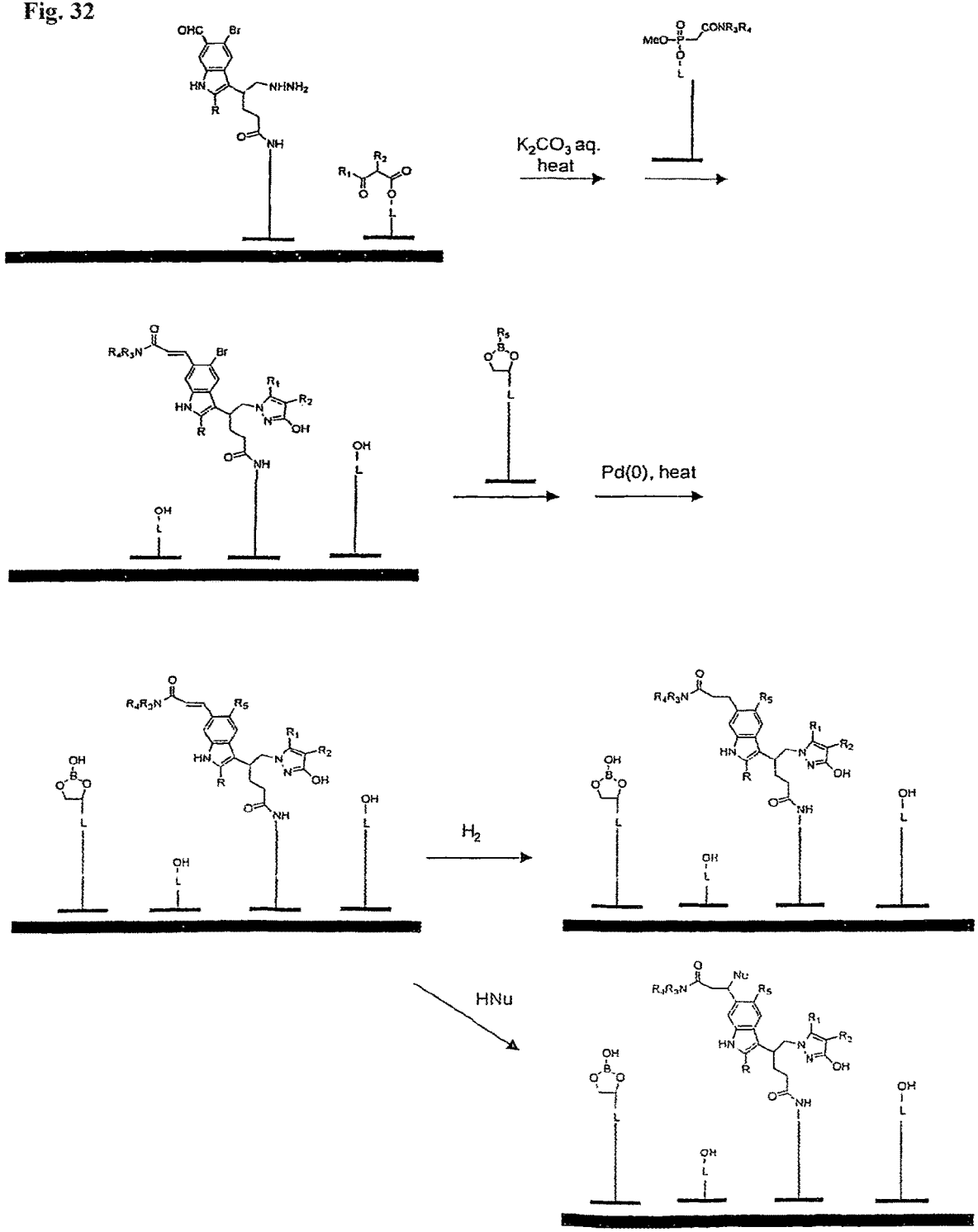
Figure 41:
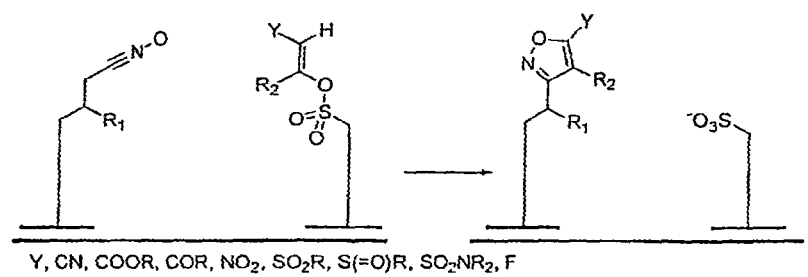

FIGS. 31 and 32 show examples of the templated synthesis of non-linear molecules.

FIG. 33 shows a schematic representation of a templated synthesis, wherein the reaction step may be performed under conditions where specific annealing of building blocks to the template is inefficient.

FIGS. 34 to 41 show examples of various reactions types allowing simultaneous reaction and cleavage.

FIGS. 42 to 44 show examples of pairs of reactive groups (X) and (Y), and the resulting bond (XY).

FIG. 45 shows a schematic representation (panel A) of the zipper box principle and an example (panel B) of two building blocks.

FIG. 46 shows a schematic representation of various methods for increasing the proximity of functional entities of different building blocks.

FIG. 47 shows examples of the chemical constitution of a linker to be able to be cleaved.

FIG. 48 schematically shows the templated synthesis by generating a new reactive group.

FIG. 49 shows a method in which reactive groups generated in a first round subsequently are reacted with introduced reactive groups.

FIGS. 50 to 52 show examples of post-templating modifications of the templated molecule.

Figure 53:
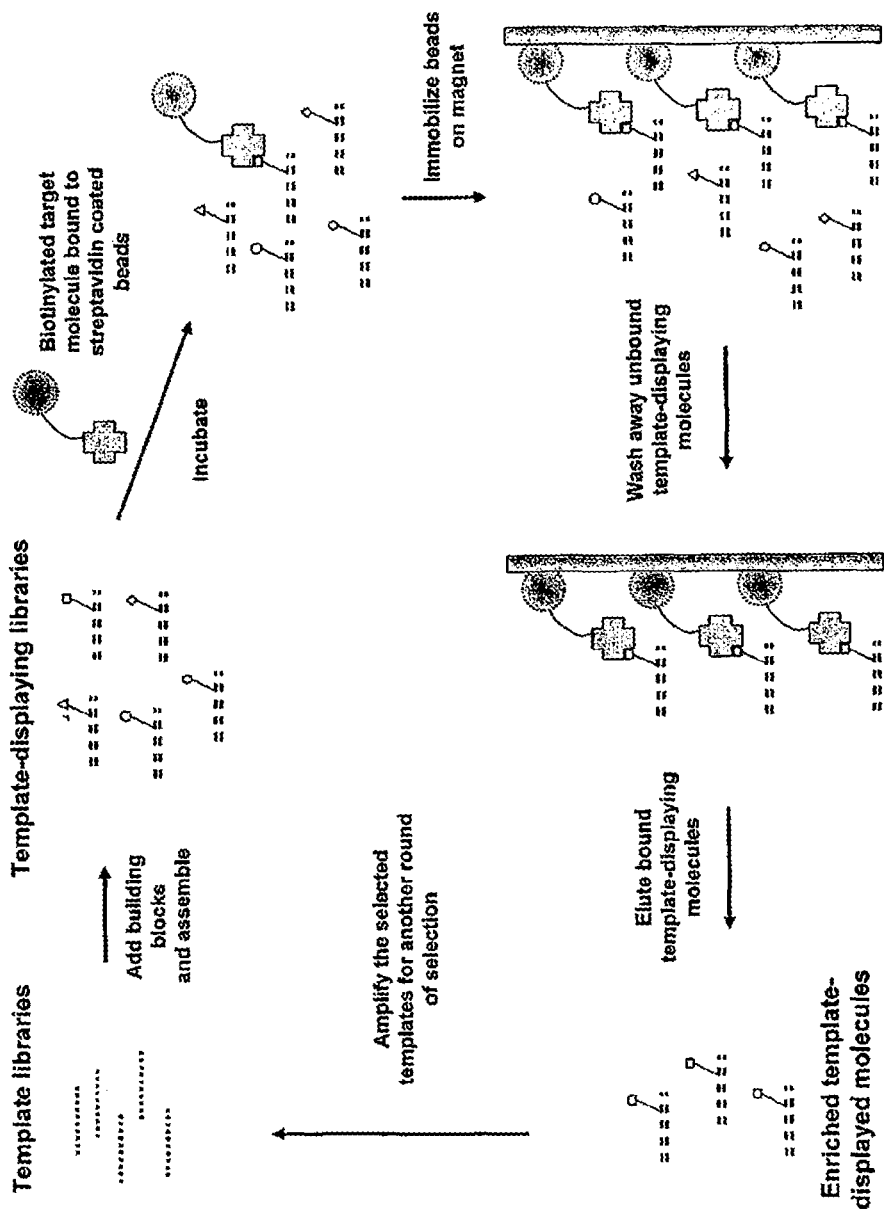

FIG. 53 illustrates one preferred method for selection of template-displaying molecules.

FIGS. 54 to 58 show the proposed complexes that may form when a reaction step is performed using set-ups that allow for stacking of DNA duplexes.

Figure 59:
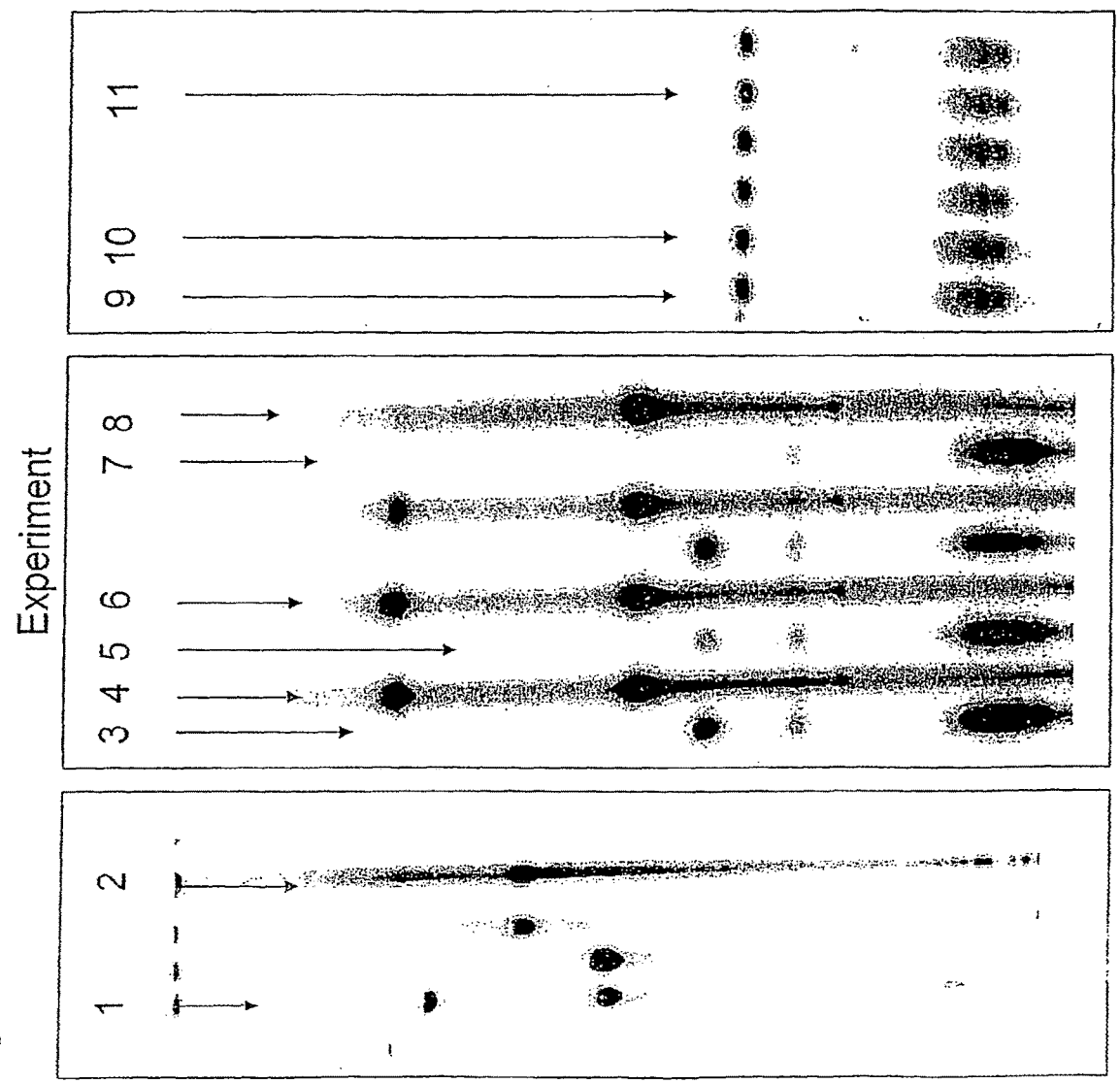

FIG. 59 shows an autoradiography of a polyacrylamide gel analysis of the reaction between building blocks.

Figure 60:
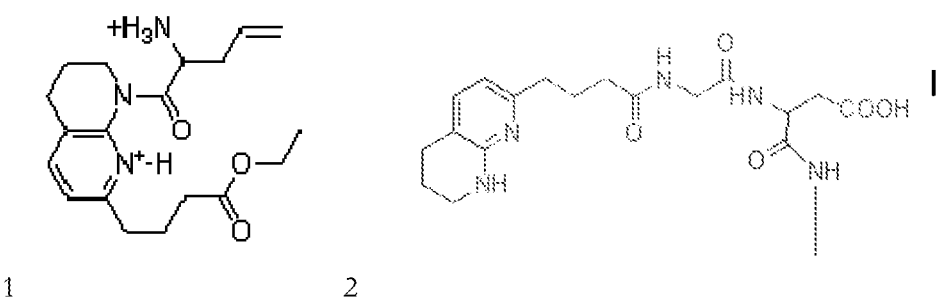

FIG. 60 shows the Feuston 3 functional entity as well as the Feuston 5 ligand.62

Figure 61:
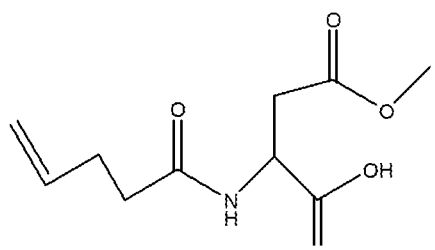

FIG. 61 shows the structure of pentenoyl protected aspartate.

Figure 62:
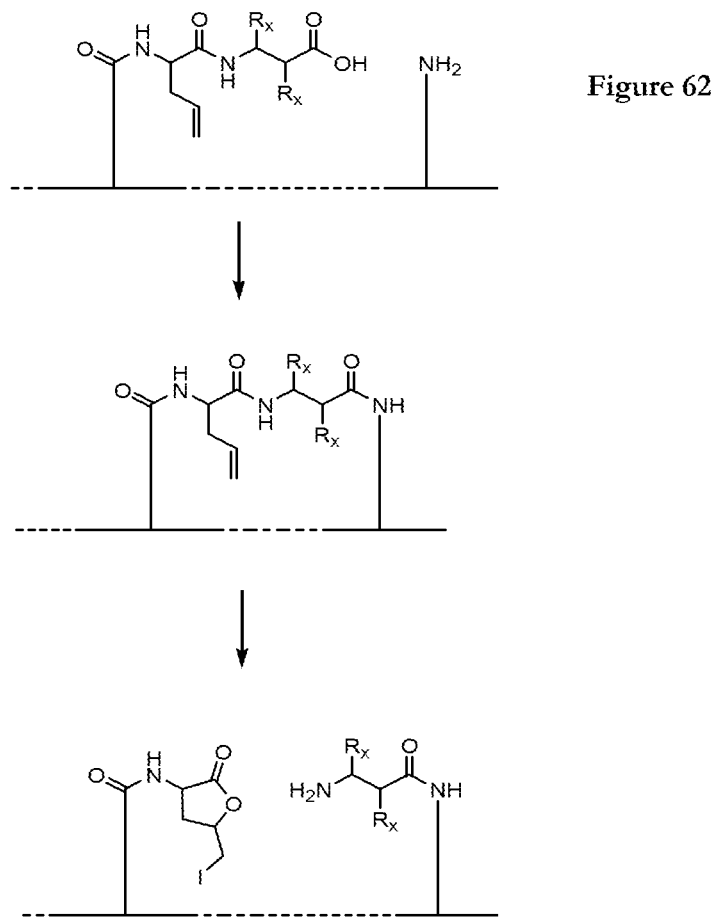

FIG. 62 shows the use of allylglycine building blocks.

Figure 63:
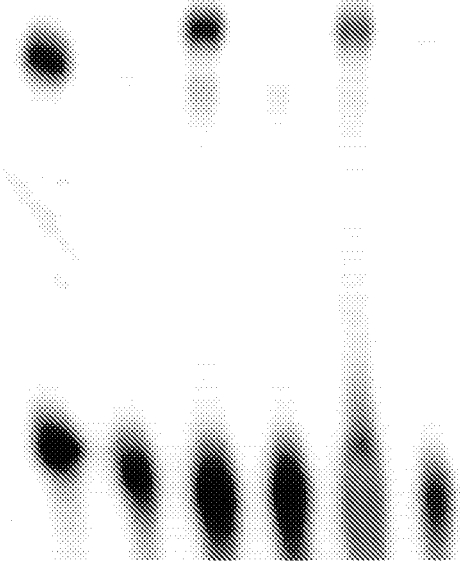

FIG. 63 shows the autoradiography of a polyacrylamide gel.

Figure 64:
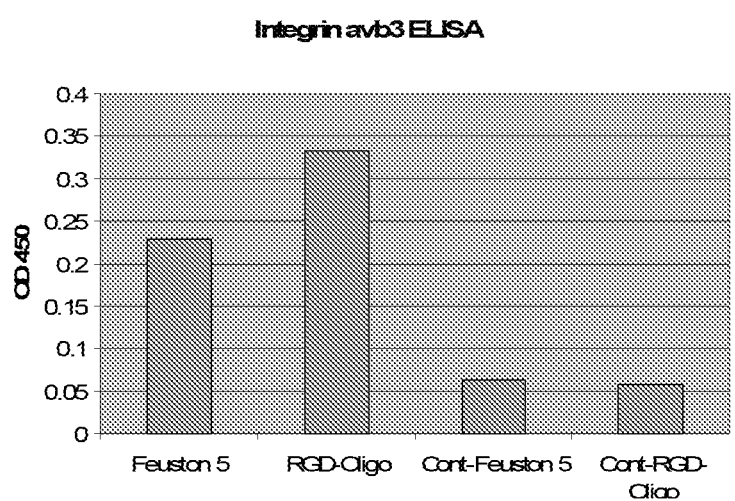

FIG. 64 shows an Elisa analysis of a product of a two-step encoding process.

DETAILED DESCRIPTION OF THE INVENTION

The following symbols are used in the figures to indicate general characteristics of the system: FIG. 9; FIG. 12; FIG. 13, FIGS. 15 to 19; FIGS. 20 to 27; FIGS. 31 to 32, FIGS. 34 to 41, FIGS. 45 to 46, FIGS. 48 and 49, and FIGS. 54 to 58 a long horizontal line symbolizes a template. Coding region 1 symbolizes sequences that anneal to type 1 building blocks. Building blocks are symbolized as shown in FIGS. 4-7. X/Y, S/T and P/Q represent pairs of reactive groups (where the reactive groups of one pair (e.g. X and Y) are partly or fully orthogonal to the reactive groups of other pairs (e.g. S/T, P/Q)). $R_1, R_2, \ldots, R_x$ symbolize functional groups. $L_1$ and $L_1, L_2, L_3, \ldots$ represent cleavable linkers, where linkers of one group (e.g., $L_1$-linkers) are cleavable under conditions where linkers of other groups ($L_2, L_3 \ldots$) are not cleaved, or are cleaved less efficiently. The proximity effect that results from incorporating two building blocks on the same template, or alternatively, as a result of incorporating a building block on a template to which is attached a reactive group, may be enhanced by any of the methods described above or below that increases this effect. For example, in order to increase the efficiency and specificity of templated synthesis, the proximity effect may be increased by the introduction of zipper boxes in most of the general concepts described here.

In all the examples, the templated molecule may be coupled to the template through the non-covalent interaction of a monomer building block with the template, or alternatively, through covalent or non-covalent coupling to the template, and may be located at either of the ends of the template, or anywhere on the template. The coupling reaction to the template may be performed before, during or after the synthesis of the templated molecule.

For clarity, in some of the figures only the reaction step, not the cleavage step, has been included.

The figures included have been drawn so as to highlight specific set-ups.

Obviously, any combination of the methods may be employed, in order to make linear, as well as non-linear molecules, to use reactive groups that lead to simultaneous cleavage, as well as reactive groups that do not lead to simultaneous cleavage, to use cleavable and non-cleavable linkers etc.

The protocol for an embodiment of a multi-step templated synthesis is shown in FIG. 1 and involves a number of steps that each result in the addition of one or more molecular moieties to a growing molecule that eventually becomes the templated molecule. Each of these steps can be divided into substeps. Initially, a number of templates (also called a library of templates) are provided. Each of the templates comprises a plurality of unique codons and a reactive group. Also, a plurality of different building blocks are provided, each of the building blocks comprises a functional entity separated from an anti-codon with a suitable linker. The anti-codon of a specific building block complements a unique codon of a template and is, therefore, capable under proper hybridisation conditions to anneal to the unique codon. The incorporation of building blocks is initiated by contacting the plurality of different templates with a subset of the entire amount of building blocks. The subset carries anti-codons which hybridise to unique codons of a distinct coding region. A connection between the reactive group of the template and the functional entity of the building blocks is obtained. In FIG. 1 the reactive group of the template is part of a building block (building block 1) and the said building block is hybridised to the template. In a preferred embodiment the building block 1 comprising the reactive group of the template and the second building block are contacted with the template simultaneously to allow for an efficient connection between the functional entities. The line between $FE_1$ and $FE_2$ symbolise a direct connection between the functional entities or an indirect connection via a bridging molecule entity. The molecule part formed by a connection of $FE_1$ to $FE_2$ is a nascent templated molecule, which may be added further functional entities resulting in a growing nascent templated molecule.

The propagation part of the method starts with the incorporation of a further building block (building block 3). The incorporation involves the hybridisation of a subset of the building blocks to the plurality of templates bearing the nascent templated molecule. The subset of building blocks is selected to have anti-codons which complement unique codons of the templates, said unique codons being in the vicinity of, preferably neighbouring to, unique codons hybridised to the building block(s) bearing the templated molecule. The functional entity of the further building block is able to form a chemical connection to the nascent templated molecule through the reaction of a reactive group attached to the functional entity. The linkage between one or more of the functional entities and the corresponding anti-codons may be cleaved if desired and the incorporation of a new building block may be performed. In the example illustrated in FIG. 1 only three functional entities are connected in the templated molecule. However the propagation step may be conducted as many times as appropriate to obtain the desired templated compound.

As a terminal phase the linkers connecting functional entities/templated molecule and anti-codons may be cleaved. The complex comprising the templated molecules (specific compositions or sequences of molecular moieties, the identity of which is determined by the template) attached to the templates that templated their synthesis, can now be taken through a screening process. This process leads to an enrichment of templated molecules complexes with appropriate characteristics. The isolated complexes may now be enriched by amplification of the templates, and a new round of templated synthesis and screening can be performed. Eventually, the templated molecules may be identified by characterization of the corresponding templates.

The stages of the process involving incorporation of building blocks may be mediated by chemicals, or enzymes such as polymerase or ligase. For example, the anti-codon part of the building blocks may be nucleotide-derivatives that are incorporated by a polymerase. Incorporation may also be solely by hybridization of building blocks to the template. If the template is a DNA molecule, the template may comprise primer binding sites at one or both ends (allowing the amplification of the template by e.g. PCR). The remaining portion of the templates may be of random or partly random sequence.

The reaction stage of the method involves reactions between the incorporated building blocks, thereby forming chemical connections between the functional entities. The chemical connection can be a direct chemical bond or the connection can be established through a suitable bridging molecule.

The optional cleavage step involves cleaving some, all but one, or all of the linkers that connect the functional entities and anti-codons. In FIG. 1 the templated molecule is displayed by cleaving the linkers of the second and third functional entities, while maintaining the linker from the first building block.

Subsequent to the production of library according to the invention a selection is performed. The selection or screening involves enriching the population of template-templated molecule pairs for a desired property. For example, passing a library of templated molecule-template complexes over a solid phase to which a protein target has been immobilized, and washing unbound complexes off, will enrich for complexes that are able to bind to the protein.

The selection may be performed more than once, for example with increasing stringency. Between each selection it is in general preferable to perform an amplification. The amplification involves producing more of the template-templated molecule complexes, by amplification of the template or complementing template, and producing more of the template-templated molecule pairs, for further rounds of selection/screening, or for sequencing or other characterization. For example, if the template is a DNA strand, the template may be amplified by PCR, where after the templated synthesis can be performed using the amplified DNA, as described above.

Cloning and sequencing may also be useful techniques and involve the cloning of the isolated templates or complementing templates, followed by characterization. In some cases, it may be desirable to sequence the population of isolated templates or complementing templates, wherefore cloning of individual sequences is not required.

Figure 2:
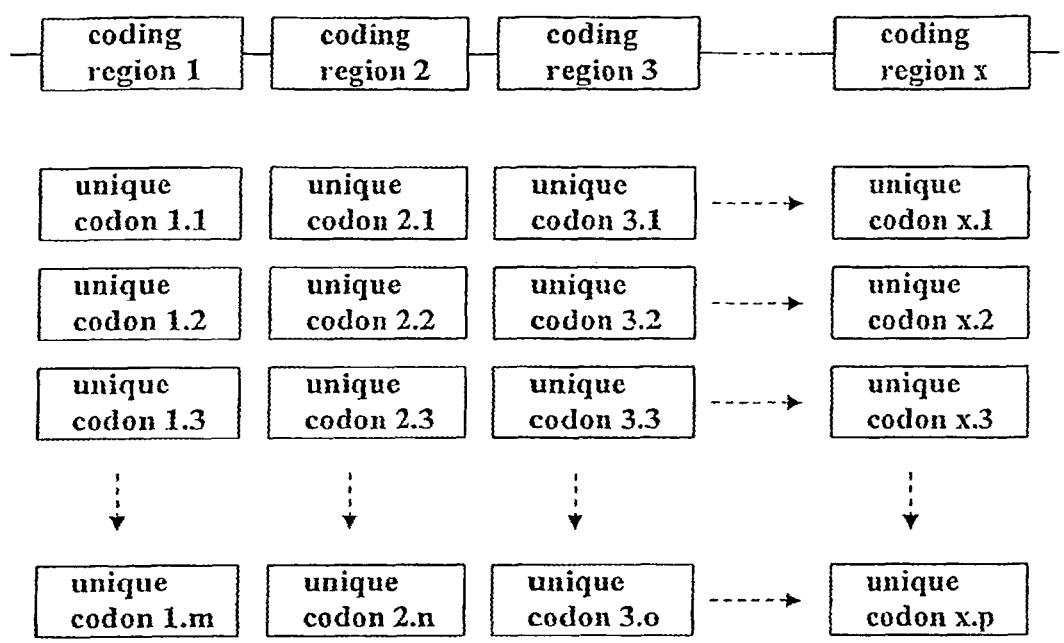
FIG. 2 shows the general structure of templates useful in the generation of a library.

In FIG. 2, in the upper part of the figure, the general structure of a template is shown. The templates comprise x coding regions. Each coding region has a unique sub-structure which differentiates it from some or all of the other coding regions. Shown below the general structure of a template are specific templates. A given specific template carries a specific set of x unique codons. A unique codon specifies (by way of interaction with a specific anti-codon of a building block) a specific functional entity. The unique codons 1.1, 1.2, 1.3, . . . , 1.m are all examples of coding region 1 sequences. The general design of the templates therefore enables the templated incorporation of building blocks, in the sense that a sub-set of building blocks can be added that will only be incorporated at the same position on the template (i.e., coding region 1 if the building blocks have anti-codons that are complementary to the unique codons of codon region 1).

FIG. 3 shows an example of a design of templates and anti-codons for oligonucleotide-based building blocks. Section A discloses the general structure of a set of templates carrying 6 coding regions, each containing a partly random sequence (X specifies either C or G), and a constant sequence that is identical for all sequences in the group (e.g., all coding region 1 sequences carries a central ATATTT sequence). By using C and G only (or, alternatively, A and T only), the building blocks that are complementary to coding regions 1 have very similar annealing temperatures wherefore misannealing is insignificant. The attachment point of the linker that connects the anti-codon and the functional entity is not specified in the figure. Ideally, the linker is attached to the constant region of the anti-codon, in order to avoid bias in the annealing process.

Section B of FIG. 3 shows examples of codon and anti-codon sequences. Example codon 1 and codon 6 sequences are shown. The example codon 1 sequence represents one specific sequence out of 1024 different sequences that anneal specifically to the complementary anti-codon 1 sequences; the example codon 6 sequence represents one specific sequence out of 128 different sequences that anneal to the complementary anti-codon 6 sequences.

FIG. 4 illustrates different general designs of building blocks. A building block comprises or essentially consists of a functional entity, connected through a (cleavable) linker to an anti-codon. Panel A shows a building block with one reactive group (X), connecting the, functional group ($R_x$) with the anti-codon. This type of building block may be used for the simultaneous reaction and cleavage protocol (e.g. FIGS. 10 and 28). The functional entity in this example comprises one reactive group, and a functional group $R_x$, also called a functionality. The reactive groups typically become part of the templated molecule. Panel B shows a building block with two reactive groups (X and Y), connecting the anti-codon and the functional group ($R_x$). The functional entity in this example comprises two reactive groups that are both part of the moiety that links the anti-codon and functional group, $R_x$. Panel C shows a building block with a reactive group (X) connecting $R_x$ and the anti-codon, and a reactive group (Y) attached to the $R_x$ group. This type of building block may be used in the simultaneous reaction and cleavage protocol (e.g., FIG. 10 and 11). The functional entity comprises two reactive groups X and Y, where X is part of the linker, and Y is attached to the functional group $R_x$. Panel D shows a building block with one reactive group (X). The reactive group (X) does not link the functional group (Rx) and the complementing element. A cleavable linker (L) is provided in order to release the functional entity from the anti-codon. This type of building block may be used in protocols that require cleavage of the linker after the reactive groups of the functional entities have reacted (e.g., FIG. 15). Panel E disclose a building block with four reactive groups and a functional group Rx. The four reactive groups and the functional group Rx may serve as a scaffold, onto which substituents (encoded by building blocks bound to codons on the same template) are coupled through reaction of reactive groups (X) of other building blocks with the reactive groups (Y) (e.g., FIG. 28). In this example, no cleavable linker is indicated. Therefore, after the templating reactions the templated molecule is attached to the template through the linker of this building block.

In FIG. 5 three different building blocks are depicted. Building block A comprises an anti-codon (horizontal line), which may be an oligonucleotide, to which a linker carrying the functional entity is attached to the central part. The portion of the linker marked "a" may represent a oligonucleotide sequence to which a single stranded nucleotide may be annealed in order to make the linker more rigid, or alternatively, "a" may represent a zipper box sequence of nucleotides or other type of zipper box moiety. The vertical line may represent a PEG (polyethylene glycol) linker, oligonucleotide linker, or any other linker that provides the functional entity with the appropriate freedom interact productively with a functional entity of a building block annealed to the same template during the templating process. In building block, the linker is attached to the terminus of the anti-codon. The anti-codon and the linker may be one continuous strand of an oligonucleotide. The horizontal part here represents the anti-codon, and the vertical part represents the linker. The linker may contain a moiety "a" that functions as a zipper box (see FIG. 45), a rigid linker, or an annealing site for another entity that rigidifies the linker upon annealing. In building block C of FIG. 5 the linker and anti-codon may be a continuous strand of an oligonucleotide. Attached to the linker is a nucleophile "Nu" which may react with a functional entity. This may be used as an anchorage point for the templated molecule. Building block C may preferably be used as the starting or the terminal building block. When used in the initial stage of the production of the complex comprising the templated molecule, building block C may provide the template with a reactive group to which the functional entities may be attached in the growing templated molecule. In a further embodiment of the invention "Nu" of building block C represents any reactive group able to participate in a reaction resulting in the formation of a connection to a functional entity of a building block.

FIGS. 6A, 6B, 6C, 6D and 6E show five different general methods for the preparation of building blocks. The general methods involves the coupling of the functional entities to oligonucleotide-based building blocks. Reactions and reagents are shown that may be used for the coupling of functional entities to modified oligonucleotides (modified With thiol, carboxylic acid, halide, or amine), without significant reaction with the unmodified part of the oligonucleotide. As an alternative approach, the functional entity may be synthesized as phosphoramidite precursor, which can then be used for oligonucleotide synthesis by standard methods, resulting in an oligonucleotide-derivative carrying a functional entity.

FIG. 7 shows the design and synthesis of exemplary building blocks. Panel A shows a general synthesis scheme for building blocks using DNA oligonucleotide as codon, and coupling amines and carboxylic esters. The oligonucleotide is purchased with an amine coupled to e.g. the base at a terminal position of the oligo. By addition of EDC (1-(3-dimethylaminopropyl)-3-ethylcarbodiimide hydrochloride) and NHS (N-hydroxysuccinimide), the oligonucleotide is coupled to the building block through an amide bond. Panel B shows specific synthesis schemes for the generation of specific classes of building blocks.

FIG. 8 illustrates an embodiment for the templated synthesis of a polymer. X and Y are reactive groups of the functional entity. X and Y may be different kinds of reactive groups (e.g., amine and carboxylic acid), of the same kind but different (e.g., different primary amines or a primary amine and a secondary amine), or identical. Reaction of X with Y to form XY either happens spontaneously when the building block has been incorporated, or is induced by a change of conditions (e.g. pH), or by the addition of an inducing factor (chemical or UV exposure, for example)

FIG. 9 show light-induced reaction between symmetric coumarin-derivatives. Light-induced reaction of the coumarin units, followed by cleavage of the linker, result in a ring structure. Examples of functional groups (phosphate and carboxylic acid) are shown. The building blocks are said to be symmetric because the two reactive groups, two coumarin units, are of the same reactivity (in fact, in this example are identical).

FIG. 10 shows an embodiment-for templated synthesis of a polymer. A population of templates, each carrying four codons are incubated with two sets of building blocks (carrying anti-codons 1 and 2, respectively), at a temperature that ensures efficient and specific annealing of anti-codons type 1 to coding regions 1, and efficient and specific annealing of anti-codons type 2 to coding regions 2. After annealing, the excess building blocks may optionally be removed. If desired, reactive groups may be deprotected (and thus activated for reaction) at this step. Then building block-template complexes are incubated under conditions that allow the reactive groups of the building blocks (i.e., reactive groups X and Y) to react. This leads to a transfer of the functional group R1 from building block 1 to building block 2, and thus results in the formation of a dimeric polymer carrying two functional groups, R1 and R2. The process is then repeated, i.e. a third monomer (with anti-codon type 3) is added, and after annealing to coding region 3, excess building block is removed, and the reaction between X and Y now leads to the formation of a trimeric polymer, coupled to the building block annealed to coding region 3. Once more, the process is repeated with building blocks of type 4, resulting in the formation of a tetrameric polymer.

The reactive groups X and Y used in this scheme thus have two functions: i) reaction between X and Y leads to coupling of the corresponding functionalities (e.g., R1 and R2), and simultaneously, ii) the linker between R1 and the anti-codon is cleaved. Examples of reactive groups X and Y with such characteristics (i.e., the ability to simultaneously react and cleave) are shown in FIGS. 34 to 41. By appropriate choice of X and Y, the nascent polymer is migrated down the template, from building block to building block, as it is being synthesized. For example, by choosing X=ester (COOR), and Y=amine ($NH_2$), the nucleophilic attack of the amine on the ester leads to transfer of the upstream functionality (e.g., $R_1$) to the downstream building block (e.g., carrying anti-codon type 2). This ensures the highest possible effect of proximity with this set-up (i.e., in each step, the reacting X and Y are carried on neighbouring monomers).

If desired, the templated polymer may be coupled to the template through the non-covalent interaction of a building block with the template (in the example given, through the interaction of building block 4 with the template), or alternatively, through covalent coupling to a reactive group on the template, located at either of the ends of the template, or anywhere on the template sequence. In the latter case, the coupling reaction to the template may be performed before, during or after the synthesis of the polymer.

FIG. 11 shows the templated synthesis of a mixed polymer. The most noticeable difference, when compared to the embodiment shown in FIG. 10 is that the reactive groups on the individual building blocks are different. The pairs of reactive groups (X/Y, S/T, and P/Q) are chosen so that the reaction of X and Y, S and T, P and Q, respectively, results in transfer of a functional group from one building block to another (i.e., the reaction both mediates the coupling of the two functional groups and the cleavage of the linker that initially connects one of the functional groups to the anti-codon). Example pairs of reactive groups that mediate this simultaneous reaction and cleavage are shown in FIGS. 34 to 41.

FIG. 12 shows two methods of obtaining different classes of compounds using simultaneous reaction and cleavage. In FIG. 12A, the formation of an alpha-peptide is disclosed and in FIG. 12C the synthesis of a polyamine is shown.

In FIG. 12A, two building blocks are incorporated by hybridization to the template. One of the building blocks is an oligonucleotide to which has been appended a thioester. The other building block is an oligonucleotide to which has been appended an amino acid thioester. The amine of the latter building block attacks the carbonyl of the other building block. This results in formation of an amide bond, which extends the peptide one unit. When the next amino acid thioester building block is incorporated, this may attack the thioester carbonyl, resulting in cleavage of the dipeptide from the anti-codon, to form a tripeptide. This process is repeated until the desired peptide has been generated. Importantly, as the reaction in each step is between the incoming subunit-precursor and the subunit of the nascent polymer that is closest to the linker that connects it to the anti-codon, the geometry of the nucleophilic attack remains unchanged. The reactivity of the amine with the ester may be tuned in several ways. Parameters that will affect the reactivity include: (i) pH and temperature, (ii) nature of ester (thio-, phosphor or hydroxy-ester); (iii) the nature of the substituent on the sulfur (see FIG. 12B below).

The general scheme presented here can be applied to most nucleophilic reactions, including formation of various types of peptides, amides, and amide-like polymers (e.g., mono-, di-, tri-, and tetra-substituted α-, β, γ-, and Ω-peptides, polyesters, polycarbonate, polycarbarmate, polyurea), using similar functional entities.

FIG. 12B shows four different thioesters with different substituents on the sulphur and therefore different reactivity towards nucleophiles.

FIG. 12C relates to the formation of a polyamine. Using the same principle as in FIG. 12A, a polyamine is formed.

FIG. 13 shows simultaneous reaction and cleavage for two reactions. In reaction A a peptoid or an α- or β-peptide is formed (FIG. 13A), and in reaction B, a hydrazino peptide is formed (FIG. 13B).

In reaction A, two building blocks are initially incorporated, one of which carries both a nucleophile (an amino group) and an electrophile (e.g. an ester); the other building block only carries an electrophile (e.g. a thioester). As a result, the nucleophilic amine will attack the electrophile of the building block attached to the same template. As a result, a dimeric structure is formed, linked to building block that initially carried the amine. Upon sequential addition of building blocks, the linear structure grows, and eventually the desired templated molecule (a peptoid or an α- or β-peptide) has been formed.

The reaction B follows the same line as in A, except that hydrazine-peptide precursor building blocks are used, leading to the formation of hydrazino peptides.

FIG. 14 shows a general reaction scheme for templated synthesis of a polymer, using non-simultaneous reaction and cleavage. In this scheme, the reaction of the reactive groups (e.g., X and Y) does not in itself lead to cleavage, wherefore the functional entity is coupled to the anti-codon via a cleavable linker. Therefore, each addition of a subunit to the growing polymer involves two steps. First, the reactive groups X and Y react to form a bond XY. Then, in a separate step, a cleavable linker L is cleaved, which releases one of the functional entities from the anti-codon. By alternating between two types of cleavable linkers (cleavable under different conditions) one may achieve migration of the nascent polymer down the template, like described in FIG. 10 and 11. This ensures the highest possible effect of proximity with this set-up (i.e., in each step, the reacting X and Y are carried on neighbouring monomers). In the example, some or all of the reactive pairs may be of the same kind (e.g., X/Y=S/T=P/Q).

Example reactions that do not mediate simultaneous reaction and cleavage are shown in FIGS. 42 to 44. Any combination of cleavable and non-cleavable linkers may be used, dependent on the nature of the reactive groups in the functional entities (e.g., dependent on whether the reaction involves a release from the anti-codon).

FIG. 15 relates to activation of reactive groups and release from anti-codon by ring-opening.

Reaction of the initiator with X in the ring structure opens the ring, resulting in activation of Y. Y can now react with X in a neighboring functional entity. As a result of ring-opening, the functional entities are released from the anti-codons. If the zipper-box principle is applied to this set-up (where each additional building block added reacts with the nascent templated molecule attached to the initiator), the initiator linker must carry half of the zipper (e.g., the "sense strand"), and all the building blocks must carry the other half of the zipper-box (the "anti-sense strand").

Ring-opening of N-thiocarboxyanhydrides, to form β-peptides.

After incorporation of two building blocks, where one of the building blocks carry an initiator reactive group (or incorporation of one building block next to a covalently attached initiator molecule), the initiator is activated, for example by deprotection or by an increase in pH. The primary amine then attacks the carbonyl of the N-thiocarboxyanhydride (NTA) unit. As a result, CSO is released, and a primary amine is generated. When the next building block is incorporated, this amine will react with the NTA, and eventually when all the building blocks have been incorporated and the NTA units have reacted, a β-peptide will have formed. Finally, the linkers that connect the β-peptide to the anti-codons are cleaved, resulting in a β-peptide attached to its template through one linker.

A number of changes to this set-up can be envisaged. For example, instead of thiocarboxyanhydrides, one might use carboboxyanhydrides. The initiator might be protected with a base- or photolabile group. If a base-labile protection group is chosen, the stability of the carboxyanhydride must be considered. At higher pH it may be advantageous to use carboxyanhydrides rather than thiocarboxyanhydrides. Other types of peptides and peptide-like polymers (e.g., mono-,di-, tri-, and tetra-substituted α-, β-, γ-, and Ω-peptides, polyesters, polycarbonate, polycarbarmate, polyurea) can be made, using a similar scheme. For example, a-peptides can be made by polymerization of 5-membered carboxyanhydride rings.

FIG. 16 shows the principle of symmetric fill-in (symmetric XX building blocks). The fill-in reaction occurs between the reactive groups ("X" in the figure) and bridging molecules "Y-Y" in figure).

For clarity, only the reaction (not the cleavage) is shown in the figure. X represents the reactive groups of the functional entity. In this case the two reactive groups are of the same kind. (Y-Y) is added to the mixture before, during or after incorporation of the building blocks.

FIG. 17 shows imine formation by fill-in reaction.

Dialdehyde is added in excess to incorporated diamines. As a result, an imine is formed. In the example, the templated molecule carries the following functional groups: cyclopentadienyl and hydroxyl.

FIG. 18 shows an example of amide formation using symmetric fill-in. After incorporation of two building blocks each carrying a di-amine, non-incorporated building blocks may be removed. Then EDC (1-Ethyl-3-(3-dimethylaminopropyl)carbodiimide), and dicarboxylic acid is added in excess to the primary amines of the building blocks. Alternatively, a di-(N-hydroxy-succinimide ester) may be added in excess. At a pH of 7-10, this will lead to the formation of two amide bonds linking the functional entities. After reaction, excess reagents may be removed by dialysis, precipitation of the building blocks and template, gel filtration or by other means that separate the reagents from the building blocks. When the process of incorporation-and-reaction has been repeated a number of times, and the desired molecule has been templated, the linkers (L) may be cleaved, and, if functional groups have been masked by protection groups (PG), these functional groups can be deprotected to expose the functional groups. Appropriate protecting groups would be for example Boc-, Fmoc, benzyloxycarbonyl (Z, cbz), trifluoracetyl, phthaloyl, or other amino protecting groups described e.g. in (T. W. Green and Peter G. M. Wuts (1991), Protective Groups in Organic Synthesis).

An alternative route to amide-bonded functional entities would be to incorporate building blocks carrying di-carboxylic acids, and then add diamines, NHS and EDC. Alternatively, the building blocks could carry N-hydroxy-succinimidyl (NHS) esters, which would react with the added amines without the need to add EDC and NHS.

FIG. 19 shows an example of urea-bond formation.

The functional entities of the incorporated building blocks react with phosgen or a phosgen-equivalent such as CDI to form a polyurea. Formaldehyde may also be used. The linkers are cleaved and the protected hydroxyl is deprotected. Appropriate leaving groups (Lv) are chloride, imidazole, nitrotriazole, or other good leaving groups.

FIG. 21 shows the formation of chiral and achiral templated molecules. In this example, the functional group Rx is used as a cleavable linker, that generates the desired functional group upon activation. In both reaction A and reaction B, a urea-bond is formed.

In reaction scheme A in FIG. 21, the functional group is attached to the backbone via a chiral carbon. The hydrogen on this carbon is drawn to emphasize this. Before bond formation, there is free rotation about the bond connecting the chiral carbon and the functional group. When the reactive groups (the amines) react with the phosgen equivalent (e.g., a carbonyldiimidazole) to form the templated molecule, the building blocks may be inserted in either of two orientations (as indicated by the position of the hydrogen, left or right). As a result, each encoded residue of the templated molecule will have two possible chiral forms. If the templated molecule was e.g. a pentameric polyurea (formed from five functional entities), this molecule would have $2^5=32$ stereoisomers. In certain cases it may be advantageous to incorporate such additional structural diversity in the library (for example when a low building block diversity is employed). In other cases such additional diversity is not desirable, as the screening efficiency may become compromised, or it may become too difficult to determine the identity of a templated molecule that has been isolated in a screening process.

In reaction scheme B in FIG. 21, the chiral carbon of reaction A has been replaced by a nitrogen. As a result, the resulting templated molecule is achiral, i.e. the template encodes one specific structure.

FIG. 22 shows the formation of a phosphodiester bond by the principle of symmetric fill-in. The incorporated building blocks react with the activated fill-in molecule to form a phosphodiester bond. Then the linkers are cleaved, releasing the templated molecule from its template. An example of an appropriate leaving group (Lv) is imidazole.

FIG. 23 shows phosphodiester formation with one reactive group in each building block.

Upon addition of a dihydroxylated compound such as 1,3-dihydroxypyridine, a phosphodiester bond is formed. Finally, the functional group Rx is liberated from the anti-codon by cleavage of the protection groups/cleavable linker that connected it to the anti-codon.

FIG. 24 shows an example of a pericyclic fill-in reaction.

First, two building blocks are incorporated. Then 1,4-benzoquinone is added in excess, resulting in the formation of a polycyclic compound. A third building block is added, reacted with the 1,4-benzoquinone, and this process is repeated a number of times until the desired templated molecule has been generated. Finally, all but one of the linkers that connect the templated molecule to the anti-codon, are cleaved.

FIG. 26 relates to asymmetric fill-in using XS building blocks.

A fill-in reaction between reactive groups (X and S) and bridging molecules (T-Y) is shown. For clarity, only the reaction (not linker cleavage) is shown. X and S represent the reactive groups of the functional entity. In this case the two reactive groups are not of the same kind. (T-Y) is added to the mixture before, during or after incorporation of the building blocks. Likewise, significant reaction between X and Y, and between S and T may take place during or after incorporation of the building blocks.

FIG. 27 shows an example of asymmetric fill-in by modified Staudinger ligation and ketone-hydrazide reaction. The reactive groups X and S of the building blocks are azide and hydrazide. The added molecule that fills the gaps between the building blocks carry a ketone and a phosphine moiety. The reactions between a ketone and a hydrazide, and between an azide and a phosphine, are very chemoselective. Therefore, most functional groups Rx can be employed without the need for protection during the reactions. Examples for the molecular moieties R, R1, X and Y may be found in (Mahal et al. (1997), Science 276, pp. 1125-1128; Saxon et al. (2000), Organic Letters 2, pp. 2141-2143).

FIG. 28 shows a general reaction scheme for templated synthesis of a non-linear molecule. A template carrying four codons is mixed with two building blocks. The functional entity of one building block comprises a reactive group X and a functional group $R_1$. The other building block comprises three reactive groups Y and a functional group $R_2$. The building block bound to codon 2 is here called the scaffold, as the functional groups are transferred to this building block during the templating process.

After incubation at a temperature that ensures efficient and specific annealing of the two building blocks to their respective codon, and optionally, excess building block has been removed, X is brought to react with one of the reactive groups Y, for example by changing the conditions, by deprotecting X or Y, or by simply exploiting the pronounced proximity of X and Y groups when the building blocks are bound to the template.

In this scheme, X and Y have been chosen so as to allow simultaneous reaction and cleavage. Thus, as a result of the reaction between X and Y, the substituent group (functional group) $R_1$ is transferred to the scaffold. Example reactive groups X and Y that mediate simultaneous reaction and cleavage are given in FIGS. 34 to 41. Any pair of reactive groups X and Y that mediates simultaneous reaction and cleavage can be used in this scheme, i.e., different X/Y pairs may be used at each substituent position.

Annealing and reacting of two more building blocks lead to the formation of a scaffolded molecule carrying three substituents ($R_1$, $R_3$ and $R_4$). The identity of the substituents is determined by the codons of the template to which the scaffolded molecule is attached.

FIG. 29 shows templated synthesis of a non-linear molecule, employing reactive groups of different kinds, and non-simultaneous reaction and cleavage. The reactive groups X, S, P and Y, T, Q may be of different kinds, and the bonds formed (XY, ST, and PQ) therefore may be of different kinds.

After reaction and then cleavage of the linker L (that attaches the functional entity of the first building block to the anti-codon), the substituent (functional group) R1 is transferred to the second building block (the scaffold). Thus, relative to the synthesis scheme of FIG. 28, here an additional step of linker cleavage is required. After repeating the processes of annealing, reacting and cleavage a number of times, a scaffolded molecule has been formed carrying encoded substituents. The identity of the substituents is determined by the codons of the template to which the scaffolded molecule is attached. The position of the substituents are determined by the identity of the reactive groups Y, T and Q of the scaffold, and therefore indirectly determined by the identity of the codon to which the scaffold building block anneals. Therefore, in this set-up, the identity and position of the substituents, as well as the identity of the scaffold, is determined by the sequence of the template. The reactive pairs may also be of the same kind (e.g., X/Y=S/T=P/Q).

FIG. 30 discloses the principle of templated synthesis of a non-linear molecule, by exploiting the increased proximity effect that arises from a "migrating" scaffold. In this set-up, the templated molecule migrates down the template as it is being synthesized. This is made possible by the use two different linkers $L_x$ and $L_y$, cleavable under different conditions. As a result, a high proximity is maintained throughout the templating process, as the building blocks that react in each reaction step are bound to adjacent coding regions on the template.

FIG. 31 shows the templated synthesis of various non-linear molecules.

- FIG. 31, panel A: Three building blocks are added and reacted one at a time. Each building block comprises an activated ester (reactive group, (X)) where the ester moiety carries a functional group Rx. Upon reaction between the esters and the amines on the scaffold (scaffold is covalently attached to the template), amide bonds are formed, and the Rx groups are now coupled to the scaffold via amide bonds. This is thus an example of simultaneous reaction (amide formation) and cleavage (release of the Rx moiety from the anti-codon), see e.g. FIG. 28.
- FIG. 31, panel B: Analogously to FIG. 31, panel A, three amines react with three esters to form three amide bonds, thereby coupling the functional groups Rx to the scaffold moiety. However, as opposed to FIG. 31, panel A, the scaffold is here encoded by the template, and therefore the scaffold is here part of the functional entity of a building block.
- FIG. 31, panel C: Three building blocks are used. The nucleophilic amine (covalently attached to the template) attacks the ester carbonyl of the building block bound to coding region 3; the amine of the third monomer attacks the thioester of the next incorporated building block, and after incorporation of the third building block, the Horner-Wittig Emmans reagent of the building block reacts with the aldehyde of the third monomer under alkaline conditions. This forms the templated molecule. The double bond may be post-templating modified by hydrogenation to form a saturated bond, or alternatively, submitted to a Michael addition.
- FIG. 31, panel D: The thiol of the scaffold reacts with the pyridine-disulfide of the incorporated building block. The amine of the scaffold reacts with the ester of the second incorporated building block. The double nitrile-activated alpha-position is acylated by the thioester of the next building block in the presence of base. Finally, the aryliodide undergoes Suzuki coupling with the arylboronate of monomer 4 to yield the biaryl moiety.
- FIG. 31, panel E: The incorporated building block acylates one of the primary amines.

The aryliodide undergoes a Suzuki coupling by reaction with the next building block, and the benzylic amine is acylated by last incorporated building block.

- FIG. 32, panel F: Acylation of the hydrazine followed by cyclization leads to formation of a hydroxypyrazole. After incorporation of the second building block, the arylbromide undergoes Suzuki coupling with the aryl boronate. Finally, the aldehyde reacts with the Horner-Wittig-Emmons reagent of the building block that is next incorporated, to yield an alpha, beta-unsaturated amide, which may be further modified or functionalized by either reduction with $H_2$/Pd—C or Michael addition with nucleophiles. Alternatively, a fourth building block might be used to template the coupling of a nucleophilic substituent at the double bond position.

FIG. 33 shows a general procedure of templated synthesis, wherein the reaction step may be performed under conditions where specific annealing of building blocks to the template is inefficient.

It may be desirable to perform the reaction step (or one of the other steps) under conditions where annealing of building blocks is in-efficient. To solve this potential problem, one may covalently link the incorporated building blocks, either chemically or by using a ligase (when the anti-codon comprises an oligonucleotide) or a polymerase (when the anti-codon is e.g. a nucleotide). In this set-up, the template is designed to fold back on itself.

In step 1, the two incorporated building blocks are incorporated and may be ligated together, and be linked to the template, during or after their incorporation. If desired, the conditions may now be changed to increase the efficiency of the reaction step that follows. Then, in step 2, the reactive groups X and Y are brought to react. Because the building blocks are covalently attached to each other (and to the template), the reaction can be performed under conditions where annealing of the building blocks to the template is inefficient. Reaction conditions that may not be compatible with efficient annealing and double helix structure include organic solvents, low salt and high temperature, all of which may be used with the set-up described in this figure.

After step 2 (reaction), the conditions are changed again, in order to allow efficient incorporation and covalent linkage of the next building block (step 3). This cycling between conditions that allow incorporation and ligation, and that allow reaction, is continued until the desired number of building blocks have been incorporated and reacted. Finally, some of the linkers are cleaved to give the templated molecule. As described above, the covalent coupling of the building blocks to each other allows the reaction between their reactive groups to be performed under more diverse conditions than would otherwise be possible. In addition, covalent coupling between building blocks makes it possible to use anti-codons comprising shorter recognition sequences. When the anti-codon comprises an oligonucleotide, it is generally preffered to use an oligonucleotide of at least fifteen nucleotides during incorporation, in order to obtain high efficiency of incorporation. However, if a ligase or chemical is used to covalently couple the building blocks, a shorter oligonucleotide (4-8 nucleotides) may be used. This will bring the reactive groups X and Y into closer proximity, and increase the local concentration of rective groups dramatically: If the distance between the reactive groups is decreased from 16 nucleotides to 4 nucleotides, this will increase the local concentration $4^3$=64. Everything else being equal, this will increase the rate of the reaction by 64-fold.

In order to change between conditions that allow incorporation and covalent coupling between building blocks, and conditions that allow the reaction to occur efficiently, the templates may be attached to a solid phase material (e.g., streptavidin beads if the templates are biotinylated), or the templates (with the building blocks associated to them) may be precipitated and resuspended in appropriate buffer during the steps of incorporation and reaction.

FIGS. 34 to 41 show various reaction types allowing simultaneous reaction and activation. Different classes of reactions are shown which mediate translocation of a functional group from one monomer building block to another, or to an anchorage point. The reactions have been grouped into three different classes: Nucleophilic substitutions, addition-elimination reactions, and transition metal catalyzed reactions. These reactions are compatible with simultaneous reaction and activation.

- FIG. 34, panel A: Reaction of nucleophiles with carbonyls. As a result of the nucleophilic substitution, the functional group R is translocated to the monomer building block initially carrying the nucleophile.
- FIG. 34, panel B: Nucleophilic attack by the amine on the thioester leads to formation of an amide bond, in effect translocating the functional group R of the thioester to the other monomer building block.
- FIG. 34, panel C: Reaction between hydrazine and β-ketoester leads to formation of pyrazolone, in effect translocating the R and R' functional groups to the other monomer building block.
- FIG. 34, panel D: Reaction of hydroxylamine with β-ketoester leads to formation of the isoxazolone, thereby translocating the R and R' groups to the other monomer building block.
- FIG. 35, panel E: Reaction of thiourea with β-ketoester leads to formation of the pyrimidine, thereby translocating the R and R' groups to the other monomer building block.
- FIG. 35, panel F: Reaction of urea with malonate leads to formation of pyrimidine, thereby translocating the R group to the other monomer building block.
- FIG. 35, panel G: Depending on whether Z=O or Z=NH, a Heck reaction followed by a nucleophilic substitution leads to formation of coumarin or quinolinon, thereby translocating the R and R' groups to the other monomer building block.
- FIG. 35, panel H: Reaction of hydrazine and phthalimides leads to formation of phthalhydrazide, thereby translocating the R and R' groups to the other monomer building block.
- FIG. 36, panel I: Reaction of amino acid esters leads to formation of diketopiperazine, thereby translocating the R group to the other monomer building block.
- FIG. 36, panel J: Reaction of urea with α-substituted esters leads to formation of hydantoin, and translocation of the R and R' groups to the other monomer building block.
- FIG. 36, panel K: Alkylation may be achieved by reaction of various nucleophiles with sulfonates. This translocates the functional groups R and R' to the other monomer building block.
- FIG. 36, panel L: Reaction of a di-activated alkene containing an electron withdrawing and a leaving group, whereby the alkene is translocated to the nucleophile.
- FIG. 37, panel M: Reaction of disulfide with mercaptane leads to formation of a disulfide, thereby translocating the R' group to the other monomer building block.
- FIG. 37, panel N: Reaction of amino acid esters and amino ketones leads to formation of benzodiazepinone, thereby translocating the R group to the other monomer building block.
- FIG. 37, panel O: Reaction of phosphonates with aldehydes or ketones leads to formation of substituted alkenes, thereby translocating the R" group to the other monomer building block.
- FIG. 38, panel P: Reaction of boronates with aryls or heteroaryls results in transfer of an aryl group to the other monomer building block (to form a biaryl).
- FIG. 38, panel Q: Reaction of arylsulfonates with boronates leads to transfer of the aryl group.
- FIG. 38, panel R: Reaction of boronates with vinyls (or alkynes) results in transfer of an aryl group to the other monomer building block to form a vinylarene (or alkynylarene).
- FIG. 39, panel S: Reaction between aliphatic boronates and arylhalides, whereby the alkyl group is translocated to yield an alkylarene.
- FIG. 39, panel T: Transition metal catalysed alpha-alkylation through reaction between an enolether and an arylhallide, thereby translocating the aliphatic part.
- FIG. 39, panel U: Condensations between e.g. enamines or enolethers with aldehydes leading to formation of alpha-hydroxy carbonyls or alpha,beta-unsaturated carbonyls. The reaction translocates the nucleophilic part.
- FIG. 40, panel V: Alkylation of alkylhalides by e.g. enamines or enolethers. The reaction translocates the nucleophilic part.
- FIG. 40, panel W: [2+4] cycloadditions, translocating the diene-part.
- FIG. 40, panel X: [2+4] cycloadditions, translocating the ene-part.
- FIG. 40, panel Y: [3+2] cycloadditions between azides and alkenes, leading to triazoles by translocation of the ene-part.
- FIG. 41, panel Z: [3+2] cycloadditions between nitriloxides and alkenes, leading to isoxazoles by translocation of the ene-part.

FIGS. 42 to 44 show pairs of reactive groups (X) and (Y), and the resulting bond (XY).

A collection of reactive groups that may be used for templated synthesis as described herein are shown, along with the bonds formed upon their reaction.

After reaction, cleavage may be required (e.g., see FIG. 8).

FIG. 45 shows a method of increasing the proximity effect of the template: The Zipper-box.

Panel A discloses linkers carrying oligonucleotide zipper boxes (a) and (b) that are complementary. By operating at a temperature that allows transient interaction of (a) and (b), the reactive groups X and Y are brought into close proximity during multiple annealing and strand-melting events, which has the effect of keeping X and Y in close proximity in a larger fraction of the time than otherwise achievable. Alternatively, one may cycle the temperature between a low temperature (where the zipper boxes pairwise interact stably), and a higher temperature (where the zipper boxes are apart, but where the anti-codon remains stably attached to the codon of the template). By cycling between the high and low temperature several times, a given reactive group X is exposed to several reactive groups Y, and eventually will react to form an XY bond. As a final alternative, the temperature may be kept appropriately low that the two strands of the zipper-box (a and b) are stably associated. Independent on which of these protocols is followed, the building blocks must be added to the reaction mix at an appropriately high temperature where the interaction between the codon and anti-codon is specific. Once the building blocks have been specifically associated with the template, the temperature can be lowered, and the alternative protocols described above followed, in order to achieve a high reaction efficiency.

When the anti-codon is an oligonucleotide (e.g., DNA, RNA) or oligonucleotide analog (e.g., PNA, LNA), it may be practical to use a continuous nucleotide strand, comprising both the anti-codon, linker and zipper-box (see (B) below).

Panel B shows sequences of two DNA oligo-based building blocks. The anti-codon ("annealing region"), linker and zipper-box are indicated. Thus, in this example, one linear DNA molecule constitutes the anti-codon, the linker that connects the functional entity and the anti-codon, and the zipper-box. The reactive groups X (a carboxylic acid) and Z (an amine) are coupled to the 3'-end of DNA oligo 1 and the 5'-end of DNA oligo 2, respectively. A template sequence to which oligo 1 and oligo 2 would anneal might contain the following sequence: 5'-CCGATGCAATCCAGAGGTCG-GCTGGATGCTCGACAGGTC.

FIG. 46 shows three methods of how the proximity effect can be increased:

FIG. 46, panel A: Helix stacking, FIG. 46, panel B Ligation and FIG. 46, panel C Rigid linkers.

FIG. 46, panel A: Helix stacking. Two building blocks with oligonucleotide-based anti-codons anneal to their respective codons (in the figure, the left building block is a "scaffold" that carries four reactive groups, and the right building block carries a functional entity with e.g. one reactive group, i.e., the latter building block may carry the substituent that will become attached to the scaffold. Double helices tend to stack, especially if the sequence of the opposing ends of the helices has been designed so as to optimize this interaction (for example by the presence of the sequence GGG at the ends of the duplex structures). This stacking tendency will bring the two building blocks into closer proximity, in turn increasing reaction efficiency between the functional entities. If the "substituent-building blocks" have anti-codons with lower melting temperatures than that of the "scaffold-building block", the substituent building block may be removed after its reaction with the scaffold building block, before the next building block is incorporated. In this way, the template region between two reacting building blocks may be kept single stranded, allowing this region to loop out and let the two duplex structures stack during the reaction between the two building blocks.

FIG. 46, panel B: Ligation of building blocks. The anti-codons of two building blocks may be chemically or enzymatically ligated together. Coupling of two anti-codons will increase the annealing efficiency. Therefore, smaller anti-codons can be used if ligated together with the previously incorporated building block. As an example, first add a building block (or just an 20-nucleotide DNA oligo) with a melting temperature of e.g. 60° C. Then add another building block (e.g., with a 8-nucleotide DNA anti-codon) with a low melting temperature and therefore only capable of transiently interacting with the template at the ambient temperature. If a DNA ligase is employed, or if the anti-codon can be ligated to the anti-codon of the first building block chemically, then the second building block will become firmly attached to the template, despite its short length of just 8 nucleotides. Thus, ligation allows the use of shorter anti-codons, which in turn brings the reactive groups into closer proximity.

FIG. 46, panel C: Rigid linkers. By using linkers comprising one or more flexible regions ("hinges") and one or more rigid regions, the probability of two functional entities getting into reactive contact may be increased.

a. Symbol used for building block with a rigid part and two flexible hinges.

b. A building block with the characteristics described in (a). The building block contains a continuous oligonucleotide-strand, constituting both the anti-codon (horizontal line), and linker (vertical line) connecting the functional entity (FE) with the anti-codon. Annealing of a complementary sequence to the central part of the linker leads to formation of a rigid double helix; at either end of the linker a single-stranded region remains, which constitutes the two flexible hinges.

FIG. 47 discloses various cleavable linkers. A number of cleavable linkers are shown, as well as the agents that cleave them and the products of the cleavage-reaction. In addition, catalysts including enzymes and ribozymes, may also be used to cleave the linker. Exemplary enzymes are proteases (e.g. chymotrypsin), nucleases, esterases and other hydrolases.

FIG. 48 shows two different ways of templated synthesis by generating a new reactive group. In cases where the reaction of X and Y leads to formation of a new reactive group Z, this may be exploited to increase the diversity of the templated molecule, by incorporating building blocks carrying reactive groups Q that react with Z. Using this approach, the templated molecules may be very compact structures, and thus, this approach describes a method to make highly substituted (functionalized and diverse) libraries of molecules of relatively low molecular weight.

FIG. 48, panel A: First, a building block carrying a reactive group X and a building block carrying a reactive group Y is incorporated, whereafter X and Y react, leading to the formation of the Z bond. Then a building block carrying a reactive group Q is added, whereafter Z reacts with Q, to form the ZQ bond. In this example, both the reaction of X with Y, and of Z with Q, are reactions that involve simultaneous reaction and cleavage.

FIG. 46, panel B: First, a building block carrying a reactive group X and a building block carrying a reactive group Y is incorporated, whereafter X and Y react, leading to the formation of the Z bond. Then a building block carrying a reactive group Q is added, whereafter Z reacts with Q, to form the ZQ bond. In this example, the reaction of Z with Q does not involve simultaneous cleavage, wherefore an additional step of linker cleavage is introduced.

FIG. 49, example 1, shows a templated synthesis by generating a new reactive group. The reaction of the functional entities of the first three building blocks leads to formation of two double bonds, which may react with two hydroxylamines carried in by the building blocks added in the latter steps, and leads to formation of an ester, which may react with the hydroxylamine, encoded by a building block. Finally, the linkers are cleaved, generating the templated molecule.

FIGS. 50 to 52 show different methods of performing post-templating modifications on templated molecule. After the templating process has been performed, the templated molecules may be modified to introduce new characteristics. This list describes some of these post-templating modifications.

FIG. 53 illustrates one preferred method for selection of template-displaying molecules.

FIGS. 54 to 58 show the proposed complexes that may form when a reaction step is performed using set-ups that allow for stacking of DNA duplexes.

FIG. 59 shows a autoradiography of a polyacrylamide gel analysis of the reaction between building blocks.

FIG. 60 shows the Feuston 3 functional entity as well as the Feuston 5 ligand. Structure 1 shows the Feuston 3 functional entity, which is needed together with Gly and Asp to create Feuston 5 (structure 2). Feuston 5 (structure 2) is a ligand that binds to the $\alpha v \beta_3$ integrin receptor (as described in press; Feuston BP et al. J Med Chem. 2002 Dec. 19;45(26):5640-8)

FIG. 61 shows the structure of the pentenoyl protected aspartate entity used to load an amino modified scaffold oligo, to create the Feuston 5 ligand.

FIG. 62 shows the use of allylglycine building blocks.

FIG. 63 shows the autoradiography of a polyacrylamide gel. The autoradiography shows the three transfers of β-Ala to an amino modified scaffold oligo, this scaffold oligo being radioactively labeled. Lanes 1, 3 and 5 shows cross-linked product between scaffold amine and functional entity β-Ala AG carboxylic acid fortransfers 1, 2 and 3. Lanes 2, 4 and 6 shows cleaved product, i.e. scaffold carming the transferred functional entity.

FIG. 64 shows an Elisa analysis of the product of the two-step encoding process. The result is from an ELISA done on the feuston 5 ligand generated by seguential transfers to a scaffold oligo (first column). The controls are the RGD peptide, which is an Integrin II and (second column;) loaded on a 20 mer oligo and uncoated wells (no Integrin immobilized; third and fourth columns).

EXAMPLES

In the following examples, building blocks are used which contain a zipper box adjacent to the functional entity. The zipper box sequences are underlined below. The following buffers and protocols are used in the same three examples.

Buffers.
Buffer A (100 mM Hepes pH=7.5; 1 M NaCl)
Buffer B (20 mM Hepes pH=7.5; 200 mM NaCl)
5'-Labeling with $^{32}$P.

Mix 5 pmol oligonucleotide, 2 µl 10× phosphorylation buffer (Promega cat#4103), 1 µl T4 Polynucleotide Kinase (Promega cat#4103), 1 µl γ-$^{32}$P ATP, add H$_2$O to 20 µl. Incubate at 37° C. 10-30 minutes.

PAGE (polyacrylamide gel electrophoresis).

The samples are mixed with formamide dye 1:1 (98% formamide, 10 mM EDTA, pH 8, 0.025 % Xylene Cyanol, 0.025% Bromphenol Blue), incubated at 80° C. for 2 minutes, and run on a denaturing 10% polyacrylamide gel. Develop gel using autoradiography (Kodak, BioMax film).

Example 1

The Effect of Alternating Temperature on Reaction Efficiency in the Zipper Box System.
DNA-oligos:
X=Carboxy-dT (Glen Research, cat.no. 10-1035)
6=Amino-Modifier 5 (cat. Nr. 10-1905)

AH 316:
(SEQ ID NO: 1)
5'- 6GTAACAGACCTGTCGAGCATCCTGCT

AH 331:
(SEQ ID NO: 2)
5'-CGACCTCTGGATTGCATCGGTGTTACX

AH140:
(SEQ ID NO: 3)
5'-AGCTGGATGCTCGACAGGTCAGGTCGATCCGCGTTACCAGTCTTGCC
TGAACGTAGTCGTCCGATGCAATCCAGAGGTCG

Experimental.

Mix 10 µl Buffer A, 1 pmol AH 331 ($^{32}$P-labelled), 10 pmol AH 316, 5 pmol AH 140, and add H$_2$0 to 50 µl.

Anneal from 80° C. to 30° C. (−1° C./30 sek). Then dilute 100 times in buffer B +50 mM DMT-MM. (Prepared according to Kunishima et al. *Tetrahedron* (2001), 57, 1551) dissolved in ddH$_2$O.

Incubate at one of 8 different temperature profiles o/n (6 different constant temperatures ( 15° C.; 17.8° C.; 22.7° C.; 28.3° C.; 31.0° C.; or 35.0° C.; or alternating between 10° C. for 5 sec. and 35° C. for 1 sec.); or alternating between 20° C. for 5 sec. and 45° C. for 1 sec). Analyze by 10% urea polyacrylamide gel electrophoresis.

Results.

The polyacrylamide gel analysis showed that a more efficient reaction results from alternating the temperature between 10 ° C. and 35 ° C., rather than performing the reaction at a constant temperature of 15° C., 17.8° C., 22.7° C., 28.3° C., 31.0° C., or 35.0° C.

Example 2

The Effect of Stacking on Reaction Efficiency.
DNA-oligos:
X=Carboxy-dT (cat.no. 10-1035)
Z=Amino-Modifier C6 dT (cat.no. 10-1039)
6=Amino-Modifier 5 (cat.no. 10-1905)

AH36:
(SEQ ID NO: 4)
5'-CGACCTCTGGATTGCATCGGTCATGGCTGACTGTCCGTCGAATGTGT
CCAGTTACX

AH38:
(SEQ ID NO: 5)
5'- AGCTGGATGCTCGACAGGTCCCGATGCAATCCAGAGGTCG

AH51:
(SEQ ID NO: 6)
5'-ZGTAACACCTGTGTAAGCTGCCTGTCAGTCGGTACTGACCTGTCGA
GCATCAGCT

AH137:
(SEQ ID NO: 7)
5'-ACGACTACGTTCAGGCAAGA

AH138:
(SEQ ID NO: 8)
5'-TCTTGCCTGAACGTAGTCGTAGGTCGATCCGCGTTACCAGAGCTGGA
TGCTCGACAGGTCCCGATGCAATCCAGAGGTCG

AH139:
(SEQ ID NO: 9)
5'-CGACCTCTGGATTGCATCGG

AH143:
(SEQ ID NO: 10)
5'-CTGGTAACGCGGATCGACCTTCATTTTTTTTTTTTTTTTTTTTGGC
TGACTGTCCGTCGAATGTGTCCAGTTACX

-continued

AH 202:
(SEQ ID NO: 11)
5'-TCTGGATTGCATCGG<u>GTTAC</u>X

AH 270:
(SEQ ID NO: 12)
5'-6<u>GTAAC</u>GACCTGTCGAGCATCCAGCT

AH 286:
(SEQ ID NO: 13)
5'-AGCTGGATGCTCGACAGGTCAAGTAACAGGTCGATCCGCGTTATATC

GTTTACGGCATTACCCGTATAGCCGCTAGATGCCCAACCATGACGGCCCA

TAGCTTGCGGCTTGC

AH 320:
(SEQ ID NO: 14)
5'-AGCTGGATGCTCGACAGGTCAGGTCGATCCGCGTTACCAGGCCCATA

GCTTGCGGCTTGCTGCAGTCGATGGACCATGCCTCTTGCCTGAACGTAGT

CGTCCGATGCAATCCAGAGGTCG

AH 321:
(SEQ ID NO: 15)
5'-CAAGAGGCAT

AH 322:
(SEQ ID NO: 16)
5'-TCAGGCAAGAGGCATGGTCC

AH 342:
(SEQ ID NO: 17)
5'-TACTTGACCTGTCGAGCATC<u>GTTAC</u>X

AH 343:
(SEQ ID NO: 18)
5'-6<u>GTAAC</u>CAGCTGCAAGCCGCAAGCTATGGGC

Experimental.

Mix buffer A and relevant oligos (see table below).

| Experiment | Oligo 1 ($^{32}$P-labelled) | Oligo 2 | Oligo 3 Template | Oligo 4 | Oligo 5 | Buffer A | H$_2$O to |
|---|---|---|---|---|---|---|---|
| 1 | 5 pmol AH 36 | 10 pmol AH 51 | 10 pmol AH 38 | | | 2 µl | 10 µl |
| 2 | 5 pmol AH 143 | 10 pmol AH 51 | 10 pmol AH 138 | 10 pmol AH 139 | 10 pmol AH 137 | 2 µl | 10 µl |
| 3 | 1 pmol AH 202 | 10 pmol AH 270 | 5 pmol AH 320 | | | 10 µl | 50 µl |
| 4 | 1 pmol AH 36 | 10 pmol AH 51 | 5 pmol AH 320 | | | 10 µl | 50 µl |
| 5 | 1 pmol AH 202 | 10 pmol AH 270 | 5 pmol AH 320 | 50 pmol AH 321 | | 10 µl | 50 µl |
| 6 | 1 pmol AH 36 | 10 pmol AH 51 | 5 pmol AH 320 | 50 pmol AH 321 | | 10 µl | 50 µl |
| 7 | 1 pmol AH 202 | 10 pmol AH 270 | 5 pmol AH 320 | 50 pmol AH 322 | | 10 µl | 50 µl |
| 8 | 1 pmol AH 36 | 10 pmol AH 51 | 5 pmol AH 320 | 50 pmol AH 322 | | 10 µl | 50 µl |
| 9 | 0.2 pmol AH 342 | 2 pmol AH 343 | 1 pmol AH 286 | | | 2 µl | 10 µl |
| 10 | 0.2 pmol AH 342 | 2 pmol AH 343 | 1 pmol AH 286 | 4 pmol AH 356 | | 2 µl | 10 µl |
| 11 | 0.2 pmol AH 342 | 2 pmol AH 343 | 1 pmol AH 286 | 4 pmol AH 357 | 4 pmol AH 358 | 2 µl | 10 µl |

Anneal from 80° C. to 30° C. (−1° C./min). Add 0.5 M DMT-MM. (Prepared according to Kunishima et al. *Tetrahedron* (2001), 57, 1551) dissolved in H$_2$O. to a final concentration of 50 mM. Incubate at 10° C. for 5 sec. and then 25° C. for 1 sec. Repeat o/n.

Analyze by 10% urea polyacrylamide gel electrophoresis. Results.

Figure 54:
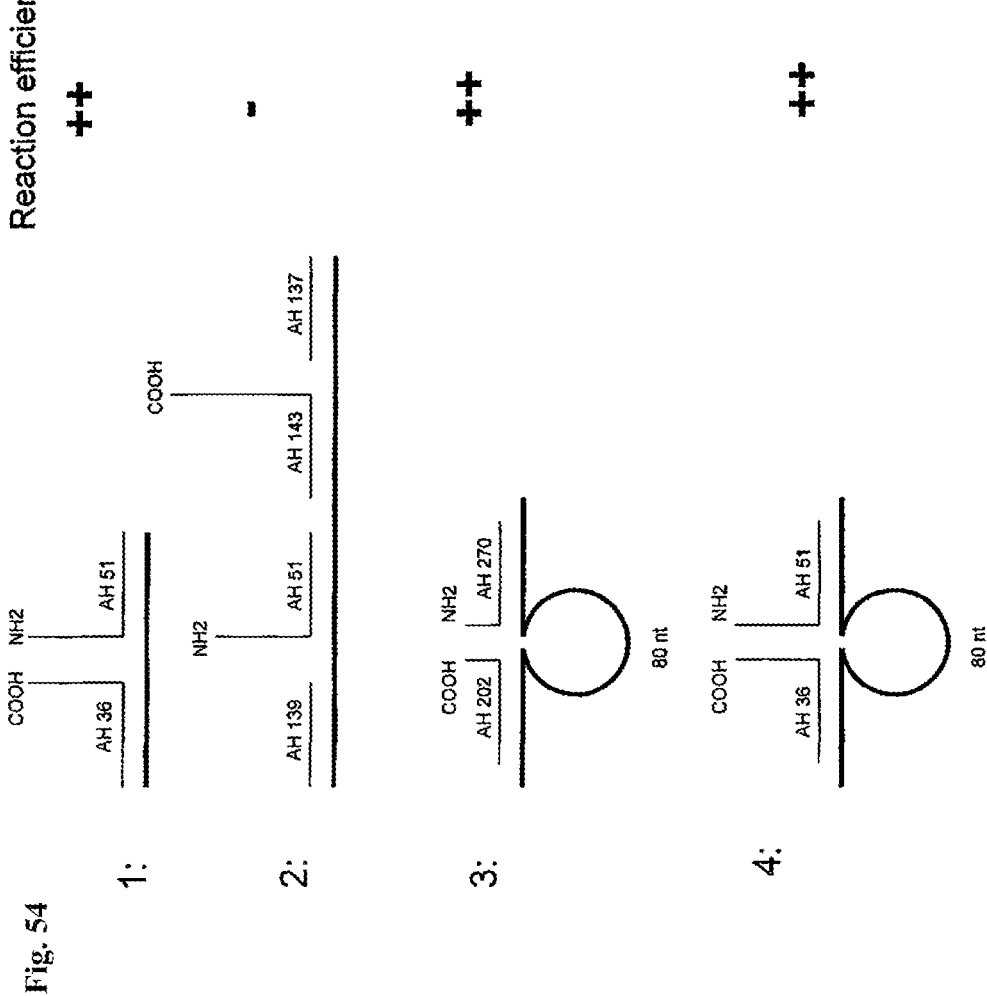
Figure 55:
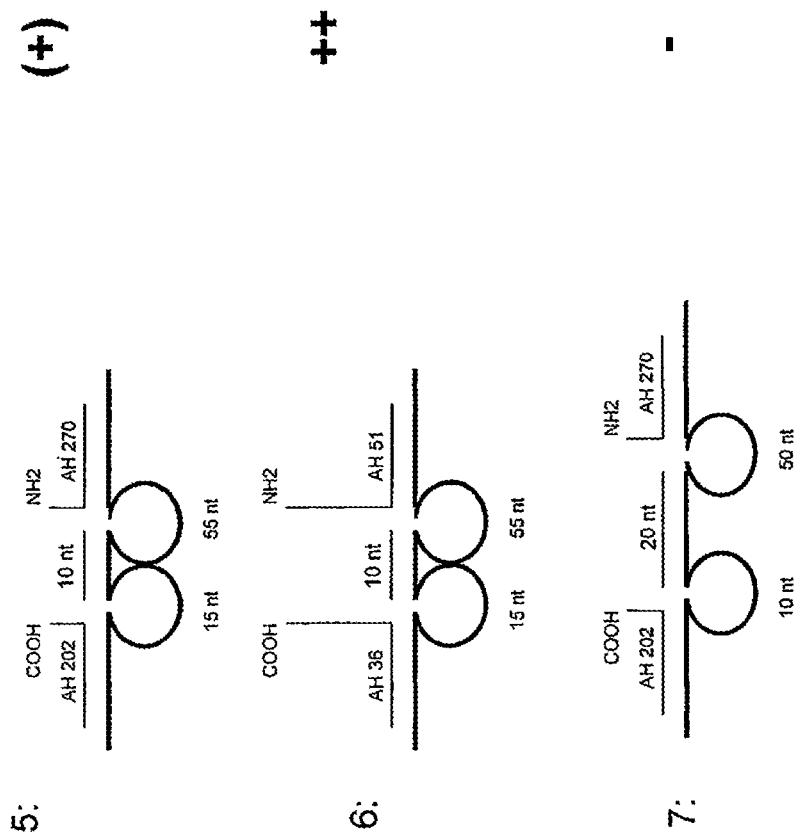

In order to test the effect of stacking of DNA duplexes on reaction efficiency, we designed a number of different set-ups of templates and building blocks (see FIGS. 54 to 58). The following conclusions were reached:

FIG. 54, panel 1 and FIG. 59, lane 1: Reference reaction between two building blocks annealed to adjacent sites on the template. As expected an efficient reaction is observed. In this set-up, the two building blocks anneal to the template and thereby form DNA duplexes that can stack onto each other.

FIG. 54, panel 2 and FIG. 59, lane 2: In this set-up, the two building blocks anneal to adjacent sites on the template. However, the two DNA-duplexes stack onto each other, basically forming one long DNA duplex. This rigid duplex does not allow the two building blocks to bend around the flexible hinge that might otherwise be present at the connection point between the two duplexes (i.e. the position of the nick in the DNA). Consequently, no significant reaction between the two building blocks is observed.

FIG. 54, panel 3 and FIG. 59, lane 3; and FIG. 54, panel 4 and FIG. 59, lane 4: Despite the fact that the two building blocks anneal to sites separated by 80 nucleotides, the reaction is still very efficient. We speculate that this is because of stacking, i.e. the intervening 80 nucleotides are looped out as a consequence of this, and therefore, the two functional entities are brought into close proximity.

In the experiment of FIG. 59, lane 3 the linker that connects the functional entity to the complementing element is short (5 nucleotides); in FIG. 59, lane 4 it is long (35 nucleotides). However, both linker lengths result in an efficient reaction.

FIG. 54, panel 5 and FIG. 59, lane 5; and FIG. 54, panel 6 and FIG. 59, lane 6: The annealing sites and separation between them are identical to those of the experiment described above (FIG. 54, panels 3 and 4; FIG. 54, lanes 3 and 4). In addition, a short oligo (10 nucleotides) has been annealed to the central region of the template. This result in a drastic decrease in reaction efficiency for the building blocks with the short linkers (lane 5); the reaction efficiency of the building blocks with the long linkers is only slightly affected if at all by the annealing of the short oligo. As indicated by the suggested structure of the complexes (FIG. 54, panels 5 and 6), we believe this is because of stacking of the 3 DNA duplexes to generate an "extended" duplex: The short linkers cannot reach across the extended duplex; the long linkers can reach across the extended duplex structure and the reaction efficiency is not significantly affected.

FIG. 54, panel 7 and FIG. 59, lane 7; and FIG. 54, panel 8 and FIG. 59, lane 8: As immediately above, except that a 20 nucleotide long oligo is annealed to the central region of the template. In this case none of the linkers (short or long) can reach across the extended duplexes, and as a result no or little reaction is observed.

Figure 56:
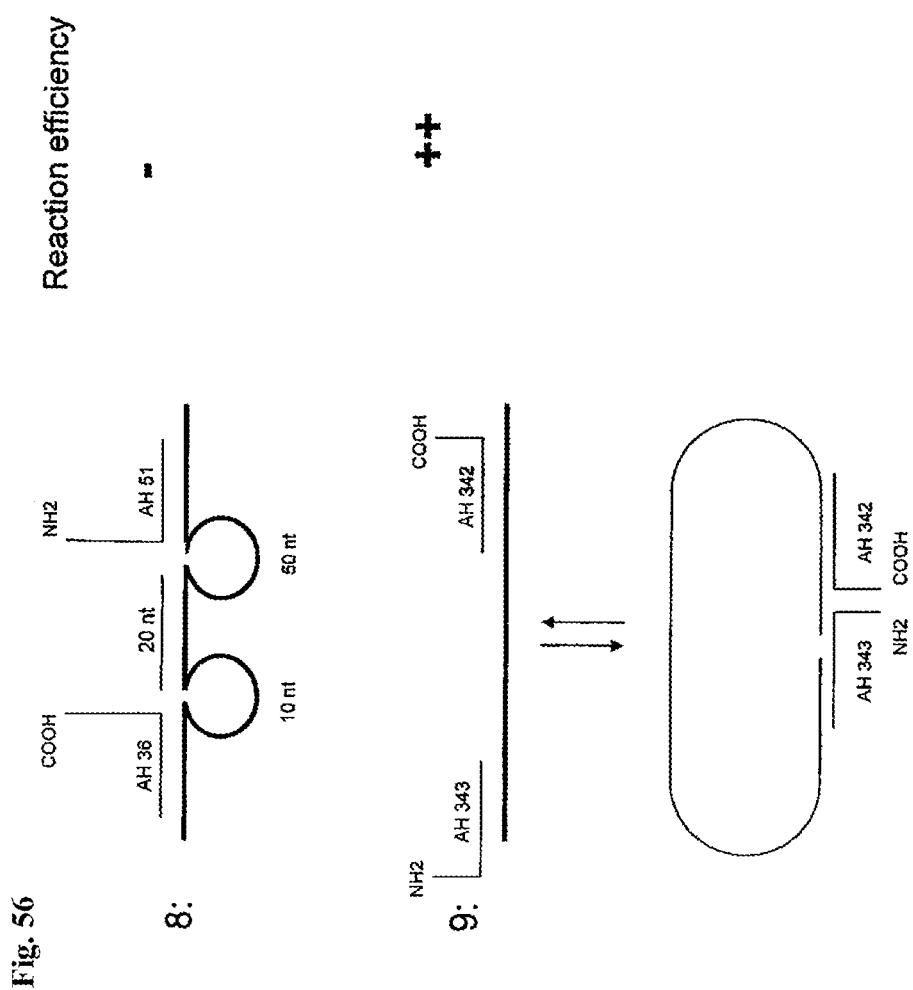
Figure 57:
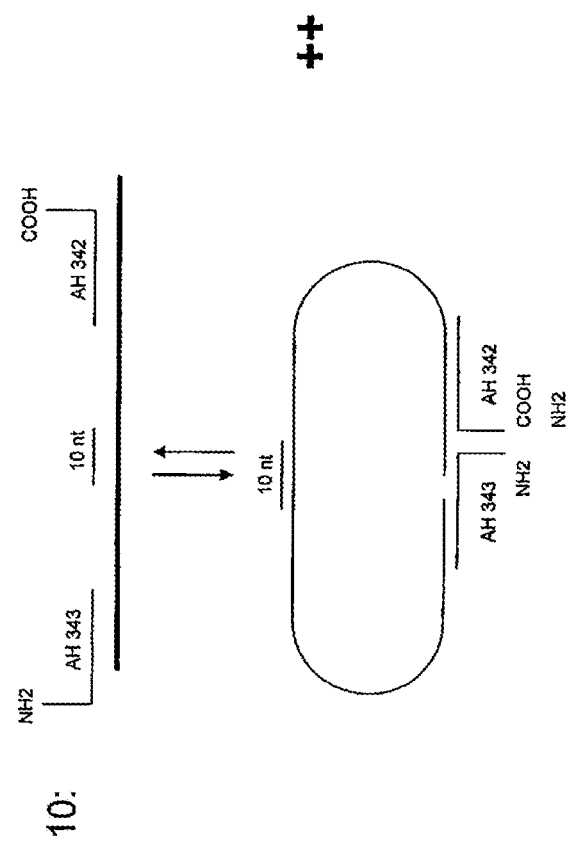
Figure 58:
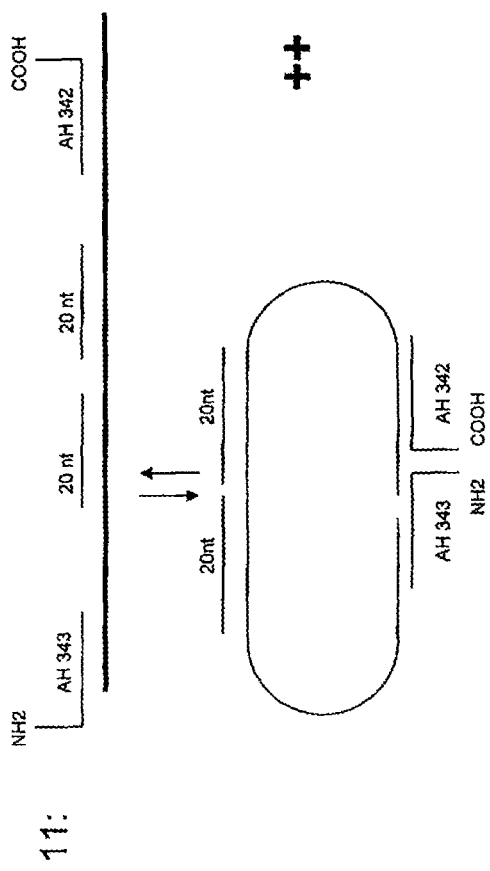

FIG. 54, panel 9 and FIG. 59, lane 9; FIG. 54, panel 10 and FIG. 59, lane 10; and FIG. 54, panel 11 and FIG. 59, lane 11: In these experiments the building blocks are oriented the "other way", i.e. the linker connecting the complementing element and the functional entity is near the ends of the template. Additionally, the complementing element of the left building block contains a 5-nucleotide sequence that is complementary to other right end of the template. As a result, the building block should be capable of circularizing the template, as depicted in FIGS. 56 to 58, panels 9-11. These circular structures should also be stabilized by an extended duplex structure across the ends of the template. In the experiments of lanes 10 and 11, a short oligo (10 nucleotides) or two longer oligos (each 20 nucleotides) are annealed to the central region. This has no effect on the reaction efficiency, in correlation with the proposal that the building blocks stack onto each other through a circularization of the template, thereby bringing the functional entities into close proximity.

Example 3

Single Step Transfers of Functional Entities.

DNA-Oligos:

7=Thiol-Modifier C6 S-S (Glen Research, cat.no.10-1936)

Z=Amino-Modifier C6 dT (10-1039)

P=PC Spacer (10-4913)

AH136:
(SEQ ID NO: 19)
5'-AGCTGGATGCTCGACAGGTCTCTTGCCTGAACGTAGTCGTCCGATGC

AATCCAGAGGTCG

AH 174:
(SEQ ID NO: 20)
5'-TACGTTCAGGCAAGAGT6CCAGTTAC7

AH 190:
5'- ZGTAACACCTGPTGACCTGTCGAGCATC (SEQ ID NO: 21 up to the P and SEQ ID NO: 39 after the P)

Experimental:

Loading of NHM on the DNA-oligo:

Dry 10 nmol DNA oligo (AH174) and then resuspended in 50 µl 100 mM DTT (1,4-Dithio-L-Threitol D-9760 Sigma) in 50 mM Phosphate buffer pH=8. Incubate at 37° C. for 1 hour.

Purification on Microspin G-25 (Amersham Biosciences, 27-5325-01).

Add 50 µl 200 mM NHM ( N-Hydroxymaleimide Fluka 55510) and incubate at 25° C. for 2 hours.

Purification on Microspin G-25 equilibrated in $H_2O$.

Loading of building blocks (4-pentenoic-acid, β-ala-Boc or $CH_3COOH$) on the NHM-DNA-oligo:

Mix 50 µl 100 mM EDC and 50 p 100 mM building block. Incubate at 25° C. for 30 minutes.

Then mix 500 pmol NHM-DNA-oligo (AH174-NHM) and 10 µl of the EDC/building block mix from above. Add 100 mM MES pH=6 to 20 µl. Incubate at 25° C. for 5 minutes.

Purification on Micro Bio-Spin Chromatography Columns P6 (Bio-Rad 732-6221) equilibrated in 100 mM MES pH=6.

Transfers:

Mix 350 pmol AH136, 300 pmol AH190 and 500 pmol building block loaded AH 174. Add Buffer A to 50 µl.

Anneal from 60° C. to 25° C. (−1° C./30 sec.)

Incubate at 10° C. for 5 sec. and then 25° C. for 1 sec. Repeat o/n.

Purification on Micro Bio-Spin Chromatography Columns P6 equilibrated in $H_2O$.

Results:

The transfers were analyzed by MS, see table below. Transfer efficiencies of 20-34% were observed.

| Transfer efficiency | | |
| --- | --- | --- |
| 4-pentenoic-acid | β-ala-Boc | $CH_3COOH$ |
| 33–34% | 20–23% | 29–33% |

Example 4

Multistep Transfer of Functional Entities to a Scaffold Oligonucleotide

In this example three functional entities are transferred to an amino modified scaffold oligo by a three step reaction, and analyzed by a denaturing acrylamide gel using radio labelling.

Loading of Functional Entities on Modified Oligonucleotides to Create Building Blocks.

5 nmoles of three carboxylic acid modified building block oligos [AH 155; 5'CTG GTA ACG CGG ATC GAC CTG TTA CT-COOH 3', SEQ ID NO:22; AH 272 5'ACG ACT ACG TTC AGG CAA GAG TTA CT-COOH 3', SEQ ID NO:23; and AH 202 5'-TCT GGA TTG CAT CGG CTG TTA CT-COOH 3', SEQ ID NO:24] (all oligonucleotides described ordered from DNA technology, Aarhus, Denmark) one from each of the three positions corresponding to the template were loaded with β-Alanine methyl ester coupled to allylglycine n-Boc followed by Boc deprotection (β-AlaOMe AG). The loading was done by incubating each of the oligos with 10 mM β-AlaOMe AG, 75 mM DMT-MM in 150 mM Hepes-OH buffer, pH 7.5 to a final volume of 50 µl at 25° C. shaking overnight. Then adding 5 µl 1 M $NH_4$-acetate, incubated at 25° C. for 10 min, then spin column purified with $ddH_2O$ equilibrated columns (Micro Bic-Spin chromatography columns P-6, Bio-Rad). The deprotection of the methyl group protected acid was done by adding 0.5 µl 2M NaOH to the oligos and incubating for 10 min. at 80° C. Lastly the oligos were spin column purified and loadings confirmed by mass spectrophotometry.

Transfers of Functional Entities to Scaffold Oligo.

In order to be able to analyze the functional entity transfers using acrylamide gel analysis, the scaffold oligo [MDL251 5'amino-C6 dT-ACC TGT CGA GCA TCC AGC T 3', SEQ ID NO:25] was radioactively labelled in the 3' end. 50 pmol of the oligo was labelled with 10 µl ddATP αP32 (Amersham Biosciences) by adding 4 µl 10×NEbuffer 4, 4µl 10×CoCl2 and 35 units of terminal deoxynucleotide transferase (New England Biolabs) and water to a final volume of 40 µl. Mixture incubated at 37° C. for 1 hour. Labeled oligo purified using ddH2O equilibrated spin column.

12.5 pmol of the labeled scaffold oligo, 125 pmol loaded building block oligo AH 202, corresponding to position three on the template and 62.5 pmol template [AH 154 5' AGC TGG ATG CTC GAC AGG TCA AGT AAC AGG TCG ATC CGC GTT ACC AGT CTT GCC TGA ACG TAG TCG TCC GAT GCA ATC AGG AGG TCG 3' as follows, SEQ ID NO:26] was incubated in a final volume of 45 µl containing 20 mM Hepes-OH pH 7.5, 200 mM NaCl buffer. The oligos were annealed by heating to 80° C. and slowly going down to 20° C. (1°/min) using a thermocycler (Eppendorf, Mastergradient) Following the annealing 5 µl 0.5M DMT-MM was added. Sample crosslinked, see FIG. 32 overnight cycling at 10° C. 10 sec/35° C. 1 sec.

The sample was spin column purified and the crosslinked product cleaved to give first transfer of β-Ala to scaffold oligo amine by adding 10 µl 25 mM I2 dissolved in 1:1 tetrahydrofuran:H2O and incubated at 37° C. for 1.5 hours. Followed by addition of 1.5 µl M β-mercapotethanol and then purified with two equilibrated spin columns. The sample was completely dried down and oligos redissolved in 30 µl ddH20. Transfer 2, oligo AH 272 and transfer 3, AH 202 were done in the exact same way as just described including the annealing, crosslinking and cleavage. For each remaining round adding same amount of building block oligo, 125 pmol.

Samples for analysis were taking out along the way, before and after crosslinking for the three transfers, which were analyzed on a 10% acrylamide denaturing gel, see FIG. 63. As can be seen, crosslinking efficiency (step 1) was approximately 50% (FIG. 63, lane 1). This was followed by an almost 100% efficient cleavage (lane 2), which results in the transfer of the β-Ala moiety onto the scaffold. This is followed by the crosslinking/cleavage of step 2 and 3 (lanes 3+4, 5+6) to generate the final product on the scaffold oligo. The product thus contains the three transferred β-Ala moieties.

Example 5

Two-step Transfer and Functional Analysis by ELISA.

In this example two entities are transferred to a scaffold oligo by a two-step reaction to produce a ligand, Feuston 5 (see FIG. 60) that binds to the αVβ3 integrin receptor. The product of the two-step process was analyzed by Elisa.

Loading of Functional Entities on Modified Oligonucleotides to Create Building Blocks.

Two building block oligos were used, AH 155 (see above) loaded with Feuston 3 allylglycine. Feuston 3 is a derivative of the Feuston 5 ligand see FIG. 60 (F3OMeAG) and AH 272 (see above) loaded with glycine allylglycine (GlyOMeAG) according to the above protocol (example Xa) for loadings of allylglycine functional entities to carboxylic acid modified oligos. 10 nmoles of each was loaded in two reactions each.

To create the Feuston 5 ligand aspartate is also needed. Therefore aspartate which was loaded as a pentenoyl (amine) and methyl (carboxylic acid) protected functional entity see FIG. 61, to an amino modified scaffold oligo [AH 270 ;5' amino-GTA ACG ACC TGT CGA GCA TCC AGC T 3', SEQ ID NO:27]. The loading was done by mixing 25 µl 150 mM EDC (N-(3-Dimethylaminopropyl)-N'-ethylcarbodiimide hydrochloride, Fluka), 25 µl NHS (N-hydroxysuccinimide, Sigma) and 5 µl 100 mM of the pentenoyl protected. aspartate functional entity, all reagents were dissolved in N,N-dimethylformamide, DMF. Incubated at 25° C. for 40 min. To this mixture 5 nmol of the scaffold oligo, AH 270 resuspended in 30 µl 150 mM Hepes-OH pH 7.5 was added and this incubated shaking over night at 25° C. The amine pentenoyl protection group was deprotected by adding 20 µl 25 mM I2 dissolved in 1:1 tetrahydrofuran: water and incubated at 37° C. for 2 hours. Followed by spin column purification, and loading confirmed by mass spectrum analysis.

Transfers of Functional Entities to Scaffold Oligo.

The transfers were done in the same manner as described above, but using larger amounts of oligo to ensure there being enough ligand created to give a sufficient signal in the ELISA. For the first round the following amounts were used: 850 pmol loaded scaffold oligo; AH 270, 7500 pmol loaded building block oligo; AH 272 and 3250 pmol template oligo AH 140 [5' AGC TGG ATG CTC GAC AGG TCA GGT CGA TCC GCG TTA CCA GTC TTG CCT GAA CGT AGT CGT CCG ATG CAA TCC AGA GGT CG 3', SEQ ID NO:28]. The second round, adding 7500 pmol loaded building block oligo AH 155 for a transfer.

The created Feuston 5 ligand on the scaffold oligo still had a methyl group protected acid on the aspartate, which was deprotected just as described before. By adding 0.5 µl 2 M NaOH to the oligos and incubating at 80° C. for 10 min. The sample this time though was pH calibrated with 0.5 µl 2 M HCl and was now ready for the ELISA analysis.

ELISA assay

Maxisorb plates (Nunc Immunomodule U8 Maxisorp. Biotecline) were coated with αVβ3 integrin receptor 0.1 µg/well in PBS over night at 4° C. The wells were blocked with 300 µl blocking buffer containing PBS, 0.05% Tween 20 (Sigma), 1% BSA (Sigma), 0.1 mg/mL herring sperm DNA (Sigma), for 3 hours at room temperature. Wells were washed 5*300 µl using wash buffer containing PBS, 0.05% Tween 20, 1% BSA. The sample prepared above containing the displayed Feuston 5 ligand on a scaffold oligo was added to a well, control for the experiment being a 20 mer oligo loaded with the RGD peptide, a well known and well described ligand for this integrin receptor (loaded according to above described method for the pentenoyl and methyl protected aspartate functional entity). The incubation with these ligands was done in ligand binding buffer containing PBS, 1 mM MnCl2, 1 mg/mL BSA at room temperature for one hour. Washed in washing buffer 5*300 µl. Incubated with 100 µl horseradish peroxidase-streptavidine (Endogen) diluted 1:10000 times in wash buffer, incubated for one hour at room temperature. Washed again in 5*300 µl wash buffer. 100 µl 3,3',5,5'-tetrametylbenzidine hydrogenperoxidase (TMB substrate, Kem-en-tec) added and incubated at room temperature until color development. 100 µl 0.2 M sulphuric acid added, color measured at 450 nm, see FIG. 64. As can be seen the Feuston 5 ligand generated by the two-step encoding procedure is active and binds the integrin receptor with relatively high efficiency.

The invention claimed is:

1. A library comprising different complexes, said complexes comprising a first entity and a second entity, wherein
the first entity comprises a double stranded oligonucleotide identifier comprising single oligonucleotide strands covalently linked by a first linker, each single strand containing from 12 to 400 nucleic acid monomers, wherein at least one nucleic acid monomer of each single strand is a deoxyribonucleotide,
wherein the second entity comprises a small non-peptide molecule and a second linker, the second linker being distinct from the first linker and covalently linking the first entity to the small-non-peptide molecule of the second entity,
wherein the small non-peptide molecule of the second entity can be identified by each and both strands of the double stranded oligonucleotide identifier of the first entity, and
wherein the small non-peptide molecule is covalently linked to the double stranded identifier oligonucleotide via an anchorage point located at a terminal region of one of the single strands.

2. The library according to claim 1, wherein the small non-peptide molecule of the complexes of the library is selected from the group consisting of monofunctional, difunctional,trifunctional and oligofunctional open-chain hydrocarbons;
monofunctional, difunctional,trifunctional and oligofunctional non-aromatic carbocycles;
monocyclic, bicyclic, tricyclic and polycyclic hydrocarbons; bridged polycyclic hydrocarbons;
monofunctional, difunctional, trifunctional, and oligofunctional non-aromatic heterocycles;
monocyclic, bicyclic, tricyclic, and polycyclic heterocycles, bridged polycyclic heterocycles;
monofunctional, difunctional,trifunctional and oligofunctional aromatic carbocycles;
monocyclic, bicyclic, tricyclic, and polycyclic aromatic carbocycles; and
monofunctional, difunctional,trifunctional and oligofunctional aromatic heterocycles.

3. The library of claim 1, wherein the number of complexes is from 2 to $10^{18}$.

4. The library of claim 1, wherein the individual nucleic acid monomers of the covalently linked oligonucleotide identifier comprise a nucleobase moiety and a sugar moiety and an internucleoside linker.

5. The library of claim 4, wherein the nucleobase moiety of the nucleic acid monomers is a natural nucleobase moiety.

6. The library of claim 5, wherein the nucleobase moieties are selected from the group consisting of deoxyadenosine, deoxyguanosine, deoxythymidine, deoxycytidine, adenosine, guanosine, uridine, cytidine and inosine.

7. The library of claim 4, wherein the sugar moiety of the nucleic acid monomers is a pentose.

8. The library of claim 7, wherein the pentose is selected from the group consisting of ribose, 2'-deoxyribose, 2'-O-methyl-ribose, 2'-flouro-ribose, and 2'-4'-O-methylene-ribose.

9. The library of claim 1, wherein the internucleoside linker linking the individual nucleic acid monomers is a phosphodiester linker.

10. The library according to claim 1, wherein the first and/or second linker is selected from the group consisting of carbohydrides, substituted carbohydrides, vinyl, polyvinyl, substituted polyvinyl, acetylene, polyacetylene, aryl /hetaryl, polyaryl/hetaryl and substituted polyaryl/polyhetaryl, ethers, polyethers, amines, polyamines, substituted polyamines; double stranded, single stranded or partially double stranded natural and unnatural polynucleotides, substituted double stranded, single stranded or partially double stranded natural and unnatural polynucleotides, polyamides, natural and un-natural polypeptides, substituted polyamides, and substituted natural and unnatural polypeptides.

11. The library according to claim 1, wherein said first and/or second linker comprises a polynucleotide linker.

12. The library according to claim 1, wherein said first and/or second linker comprises a polyether linker.

13. The library according to claim 12 wherein said first and/or second linker comprises a polyethyleneglycol linker.

14. The library according to claim 12 wherein said first and/or second linker comprises a substituted polyether linker.

15. The library of claim 4, wherein the nucleobase moiety of the nucleic acid monomers is selected from the group consisting of adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C_3$-$C_6$)-alkynylcytosine, 5-fluorouracil, 5- bromouracil, pseudoisocytosine, 2-hydroxy-5-methyl-4-triazolopyridine, isocytosine, isoguanine, and inosine.

16. The library of claim 1, wherein the first linker of the double stranded identifier oligonucleotide comprises a hair-pin loop of nucleotides covalently linking the two strands of the double stranded identifier oligonucleotide at one end of the strands.

17. The library of claim 1, wherein the small non-peptide molecule is covalently linked to the double stranded identifier oligonucleotide via an anchorage point located at a first terminal region of one of the single strands, and wherein the first linker comprises a hair-pin loop of nucleotides covalently linking the two strands of the double stranded identifier oligonucleotide at a different, second terminal region of the single strands.

18. A method for the enrichment of the library according to claim 1 for small non-peptide molecules having a predetermined activity or functionality, said method comprising the steps of:
(i) subjecting said library one or more times to an enrichment condition, and
(ii) obtaining an enriched library having a higher relative amount of small non-peptide molecules having said predetermined activity or functionality.

19. The method of claim 18, wherein the oligonucleotide identifiers of the enriched complexes are amplified.

20. The method of claim 18, wherein the small non-peptide molecules of the enriched library are identified by sequencing the oligonucleotide identifier.

21. The method of claim 18, wherein the enrichment condition is an affinity of the small non-peptide molecules of the library of claim 1 for a target molecule or target entity.

22. The library according to claim 11, wherein each of the first and the second linker comprises a polynucleotide linker.

23. The library according to claim 12, wherein each of the first and the second linker comprises a polyether linker.

24. The library according to claim 13, wherein each of the first and the second linker comprises a polyethyleneglycol linker.

25. A library comprising different complexes, wherein each complex comprises
i) a first entity comprising a double stranded oligonucleotide identifier comprising single oligonucleotide strands covalently linked by a first linker,
ii) a second entity comprising a small non-peptide molecule, and
iii) a second linker covalently linking the first entity to the small non-peptide molecule of the second entity,
wherein the small non-peptide molecule of the second entity can be identified by each and both of the single strands of the double stranded oligonucleotide identifier of the first entity, wherein the small non-peptide molecule is covalently linked to the double stranded identifier oligonucleotide via an anchorage point located at a terminal region of one of the single strands.

26. The library according to claim 25, wherein the small non-peptide molecule of the complexes of the library is selected from the group consisting of
monofunctional, difunctional, trifunctional and oligofunctional open-chain hydrocarbons;
monofunctional, difunctional, trifunctional and oligofunctional non-aromatic carbocycles;
monocyclic, bicyclic, tricyclic and polycyclic hydrocarbons; bridged polycyclic hydrocarbons;
monofunctional, difunctional, trifunctional, and oligofunctional non-aromatic heterocycles;
monocyclic, bicyclic, tricyclic, and polycyclic heterocycles, bridged polycyclic heterocycles;
monofunctional, difunctional, trifunctional and oligofunctional aromatic carbocycles;
monocyclic, bicyclic, tricyclic, and polycyclic aromatic carbocycles; and monofunctional, difunctional, trifunctional and oligofunctional aromatic heterocycles.

27. The library of claim 25, wherein the number of complexes is from 2 to $10^{18}$.

28. The library of claim 25, wherein the individual nucleic acid monomers of the covalently linked oligonucleotide identifier comprise a nucleobase moiety and a sugar moiety and an internucleoside linker.

29. The library according to claim 25, wherein the first and/or second linker is selected from the group consisting of carbohydrates, substituted carbohydrates, vinyl, polyvinyl, substituted polyvinyl, acetylene, polyacetylene, aryl /hetaryl, polyaryl/hetaryl and substituted polyaryl/polyhetaryl, ethers, polyethers, amines, polyamines, substituted polyamines; double stranded, single stranded or partially double stranded natural and unnatural polynucleotides, substituted double stranded, single stranded or partially double stranded natural and unnatural polynucleotides, polyamides, natural and un-natural polypeptides, substituted polyamides, and substituted natural and unnatural polypeptides.

30. The library according to claim 25, wherein said first and/or second linker comprises a polynucleotide linker.

31. The library according to claim 25, wherein said first and/or second linker comprises a polyether linker.

32. The library according to claim 25 wherein said first and/or second linker comprises a polyethyleneglycol linker.

33. The library according to claim 25 wherein said first and/or second linker comprises a substituted polyether linker.

34. The library according to claim 30, wherein each of the first and the second linker comprises a polynucleotide linker.

35. The library according to claim 31, wherein each of the first and the second linker comprises a polyether linker.

36. The library according to claim 32 wherein each of the first and the second linker comprises a polyethyleneglycol linker.

37. The library of claim 25, wherein the first linker of the double stranded identifier oligonucleotide comprises a hair-pin loop of nucleotides covalently linking the two strands of the double stranded identifier oligonucleotide at one end of the strands.

38. The library of claim 25, wherein the small non-peptide molecule is covalently linked to the double stranded identifier oligonucleotide via an anchorage point located at a first terminal region of one of the single strands, and wherein the first linker comprises a hair-pin loop of nucleotides covalently linking the two strands of the double stranded identifier oligonucleotide at a different, second terminal region of the single strands.

39. A method for the enrichment of the library according to claim 25 for small non-peptide molecules having a predetermined activity or functionality, said method comprising the steps of:
(i) subjecting said library one or more times to an enrichment condition, and
(ii) obtaining an enriched library having a higher relative amount of small non-peptide molecules having said predetermined activity or functionality.

40. The method of claim 39, wherein the oligonucleotide identifiers of the enriched complexes are amplified.

41. The method of claim 39, wherein the small non-peptide molecules of the enriched library are identified by sequencing the oligonucleotide identifier.

42. The method of claim 39, wherein the enrichment condition is an affinity of the small non-peptide molecules of the library of claim 25 for a target molecule or target entity.

43. The library according to claim 1, wherein each nucleic acid monomer present in the oligonucleotide identifier comprises a naturally occurring nucleobase and a backbone moiety.

44. The library according to claim 1, wherein the nucleobases of the nucleic acid monomers of the oligonucleotide identifier are selected from the groupd consisting of naturally occurring nucleobases and non-naturally occurring nucleobases, wherein the nucleobases are connected by backbone moieties comprising a pentose sugar moiety and an internucleoside linker.

45. The library according to claim 44, wherein the nucleobases of the nucleic acid monomers of the identifier are selected from the group consisting of purine and pyrimidine hetero-cycles, including heterocyclic analogues and tautomers thereof.

46. The library according to claim 45, wherein the nucleobases of the nucleic acid monomers are selected from the group consisting of
adenine, 8-oxo-$N^6$-methyladenine;
guanine, isoguanine, 7-deazaguanine;
cytosine, isocytosine, pseudoisocytosine, $N^4,N^4$-ethanocytosine, 5-methylcytosine, 5-($C^3$-$C^6$)-alkynylcytosine;
thymine;
uracil, 5-bromouracil, 5-fluorouracil;
inosine;
purine, diaminopurine, $N^6,N^6$-ethano-2,6-diamino-purine;
xanthine, 7-deazaxanthine;
pyrimidine and 2-hydroxy-5-methyl-4-triazolopyridine;
including heterocyclic analogues and tautomers thereof.

47. The library according to claim 44, wherein each backbone moiety is independently selected from the group consisting of

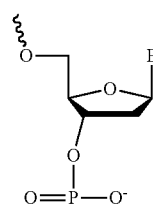
DNA

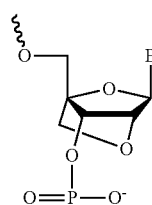
Oxy-LNA

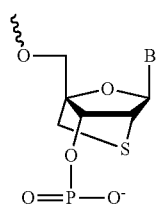
Thio-LNA

-continued

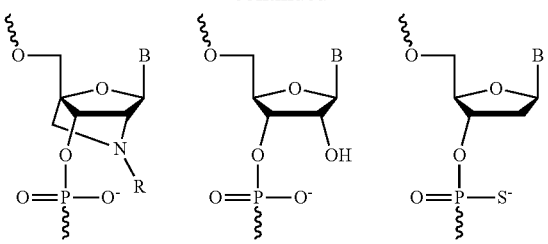
Amino-LNA
R = -H, -CH$_3$
    RNA    Phosphorthioate

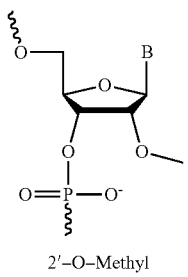
2'-O-Methyl

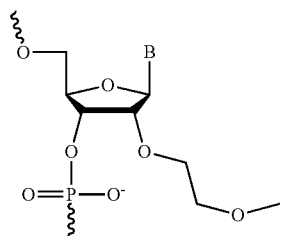
2'-MOE

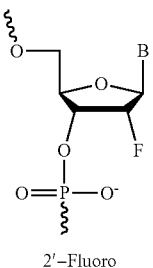
2'-Fluoro

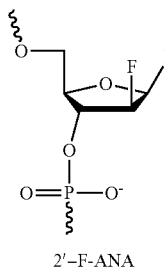
2'-F-ANA

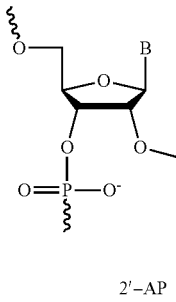
2'-AP

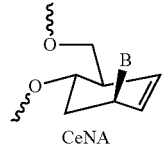
CeNA

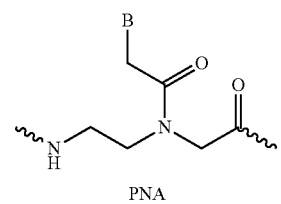
HNA

PNA

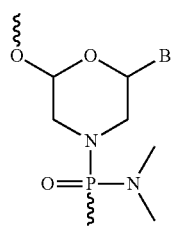
Morpholino

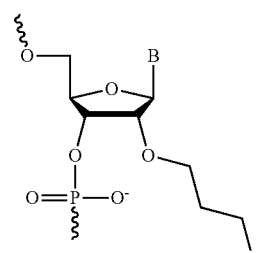
2'-(3-hydoxy)propyl

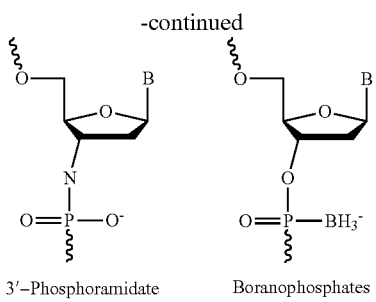

3'-Phosphoramidate  Boranophosphates wherein B denotes a nucleobase.

48. The library according to claim 1, wherein each nucleic acid monomer present in the oligonucleotide identifier is composed of a nucleobase and a backbone moiety, wherein each nucleobase is selected from the group consisting of naturally occurring nucleobases and non-naturally occurring nucleobases, and wherein each backbone moiety comprises a pentose sugar moiety and an internucleoside linker.

49. The library according to claim 48, wherein the pentose sugar moiety is selected from the group consisting of ribose, 2'-deoxyribose, 2'-O-methyl-ribose, 2'-flouro-ribose, and 2'-4'-O-methylene-ribose (LNA), and wherein each nucleobase is attached to the 1' position of each pentose sugar moiety.

50. The library according to claim 48, wherein each internucleoside linker is connecting the 3' end of a preceding pentose monomer to a 5' end of a succeeding pentose monomer in the identifier oligonucleotide.

51. The library according to claim 50, wherein each internucleoside linker is independently selected from the group of consisting of a phosphodiester linker, a phosphorothioate linker, a methylphosphonate linker, a phosphoramidate linker, a phosphotriester linker, a phosphodithioate linker, and a non-phosphorous-containing linker.

52. The library according to claim 1, wherein the olgionucleotide identifier comprises nucleic acid monomers selected from the group consisting of nucleosides consisting of deoxyadenosine, deoxyguanosine, deoxythymidine, and deoxycytidine, wherein said nucleosides are connected through phosphodiester linkages.

53. The library according to claim 1, wherein the oligonucleotide identifier comprises nucleic acid monomers selected from the group consisting of nucleosides consisting of adenosine, guanosine, uridine, cytidine, and inosine, wherein said nucleosides are connected through phosphodiester linkages.

54. The library according to claim 1, wherein the oligonucleotide identifier comprises nucleic acid monomers selected from a first group consisting of nucleosides consisting of deoxyadenosine, deoxyguanosine, deoxythymidine, and deoxycytidine, as well as nucleosides selected from a second group consisting of nucleosides consisting of adenosine, guanosine, uridine, cytidine, and inosine, wherein said nucleosides are connected through phosphodiester linkages.

55. The library according to claim 1, wherein the second linker is a polyethylene glycol (PEG) linker.

56. The library according to claim 55, wherein the small non-peptide small non-peptide molecules of the library are selected from the group consisting of
monofunctional, difunctional, trifunctional and oligofunctional, open-chain hydrocarbons, monocyclic, bicyclic, tricyclic and polycyclic hydrocarbons, bridged polycyclic hydrocarbons;
monofunctional, difunctional trifunctional and oligofunctional, non-aromatic carbocycles, monofunctional, difunctional, trifunctional and oligofunctional, aromatic carbocycles, monocyclic, bicyclic, tricyclic and polycyclic, aromatic carbocycles;
monofunctional, difunctional, trifunctional and oligofunctional, non-aromatic heterocycles, monofunctional, difunctional, trifunctional and oligofunctional, aromatic heterocycles monocyclic, bicyclic, tricyclic and polycyclic heterocycles, and bridged polycyclic heterocycles.

57. The library according to claim 25, wherein each nucleic acid monomer present in the oligonucleotide identifier comprises a naturally occurring nucleobase and a backbone moiety.

58. The library according to claim 25, wherein the nucleobases of the nucleic acid monomers of the oligonucleotide identifier are selected from the group consisting of naturally occurring nucleobases and non-naturally occurring nucleobases, wherein the nucleobases are connected by backbone moieties comprising a pentose sugar moiety and an internucleoside linker.

59. The library according to claim 58, wherein the nucleobases of the nucleic acid monomers of the oligonucleotide identifier are selected from the group consisting of purine and pyrimidine hetero-cycles, including heterocyclic analogues and tautomers thereof.

60. The library according to claim 59, wherein the nucleobases of the nucleic acid monomers are selected from the group consisting of adenine, 8-oxo-N$^6$-methyladenine;

guanine, isoguanine, 7-deazaguanine;

cytosine, isocytosine, pseudoisocytosine, N$^4$,N$^4$-ethanocytosine, 5-methylcytosine, 5-(C$^3$-C$^6$)-alkynylcytosine;

thymine;

uracil, 5-bromouracil, 5-fluorouracil;

inosine;

purine, diaminopurine, N$^6$,N$^6$-ethano-2,6-diamino-purine;

xanthine, 7-deazaxanthine;

pyrimidine and 2-hydroxy-5-methyl-4-triazolopyridine;

including heterocyclic analogues and tautomers thereof.

61. The library according to claim 58, wherein each backbone moiety is independently selected from the group consisting of

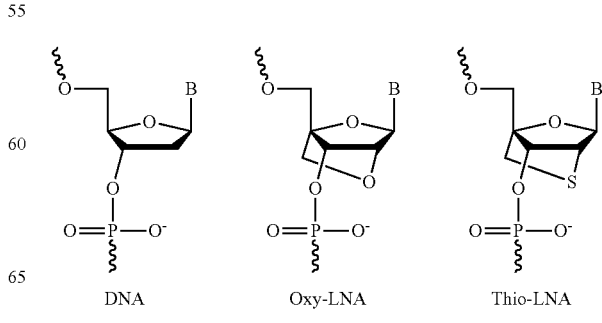

DNA  Oxy-LNA  Thio-LNA

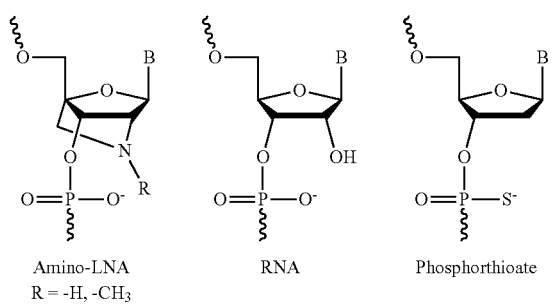

Amino-LNA  R = -H, -CH₃  RNA  Phosphorthioate

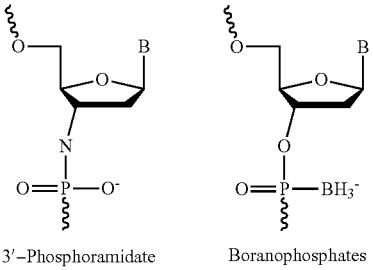

3'–Phosphoramidate   Boranophosphates

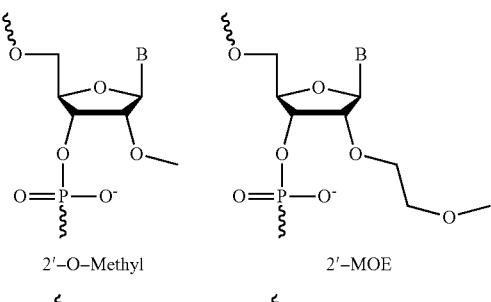

2'–O–Methyl   2'–MOE

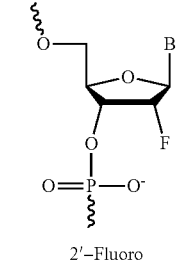
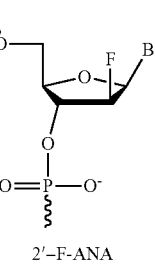

2'–Fluoro   2'–F-ANA

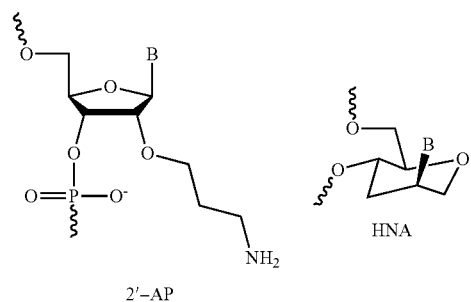

2'–AP   HNA

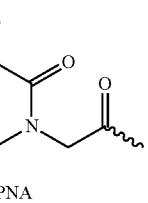

CeNA   PNA

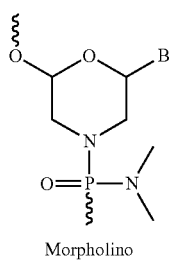
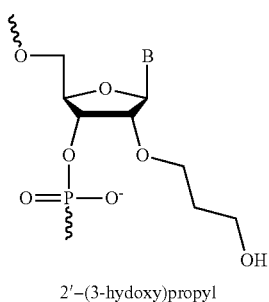

Morpholino   2'–(3-hydoxy)propyl wherein B denotes a nucleobase.

62. The library according to claim 25, wherein each nucleic acid monomer present in the oligonucleotide identifier is composed of a nucleobase and a backbone moiety, wherein each nucleobase is selected from the group consisting of naturally occurring nucleobases and non-naturally occurring nucleobases, and wherein each backbone moiety comprises a pentose sugar moiety and an internucleoside linker.

63. The library according to claim 62, wherein the pentose sugar moiety is selected from the group consisting of ribose, 2'-deoxyribose, 2'-O-methyl-ribose, 2'-flouro-ribose, and 2'-4'-O-methylene-ribose (LNA), and wherein each nucleobase is attached to the 1' position of each pentose sugar moiety.

64. The library according to claim 62, wherein each internucleoside linker is connecting the 3' end of a preceding pentose monomer to a 5' end of a succeeding pentose monomer in the identifier oligonucleotide.

65. The library according to claim 64, wherein each internucleoside linker is independently selected from the group of consisting of a phosphodiester linker, a phosphorothioate linker, a methylphosphonate linker, a phosphoramidate linker, a phosphotriester linker, a phosphodithioate linker, and a non-phosphorous-containing linker.

66. The library according to claim 25, wherein the oligonucleotide identifier comprises nucleic acid monomers selected from the group consisting of nucleosides consisting of deoxyadenosine, deoxyguanosine, deoxythymidine, and deoxycytidine, wherein said nucleosides are connected through phosphodiester linkages.

67. The library according to claim 25, wherein the oligonucleotide identifier comprises nucleic acid monomers selected from the group consisting of nucleosides consisting of adenosine, guanosine, uridine, cytidine, and inosine, wherein said nucleosides are connected through phosphodiester linkages.

68. The library according to claim 25, wherein the oligonucleotide identifier comprises nucleic acid monomers selected from a first group consisting of nucleosides consisting of deoxyadenosine, deoxyguanosine, deoxythymidine, and deoxycytidine, as well as nucleosides selected from a second group of nucleosides consisting of adenosine, guanosine, uridine, cytidine, and inosine, wherein said nucleosides are connected through phosphodiester linkages.

69. The library according to claim 25, wherein the second linker is a polyethylene glycol (PEG) linker.

70. The library according to claim 69, wherein the small non-peptide molecules of the library are selected from the group consisting of monofunctional, difunctional, trifunctional and oligofunctional, open-chain hydrocarbons, monocyclic, bicyclic, tricyclic and polycyclic hydrocarbons, bridged polycyclic hydrocarbons;

monofunctional, difunctional trifunctional and oligofunctional, non-aromatic carbocycles, monofunctional, difunctional, trifunctional and oligofunctional, aromatic carbocycles, monocyclic, bicyclic, tricyclic and polycyclic, aromatic carbocycles;

monofunctional, difunctional, trifunctional and oligofunctional, non-aromatic heterocycles, monofunctional, difunctional, trifunctional and oligofunctional, aromatic heterocycles monocyclic, bicyclic, tricyclic and polycyclic heterocycles, and bridged polycyclic heterocycles.

71. A library comprising different complexes, wherein each complex comprises
   i) a first entity comprising a double stranded oligonucleotide identifier comprising single oligonucleotide strands covalently linked by a first linker, wherein the first linker links oligonucleotide strand 3' and 5' ends,
   ii) a second entity comprising a small non-peptide molecule, and
   iii) a second linker covalently linking the first entity to the second entity,
   wherein the small non-peptide molecule of the second entity can be identified by each and both of the single strands of the double stranded oligonucleotide identifier,
   wherein the first entity is covalently linked to the second entity at or near the 3' or 5' end of a single strand of the double stranded oligonucleotide identifier.

72. The library of claim 71, wherein the number of complexes is from 2 to $10^{18}$.

73. The library according to claim 72, wherein the small non-peptide molecule of the complexes of the library is selected from the group consisting of monofunctional, difunctional,trifunctional and oligofunctional open-chain hydrocarbons; monofunctional, difunctional,trifunctional and oligofunctional non-aromatic carbocycles; monocyclic, bicyclic, tricyclic and polycyclic hydrocarbons; bridged polycyclic hydrocarbons; monofunctional, difunctional, trifunctional, and oligofunctional non-aromatic heterocycles; monocyclic, bicyclic, tricyclic, and polycyclic heterocycles, bridged polycyclic heterocycles; monofunctional, difunctional,trifunctional and oligofunctional aromatic carbocycles; monocyclic, bicyclic, tricyclic, and polycyclic aromatic carbocycles; and monofunctional, difunctional, trifunctional and oligofunctional aromatic heterocycles.

74. The library according to claim 73, wherein the first and/or second linker is selected from the group consisting of carbohydrides, substituted carbohydrides, vinyl, polyvinyl, substituted polyvinyl, acetylene, polyacetylene, aryl /hetaryl, polyaryl/hetaryl and substituted polyaryl/polyhetaryl, ethers, polyethers, amines, polyamines, substituted polyamines; double stranded, single stranded or partially double stranded natural and unnatural polynucleotides, substituted double stranded, single stranded or partially double stranded natural and unnatural polynucleotides, polyamides, natural and un-natural polypeptides, substituted polyamides, and substituted natural and unnatural polypeptides.

75. The library according to claim 74, wherein said first and/or second linker comprises a polynucleotide linker.

76. The library according to claim 74, wherein said first and/or second linker comprises an optionally substituted polyether linker.

77. The library according to claim 74, wherein said first and/or second linker comprises a polyethyleneglycol linker.

78. The library of claim 75, wherein the first linker comprises a hair-pin loop of nucleotides.

79. The library of claim 78, wherein the second entity is covalently linked to the first entity at or near the 5' or 3' end of a single strand of double stranded identifier oligonucleotide, and wherein the first linker comprises a hair-pin loop comprising nucleotides covalently linking the two strands of the double stranded identifier oligonucleotide at the opposite end of the single strand.

80. The library according to claim 76, wherein the second linker comprises an optionally substituted polyether linker.

81. The library according to claim 77, wherein the second linker comprises a polyethylene glycol.

82. The library according to claim 80, wherein the polyether linker is not substituted.

83. The library according to claim 71, wherein each nucleic acid monomer present in the oligonucleotide identifier is composed of a nucleobase and a backbone moiety, wherein each nucleobase is selected from the group consisting of naturally occurring nucleobases and non-naturally occurring nucleobases, and wherein each backbone moiety comprises a pentose sugar moiety and an internucleoside linker.

84. The library according to claim 83, wherein the pentose sugar moiety is selected from the group consisting of ribose, 2'-deoxyribose, 2'-O-methyl-ribose, 2'-flouro-ribose, and 2'-4'-O-methylene-ribose (LNA).

85. The library according to claim 83, wherein each internucleoside linker connects the 3' end of a preceding pentose monomer to a 5' end of a succeeding pentose monomer, and wherein each internucleoside linker is independently selected from the group consisting of a phosphodiester linker, a phosphorothioate linker, a methylphosphonate linker, a phosphoramidate linker, a phosphotriester linker, a phosphodithioate linker and a non-phosphorous-containing linker.

86. The library according to claim 85, wherein at least one internucleoside linker is a non-phosphorous-containing linker.

87. A library comprising different complexes, wherein each complex comprises
   i) a first entity comprising a double stranded oligonucleotide identifier comprising single oligonucleotide strands covalently linked by a terminally located hair-pin loop comprising nucleotides, wherein the hairpin loop covalently links oligonucleotide strand 3' and 5' ends.
   ii) a second entity comprising a molecule selected from the group consisting of monofunctional, difunctional, trifunctional and oligofunctional open-chain hydrocarbons; monofunctional, difunctional, trifunctional and oligofunctional non-aromatic carbocycles; monocyclic, bicyclic, tricyclic and polycyclic hydrocarbons; bridged polycyclic hydrocarbons; monofunctional, difunctional, trifunctional, and oligofunctional non-aromatic heterocycles; monocyclic, bicyclic, tricyclic, and polycyclic heterocycles, bridged polycyclic heterocycles; monofunctional, difunctional, trifunctional and oligofunctional aromatic carbocycles; monocyclic, bicyclic, tricyclic, and polycyclic aromatic carbocycles; and monofunctional, difunctional, trifunctional and oligofunctional aromatic heterocycles,
   iii) a linker covalently linking the first entity and the second entity,
   wherein the molecule of the second entity can be identified by each and both of the single strands of the double stranded oligonucleotide identifier,
   wherein the first entity is covalently linked to the second entity at a terminal location of the first entity.

88. The library according to claim 87, wherein the linker covalently linking the first entity and the second entity is selected from the group consisting of carbohydrides, substituted carbohydrides, vinyl, polyvinyl, substituted polyvinyl, acetylene, polyacetylene, aryl/hetaryl, polyaryl/hetaryl and substituted polyaryl/polyhetaryl, ethers, polyethers, amines, polyamines, substituted polyamines; double stranded, single stranded or partially double stranded natural and unnatural polynucleotides, substituted double stranded, single stranded or partially double stranded natural and unnatural polynucleotides, polyamides, natural and un-natural polypeptides, substituted polyamides, and substituted natural and unnatural polypeptides.

89. The library according to claim 87, wherein the linker covalently linking the first entity and the second entity comprises an optionally substituted polyether linker.

90. The library according to claim 87, wherein the linker covalently linking the first entity and the second entity comprises a polyethylene glycol.

91. The library according to claim 89, wherein the polyether is not substituted.

92. The library according to claim 87, wherein each nucleic acid monomer present in the oligonucleotide identifier is composed of a nucleobase and a backbone moiety, wherein each nucleobase is selected from the group consisting of naturally occurring nucleobases and non-naturally occurring nucleobases, and wherein each backbone moiety comprises a pentose sugar moiety and an internucleoside linker.

93. The library according to claim 92, wherein the pentose sugar moiety is selected from the group consisting of ribose, 2'-deoxyribose, 2'-O-methyl-ribose, 2'-flouro-ribose, and 2'-4'-O-methylene-ribose (LNA).

94. The library according to claim 92, wherein each internucleoside linker connects the 3' end of a preceding pentose monomer to a 5' end of a succeeding pentose monomer, and wherein each internucleoside linker is independently selected from the group consisting of a phosphodiester linker, a phosphorothioate linker, a methylphosphonate linker, a phosphoramidate linker, a phosphotriester linker, a phosphodithioate linker, and a non-phosphorous-containing linker.

95. The library according to claim 94, wherein at least one internucleoside linker is a non-phosphorous-containing linker.

96. The library according to claim 95, wherein further internucleoside linkers of the identifier oligonucleotide are independently selected from the group of consisting of a phosphodiester linker, a phosphorothioate linker, a methylphosphonate linker, a phosphoramidate linker, a phosphotriester linker and a phosphodithioate linker.

97. The method of claim 87, wherein the terminal location of the first entity is a terminal region of either of the covalently linked single strands of the double stranded oligonucleotide identifier.

98. The library according to claim 87, wherein the second entity is covalently linked to the first entity at a terminal region of a single strand of the double stranded identifier oligonucleotide, and wherein the hair-pin loop covalently links the two strands of the double stranded identifier oligonucleotide at the opposite end of the single strand.

* * * * *

SEQUENCE LISTING

<160> NUMBER OF SEQ ID NOS: 39

<210> SEQ ID NO 1
<211> LENGTH: 27
<212> TYPE: DNA
<213> ORGANISM: Artificial Sequence
<220> FEATURE:
<223> OTHER INFORMATION: synthetic construct (AH316)
<220> FEATURE:
<221> NAME/KEY: modified_base
<222> LOCATION: (1)..(1)
<223> OTHER INFORMATION: g modified with Amino-modifier 5 (obtainable from Glen Research cat. No 10-1905

<400> SEQUENCE: 1
ngtaacagac ctgtcgagca tccagct                                27

<210> SEQ ID NO 2
<211> LENGTH: 27
<212> TYPE: DNA
<213> ORGANISM: Artificial Sequence
<220> FEATURE:
<223> OTHER INFORMATION: synthetic construct (AH331)
<220> FEATURE:
<221> NAME/KEY: modified_base
<222> LOCATION: (27)..(27)
<223> OTHER INFORMATION: modified uracil, namely Carboxy dT (Glen Research, cat. No 10-1035)

<400> SEQUENCE: 2
cgacctctgg attgcatcgg tgttacn                                27

<210> SEQ ID NO 3
<211> LENGTH: 80
<212> TYPE: DNA
<213> ORGANISM: Artificial Sequence
<220> FEATURE:
<223> OTHER INFORMATION: synthetic construct (AH140)

<400> SEQUENCE: 3
agctggatgc tcgacaggtc aggtcgatcc gcgttaccag tcttgcctga acgtagtcgt    60
ccgatgcaat ccagaggtcg                                              80

<210> SEQ ID NO 4
<211> LENGTH: 56
<212> TYPE: DNA
<213> ORGANISM: Artificial Sequence
<220> FEATURE:
<223> OTHER INFORMATION: synthetic construct (AH36)
<220> FEATURE:
<221> NAME/KEY: modified_base
<222> LOCATION: (56)..(56)
<223> OTHER INFORMATION: modified uracil, namely Carboxy-dT (Glen Research cat.no. 10-1035)

<400> SEQUENCE: 4
cgacctctgg attgcatcgg tcatggctga ctgtccgtcg aatgtgtcca gttacn        56

<210> SEQ ID NO 5
<211> LENGTH: 40
<212> TYPE: DNA
<213> ORGANISM: Artificial Sequence
<220> FEATURE:
<223> OTHER INFORMATION: synthetic construct (AH38)

<400> SEQUENCE: 5
agctggatgc tcgacaggtc ccgatgcaat ccagaggtcg                          40

```
<210> SEQ ID NO 6
<211> LENGTH: 56
<212> TYPE: DNA
<213> ORGANISM: Artificial Sequence
<220> FEATURE:
<223> OTHER INFORMATION: synthetic construct (AH51)
<220> FEATURE:
<221> NAME/KEY: modified_base
<222> LOCATION: (1)..(1)
<223> OTHER INFORMATION: modified uracil, namely Amino-Modifier C6 dT
      (Glen Research cat.no. 10-1039)

<400> SEQUENCE: 6
ngtaacacct gtgtaagctg cctgtcagtc ggtactgacc tgtcgagcat ccagct        56

<210> SEQ ID NO 7
<211> LENGTH: 20
<212> TYPE: DNA
<213> ORGANISM: Artificial Sequence
<220> FEATURE:
<223> OTHER INFORMATION: synthetic construct (AH137)

<400> SEQUENCE: 7
acgactacgt tcaggcaaga                                                20

<210> SEQ ID NO 8
<211> LENGTH: 80
<212> TYPE: DNA
<213> ORGANISM: Artificial Sequence
<220> FEATURE:
<223> OTHER INFORMATION: synthetic construct (AH138)

<400> SEQUENCE: 8
tcttgcctga acgtagtcgt aggtcgatcc gcgttaccag agctggatgc tcgacaggtc    60
ccgatgcaat ccagaggtcg                                                80

<210> SEQ ID NO 9
<211> LENGTH: 20
<212> TYPE: DNA
<213> ORGANISM: Artificial Sequence
<220> FEATURE:
<223> OTHER INFORMATION: synthetic construct (AH139)

<400> SEQUENCE: 9
cgacctctgg attgcatcgg                                                20

<210> SEQ ID NO 10
<211> LENGTH: 76
<212> TYPE: DNA
<213> ORGANISM: Artificial Sequence
<220> FEATURE:
<223> OTHER INFORMATION: synthetic construct (AH143)
<220> FEATURE:
<221> NAME/KEY: modified_base
<222> LOCATION: (76)..(76)
<223> OTHER INFORMATION: modified uracil, namely Carboxy-dT (Glen
      Research cat.no. 10-1035)

<400> SEQUENCE: 10
ctggtaacgc ggatcgacct tcatttttt ttttttttt ttttggctga ctgtccgtcg      60
aatgtgtcca gttacn                                                    76

<210> SEQ ID NO 11
<211> LENGTH: 21
<212> TYPE: DNA
<213> ORGANISM: Artificial Sequence
```

-continued

```
<220> FEATURE:
<223> OTHER INFORMATION: synthetic construct (AH202)
<220> FEATURE:
<221> NAME/KEY: modified_base
<222> LOCATION: (21)..(21)
<223> OTHER INFORMATION: modified uracil, namely Carboxy-dT (Glen
      Research cat.no. 10-1035)

<400> SEQUENCE: 11
tctggattgc atcgggttac n                                              21

<210> SEQ ID NO 12
<211> LENGTH: 25
<212> TYPE: DNA
<213> ORGANISM: Artificial Sequence
<220> FEATURE:
<223> OTHER INFORMATION: synthetic construct (AH 270)
<220> FEATURE:
<221> NAME/KEY: modified_base
<222> LOCATION: (1)..(1)
<223> OTHER INFORMATION: g modified with Amino-Modifier 5 (cat.no.
      10-1905)

<400> SEQUENCE: 12
ntaacgacct gtcgagcatc cagct                                          25

<210> SEQ ID NO 13
<211> LENGTH: 112
<212> TYPE: DNA
<213> ORGANISM: Artificial Sequence
<220> FEATURE:
<223> OTHER INFORMATION: synthetic construct (AH286)

<400> SEQUENCE: 13
agctggatgc tcgacaggtc aagtaacagg tcgatccgcg ttatatcgtt tacggcatta    60
cccgtatagc cgctagatgc ccaaccatga cggcccatag cttgcggctt gc           112

<210> SEQ ID NO 14
<211> LENGTH: 120
<212> TYPE: DNA
<213> ORGANISM: Artificial Sequence
<220> FEATURE:
<223> OTHER INFORMATION: synthetic construct (AH320)

<400> SEQUENCE: 14
agctggatgc tcgacaggtc aggtcgatcc gcgttaccag gcccatagct tgcggcttgc    60
tgcagtcgat ggaccatgcc tcttgcctga acgtagtcgt ccgatgcaat ccagaggtcg   120

<210> SEQ ID NO 15
<211> LENGTH: 10
<212> TYPE: DNA
<213> ORGANISM: Artificial Sequence
<220> FEATURE:
<223> OTHER INFORMATION: synthetic construct (AH321)

<400> SEQUENCE: 15
caagaggcat                                                           10

<210> SEQ ID NO 16
<211> LENGTH: 20
<212> TYPE: DNA
<213> ORGANISM: Artificial Sequence
<220> FEATURE:
<223> OTHER INFORMATION: synthetic construct (AH322)

<400> SEQUENCE: 16
```
tcaggcaaga ggcatggtcc                                              20

<210> SEQ ID NO 17
<211> LENGTH: 26
<212> TYPE: DNA
<213> ORGANISM: Artificial Sequence
<220> FEATURE:
<223> OTHER INFORMATION: synthetic construct (AH342)
<220> FEATURE:
<221> NAME/KEY: modified_base
<222> LOCATION: (26)..(26)
<223> OTHER INFORMATION: modified uracil, namely Carboxy-dT (Glen
      Research cat.no. 10-1035)

<400> SEQUENCE: 17
tacttgacct gtcgagcatc gttacn                                       26

<210> SEQ ID NO 18
<211> LENGTH: 30
<212> TYPE: DNA
<213> ORGANISM: Artificial Sequence
<220> FEATURE:
<223> OTHER INFORMATION: synthetic construct (AH343)
<220> FEATURE:
<221> NAME/KEY: modified_base
<222> LOCATION: (1)..(1)
<223> OTHER INFORMATION: g modified with Amino-Modifier 5 (cat.no.
      10-1905)

<400> SEQUENCE: 18
gtaaccagct gcaagccgca agctatgggc                                   30

<210> SEQ ID NO 19
<211> LENGTH: 60
<212> TYPE: DNA
<213> ORGANISM: Artificial Sequence
<220> FEATURE:
<223> OTHER INFORMATION: synthetic construct (AH136)

<400> SEQUENCE: 19
agctggatgc tcgacaggtc tcttgcctga acgtagtcgt ccgatgcaat ccagaggtcg   60

<210> SEQ ID NO 20
<211> LENGTH: 26
<212> TYPE: DNA
<213> ORGANISM: Artificial Sequence
<220> FEATURE:
<223> OTHER INFORMATION: synthetic construct (AH174)
<220> FEATURE:
<221> NAME/KEY: modified_base
<222> LOCATION: (18)..(18)
<223> OTHER INFORMATION: t modified with Amino modifier 5 (obtainable
      from Glen research
      cat No. 10-1905)
<220> FEATURE:
<221> NAME/KEY: modified_base
<222> LOCATION: (26)..(26)
<223> OTHER INFORMATION: c modified with Thiol-Modifier C6 S-S (Glen
      Research, cat.no.10-1936)

<400> SEQUENCE: 20
tacgttcagg caagagtncc agttan                                       26

<210> SEQ ID NO 21
<211> LENGTH: 11
<212> TYPE: DNA
<213> ORGANISM: Artificial Sequence
<220> FEATURE:
<223> OTHER INFORMATION: first part of synthetic construct (AH190)
<220> FEATURE:

```
<221> NAME/KEY: modified_base
<222> LOCATION: (1)..(1)
<223> OTHER INFORMATION: modified uracil, namely Amino-Modifier C6 dT
      (Glen Research Cat. No. 10-1039)
<220> FEATURE:
<221> NAME/KEY: modified_base
<222> LOCATION: (11)..(11)
<223> OTHER INFORMATION: g linked by PC Spacer phosphoramidite
      (obtainable from Glen Research, cat. No. 10-4913) to base 1 of
      SEQ ID NO:39

<400> SEQUENCE: 21
ngtaacacct n                                                              11

<210> SEQ ID NO 22
<211> LENGTH: 26
<212> TYPE: DNA
<213> ORGANISM: Artificial Sequence
<220> FEATURE:
<223> OTHER INFORMATION: synthetic construct (AH155)
<220> FEATURE:
<221> NAME/KEY: modified_base
<222> LOCATION: (25)..(25)
<223> OTHER INFORMATION: t modified with -COOH 3'

<400> SEQUENCE: 22
ctggtaacgc ggatcgacct gttact                                              26

<210> SEQ ID NO 23
<211> LENGTH: 26
<212> TYPE: DNA
<213> ORGANISM: Artificial Sequence
<220> FEATURE:
<223> OTHER INFORMATION: synthetic construct (AH272)
<220> FEATURE:
<221> NAME/KEY: modified_base
<222> LOCATION: (26)..(26)
<223> OTHER INFORMATION: t modified with -COOH 3'

<400> SEQUENCE: 23
acgactacgt tcaggcaaga gttacn                                              26

<210> SEQ ID NO 24
<211> LENGTH: 23
<212> TYPE: DNA
<213> ORGANISM: Artificial Sequence
<220> FEATURE:
<223> OTHER INFORMATION: synthetic construct (AH202)
<220> FEATURE:
<221> NAME/KEY: modified_base
<222> LOCATION: (23)..(23)
<223> OTHER INFORMATION: t modified with -COOH 3'

<400> SEQUENCE: 24
tctggattgc atcggctgtt act                                                 23

<210> SEQ ID NO 25
<211> LENGTH: 20
<212> TYPE: DNA
<213> ORGANISM: Artificial Sequence
<220> FEATURE:
<223> OTHER INFORMATION: synthetic construct (MDL251)
<220> FEATURE:
<221> NAME/KEY: modified_base
<222> LOCATION: (1)..(1)
<223> OTHER INFORMATION: modified uracil, namely 5'amino-C6 dT (Glen
      Research Cat. No. 10-1039)

<400> SEQUENCE: 25
nacctgtcga gcatccagct                                                     20
```

<210> SEQ ID NO 26
<211> LENGTH: 87
<212> TYPE: DNA
<213> ORGANISM: Artificial Sequence
<220> FEATURE:
<223> OTHER INFORMATION: synthetic construct (AH154)

<400> SEQUENCE: 26
agctggatgc tcgacaggtc aagtaacagg tcgatccgcg ttaccagtct tgcctgaacg    60
tagtcgtccg atgcaatcca gaggtcg                                        87

<210> SEQ ID NO 27
<211> LENGTH: 25
<212> TYPE: DNA
<213> ORGANISM: Artificial Sequence
<220> FEATURE:
<223> OTHER INFORMATION: synthetic construct (AH270)
<220> FEATURE:
<221> NAME/KEY: modified_base
<222> LOCATION: (1)..(1)
<223> OTHER INFORMATION: g modified by 5'amino

<400> SEQUENCE: 27
ntaacgacct gtcgagcatc cagct                                          25

<210> SEQ ID NO 28
<211> LENGTH: 80
<212> TYPE: DNA
<213> ORGANISM: Artificial Sequence
<220> FEATURE:
<223> OTHER INFORMATION: synthetic construct (AH140)

<400> SEQUENCE: 28
agctggatgc tcgacaggtc aggtcgatcc gcgttaccag tcttgcctga acgtagtcgt    60
ccgatgcaat ccagaggtcg                                                80

<210> SEQ ID NO 29
<211> LENGTH: 16
<212> TYPE: DNA
<213> ORGANISM: Artificial
<220> FEATURE:
<223> OTHER INFORMATION: synthetic construct, building block for coding
      region 1, Fig. 3A

<400> SEQUENCE: 29
sssssatatt tsssss                                                    16

<210> SEQ ID NO 30
<211> LENGTH: 16
<212> TYPE: DNA
<213> ORGANISM: Artificial
<220> FEATURE:
<223> OTHER INFORMATION: synthetic construct, building block for coding
      region 2, Fig. 3A

<400> SEQUENCE: 30
sssattttas ssssss                                                    16

<210> SEQ ID NO 31
<211> LENGTH: 16
<212> TYPE: DNA
<213> ORGANISM: Artificial
<220> FEATURE:
<223> OTHER INFORMATION: synthetic construct, building block for coding
      region 3, Fig. 3A

<400> SEQUENCE: 31
staatttsss ssssss                                              16

<210> SEQ ID NO 32
<211> LENGTH: 16
<212> TYPE: DNA
<213> ORGANISM: Artificial
<220> FEATURE:
<223> OTHER INFORMATION: synthetic construct, building block for coding
      region 4, Fig. 3A

<400> SEQUENCE: 32
ssatssatss atssss                                              16

<210> SEQ ID NO 33
<211> LENGTH: 16
<212> TYPE: DNA
<213> ORGANISM: Artificial
<220> FEATURE:
<223> OTHER INFORMATION: synthetic construct, buidling blocks for coding
      region 5, Fig. 3A

<400> SEQUENCE: 33
gcccgattaa assccg                                              16

<210> SEQ ID NO 34
<211> LENGTH: 16
<212> TYPE: DNA
<213> ORGANISM: Artificial
<220> FEATURE:
<223> OTHER INFORMATION: synthetic construct, building blocks for coding
      region 6, Fig. 3A

<400> SEQUENCE: 34
sasasttstt sssggg                                              16

<210> SEQ ID NO 35
<211> LENGTH: 16
<212> TYPE: DNA
<213> ORGANISM: Artificial
<220> FEATURE:
<223> OTHER INFORMATION: synthetic construct, codon 1, Fig. 3B

<400> SEQUENCE: 35
gcgcgatatt tgggcc                                              16

<210> SEQ ID NO 36
<211> LENGTH: 16
<212> TYPE: DNA
<213> ORGANISM: Artificial
<220> FEATURE:
<223> OTHER INFORMATION: synthetic construct, anti-codon 1, Fig. 3B

<400> SEQUENCE: 36
ggcccaaata tcgcgc                                              16

<210> SEQ ID NO 37
<211> LENGTH: 16
<212> TYPE: DNA
<213> ORGANISM: Artificial
<220> FEATURE:
<223> OTHER INFORMATION: synthetic construct, codon 6, Fig. 3B

<400> SEQUENCE: 37
gagagttctt cgcggg                                              16

```
<210> SEQ ID NO 38
<211> LENGTH: 16
<212> TYPE: DNA
<213> ORGANISM: Artificial
<220> FEATURE:
<223> OTHER INFORMATION: synthetic construct, anti-codon 6, Fig. 3B

<400> SEQUENCE: 38
cccgcgaaga actctc                                                   16

<210> SEQ ID NO 39
<211> LENGTH: 16
<212> TYPE: DNA
<213> ORGANISM: Artificial
<220> FEATURE:
<223> OTHER INFORMATION: second part of synthetic construct (AH 190)
<220> FEATURE:
<221> NAME/KEY: modified_base
<222> LOCATION: (1)..(1)
<223> OTHER INFORMATION: t linked by PC spacer phosphoramidite (Glen
      Research Cat. No. 10-1039) to last base of SEQ ID NO:21

<400> SEQUENCE: 39
ngacctgtcg agcatc                                                   16
```